United States Patent
Mizui et al.

(10) Patent No.: US 7,026,352 B1
(45) Date of Patent: Apr. 11, 2006

(54) PHYSIOLOGICALLY ACTIVE SUBSTANCES

(75) Inventors: Yoshiharu Mizui, Ibaraki (JP); Takashi Sakai, Ibaraki (JP); Satoshi Yamamoto, Ibaraki (JP); Keisuke Komeda, Ibaraki (JP); Masanori Fujita, Ibaraki (JP); Akifumi Okuda, Ibaraki (JP); Kumiko Kishi, Ibaraki (JP); Jun Niijima, Ibaraki (JP); Mitsuo Nagai, Ibaraki (JP); Kiyoshi Okamoto, Ibaraki (JP); Masao Iwata, Ibaraki (JP); Yoshihiko Kotake, Ibaraki (JP); Toshimitsu Uenaka, Ibaraki (JP); Naoki Asai, Ibaraki (JP); Motoko Matsufuji, Tokyo (JP); Tomohiro Sameshima, Shizuoka (JP); Naoto Kawamura, Kanagawa (JP); Kazuyuki Dobashi, Kanagawa (JP); Takashi Nakashima, Shizuoka (JP); Masashi Yoshida, Shizuoka (JP); Toshio Tsuchida, Shizuoka (JP); Susumu Takeda, Shizuoka (JP); Tomonari Yamada, Shizuoka (JP); Koji Norihisa, Shizuoka (JP); Takao Yamori, Tokyo (JP)

(73) Assignees: Mercian Corporation, Tokyo (JP); Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/470,806

(22) PCT Filed: Feb. 1, 2002

(86) PCT No.: PCT/JP02/00848

§ 371 (c)(1),
(2), (4) Date: Aug. 1, 2003

(87) PCT Pub. No.: WO02/060890

PCT Pub. Date: Aug. 8, 2002

(30) Foreign Application Priority Data

Feb. 1, 2001 (JP) .............................. 2001-025458

(51) Int. Cl.
*A61K 31/365* (2006.01)
*C07D 313/00* (2006.01)

(52) U.S. Cl. .................. 514/450; 514/218; 514/232.8; 514/320; 514/336; 514/422; 540/575; 544/149; 544/376; 546/207; 546/281.7; 548/517; 549/265; 549/270; 549/271

(58) Field of Classification Search ................ 549/271, 549/265, 270; 514/450, 218, 252.2, 320, 514/336, 422; 540/575; 544/149, 376; 546/207, 546/281.7; 548/517
See application file for complete search history.

(56) References Cited

FOREIGN PATENT DOCUMENTS

| JP | 4-352783 A | 12/1992 |
| WO | WO00/75126 A1 | 12/2000 |
| WO | WO02/12533 A2 | 2/2002 |

OTHER PUBLICATIONS

Bestmann, Hans Jurgen. SYNTHESIS, 1989, vol. 6, pp. 419-423.
Bestmann, Jans Jurgen. Angew. Chem., 1983, vol. 95, No. 10, pp. 810-811.
Furstner, Alois et al. Efficient Total Syntheses of Resin Glycosides and Analogues by Ring-Closing Olefin Metathesis, 1999, vol. 121, pp. 7814-7821.
Seki-Asano, Mitsuko, et al. J. Antibiot., 1994, vol. 47, No. 12, pp. 1395-1401.
Gunawardana, Geewananda, et al. J. Am. Chem. Soc. 1999, vol. 121, pp. 6092-6093.
Rohr, Jurgen. Angew Chem. Int. Ed., 2000, vol. 39, No. 16, pp. 2847-2849.
Kobayashi, Jun'ichi et al. Tetrahedron Letters, 1996, vol. 37, No. 9, pp. 1449-1450.
Hamberg, Mats. LIPIDS, 2000, vol. 35, No. 4, pp. 353-363.
Hamberg, Mats. Chem. Phys. Lipids, 1988, vol. 46, No. 4, pp. 235-243.

*Primary Examiner*—Bernard Dentz
(74) *Attorney, Agent, or Firm*—Birch, Stewart, Kolasch & Birch, LLP

(57) ABSTRACT

The present invention provides a novel bioactive substance having an antitumor activity and a process for producing it, and a medical use thereof. Namely, it provides a 12-membered ring macrolide compound represented by the following formula obtained from the incubation solution of *Streptomyces* sp. Mer. 11107 or a variant thereof, a pharmacologically acceptable salt thereof or a hydrate of them, and a process for producing it 92 Claims, No Drawings

1

PHYSIOLOGICALLY ACTIVE SUBSTANCES

This application is the national phase under 35 U.S.C. § 371 of PCT International Application No. PCT/JP02/00848 which has an International filing date of Feb. 1, 2002, which designated the United States of America.

TECHNICAL FIELD

The present invention relates to a 12-membered ring macrolide compound and antitumor activity thereof. More specifically, it relates to an agent for treating cancer, in particular, an agent for treating a solid cancer, an agent for suppressing cancer metastasis, an agent for treating diabetic retinopathy, an agent for treating rheumatoid arthritis and an agent for treating hematoma, which suppresses an angiogenesis by varying gene expression, for example, by inhibiting VEGF production.

PRIOR ART

Compounds having cytotoxicity have been used as anticancer agents, and many screenings have been carried out using cytotoxicity as an index. As a result, almost all of anticancer agents give affection to cancer cell and simultaneously to tissue in which cell proliferation is active, for example, to bone marrow, intestine epithelium and the like. Thus, the improvement of QOL of a patient has not been accomplished out yet.

Further, although it can be expected that treatment by the anticancer agents is rather effective for leukemia, it cannot be always said that they are effective for solid cancer, therefore it is status quo that the anticancer agents being effective for solid cancer are very few in number.

Screening fermentaion products of microorganism has been carried out using the cytotoxicity in vitro as an index, expecting that they might also be used as a anticancer agent. Many compounds having cytotoxicity have been found, however, it is confirmed that many of them are only cytotoxic, and few compounds show anticancer effect in vivo, and further few compounds exhibit effectiveness for solid cancer.

DISCLOSURE OF THE INVENTION

It is the object of the present invention to find a compound which is effective in vivo and can be further expected to have an effect for solid cancer from fermentation products of microorganism.

It is considered that tumorgenesis is caused by that a gene of normal cell is varied and a gene different from the normal cell is expressed. Accordingly, the present inventors have considered that the growth of a cancer cell can be suppressed by varying the gene expression of the cancer cell. For example, they have considered that the growth of the cancer cell can be varied by varying the gene expression of oncogene or tumor suppressor gene, or by varying the gene expression involving in cell cycle.

The present inventors have considered that a compound causing the variation of the gene expression, in particular, a compound suppressing VEGF production at a low oxygen condition could suppress angiogenesis by a cancer and is also effective for solid cancer. Then, they carried out screening fermentation products of microorganism using the VEGF production of low oxygen stimulating U251 cell as an index, have found out novel bioactive compounds, 12-membered ring macrolide compounds (hereinafter, these are referred to as 11107A to 11107BJ) which suppress the growth of vascular endothelial cell by suppressing VEGF production, and further suppress the growth of solid cancer in vivo. Further, they have found that compounds which were obtained by chemically modifying these microbial products (hereinafter, these are referred to as 11107 derivative) also have an activity for suppressing the growth of solid cancer.

The present invention provides the compound defined below, a pharmacologically acceptable salt thereof or a hydrate thereof. The hydrate is preferably a pharmacologically acceptable hydrate.

Hereafter, the respective title compounds are defined by the respective formulae. Any of these are reduced by the restricted clauses 1 and 2. Further, the compound described in the restricted clause 3 is not included.

The substituents such as $R^2$ in the respective formulae are defined by each formula.

Further, the present invention also provides medical uses of the respective compounds, a pharmacologically acceptable salt thereof or a hydrate of them. Namely, they are a pharmaceutical composition containing any one of them, medicament, the method for preventing, treating or improving diseases, the use of the compound for producing an agent for treating them, etc.

1. A compound represented by the formula (1), a pharmacologically acceptable salt thereof or a hydrate of them.

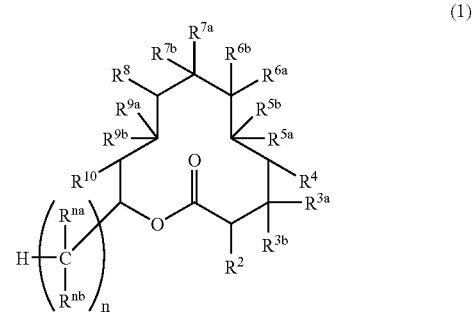

(1)

In the formula (1), n represents an integer of 3 to 12; and $R^2$, $R^{3a}$, $R^{3b}$, $R^4$, $R^{5a}$, $R^{5b}$, $R^{6a}$, $R^{6b}$, $R^{7a}$, $R^{7b}$, $R^8$, $R^{9a}$, $R^{9b}$, $R^{10}$, $R^{na}$ and $R^{nb}$ are the same as or different from each other and each means (1) hydrogen, (2) hydroxy or (3) <1> methyl, <2> $C_{1\text{-}22}$ Alkoxy, <3> $ArCH_2O$— (wherein Ar represents $C_{6\text{-}14}$ Aryl or 5-membered to 14-membered heteroaryl, each of which may have substituents), <4> $C_{2\text{-}22}$ Acyloxy, <5> unsaturated $C_{3\text{-}22}$ acyloxy, <6> $R^{CO}COO$— (wherein $R^{CO}$ represents $C_{6\text{-}14}$ Aryl, 5-membered to 14-membered heteroaryl, $C_{1\text{-}22}$ Alkoxy, unsaturated $C_{2\text{-}22}$ Alkoxy, $C_{6\text{-}14}$ Aryloxy or 5-membered to 14-membered heteroaryloxy, each of which may have substituents), <7> $C_{1\text{-}22}$ Alkylsulfonyloxy, <8> benzenesulfonyloxy or <9> $R^{s1}R^{s2}R^{s3}SiO$— (wherein $R^{s1}$, $R^{s2}$ And $R^{s3}$ are the same as or different from each other and each represents methyl, ethyl, i-propyl, t-butyl or phenyl), each of which may have substituents, (4) halogen or (5) $R^{N1}R^{N2}N$—$R^M$— (wherein $R^M$ represents a single bond or —CO—O—; and $R^{N1}$ and $R^{N2}$ are 1) the same as or different from each other and each represents <1> hydrogen or <2> (i) $C_{1\text{-}22}$ alkyl, (ii) unsaturated $C_{3\text{-}22}$ Alkyl, (iii) $C_{2\text{-}22}$ Acyl, (iv) unsaturated $C_{3\text{-}22}$ Acyl, (v) $C_{6\text{-}14}$ Aryl, (vi) 5-membered to 14-membered heteroaryl, (vii) benzyl, (viii) $C_{1\text{-}22}$ alkylsulfonyl or (ix) benzenesulfonyl, each of which may have substituents, or 2) —$NR^{N1}R^{N2}$ may be bound together to represent 3-membered to 14-membered nitrogen-containing non-aromatic heterocyclic ring which may have substituents); further, $R^2$ may form a single bond with either of $R^{3a}$ or $R^{3b}$ to represent the partial structure

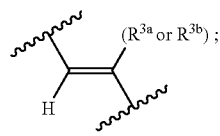

further, $R^{3a}$ and $R^{3b}$ may be bound together to represent a ketone structure (=O) or an oxime structure {=NOR$^{OX}$ (wherein $R^{OX}$ represents $C_{1-22}$ Alkyl, unsaturated $C_{3-22}$ alkyl, $C_{6-14}$ Aryl, 5-membered to 14-membered heteroaryl or benzyl, each of which may have substituents)}; further, either of $R^{3a}$ or $R^{3b}$ and either of $R^{6a}$ or $R^{6b}$ may be bound with oxygen to represent the partial structure

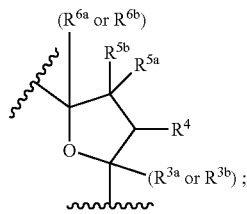

further, $R^4$ may form a single bond with either of $R^{5a}$ or $R^{5b}$ and may represent the partial structure

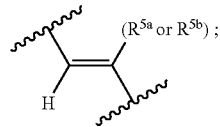

further, $R^{5a}$ and $R^{5b}$ may be bound together to represent a ketone structure (=O) or an oxime structure (=NOR$^{OX}$); further, $R^{6a}$ and $R^{6b}$ may be bound together to represent a spirooxyrane ring or exomethylene; further, either of $R^{6a}$ or $R^{6b}$ and either of $R^{7a}$ or $R^{7b}$ may be bound together to form a 1,3-dioxolane ring; further, $R^{7a}$ and $R^{7b}$ may be bound together to represent a ketone structure (=O) or an oxime structure (=NOR$^{OX}$); further, $R^8$ may form a single bond with either of $R^{9a}$ or $R^{9b}$ to represent the partial structure

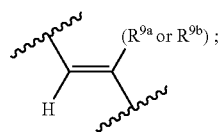

further, $R^{9a}$ and $R^{9b}$ may be bound together to represent a ketone structure (=O) or an oxime structure (=NOR$^{OX}$);

further, two adjacent $R^{na}$s may form 0 to 3 ethylene structures where one $R^{na}$ and one other $R^{na}$ forme a single bond; further, two $R^{na}$s may form 0 to 2 epoxy structures together with oxygen; further two $R^{na}$s may form one 2-oxo-1,3-dioxane structure; further, $R^{na}$ and $R^{nb}$ on the same carbon may be bound together to represent a ketone structure (=O) or an oxime structure (=NOR$^{OX}$), provided that (Restricted clause 1) when the above-mentioned compound is represented by the following formula (2):


at least one of $R^7$ and $R^{21}$ is hydroxy, acetoxy or methoxy; (Restricted clause 2) when the above-mentioned compound is represented by the following formula (3):

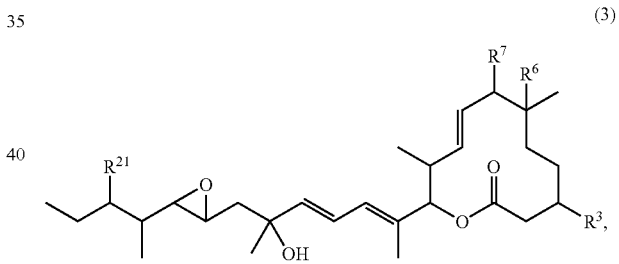

$R^7$ is hydroxy or acetoxy; and $R^3$, $R^6$ and $R^{21}$ are OH; and (Restricted clause 3) a compound represented by the formula (4) is excluded.

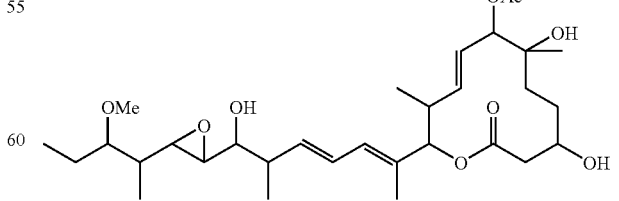

2. A compound represented by the formula (5), a pharmacologically acceptable salt thereof or a hydrate of them.

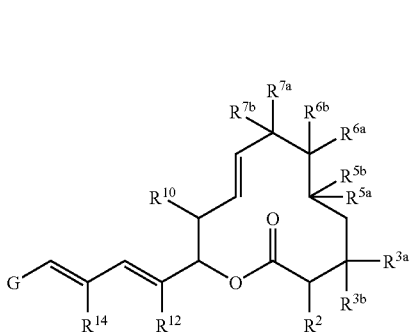

(5)

In the formula (5)

$R^2$, $R^{10}$, $R^{12}$ and $R^{14}$ are the same as or different from each other and each represents hydrogen or methyl;

$R^{3a}$, $R^{3b}$, $R^{5a}$, $R^{5b}$, $R^{6a}$ and $R^{6b}$ are the same as or different from each other and each represents
(1) hydrogen,
(2) hydroxy,
(3) <1> $C_{1-22}$ Alkyl,
   <2> $C_{1-22}$ Alkoxy,
   <3> ArCH$_2$O— (wherein Ar represents $C_{6-14}$ Aryl or 5-membered to 14-membered heteroaryl which may have substituents),
   <4> $C_{2-22}$ Acyloxy,
   <5> unsaturated $C_{3-22}$ Acyloxy,
   <6> —OCOR$^{CO}$ (wherein R$^{CO}$ represents (i) $C_{6-14}$ Aryl, (ii) 5-membered to 14-membered heteroaryl, (iii) $C_{1-22}$ alkoxy, (iv) unsaturated $C_{2-22}$ Alkoxy, (v) $C_{6-14}$ Aryloxy or (vi) 5-membered to 14-membered heteroaryloxy, each of which may have substituents),
   <7> $C_{1-22}$ Alkylsulfonyloxy,
   <8> benzenesulfonyloxy or
   <9> —OSiR$^{s1}$R$^{s2}$R$^{s3}$ (wherein R$^{s1}$, R$^{s2}$ and R$^{s3}$ are the same as or different from each other and each represents methyl, ethyl, i-propyl, t-butyl or phenyl,
(4) halogen or
(5) —R$^M$—NR$^{N1}$R$^{N2}$ (wherein R$^M$ represents a single bond or —CO—O—; and R$^{N1}$ and R$^{N2}$ are 1) the same as or different from each other and each represents <1> hydrogen or <2> (i) $C_{1-22}$ alkyl, (ii) unsaturated $C_{3-22}$ Alkyl, (iii) $C_{2-22}$ Acyl, (iv) unsaturated $C_{3-22}$ Acyl, (v) $C_{6-14}$ Aryl, (vi) 5-membered to 14-membered heteroaryl, (vii) benzyl, (viii) $C_{1-22}$ alkylsulfonyl or (ix) benzenesulfonyl, each of which may have substituents, or 2) NR$^{N1}$R$^{N2}$ may be bound together to represent 3-membered to 14-membered nitrogen-containing non-aromatic heterocyclic ring which may have substituents);

$R^{7a}$ and $R^{7b}$ Are
(1) different from each other and each represents
   1) hydrogen,
   2) —OR$^H$ (wherein R$^H$ is hydrogen, methyl or acetyl),
   3) —OR$^D$ (wherein R$^D$ represents
      (i) $C_{1-22}$ Alkyl (provided that in case of methyl, it always has substituents),
      (ii) —CH$_2$Ar,
      (iii) $C_{3-22}$ Acyl,
      (iv) unsaturated $C_{3-22}$ Acyl,
      (v) —COR$^{CO}$,
      (vi) $C_{1-22}$Alkylsulfonyl,
      (vii) benzenesulfonyl or
      (viii) SiR$^{s1}$R$^{s2}$R$^{s3}$) or
   4) —R$^M$—NR$^{N1}$R$^{N2}$, or (2) $R^{7a}$ and $R^{7b}$ may be bound together to represent <1> a ketone structure (=O) or represent an oxime structure (=NOR$^{OX}$; wherein R$^{OX}$ represents <1> $C_{1-22}$ Alkyl, <2> unsaturated $C_{3-22}$ Alkyl, <3> $C_{6-14}$ Aryl, <4> 5-membered to 14-membered heteroaryl or <5> benzyl, each of which may have substituents);

further, $R^{3a}$ and $R^{3b}$ may be bound together to represent a ketone structure (=O) or an oxime structure (=NOR$^{OX}$);

further, $R^{6a}$ or $R^{6b}$ may be bound together to represent a spirooxyrane ring or exomethylene;

further, either of $R^{6a}$ or $R^{6b}$ and either of $R^{7a}$ or $R^{7b}$ may be bound together to form a 1,3-dioxolane ring;

G is represented by

[1]

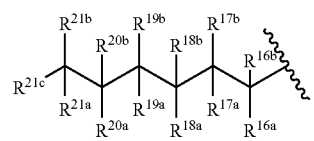

(G-I)

{wherein $R^{16a}$ and $R^{16b}$ are the same as or different from each other and each represents hydrogen, methyl or hydroxy;

$R^{17a}$, $R^{17b}$, $R^{18a}$, $R^{18b}$, $R^{19a}$, $R^{19b}$, $R^{20a}$, $R^{20b}$, $R^{21a}$, and $R^{21b}$ are the same as or different from each other and each represents
(1) hydrogen,
(2) methyl which may optionally have substituents,
(3) —OR$^H$,
(4) —OR$^D$,
(5) halogen or
(6) —R$^M$—NR$^{N1}$R$^{N2}$; and $R^{21c}$ means (1) hydrogen or (2)

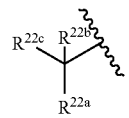

(wherein R$^{22a}$, R$^{22b}$ and R$^{22c}$ are the same as or different from each other and each represents <1> hydrogen, <2> methyl, <3> hydroxy, <4>—OR$^H$, <5> —OR$^D$, <6> —R$^M$—NR$^{N1}$RN2 or <7> halogen); further, either of R$^{18a}$ or R$^{18b}$ and either of R$^{19a}$ or R$^{19b}$ may form a single bond together to represent the partial structure

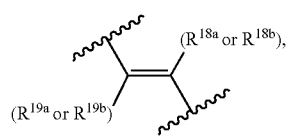

(R$^{18a}$ or R$^{18b}$), (R$^{19a}$ or R$^{19b}$)

or may be bonded with an oxygen to represent the partial structure

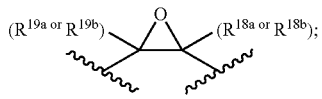

further, either of $R^{19a}$ or $R^{19b}$ and either of $R^{20a}$ or $R^{20b}$ may form a single bond together to represent

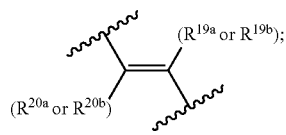

further, $R^{21a}$ and $R^{21b}$ may be bound together to represent <1> a ketone structure (=O) or represent <2> an oxime structure (=NOR$^{OX}$);
further, either of $R^{21a}$ or $R^{21b}$ and either of $R^{22a}$ or $R^{22b}$ may be bound together to represent the partial structure

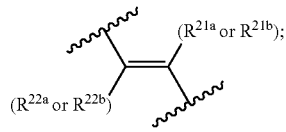

further, either of $R^{19a}$ or $R^{19b}$ and either of $R^{21a}$ or $R^{21b}$ may be bound together to represent the partial structure

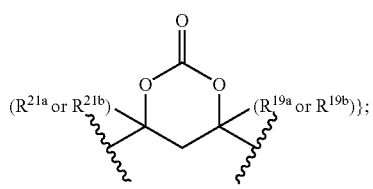

[2]

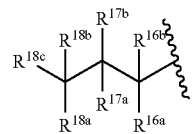

(G-II)

{wherein $R^{16a}$, $R^{16b}$, $R^{17a}$, $R^{17b}$, $R^{18a}$ and $R^{18b}$ have the same meanings as the definitions in the formula (G-I); and $R^{18c}$ represents (1) hydrogen or (2) the formula

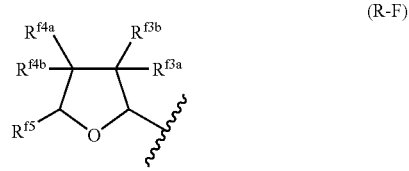

(R-F)

(wherein $R^{f3a}$, $R^{f3b}$, $R^{f4a}$ and $R^{f4b}$ are the same as or different from each other and each represents hydrogen, methyl, hydroxy, methoxy or acetoxy; and $R^{f5}$ represents methyl or ethyl)}; or

[3]

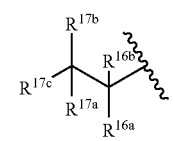

(G-III)

{wherein $R^{16a}$, $R^{16b}$, $R^{17a}$ and $R^{17b}$ have the same meanings as the definitions in the formula (G-I); and $R^{17c}$ represents (1) hydrogen or (2) the formula

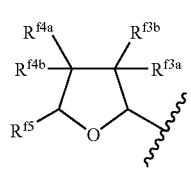

(R-F)

(wherein $R^{f3a}$, $R^{f3b}$, $R^{f4a}$ and $R^{f4b}$ are the same as or different from each other and each represents hydrogen, methyl, hydroxy, methoxy or acetoxy; and $R^{f5}$ represents methyl or ethyl)}, provided that the restricted clauses 1, 2 and 3 Are included.

3. A compound represented by the formula (6), a pharmacologically acceptable salt thereof or a hydrate of them.

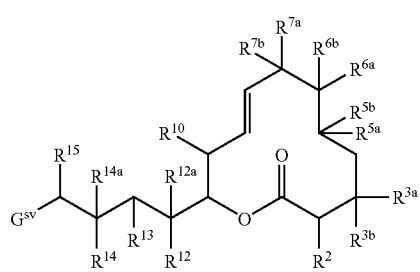

(6)

In the formula (6), $R^2$, $R^{3a}$, $R^{3b}$, $R^{5a}$, $R^{5b}$, $R^{6a}$, $R^{6b}$, $R^{7a}$, $R^{7b}$, $R^{10}$, $R^{12}$ and $R^{14}$ have the same meanings as the definitions of the formula 5;

$R^{12a}$ and $R^{13}$ (1) each represents hydrogen, or (2) are bound together to <1> form a single bond and represent

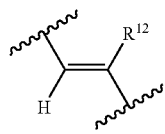

or <2> form epoxy and represent

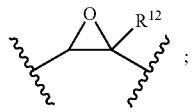;

$R^{14a}$ and $R^{15}$ (1) each represents hydrogen, or (2) are bound together to <1> form a single bond and represent

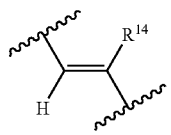

or <2> form epoxy and represent

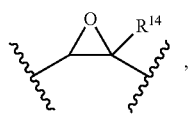, provided that (1) when $R^{12a}$ and $R^{13}$ are bound together to form a single bond in the formula (6), $R^{14a}$ and $R^{15}$ <1> are each hydrogen or <2> are bound together to be an epoxy; and (2) when $R^{14a}$ and $R^{15}$ are bound together to form a single bond, $R^{12a}$ and $R^{13}$ <1> are each hydrogen or <2> are bound together to be an epoxy; and $G^{sv}$ (1) has the same meaning as the definition of G in the formula 5, or (2) represents

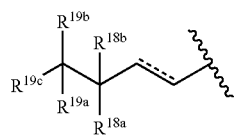

(wherein ═══ represents a single bond or a double bond; $R^{18a}$, $R^{18b}$, $R^{19a}$ and $R^{19b}$ have the same meanings as the definitions in the formula (5); $R^{19c}$ is hydrogen or $C_{1-4}$ Alkyl).

4. A compound represented by the formula (7), a pharmacologically acceptable salt thereof or a hydrate of them.

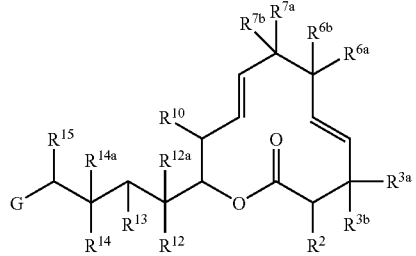

(7)

In the formula (7), $R^2$, $R^{3a}$, $R^{3b}$, $R^{6a}$, $R^{6b}$, $R^{7a}$, $R^{7b}$, $R^{10}$, $R^{12}$, $R^{14}$ and G have the same meanings as the definitions in the formula 5; $R^{12a}$ and $R^{13}$ (1) each represents hydrogen or (2) are bound together to <1> form a single bond and represent

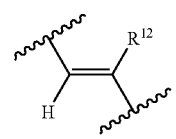

or <2> form epoxy and represent

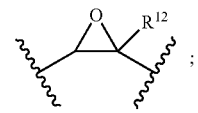;

and $R^{14a}$ and $R^{15}$ (1) each represents hydrogen or (2) are bound together to <1> form a single bond and represent

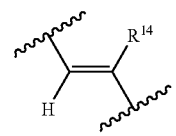

or <2> form epoxy and represent

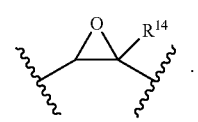.

5. A compound represented by the formula (8), a pharmacologically acceptable salt thereof or a hydrate of them.

(8)

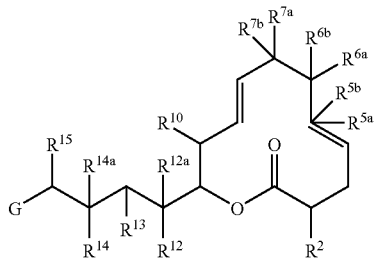

In the formula (8), $R^2$, $R^{5a}$, $R^{5b}$, $R^{6a}$, $R^{6b}$, $R^{7a}$, $R^{7b}$, $R^{10}$, $R^{12}$, $R^{14}$ and G have the same meanings as the definitions in the formula 5; and $R^{12a}$, $R^{13}$, $R^{14a}$ and $R^{15}$ have the same meanings as the definitions in the formula 7.

6. A compound represented by the formula (9), a pharmacologically acceptable salt thereof or a hydrate of them.

(9)

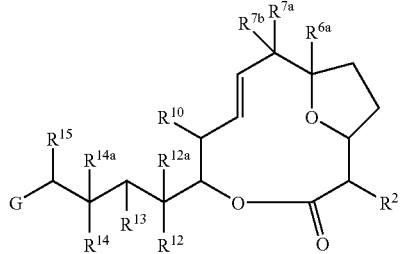

In the formula (9), $R^2$, $R^{6a}$, $R^{7a}$, $R^{7b}$, $R^{10}$, $R^{12}$, $R^{14}$ and G have the same meanings as the definitions in the formula 5; and $R^{12a}$, $R^{13}$, $R^{14a}$ and $R^{15}$ have the same meanings as the definitions in the formula 7.

7. A compound represented by the formula (10), a pharmacologically acceptable salt thereof or a hydrate of them.

(10)

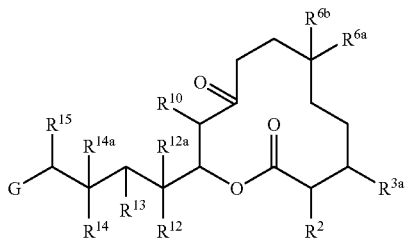

In the formula (10), $R^2$, $R^{3a}$, $R^{6a}$, $R^{6b}$, $R^{10}$, $R^{12}$, $R^{14}$ and G have the same meanings as the definitions in the formula 5; and $R^{12a}$, $R^{13}$, $R^{14a}$ and R have the same meanings as the definitions in the formula 7.

8. A compound represented by the formula (11), a pharmacologically acceptable salt thereof or a hydrate of them.

(11)

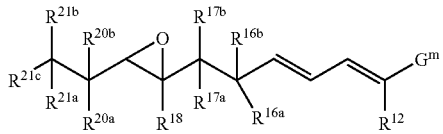

In the formula (11), $R^{12}$, $R^{16a}$, $R^{16b}$, $R^{17a}$, $R^{17b}$, $R^{20a}$, $R^{20b}$, $R^{21a}$, $R^{21b}$ and $R^{21c}$ have the same meanings as the definitions in the formula 5; $R^{18}$ represents hydrogen or methyl; and $G^M$ is represented by (1)

(GM-I)

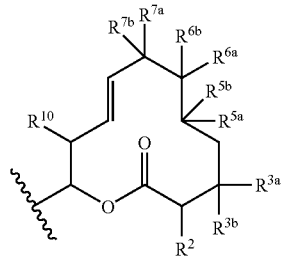

(wherein $R^2$, $R^{3a}$, $R^{3b}$, $R^{5a}$, $R^{5b}$, $R^{6a}$, $R^{6b}$, $R^{7a}$, $R^{7b}$ and $R^{10}$ have the same meanings as the definitions in the formula 5 of), (2)

(GM-II)

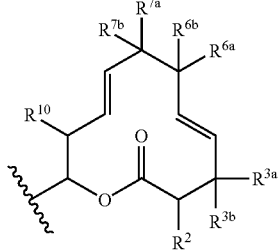

(wherein $R^2$, $R^{3a}$, $R^{3b}$, $R^{6a}$, $R^{6b}$, $R^{7a}$, $R^{7b}$ and $R^{10}$ have the same meanings as the definitions in the formula 7), (3)

(GM-III)

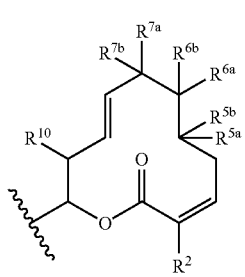

(wherein $R^2$, $R^{5a}$, $R^{5b}$, $R^{6a}$, $R^{6b}$, $R^{7a}$, $R^{7b}$ and $R^{10}$ have the same the definitions in the formula 8), (4)

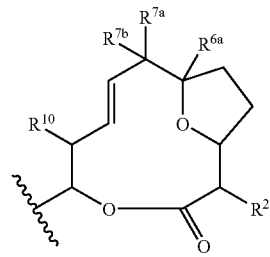

(GM-IV)

(wherein $R^2$, $R^{6a}$, $R^{7a}$, $R^{7b}$ and $R^{10}$ have the same meanings as the definitions in the formula 9) or (5)

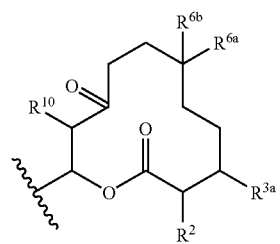

(GM-V)

(wherein $R^2$, $R^{3a}$, $R^{6a}$, $R^{6b}$ and $R^{10}$ have the same meanings as the definitions in the formula 10), provided that the restricted clauses 1, 2 and 3 are included.

9. A compound represented by the formula (12), a pharmacologically acceptable salt thereof or a hydrate of them.

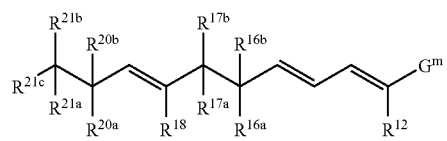

(12)

In the formula (12), $R^{12}$, $R^{16a}$, $R^{16b}$, $R^{17}$, $R^{17a}$, $R^{17b}$, $R^{20a}$, $R^{20b}$, $R^{21a}$, $R^{21b}$ and $R^{21c}$ have the same meanings as the definitions in the formula 5; and $R^{18}$ and $G^M$ have the same meanings as the definitions in the formula 11.

10. A compound represented by the formula (13), a pharmacologically acceptable salt thereof or a hydrate of them.

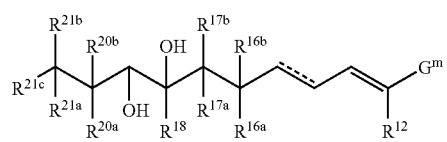

(13)

In the formula (13), ====represents a single bond or a double bond; $R^{12}$, $R^{16a}$, $R^{16b}$, $R^{17a}$, $R^{17b}$, $R^{20a}$, $R^{20b}$, $R^{21a}$, $R^{21b}$ and $R^{21c}$ have the same meanings as the definitions in the formula 5; and $R^{18}$ and $G^M$ have the same meanings as the definitions in the formula 11.

11. A compound represented by the formula (14), a pharmacologically acceptable salt thereof or a hydrate of them.

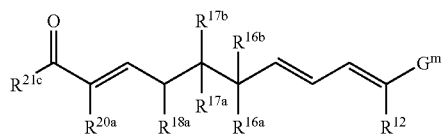

(14)

In the formula (14), $R^{12}$, $R^{16a}$, $R^{16b}$, $R^{17a}$, $R^{17b}$, $R^{18a}$, $R^{20a}$, $R^{20b}$ and $R^{21c}$ have the same meanings as the definitions in the formula 5; and $G^M$ has the same meaning as the definition in the formula 11.

12. A compound represented by the formula (H-I), a pharmacologically acceptable salt thereof or a hydrate of them.

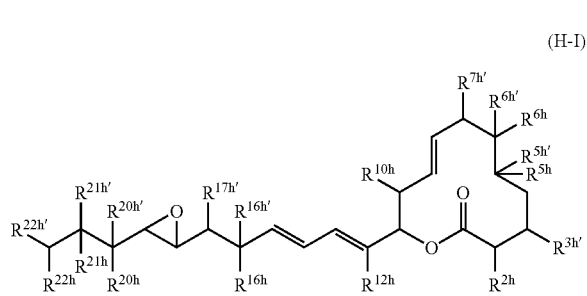

(H-I)

In the formula (H-I), $R^{2h}$, $R^{5h}$, $R^{6h}$, $R^{10h}$, $R^{12h}$, $R^{16h}$, $R^{20h}$, $R^{21h}$ and $R^{22h}$ are the same as or different from each other and each represent (1) hydrogen,
(2) methyl,
(3) hydroxymethyl or
(4) $C_{2-8}$ Acyloxymethyl;

$R^{3h'}$, $R^{5h'}$, $R^{6h'}$, $R^{7h'}$, $R^{16h'}$, $R^{17h'}$, $R^{20h'}$, $R^{21h'}$ and $R^{21h'}$ are the same as or different from each other and each represents (1) hydrogen,
(2) hydroxy,
(3) methoxy or
(4) $C_{2-8}$ Acyloxy;

$R^{5h}$ and $R^{5h'}$ may be bound together to form a ketone structure (=O); $R^{21h}$ and $R^{21h'}$ may be bound together to form a ketone structure (=O); and $R^{6h}$ and $R^{6h'}$ may be bound together to form a spirooxyrane structure, provided that the restricted clauses 1, 2 and 3 are included.

13. A compound represented by the formula (H-1), a pharmacologically acceptable salt thereof or a hydrate of them, which is selected from the group consisting of a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, both of $R^{21h}$ and $R^{21h'}$ are bound together to form a ketone structure, $R^{22h'}$ is hydrogen and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydroxy $R^{17h'}$ is hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydroxy, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is hydroxy, all of $R^{10h}$, $R^{12h}$ and $R^{16h}$ are methyl, $R^{16h'}$ is hydroxy, $R^{17h'}$ is hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydroxy, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is propanoyloxy, all of $R^{10h}$, $R^{12h}$ and $R^{16h}$ Are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, and all of $R^{21h}$, $R^{22h'}$ and $R^{22h}$ Are hydrogen;

a compound in which $R^{2h}$ is hydrogen, $R^{3h'}$ is hydroxy, $R^{5h}$ is hydrogen, $R^{5h'}$ is hydroxy, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, $R^{5h}$ is hydrogen, $R^{5h'}$ is acetoxy, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is acetoxy, both of $R^{5h}$ and $R^{5h'}$ are hydrogen, $R^{6h}$ is methyl, $R^{6h'}$ is hydroxy, $R^{5h}$ is acetoxy, all of $R^{5h'}$, $R^{6h}$ and $R^{6h'}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is acetoxymethyl, $R^{6h'}$ is hydroxy, $R^{7h'}$ is acetoxy, all of $R^{10h}$, $R^{12h}$ and $R^{16h}$ Are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydrogen, $R^{17h'}$ are hydroxy, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, both of $R^{20h}$ and $R^{20h'}$ are hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, both of $R^{10h}$ and $R^{12h}$ are methyl, all of $R^{16h}$, $R^{16h'}$ and $R^{17h'}$ are hydrogen, $R^{20h}$ is methyl, $R^{20h'}$ is hydroxy, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, both of $R^{10h}$ and $R^{16h}$ are methyl, all of $R^{12h}$, $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, both of $R^{12h}$ and $R^{16h}$ are methyl, all of $R^{10h}$, $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is acetoxymethyl, $R^{6h'}$ is hydroxy, $R^{7h'}$ is hydroxy, all of $R^{10h}$, $R^{12h}$ and $R^{16h}$ Are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is hydroxy, all of $R^{10}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ and $R^{21h}$ are bound together to form a ketone structure, $R^{22h'}$ is hydrogen, and $R^{22h}$ is methyl;

a compound in which $R^{2h}$ is hydrogen, $R^{3h'}$ is hydroxy, all of $R^{5h}$, $R^{5h'}$ and $R^{6h}$ are hydrogen, $R^{6h'}$ is acetoxy, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is methyl, $R^{3h'}$ is hydroxy, both of $R^{5h}$ and $R^{5h'}$ are hydrogen, $R^{6h}$ is methyl, $R^{6h'}$ is hydroxy, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is methyl, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, $R^{5h}$ is hydrogen, $R^{5h'}$ is hydroxy, $R^{6h}$ is methyl, $R^{6h'}$ is hydrogen, $R^{7h'}$ is acetoxy, all of $R^{10h}$, $R^{12h}$ and $R^{16h}$ Are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, all of $R^{5h}$, $R^{5h'}$, $R^{6h}$ and $R^{6h'}$ are hydrogen, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ and $R^{6h'}$ are bound together to form a spirooxyrane structure, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ and $R^{6h'}$ are bound together to form a spirooxyrane structure, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is acetoxy, $R^{7h'}$ is acetoxy, all of $R^{10}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydroxy, $R^{17h'}$ is hydrogen, $R^{20h}$ is methyl, $R^{20h'}$ is hydrogen, $R^{21h}$ and $R^{21h'}$ are bound together to form a ketone structure, $R^{22h'}$ is hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h}$ is hydrogen, both of $R^{21h'}$ and $R^{22h'}$ are hydroxy, and $R^{22h}$ is methyl;

a compound in which $R^{2h}$ is hydrogen, $R^{3h'}$ is hydroxy, $R^{5h}$ is hydrogen, $R^{5h'}$ is hydroxy, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h}$ is hydrogen, both of $R^{21h'}$ and $R^{22h'}$ are hydroxy, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is hydroxy, both of $R^{10h}$ and $R^{16h}$ are methyl, all of $R^{12h}$, $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl; and a compound in which $R^{2h}$ is hydrogen, $R^{3h'}$ is hydroxy, both of $R^{5h}$ and $R^{5h'}$ are bound together to form a ketone structure, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl.

14. A compound represented by the formula (H-II), a pharmacologically acceptable salt thereof or a hydrate of them.

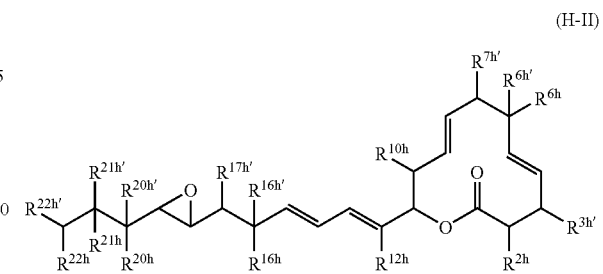

In the formula (H-II), $R^{2h}$, $R^{6h}$, $R^{10h}$, $R^{12h}$, $R^{16h}$, $R^{20h}$, $R^{21h}$ And $R^{22h}$ are the same as or different from each other and each represents
(1) hydrogen,
(2) methyl,
(3) hydroxymethyl or
(4) $C_{2-8}$ Acyloxymethyl;

$R^{3h'}$, $R^{6h'}$, $R^{7h'}$, $R^{16h'}$, $R^{17h'}$, $R^{20h'}$, $R^{21h'}$ and $R^{22h'}$ are the same as or different from each other and each represents
(1) hydrogen,
(2) hydroxy,
(3) methoxy or
(4) $C_{2-8}$ Acyloxy;

further, $R^{21h}$ and $R^{21h'}$ may be bound together to form a ketone structure (=O); and further, $R^{6h}$ and $R^{6h'}$ may be bound together to form a spirooxyrane structure.

15. A compound represented by the formula (H-II), a pharmacologically acceptable salt thereof or a hydrate of them, which is selected from the group consisting of a compound in which $R^{2h}$ is hydrogen, $R^{3h'}$ is hydroxy, $R^{6h}$ is methyl, $R^{6h'}$ is hydroxy, $R^{7h'}$ is acetoxy, all of $R^{10h}$, $R^{12h}$ And $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ And $R^{22h'}$ are hydrogen and $R^{22h}$ is methyl;

a compound in which $R^{2h}$ is hydrogen, $R^{3h'}$ is hydroxy, $R^{6h}$ is methyl, $R^{6h'}$ is hydroxy, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, both of $R^{21h}$ and $R^{21h'}$ are bound together to form a ketone structure, $R^{22h'}$ is hydrogen, and $R^{22h}$ is methyl;

a compound in which $R^{2h}$ is hydrogen, $R^{3h'}$ is hydroxy, $R^{6h}$ and $R^{6h'}$ are bound together to form a spirooxyrane structure, $R^{7h'}$ is acetoxy, all of $R^{10h}$, $R^{12h}$ and $R^{16h}$ Are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, $R^{6h}$ is methyl, $R^{6h'}$ is acetoxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl; and a compound in which $R^{2h}$ is hydrogen, $R^{3h'}$ is hydroxy, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydrogen, $R^{17h'}$ is hydroxy, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl.

16. A compound represented by the formula (H-III), a pharmacologically acceptable salt thereof or a hydrate of them.

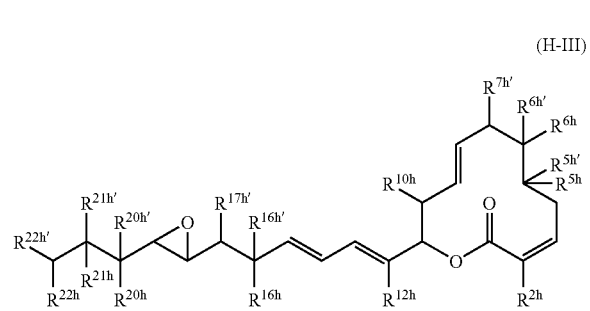

(H-III)

In the formula, $R^{2h}$, $R^{5h}$, $R^{6h}$, $R^{10h}$, $R^{12h}$, $R^{16h}$, $R^{20h}$, $R^{21h}$ And $R^{22h}$ are the same as or different from each other and each represents (1) hydrogen,
(2) methyl,
(3) hydroxymethyl or
(4) $C_{2-8}$ Acyloxymethyl;

$R^{5h'}$, $R^{6h'}$, $R^{7h'}$, $R^{16h'}$, $R^{17h'}$, $R^{20h'}$, $R^{21h'}$ and $R^{21h'}$ are the same as or different from each other and each represents (1) hydrogen,
(2) hydroxy,
(3) methoxy or
(4) $C_{2-8}$ Acyloxy;

further, $R^{5h}$ and $R^{5h'}$ may be bound together to form a ketone structure (=O); further, $R^{21h}$ and $R^{21h'}$ may be bound together to form a ketone structure (=O); further, $R^{6h}$ and $R^{6h'}$ may be bound together to form a spirooxyrane structure.

17. A compound represented by the formula (H-III), a pharmacologically acceptable salt thereof or a hydrate of them, which is selected from the group consisting of a compound in which $R^{2h}$ is hydrogen, both of $R^{5h'}$ and $R^{5h'}$ are hydrogen, $R^{6h}$ is methyl, $R^{6h'}$ is hydroxy, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen and $R^{22h}$ is methyl;

a compound in which $R^{2h}$ is hydrogen, both of $R^{5h}$ And $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is acetoxy, both of $R^{21h}$ and $R^{22h'}$ are hydrogen and $R^{22h}$ is methyl; and a compound in which $R^{2h}$ is hydrogen, both of $R^{5h}$ And $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen and $R^{22h}$ is methyl.

18. A compound represented by the formula (H-IV), a pharmacologically acceptable salt thereof or a hydrate of them.

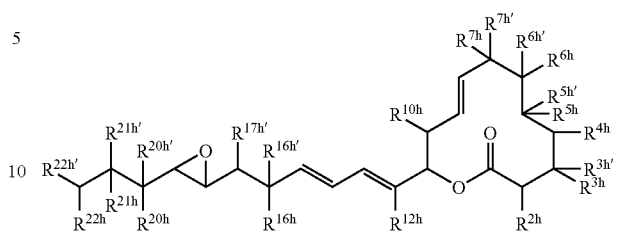

(H-IV)

In the formula, $R^{2h}$, $R^{3h}$, $R_4 h$, $R^{5h}$, $R^{6h}$, $R^{7h}$, $R^{10h}$, $R^{12h}$, $R^{16h}$, $R^{20h}$, $R^{21h}$ and $R^{22h}$ are the same as or different from each other and each represents (1) hydrogen,
(2) methyl,
(3) hydroxymethyl or
(4) $C_{2-8}$ Acyloxymethyl;

$R^{3h'}$, $R^{5h'}$, $R^{6h'}$, $R^{7h'}$, $R^{16h'}$, $R^{17h'}$, $R^{20h'}$, $R^{21h'}$ and $R^{22h}$ are the same as or different from each other and each represents (5) hydrogen,
(6) hydroxy,
(7) methoxy or
(8) $C_{2-8}$ Acyloxy;

further, $R^{3h}$ and $R^{3h'}$ may be bound together to form a ketone structure (=O); further, $R^{5h}$ and $R^{5h'}$ may be bound together to form a ketone structure (=O); further, further, $R^{7h}$ And $R^{7h'}$ may be bound together to form a ketone structure (=0); $R^{21h}$ and $R^{21h'}$ may be bound together to form a ketone structure (=O); further, $R^{4h}$ and $R^{5h}$ may form a single bond to represent

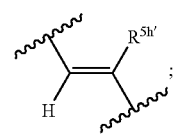

and further, $R^{6h}$ and $R^{6h'}$ may be bound together to form a spirooxyrane structure, provided that the restricted clauses 1, 2 and 3 are included.

19. The compound represented by the formula (H-IV), a pharmacologically acceptable salt thereof or a hydrate of them, which is selected from the group consisting of a compound in which $R^{2h}$ is hydrogen, $R^{3h}$ and $R^{3h'}$ are bound together to form a ketone structure, $R^{4h}$ and $R^{5h}$ form a single bond to represent

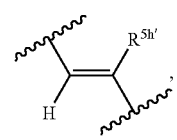

$R^{5h'}$ is hydrogen, $R^{6h}$ is methyl, $R^{6h'}$ is hydroxy, $R^{7h}$ is hydrogen, $R^{7h'}$ is acetoxy, all of $R^{10h}$, $R^{12h}$ and $R^{16}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl; and a compound in which $R^{2h}$ is hydrogen, $R^{3h}$ is hydrogen, $R^{3h'}$ is hydroxy, all of $R^{4h}$, $R^{5h}$ and $R^{5h'}$ are hydrogen, $R^{6h}$ is methyl, $R^{6h'}$ is hydroxy, $R^{7h}$ and $R^{7h'}$ are bound together to form a ketone structure, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl.

20. A compound represented by the formula (H-V), a pharmacologically acceptable salt thereof or a hydrate of them.

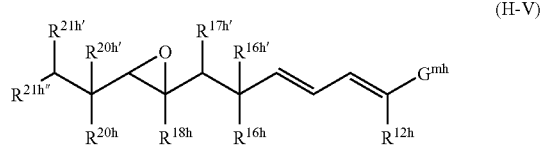
(H-V)

In the formula (H-V), $R^{12h}$, $R^{16h}$, $R^{16h'}$, $R^{17h'}$, $R^{20h}$, $R^{20h'}$ and $R^{21h'}$ have the same meanings as the definitions in the formula (H-I); $R^{18h}$ represents hydrogen or methyl; $R^{21h'}$ represents hydrogen, methyl or ethyl; and $G^{mh}$ is represented by the formula (1):

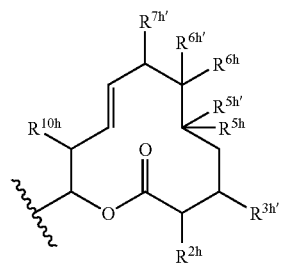
(MH-I)

(wherein $R^{2h}$, $R^{3h'}$, $R^{5h}$, $R^{5h'}$, $R^{6h}$, $R^{6h'}$, $R^{7h'}$ and $R^{10h}$ have the same meanings as the definitions in the formula (H-I)), the formula (2):

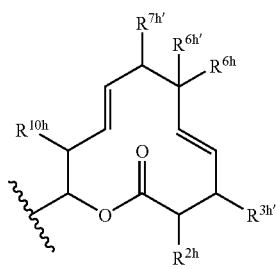
(MH-II)

(wherein $R^{2h}$, $R^{3h'}$, $R^{6h}$, $R^{6h'}$, $R^{7h'}$ and $R^{10h}$ have the same meanings as the definitions in the formula (H-II)), the formula (3):

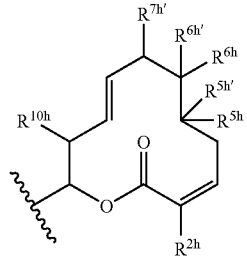
(MH-III)

(wherein $R^{2h}$, $R^{5h}$, $R^{5h'}$, $R^{6h}$, $R^{6h'}$, $R^{7h'}$ and $R^{10h}$ have the same meanings as the definitions in the formula (H-III)), the formula (4):

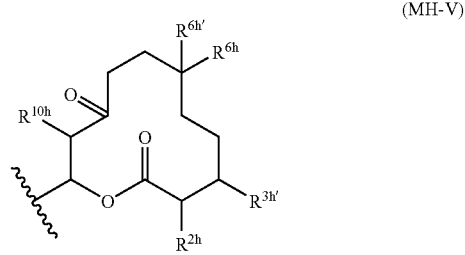
(MH-IV)

(wherein $R^{2h}$, $R^{6h}$, $R^{7h'}$ and $R^{10h}$ have the same meanings as the definitions in the formula (H-I)), or the formula (5):

(MH-V)

(wherein $R^{2h}$, $R^{3h'}$, $R^{6h}$, $R^{6h'}$ and $R^{10h}$ have the same meanings as the definitions in the formula (H-I)), provided that the restricted clauses 1, 2 and 3 are included.

21. A compound represented by the formula (H-V), a pharmacologically acceptable salt thereof or a hydrate of them, which is selected from the group consisting of a compound in which $G^{mh}$ is represented by the formula (MH-I), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, all of $R^{16h'}$, $R^{17h'}$ and $R^{18h}$ are hydrogen, all of $R^{20h}$, $R^{21h'}$ and $R^{21h''}$ are hydrogen and $R^{20h'}$ is hydroxy;

a compound in which $G^{mh}$ is represented by the formula (MH-I), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydrogen, $R^{17h'}$ is hydroxy, and all of $R^{18h}$, $R^{20h}$, $R^{20h'}$, $R^{21h'}$ and $R^{21h''}$ are hydrogen;

a compound in which $G^{mh}$ is represented by the formula (MH-I), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydroxy, and all of $R^{17h'}$, $R^{18h}$, $R^{20h}$, $R^{20h'}$, $R^{21h'}$ and $R^{21h''}$ are hydrogen;

a compound in which $G^{mh}$ is represented by the formula (MH-I), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydrogen, $R^{17h'}$ is hydroxy, $R^{18h}$ is methyl, and all of $R^{20h}$, $R^{20h'}$, $R^{21h'}$ and $R^{21h''}$ are hydrogen;

a compound in which $G^{mh}$ is represented by the formula (MH-V), $R^{2h}$ is hydrogen, $R^{3h'}$ is hydroxy, $R^{6h}$ is methyl, $R^{6h'}$ is hydroxy, all of $R^{10h}$, $R^{12h}$ and $R^{16h}$ are methyl, all of $R^{16h'}$ $R^{17h'}$ $R^{18h}$ and $R^{20h'}$ are hydrogen, $R^{20h}$ is methyl, $R^{21h'}$ is hydroxy, and $R^{21h''}$ is ethyl.

22. A compound represented by the formula (H-VI), a pharmacologically acceptable salt thereof or a hydrate of them.

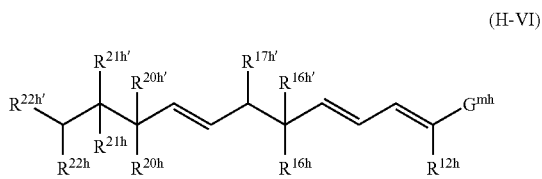

(H-VI)

In the formula, $R^{12h}$, $R^{16h}$, $R^{16h'}$, $R^{17h'}$, $R^{20h}$, $R^{20h'}$, $R^{21h}$, $R^{21h'}$, $R^{22h}$ and $R^{22h'}$ have the same meanings as the definitions in the formula (H-I); $G^{mh}$ has the same meaning as the definition in the formula (H-V).

23. A compound represented by the formula (H-VI), a pharmacologically acceptable salt thereof or a hydrate of them, which is selected from the group consisting of a compound in which $G^{mh}$ is represented by the formula (MH-I), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, both of $R^{20h'}$ and $R^{21h}$ Are hydrogen, both of $R^{21h'}$ and $R^{22h'}$ are hydroxy, and $R^{22h}$ is methyl; and a compound in which $G^{mh}$ is represented by the formula (MH-I), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, all of $R^{20h'}$, $R^{21h}$ and $R^{22h'}$ are hydrogen, $R^{21h'}$ is hydroxy, and $R^{22h}$ is methyl.

24. A compound represented by the formula (H-VII), a pharmacologically acceptable salt thereof or a hydrate of them.

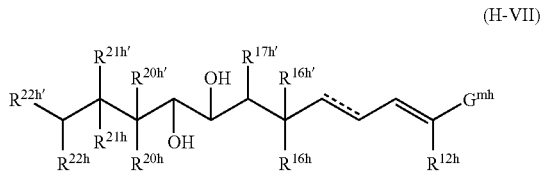

(H-VII)

In the formula, $G^{mh}$ has the same meaning as the definition in the formula (H-V); ====represents a single bond or a double bond; and $R^{12h}$, $R^{16h}$, $R^{16h'}$, $R^{17h'}$, $R^{20h}$, $R^{20h'}$, $R^{21h}$, $R^{21h'}$ $R^{22h}$ and $R^{22h'}$ have the same meanings as the definitions in the formula (H-I).

25. A compound represented by the formula (H-VII), a pharmacologically acceptable salt thereof or a hydrate of them, which is selected from the group consisting of a compound in which $G^{mh}$ is represented by the formula (MH-I), ====represents a double bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ Are methyl, both of $R^{16h'}$ and $R^{17h'}$ are hydrogen, $R^{20h}$ is methyl, all of $R^{20h'}$, $R^{21h}$ and $R^{22h'}$ are hydrogen, $R^{21h'}$ is hydroxy, and $R^{22h}$ is methyl;

a compound in which $G^{mh}$ is represented by the formula (MH-I), ====represents a single bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ Are methyl, both of $R^{16h'}$ and $R^{17h'}$ are hydrogen, $R^{20h}$ is methyl, all of $R^{20h'}$, $R^{21h}$ and $R^{22h'}$ are hydrogen, $R^{21h'}$ is hydroxy, and $R^{22h}$ is methyl; and a compound in which $G^{mh}$ is represented by the formula (MH-II), ====represents a double bond, $R^{2h}$ is hydrogen, $R^{3h'}$ is hydroxy, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, all of $R^{20h'}$, $R^{21h}$ and $R^{22h'}$ are hydrogen, $R^{21h'}$ is hydroxy, and $R^{22h}$ is methyl.

26. A compound represented by the formula (H-VIII), a pharmacologically acceptable salt thereof or a hydrate of them.

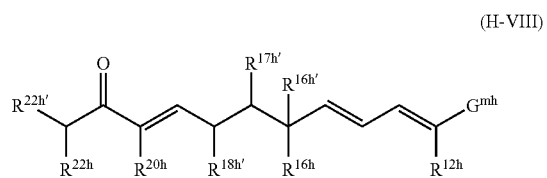

(H-VIII)

In the formula, $G^{mh}$, $R^{12h}$, $R^{16h}$, $R^{16h'}$, $R^{17h'}$, $R^{20h}$, $R^{22h}$ and $R^{22h'}$ have the same meanings as the formula (H-I); and $R^{18h'}$ represents hydrogen or hydroxy.

27. A compound, a pharmacologically acceptable salt thereof or a hydrate of them in the formula (H-VIII), which is selected from the group consisting of a compound in which $G^{mh}$ is represented by the formula (MH-I), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{18h'}$ is hydroxy, $R^{20h}$ is methyl, $R^{22h'}$ is hydroxy, and $R^{22h}$ is methyl; and a compound in which $G^{mh}$ is represented by the formula (MH-I), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{18h'}$ is hydroxy, $R^{20h}$ is methyl, $R^{22h'}$ are hydrogen, and $R^{22h}$ is methyl.

28. A compound represented by the formula (H-IX), a pharmacologically acceptable salt thereof or a hydrate of them.

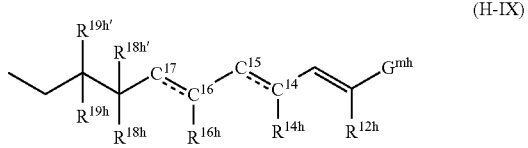

(H-IX)

In the formula, $G^{mh}$ has the same meaning as the definition in the formula (H-V); $C^{14}$===$C^{15}$ and $C^{16}$===$C^{17}$ are the same as or different from each other and each represents a single bond or a double bond; $R^{12h}$, $R^{16h}$ and $R^{18h}$ have the same meanings as the definition in the formula (H-V); $R^{14h}$ represents hydrogen or methyl; $R^{18h'}$ represents hydrogen or hydroxy; $R^{19h}$ and $R^{19h'}$ are (1) the same as or different from each other and each represents hydrogen, methyl or hydroxy, or (2) $R^{19h}$ and $R^{19h'}$ are bound together to represent a ketone structure (=O).

29. A compound represented by the formula (H-IX), a pharmacologically acceptable salt thereof or a hydrate of them, which is selected from the group consisting of a compound in which $G^{mh}$ is represented by the formula (MH-I), $C^{14}$===$C^{15}$ is a double bond, $C^{16}$===$C^{17}$ is a single bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, all of $R^{14h}$, $R^{18h}$ and $R^{19h}$ Are hydrogen, and both of $R^{18h'}$ and $R^{19h'}$ are hydroxy;

a compound in which $G^{mh}$ is represented by the formula (MH-I), $C^{14}$===$C^{15}$ is a single bond, $C^{16}$===$C^{17}$ is a double bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, both of $R^{10h}$ and $R^{14h}$ are methyl, both of $R^{12h}$ and $R^{16h}$ Are hydrogen, $R^{18h}$ is methyl, $R^{18h'}$ is hydroxy, and $R^{19h}$ and $R^{19h'}$ are bound together to form a ketone structure (=O); and a compound in which $G^{mh}$ is represented by the formula (MH-I), $C^{14}$===$C^{15}$ is a single bond, $C^{16}$===$C^{17}$ is a double bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, both of $R^{10h}$ and $R^{14h}$ are methyl, both of $R^{12h}$ and $R^{16h}$ Are hydrogen, $R^{18h}$ is methyl, $R^{18h'}$ is hydroxy, $R^{19h}$ is hydrogen, and $R^{19h'}$ is hydroxy.

30. A compound represented by the formula (H-X), a pharmacologically acceptable salt thereof or a hydrate of them.

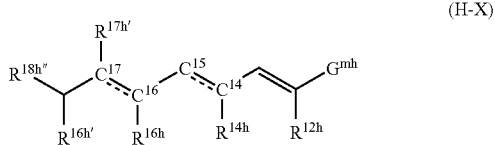

(H-X)

In the formula, $G^{mh}$, $R^{16h}$ and $R^{17h'}$ have the same meanings as the definitions in the formula (H-V); $R^{14h}$ represents hydrogen or methyl; $C^{14}$===$C^{15}$ and $C^{16}$===$C^{17}$ are the same as or different from each other and each represents a single bond or a double bond; $R^{18h'}$ is hydrogen or hydroxy; and $R^{18h''}$ represents (1) methyl or (2) the formula (R-F).

31. A compound, a pharmacologically acceptable salt thereof or a hydrate of them in the formula (H-X), which is selected from the group consisting of a compound in which $G^{mh}$ is represented by the formula (MH-I), $R^{18h''}$ is represented by the formula (R-F), $C^{14}$===$C^{15}$ is a double bond, $C^{16}$===$C^{17}$ is a single bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{14h}$ and $R^{17h'}$ are hydrogen, $R^{18h'}$ is hydroxy, both of $R^{f3a}$ and $R^{f5}$ are methyl, both of $R^{f3b}$ and $R^{f4b}$ are hydrogen, and $R^{f4b}$ is hydroxy;

a compound in which $G^{mh}$ is represented by the formula (MH-I), $C^{14}$===$C^{15}$ is a single bond, $C^{16}$===$C^{17}$ is a double bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, both of $R^{10h}$ and $R^{14h}$ are methyl, all of $R^{12h}$, $R^{16h}$ and $R^{17h'}$ are hydrogen, $R^{18h'}$ is hydroxy, and $R^{18h''}$ is methyl; and a compound in which $G^{mh}$ is represented by the formula (MH-I), $C^{14}$===$C^{15}$ is a double bond, $C^{16}$===$C^{7}$ is a single bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{14h}$ and $R^{18h'}$ are hydrogen, $R^{17h'}$ is hydroxy, and $R^{18h''}$ is methyl.

32. A compound represented by the formula (H-XI), a pharmacologically acceptable salt thereof or a hydrate of them.

(H-XI)

In the formula, $G^{mh}$ and $R^{12h}$ have the same meanings as the definitions in the formula (H-V); $R^{16h''}$ represents hydrogen, methyl or hydroxy; and $R^{17h''}$ represents (1) hydrogen or (2) the formula (R-F).

33. A compound represented by the formula (H-XI), a pharmacologically acceptable salt thereof or a hydrate of them, which is selected from the group consisting of a compound in which $G^{mh}$ is represented by the formula (MH-I), $R^{17h''}$ is represented by the formula (R-F), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ And $R^{16h''}$ are methyl, both of $R^{f3a}$ and $R^{f4a}$ are hydroxy, $R^{f3b}$ is hydrogen, $R^{f4b}$ is methyl, and $R^{f5}$ is ethyl; and a compound in which $G^{mh}$ is represented by the formula (MH-I), $R^{2h}$ is hydrogen, $R^{3h'}$ is hydroxy, all of $R^{5h}$, $R^{5h'}$ and $R^{6h'}$ are hydrogen, $R^{6h}$ is methyl, $R^{7h'}$ is acetoxy, both of $R^{10h}$ and $R^{12h}$ are methyl, $R^{16h''}$ is hydroxy, and $R^{17h''}$ is hydrogen.

34. A compound represented by the formula (15), a pharmacologically acceptable salt thereof or a hydrate of them.

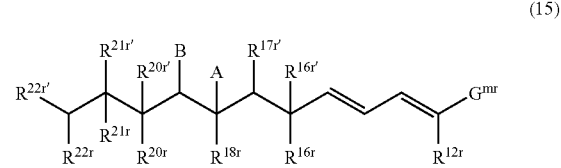

(15)

In the formula (15), $G^{mr}$ is represented by the formula (1):

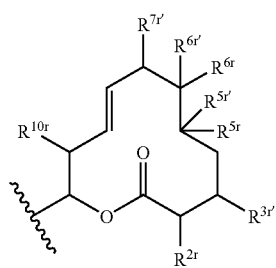
(MD-I)

(wherein $R^{2r}$, $R^{3r'}$, $R^{5r}$, $R^{5r'}$, $R^{6r}$, $R^{6r'}$, $R^{7r'}$ and $R^{10r}$ are the same as or different from each other and each represents
1) hydrogen,
2) methyl which may have substituents,
3) —$OR^H$ (wherein $R^H$ is <1> hydrogen, <2> methyl or <3> acetyl),
4) —$OR^D$ (wherein $R^D$ represents
  <1> $C_{1-22}$ Alkyl (provided that in case of methyl, it has always substituents),
  <2> —$CH_2Ar$,
  <3> $C_{3-22}$ Acyl,
  <4> unsaturated $C_{3-22}$ Acyl,
  <5> —$COR^{CO}$,
  <6> $C_{1-22}$ Alkylsulfonyl,
  <7> benzenesulfonyl or
  <8> —$SiR^{s1}R^{s2}R^{s3}$, each of which may have substituents)
5) halogen or
6) —$R^M$—$NR^{N1}R^{N2}$ (Ar, $R^{CO}$, $R^{s1}$, $R^{s2}$, $R^{s3}$, $R^M$, $R^{N1}$ and $R^{N2}$ have the same meanings as the definitions of the formula 5),
further, $R^{5r}$ and $R^{5r'}$ may be bound together to represent a ketone structure;
further, $R^{6r}$ or $R^{6r'}$ may be bound together to represent a spirooxyrane structure or an exo-methylene structure; further, either of $R^{6r}$ or $R^{6r'}$, and $R^{7r'}$ may be bound together to represent a 1,3-dioxolane ring), the formula (2):

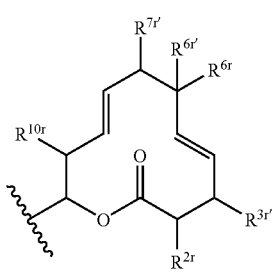
(MD-II)

(wherein $R^{2r}$, $R^{3r'}$, $R^{6r}$, $R^{6r'}$, $R^{7r'}$ and $R^{10r}$ have the same meanings as the above-mentioned definition), the formula (3):

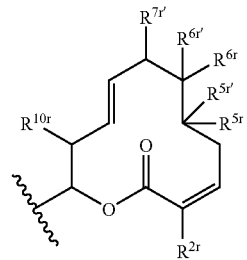
(MD-III)

(wherein $R^{2r}$, $R^{5r}$, $R^{5r'}$, $R^{6r}$, $R^{6r'}$, $R^{7r'}$ and $R^{10r}$ have the same meanings as the above-mentioned definition), the formula (4):

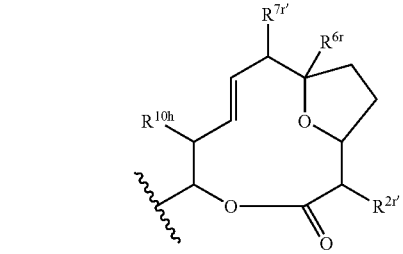
(MH-IV)

(wherein $R^{2r}$, $R^{6r}$, $R^{7r'}$ and $R^{10r}$ have the same meanings as the above-mentioned definition), or the formula (5):

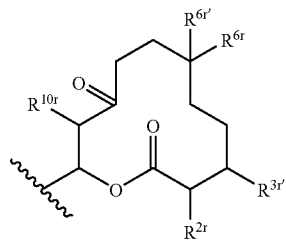
(MD-V)

(wherein $R^{2r}$, $R^{3r'}$, $R^{6r}$, $R^{6r'}$ and $R^{10r}$ have the same meanings as the above-mentioned definition);
$R^{12r}$, $R^{16r}$, $R^{16r'}$, $R^{17r'}$, $R^{18r}$, $R^{20r}$, $R^{20r'}$, $R^{21r}$, $R^{21r'}$, $R^{22r}$ And $R^{22r'}$ are the same as or different from each other and each represents
1) hydrogen,
2) methyl which may be optionally substituted,
3) —$OR^H$ (wherein $R^H$ represents <1> hydrogen, <2> methyl or <3> acetyl),
4) —$OR^D$ (wherein $R^D$ represents
  <1> $C_{1-22}$ Alkyl (provided that in case of methyl, it has always substituents),
  <2> —$CH_2Ar$,
  <3> $C_{3-22}$ Acyl,
  <4> unsaturated $C_{3-22}$ Acyl,
  <5> —$COR^{CO}$,
  <6> $C_{1-22}$ Alkylsulfonyl,
  <7> benzenesulfonyl, or <8> —SiR$^{s1}$R$^{s2}$R$^{s3}$, each of which may have substituents), 5) halogen or 6) —R$^M$—NR$^{N1}$R$^{N2}$ (Ar, R$^{CO}$, R$^{s1}$, R$^{s2}$, R$^{s3}$, R$^M$, R$^{N1}$ and R$^{N2}$ have the same meanings as the definitions in the formula 5);

further, R$^{21r}$ and R$^{21r'}$ may be bound together to represent <1> a ketone structure (=O) or an oxime structure (=NOR$^{OX}$: wherein Rox has the same meaning as the definition in the formula 5);

when either one of A and B is 1) halogen, or 2) <1> alkylsulfonyloxy, <2> benzenesulfonyloxy or <3> C$_{1-22}$ Alkoxy, each of which may have substituents, the other is 1) hydroxy, or 2) <1> C$_{1-22}$ Alkoxy or <2> C$_{2-22}$ Acyloxy, each of which may have substituents.

35. A compound represented by the formula (16), a pharmacologically acceptable salt thereof or a hydrate of them.

(16)

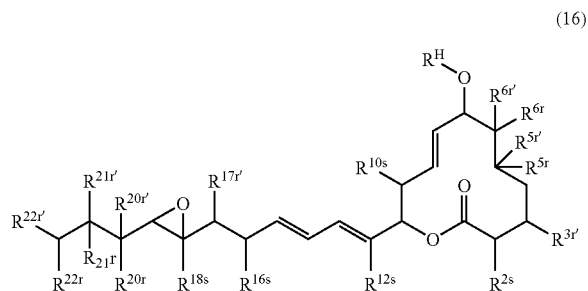

In the formula (16), R$^{3r'}$, R$^{5r}$, R$^{5r'}$, R$^{6r}$, R$^{6r'}$, R$^H$, R$^{17r'}$, R$^{20r}$, R$^{20r'}$, R$^{21r}$, R$^{21r'}$, R$^{22r}$ and R$^{22r'}$ have the same meanings as the definitions in the formula 15; and R$^{2s}$, R$^{10s}$, R$^{12s}$, R$^{16s}$ And R$^{18s}$ are the same as or different from each other and each represents hydrogen or methyl, provided that the restricted clause 3 is included.

36. A compound represented by the formula (17), a pharmacologically acceptable salt thereof or a hydrate of them.

(17)

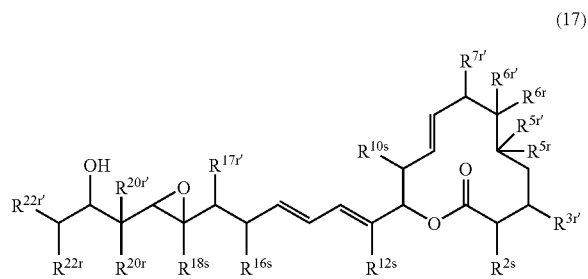

In the formula (17), R$^{3r'}$, R$^{5r}$, R$^{5r'}$, R$^{6r}$, R$^{6r'}$, R$^{7r'}$, R$^{17r'}$, R$^{20r}$, R$^{20r'}$, R$^{22r}$ and R$^{22r'}$ have the same meanings as the definitions in the formula 15; and R$^{2s}$, R$^{10s}$, R$^{12s}$, R$^{16s}$ And R$^{18s}$ have the same meanings as the definitions in the formula 16, provided that the restricted clauses 3 is included.

37. A compound represented by the formula (18), a pharmacologically acceptable salt thereof or a hydrate of them.

(18)

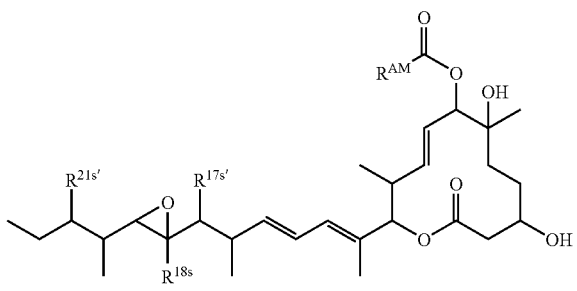

In the formula (18), R$^{17s'}$ represents hydrogen or hydroxy; R$^{18s}$ represents hydrogen or methyl; R$^{21s}$ represents hydroxy or methoxy; and R$^{AM}$ represents —NR$^{am1}$R$^{am2}$ (wherein R$^{am1}$ And R$^{am2}$ are (1) the same as or different from each other and each represents 1) hydrogen, or 2) <1> C$_{1-22}$ Alkyl, <2> C$_{3-8}$ cycloalkyl, <3> unsaturated C$_{3-22}$ Alkyl, <4> C$_{2-22}$ Acyl, <5> unsaturated C$_{3-22}$ Acyl, <6> C$_{6-14}$ Aryl, <7> C$_{3-8}$ cycloalkenyl, <8> 5-membered to 14-membered heteroaryl, <9> aralkyl, <10> heteroaralkyl, <11> C$_{1-22}$ Alkylsulfonyl, <12> benzenesulfonyl, <13> azetidin-2-yl, <14> pyrrolidin-3-yl, <15> piperazin-4-yl or <16> homopiperazin-4-yl, each of which may have substituents, or (2) —NR$^{am1}$R$^{am2}$ is bound together to represents an optionally substituted 3-membered to 14-membered nitrogen-containing non-aromatic heterocyclic ring).

38. A compound represented by the formula (18), a pharmacologically acceptable salt thereof or a hydrate of them, which is selected from the group of compounds consisting of, (1) a compound in which R$^{AM}$ is represented by

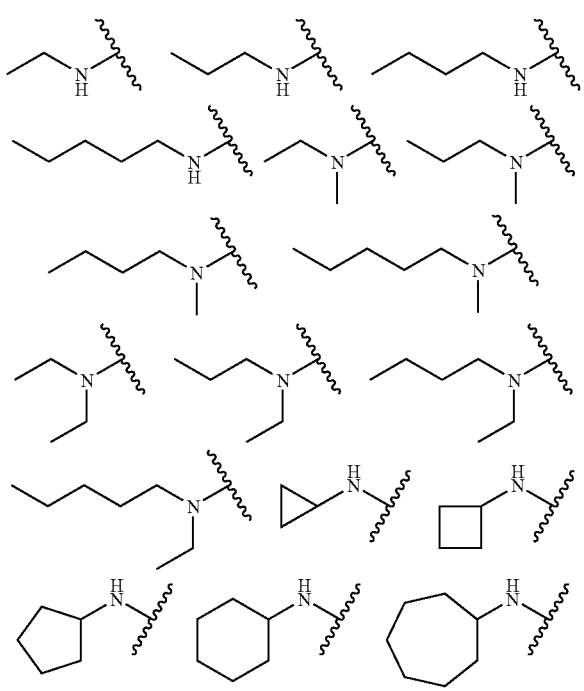

-continued

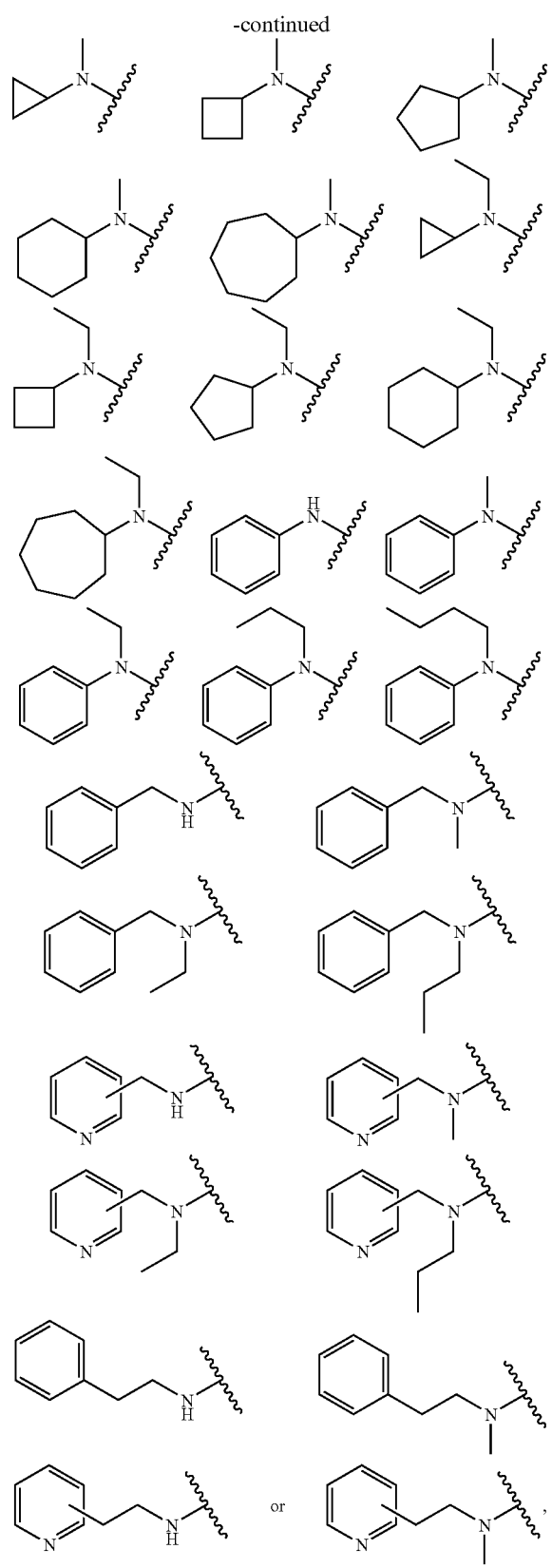

and further which may optionally have one to four of substituents selected from hydroxy, amino, N-methylamino, N-ethylamino, N,N-dimethylamino, N,N-diethylamino, N-ethyl-N-methylamino, azetidin-1-yl, pyrrolidin-1-yl, piperidin-1-yl, morpholin-1-yl, thiomorpholin-1-yl, piperazin-1-yl, 4-methylpiperazin-1-yl, 4-ethylpiperazin-1-yl, N-(2-hydroxyethyl)amino, N-(3-hydroxypropyl)amino, N-(2-hydroxyethyl)-N-methylamino, N(3-hydroxypropyl)-N-methylamino, N-(2-hydroxyethyl)-N-ethylamino or N-(3-hydroxypropyl)-N-ethylamino; (2) a compound in which $R^{AM}$ is represented by

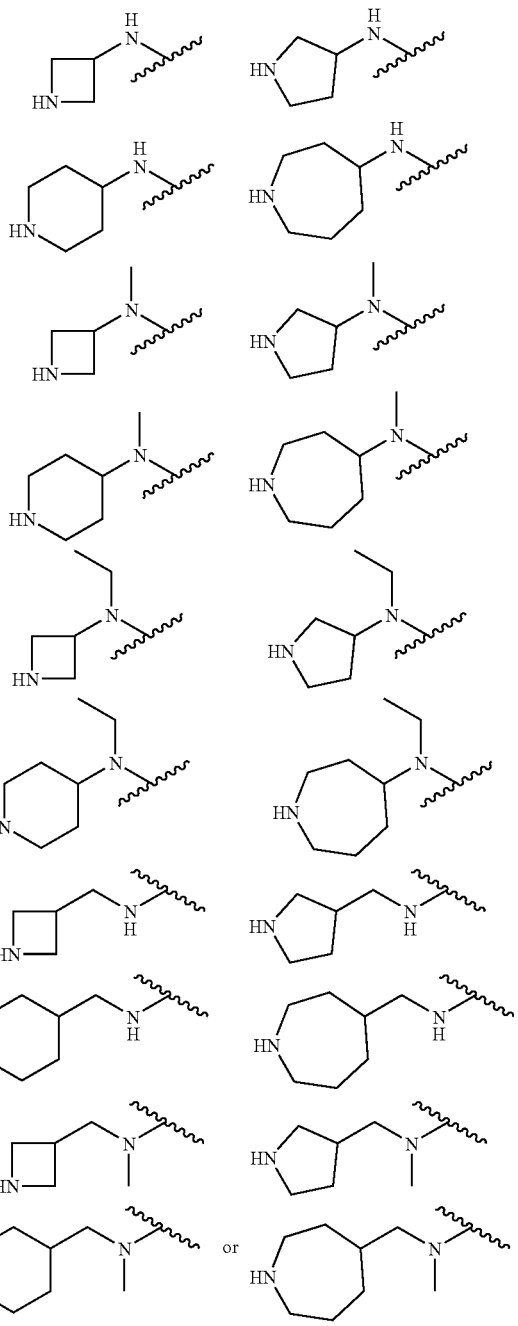

and further, which may optionally have one to four of substituents selected from methyl, ethyl, n-propyl, hydroxy, hydroxymethyl, 2-hydroxyethyl and 3-hydroxypropyl; and (3) a compound in which $R^{AM}$ is represented by

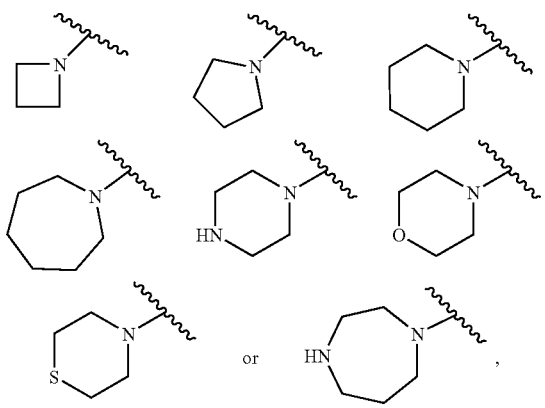

and further, which may optionally have one or two of substituents selected from methyl, ethyl, n-propyl, hydroxy, hydroxymethyl, 2-hydroxyethyl, 3-hydroxypropyl, amino, N-methylamino, N-ethylamino, N,N-dimethylamino, N,N-diethylamino, N-ethyl-N-methylamino, azetidin-1-yl, pyrrolidin-1-yl, piperidin-1-yl, morpholin-1-yl and thiomorpholin-1-yl.

39. A compound represented by the formula (19), a pharmacologically acceptable salt thereof or a hydrate of them.

 (19)

In the formula, $G^{mr}$ and $R^{12r}$ have the same meanings as the definitions in the formula (15); and Z represents oxygen or the formula:

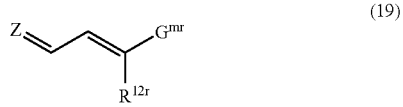

(wherein $R^Z$ represents (1) hydrogen or (2) a and $C_{1-8}$ Alkyl, $C_{1-8}$ Alkenyl or $C_{1-8}$ Alkynyl which may have substituents and an epoxy structure).

40. A compound represented by the formula (20), a pharmacologically acceptable salt thereof or a hydrate of them.

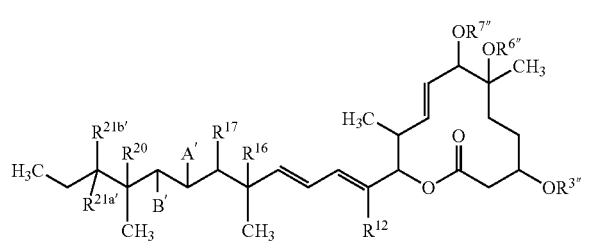 (20)

In the formula (20), a' and B' are bound together with oxygen to represent an epoxy structure, or either one of them represents hydroxy and the other represents any one of chlorine, bromine, hydroxy and methoxy; $R^{21a'}$ and $R^{21b'}$ are bound together with oxygen to represent a ketone structure, or either one of them represents hydrogen and the other represents any one of hydroxy, methoxy and —$OR^M$; $R^{3''}$, $R^{6''}$ and $R^{7''}$ are the same as or different from each other and each represents hydrogen, acetyl or —$R^M$; $R^{16}$, $R^{17}$ and $R^{20}$ Are the same as or different from each other and each represents hydrogen, hydroxy or —$OR^M$; $R^{12}$ represents methyl, —$CH_2OH$ or —$CH_2OR^M$ (wherein $R^M$ represents $C_1$–$C_8$ Alkyl, $C_2$–$C_8$ acyl, $R^{bn}CH_2$, $R^{bn}CO$ or $R^{n1}R^{n2}NCO$; $R^{bn}$ represents $C_6$–$C_{10}$ Aryl or $C_5$–$C_{1-4}$ heteroacyl which may optionally have one or more substituents described below, $R^{n1}$ and $R^{n2}$ are the same as or different from each other and each represents hydrogen, $C_1$–$C_8$ Alkyl, $C_3$–$C_7$ cycloalkyl, benzyl which may optionally have one or more substituents described below, or $R^{n1}$ and $R^{n2}$ Are bound together to represent pyrrolidine, piperidine, piperazine, N-substituted piperazine or morpholine;

The substituent described here indicates the following.
a) $C_1$–$C_8$ Alkyl, $C_1$–$C_8$ Alkoxy, $C_2$–$C_8$ Acyl,
b) fluoro, chloro, bromo, iodo,
c) carboxylic acid, sulfonic acid, carboxylic acid ester, carboxamide which may optionally have substituents on nitrogen,
d) nitro, amino, N-monosubstituted amino, N,N-disubstituted amino,
e) a hydroxy group, mercaptane, $C_1$–$C_8$ Alkylthio, $C_1$–$C_8$ alkylsulfoxide, $C_1$–$C_8$ Alkylsulfone, provided that the restricted clauses 1, 2 An 3 are included.

41. A compound represented by the formula (21), a pharmacologically acceptable salt thereof or a hydrate of them.

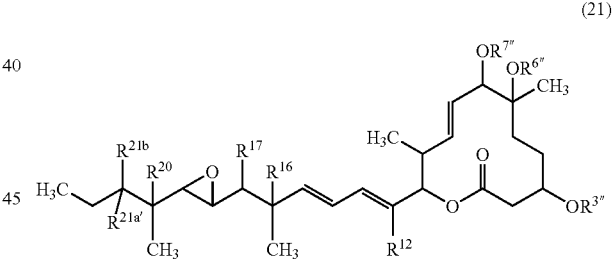 (21)

In the formula (21), $R^{3''}$ and $R^{6''}$ represent hydrogen; $R^{7''}$ represents hydrogen or acetyl; $R^{16}$, $R^{17}$ and $R^{20}$ are the same as or different from each other and each represents hydrogen or hydroxy; $R^{21a}$ and $R^{21b}$ are bound together with oxygen to represent a ketone structure, or either one of them represents hydroxy or methoxy and the other represents hydrogen; and $R^{12}$ represents methyl or —$CH_2OH$, provided that the restricted clauses 1, 2 and 3 are included.

42. The compound, a pharmacologically acceptable salt thereof or a hydrate of them, wherein in the formula (21), $R^{3''}$, $R^{6''}$ and $R^{17}$ are hydrogen; $R^{7''}$ is hydrogen or acetyl; $R^{16}$ and $R^{20}$ are the same as or different from each other and each represents hydrogen or hydroxy; $R^{21a'}$ and $R^{21b'}$ are bound together with oxygen, or either one of them represents hydroxy and the other is hydrogen; and $R^{12'}$ is methyl.

43. The compound, a pharmacologically acceptable salt thereof or a hydrate of them, wherein in the formula (21), R$^{3''}$, R$^{6''}$ and R$^{17}$ are hydrogen; R$^{7''}$ is acetyl; R$^{16}$ and R$^{17}$ Are the same as or different from each other and each represents hydrogen or hydroxy; R$^{21a}$ and R$^{21b}$ are bound together with oxygen, or either one of them represents hydroxy and the other is hydrogen; and R$^{12}$ represents methyl or —CH$_2$OH.

44. The compound, or a pharmacologically acceptable salt thereof or a hydrate of them, wherein in the formula (21), R$^{3''}_{21b}$, R$^{6''}$, R$^{7''}$, R$^{17}$, R$^{20}$ and R$^{21a}$ are hydrogen; R$^{16}$ and R$^{21b}$ are hydroxy; and R$^{12}$ is methyl.

45. The compound, a pharmacologically acceptable salt thereof or a hydrate of them, wherein in the formula (21), R$^{3''}_{21a}$, R$^{6''}$, R$^{7''}$, R$^{16}$, R$^{17}$ and R$^{21a}$ are hydrogen; R$^{20}$ and R$^{21a}$ Are hydroxy; and R$^{12}$ is methyl.

46. The compound, a pharmacologically acceptable salt thereof or a hydrate of them, wherein in the formula (21), R$^{3''}$, R$^{6''}$, R$^{7''}$, R$^{16}$, R$^{17}$, R$^{20}$ and R$^{21a}$ are hydrogen; R$^{21b}$ is hydroxy; and R$^{12}$ is methyl.

47. The compound, a pharmacologically acceptable salt thereof or a hydrate of them, wherein in the formula (21), R$^{3''}$, R$^{6''}$, R$^{17}$, R$^{20}$ and R$^{21a}$ are hydrogen; R$^{16}$ and R$^{21b}$ Are hydroxy; R$^{7''}$ is acetyl; and R$^{12}$ is methyl.

48. The compound, a pharmacologically acceptable salt thereof or a hydrate of them, wherein in the formula (21), R$^{3''}$, R$^{6''}$, R$^{17}$, R$^{20}$ and R$^{21a}$ are hydrogen; R$^{16}$ and R$^{21b}$ Are hydroxy; R$^{7''}$ is acetyl; and R$^{12}$ is methyl.

49. The compound, a pharmacologically acceptable salt thereof or a hydrate of them, wherein in the formula (21), R$^{3''}$, R$^{6''}$, R$^{16}$, R$^{17}$ and R$^{20}$ are hydrogen; R$^{21a}$ and R$^{21b}$ are bound together with oxygen; R$^{7''}$ is acetyl; and R$^{12}$ is methyl.

50. The compound, a pharmacologically acceptable salt thereof or a hydrate of them, wherein in the formula (21), R$^{3''}$, R$^{6''}$, R$^{16}$, R$^{17}$, R$^{20}$ and R$^{21a}$ are hydrogen; R$^{21b}$ is hydroxy; R$^{7''}$ is acetyl; and R$^{12}$ is methyl.

51. A medicament comprising at least one selected from compounds, a pharmacologically acceptable salt thereof or a hydrate of them an active ingredient.

Pharmaceuticals are preferably, an agent for preventing or treating a disease against which gene expression control is efficacious, an agent for preventing or treating a disease against which VEGF production suppressing action is efficacious, an agent for preventing or treating a disease against which an antiangiogenic effect is efficacious, an antiangiogenic agent, an antitumor agent, an agent for treating hematoma, an agent for suppressing cancer metastasis, an agent for treating retina angiogenic disease or an agent for treating diabetic retinopathy, an agent for treating inflammatory disease, an agent for treating inflammatory diseases consisting of osteoarthritis, rheumatoid arthritis, psoriasis or delayed hypersensitivity reaction, an agent for treating atherosclerosis, an agent for treating solid cancer, especially a medicament in which the solid cancer is lung cancer, brain tumor, breast cancer, prostate cancer, ovarian cancer, colon cancer or melanoma, an agent for treating leukemia, an antitumor agent based on gene expression control, an antitumor agent based on VEGF production suppressing action or an antitumor agent based on an antiangiogenic effect.

Further, the present invention provides a method for preventing or treating a disease against which gene expression control is efficacious, by administering a pharmacologically effective dose of the above-mentioned medicament to a patient. In particular, the method is a method for preventing or treating a disease against which the VEGF production action is efficacious or against which an antiangiogenic action is efficacious.

Further, it provides use of the any one of compounds of the present invention, a pharmacologically acceptable salt thereof or a hydrate of them for producing the above-mentioned medicament or an agent for preventing or treating. In particular, it is occasionally used for producing an agent for preventing or treating a disease against which gene expression control is efficacious, a disease against which the VEGF production suppressing action is efficacious, a disease against which an antiangiogenic action is efficacious or a solid cancer.

Further, the present invention provides the production process of the compound of the present invention, a pharmacologically acceptable salt thereof or a hydrate of them, which comprises culturing *Streptomyces* sp. Mer. 11107, FERM P-18144 or its variant in a nutrient culture medium, collecting the compounds described in any of the above are from the culture solution, and carrying out various modification synthesis by using the obtained compounds as a starting material to obtain derivatives thereof.

Further, the present invention provides an agent for preventing or treating a disease against which the gene expression control is efficacious, a disease against which the VEGF production suppressing action is efficacious, a disease against which the antiangiogenic action is efficacious or solid cancers, which comprises the compound represented by the formula (4), a pharmacologically acceptable salt thereof or a hydrate of them. Further, it provides a method for preventing or treating by using it, and use of it for producing an agent for preventing or treating. The agent for preventing or treating is preferably an agent for treating hematoma, an agent for suppressing cancer metastasis, an agent for treating retina angiogenic disease or an agent for treating diabetic retinopathy, an agent for treating inflammatory diseases an agent for treating osteoarthritis, an agent for treating rheumatoid arthritis, an agent for treating psoriasis, an agent for treating atherosclerosis or an agent for treating solid cancer. When the solid cancer is lung cancer, brain tumor, breast cancer, prostate cancer, ovarian cancer, colon cancer or melanoma, it is effective in particular.

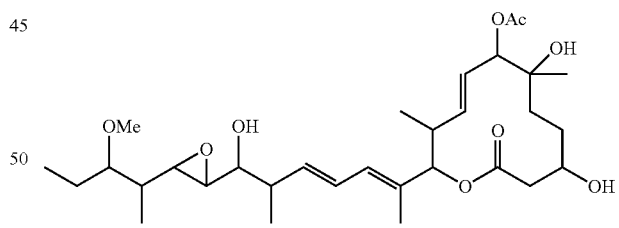

(4)

As the 12-membered ring macrolide compound which is similar as the present invention, FD895 (JP-A 4-352783) is known. However, although cell inhibitory action in vitro is indicated, it was ineffective in an animal experiment using P388 mouse leukemia cell (Seki-Asano M. et al, J. Antibiotics Vol. 47, 1395–1401, 1994).

The following deposit microorganism can be used for the microorganism for producing the compound of the present invention. The fungus strain was internationally deposited to International Patent Organism Depositary (IPOD) National Institute of Advanced Industrial Science and Technology (Tsukuba Central 6, 1–1, Higashi 1-Chome Tsukuba-shi, Ibaraki-ken 305-8566 Japan).

*Streptomyces* sp. Mer-11107 was deposited as FERM P18144 at the National Institute of Bioscience and Human-Technology Agency of Industrial Science and Technology (1-3, Higashi 1 chome Tsukuba-shi Ibaraki-ken 305-8566, Japan). Further, this was transferred to International Deposit FERM BP-7812 At International Patent Organism Depositary (IPOD) National Institute of Advanced Industrial Science and Technology (Tsukuba Central 6, 1-1, Higashi 1-Chome Tsukuba-shi, Ibaraki-ken 305-8566 Japan).

Additionally, *Streptomyces* sp. A-1532, *Streptomyces* sp. A-1533 and *Streptomyces* sp. A-1534 were also internationally deposited to International Patent Organism Depositary (IPOD) National Institute of Advanced Industrial Science and Technology (Tsukuba Central 6, 1-1, Higashi 1-Chome Tsukuba-shi, Ibaraki-ken 305-8566 Japan) as FERM BP-7849, FERM BP-7850 and FERM BP-7851, respectively.

The meanings of terms, symbols and the like used in the specification of the present application will be illustrated below, and the present invention will be specifically illustrated.

In the specification of the present application, the structural formula of the compound represents occasionally a fixed isomer for convenience. In the specification of the present application, there are included all isomers and mixtures of the isomers such as a geometric isomer which are generated from the configuration of the compound, an optical isomer based on an asymmetric carbon, a rotamer, a stereoisomer and a tautomer. It is not limited to the description of the formula for convenience, and may be either of isomers or a mixture thereof. Accordingly, the compound of the present invention occasionally has an asymmetric carbon in the molecule, and its optically active substance and a racemate may exist, but it is not specifically limited and any one is included. Further, polymorphic crystals may exist, but it is not specifically limited in the present invention and any one of the crystal forms may be single or a mixture of the crystal form. The compound (1) according to the present invention or a salt thereof may be an anhydride or a hydrate, and both are included in the present invention. The metabolite which is generated by decomposing the compound (1) according to the present invention in vivo and the prodrug of the compound (1) according to the present invention or a salt thereof are also included in the present invention.

The "halogen" used in the specification of the present application means a fluorine atom, a chlorine atom, a bromine atom and an iodine atom.

The "$C_{1-22}$ Alkyl" used in the specification of the present application indicates alkyl groups having 1 to 22 carbons, and as the preferable group, linear or branched alkyl groups such as a methyl group, an ethyl group, an n-propyl group, an isopropyl group, a n-butyl group, an isobutyl group, a sec-butyl group, a tert-butyl group, a n-pentyl group, a 1,1-dimethylpropyl group, a 1,2-dimethylpropyl group, a 2,2-dimethylpropyl group, a 1-ethylpropyl group, a 2-ethylpropyl group, a n-hexyl group, a 1-methyl-2-ethylpropyl group, a 1-ethyl-2-methylpropyl group, a 1,1,2-trimethylpropyl group, a 1-propylpropyl group, a 1-methylbutyl group, a 2-methylbutyl group, a 1,1-dimethylbutyl group, a 1,2-dimethylbutyl group, a 2,2-dimethylbutyl group, a 1,3-dimethylbutyl group, a 2,3-dimethylbutyl group, a 2-ethylbutyl group, a 2-methylpentyl group or a 3-methylpentyl group may be proposed.

The "unsaturated $C_{2-22}$ Alkyl" used in the specification of the present application indicates an alkenyl group having 2 to 22 carbons or an alkynyl group having 2 to 22 carbons, and as the preferable group, a vinyl group, an allyl group, a 1-propenyl group, a 2-propenyl group, an isopropenyl group, a 2-methyl-1-propenyl group, a 3-methyl-1-propenyl group, a 2-methyl-2-propenyl group, a 3-methyl-2-propenyl group, a 1-butenyl group, a 2-butenyl group, a 3-butenyl group, a 1-pentenyl group, a 1-hexenyl group, a 1,3-hexanedienyl group, a 1,6-hexanedienyl group, an ethynyl group, a 1-propynyl group, a 2-propynyl group, a 1-butynyl group, a 2-butynyl group, a 3-butynyl group, a 3-methyl-1-propynyl group, a 1-ethynyl-2-propynyl group, a 2-methyl-3-propynyl group, a 1-pentynyl group, a 1-hexynyl group, a 1,3-hexanediynyl group, a 1,6-hexanediynyl group, etc. may be proposed.

The "$C_{2-22}$ Acyl" used in the specification of the present application indicates an acyl group having 2 to 22 carbons, and as the preferable group, linear chain or branched acyl groups such an acetyl group, a propionyl group, a butyryl group, an isobutyryl group, a valeryl group, an isovaleryl group, a pivaloyl group, a caproyl group, a decanoyl group, a lauroyl group, a myristoyl group, a palmitoyl group, a stearoyl group or an arachidonyl group may be proposed. Further, the "$C_{2-22}$ Acyloxy" used in the present specification has the partial structure corresponding to the "$C_{2-22}$ Acyl".

The "unsaturated $C_{3-22}$ Acyl" used in the specification of the present application indicates an acyl group consisting of 3 to 22 carbons and having a double bond or a triple bond, and as the preferable group, linear chain or branched acyl groups such as an acryl group, a propioloyl group, a crotonoyl group, an isocrotonoyl group, an oleoyl group or a linolenoyl group may be proposed. Further, the "unsaturated $C_{3-22}$ Acyloxy" used in the specification of the present application has the partial structure corresponding to the "unsaturated $C_{3-22}$ Acyl".

The "$C_{1-22}$ Alkoxy" used in the specification of the present application indicates an alkoxy group having 1 to 22 carbons, and as the preferable group, a methoxy group, an ethoxy group, an n-propoxy group, an isopropoxy group, an n-butoxy group, an isobutoxy group, a sec-butoxy group, a tert-butoxy group, a n-pentyloxy group, an isopentyloxy group, a sec-pentyloxy group, an n-hexyloxy group, an isohexyloxy group, a 1,1-dimethylpropyloxy group, a 1,2-dimethylpropoxy group, a 2,2-dimethylpropyloxy group, a 2-ethylpropoxy group, a 1-methyl-2-ethylpropoxy group, a 1-ethyl-2-methylpropoxy group, a 1,1,2-trimethylpropoxy group, a 1,1,2-trimethylpropoxy group, a 1,1-dimethylbutoxy group, a 1,2-dimethylbutoxy group, a 2,2-dimethylbutoxy group, a 2,3-dimethylbutoxy group, a 1,3-dimethylbutyloxy group, a 2-ethylbutoxy group, a 1,3-dimethylbutoxy group, a 2-methylpentoxy group, a 3-methylpentyloxy group, a hexyloxy group etc. may be proposed.

The "unsaturated $C_{2-22}$ Alkoxy" used in the specification of the present application indicates an alkenyloxy group or an alkynyloxy group having 2 to 22 carbons, and as the preferable group, for example, a vinyloxy group, an allyloxy group, a 1-propenyloxy group, a 2-propenyloxy group, an isopropenyloxy group, a 2-methyl-1-propenyloxy group, a 3-methyl-1-propenyloxy group, a 2-methyl-2-propenyloxy group, a 3-methyl-2-propenyloxy group, a 1-butenyloxy group, a 2-butenyloxy group, a 3-butenyloxy group, a 1-pentenyloxy group, a 1-hexenyloxy group, a 1,3-hexanedienyloxy group, a 1,6-hexanedienyloxy group, a propargyloxy group, a 2-butynyloxy group etc. may be proposed.

The "$C_{3-8}$ cycloalkyl" used in the specification of the present application indicates a cycloalkyl group having 3 to 8 carbons, and as the preferable group, a cyclopropyl group, a cyclobutyl group, a cyclopentyl group, a cyclohexyl group, a cycloheptyl group, a cyclooctyl group etc. may be proposed.

The "$C_{3-8}$ cycloalkenyl" used in the specification of the present application indicates a cycloalkenyl group having 3 to 8 carbons, and as the preferable group, cyclopropen-1-yl, cyclopropen-3-yl, cyclobuten-1-yl, cyclobuten-3-yl, 1,3-cyclobutadien-1-yl, cyclopenten-1-yl, cyclopenten-3-yl, cyclopenten-4-yl, 1,3-cyclopentadien-1-yl, 1,3-cyclopentadien-2-yl, 1,3-cyclopentadien-5-yl, cyclohexen-1-yl, cyclohexen-3-yl, cyclohexen-4-yl, 1,3-cyclohexadien-1-yl, 1,3-cyclohexadien-2-yl, 1,3-cyclohexadien-5-yl, 1,4-cyclohexadien-3-yl, 1,4-cyclohexadien-1-yl, cyclohepten-1-yl, cyclohepten-3-yl, cyclohepten-4-yl, cyclohepten-5-yl, 1,3-cyclohepten-2-yl, 1,3-cyclohepten-1-yl, 1,3-cycloheptadien-5-yl, 1,3-cycloheptadien-6-yl, 1,4-cycloheptadien-3-yl, 1,4-cycloheptadien-2-yl, 1,4-cycloheptadien-1-yl, 1,4-cycloheptadien-6-yl, 1,3,5-cycloheptatrien-3-yl, 1,3,5-cycloheptatrien-2-yl, 1,3,5-cycloheptatrien-1-yl, 1,3,5-cycloheptatrien-7-yl, cycloocten-1-yl, cycloocten-3-yl, cycloocten-4-yl, cycloocten-5-yl, 1,3-cyclooctadien-2-yl, 1,3-cyclooctadien-1-yl, 1,3-cyclooctadien-5-yl, 1,3-cyclooctadien-6-yl, 1,4-cyclooctadien-3-yl, 1,4-cyclooctadien-2-yl, 1,4-cyclooctadien-1-yl, 1,4-cyclooctadien-6-yl, 1,4-cyclooctadien-7-yl, 1,5-cyclooctadien-3-yl, 1,5-cyclooctadien-2-yl, 1,3,5-cyclooctatrien-3-yl, 1,3,5-cyclooctatrien-2-yl, 1,3,5-cyclooctatrien-1-yl, 1,3,5-cyclooctatrien-7-yl, 1,3,6-cyclooctatrien-2-yl, 1,3,6-cyclooctatrien-1-yl, 1,3,6-cyclooctatrien-5-yl, 1,3,6-cyclooctatrien-6-yl etc. may be proposed.

The "$C_{6-14}$ Aryl" used in the specification of the present application means an aromatic hydrocarbon cyclic group which was constituted by 6 to 14 carbons, and condensed rings such as a monocyclic group, a dicyclic group and a tricyclic group are included. As the preferable examples, a phenyl group, an indenyl group, a 1-naphthyl group, a 2-naphthyl group, an azulenyl group, a hepthalenyl group, a biphenyl group, an indacenyl group, an acenaphthyl group, a fluorenyl group, a phenalenyl group, a phenanthrenyl group, an anthracenyl group, a cyclopentacyclooctenyl group, a benzocyclooctenyl group etc. may be proposed.

The "5- to 14-membered heteroaryl" used in the specification of the present application means a monocyclic, dicyclic or tricyclic 5- to 14-membered aromatic heterocyclic group which contains one or more of hetero atoms selected from the group consisting of a nitrogen atom, a sulfur atom and an oxygen atom. As the preferable group, the nitrogen-containing aromatic heterocyclic group includes a pyrrolyl group, a pyridyl group, a pyridazinyl group, a pyrimidinyl group, a pyrazinyl group, a triazolyl group, a tetrazolyl group, a benzotriazolyl group, a pyrazolyl group, an imidazolyl group, a benzimidazolyl group, an indolyl group, an isoindolyl group, an indolizinyl group, a purinyl group, an indazolyl group, a quinolyl group, an isoquinolyl group, a quinolizinyl group, a phthalazinyl group, a naphthylidinyl group, a quinoxalinyl group, a quinazolinyl group, a cinnolinyl group, a pteridinyl group, an imidazotriazinyl group, a pyrazinopyridazinyl group, an acridinyl group, a phenanthridinyl group, a carbazolyl group, a carbolinyl group, a perimidinyl group, a phenanthrolinyl group, a phenazinyl group, an imidazopyridinyl group, an imidazopyrimidinyl group, a pyrazolopyridinyl group, and the like; the aromatic heterocyclic group containing sulfur includes a thienyl group, a benzothienyl group and the like; the aromatic heterocyclic group containing oxygen includes, a furyl group, a pyranyl group, a cyclopentapyranyl group, a benzofuryl group, an isobenzofuryl group and the like; the aromatic heterocyclic group containing 2 or more of different kind of hetero atoms includes, a thiazolyl group, an isothiazolyl group, a benzothiazolyl group, a benzothiadiazolyl group, a phenothiazinyl group, an isoxazolyl group, a furazanyl group, a phenoxazinyl group, an oxazolyl group, an isooxazoyl group, a benzoxazolyl group, an oxadiazolyl group, a pyrazolooxazolyl group, an imidazothiazolyl group, a thienofuranyl group, a furopyrrolyl group, a pyridoxazinyl group and the like.

The "3- to 14-membered nitrogen-containing non-aromatic hetero ring" used in the specification of the present application means a monocyclic, dicyclic or tricyclic 3- to 14-membered non-aromatic heterocyclic group which contains one or more of hetero atoms selected from the group consisting of a nitrogen atom, a sulfur atom and an oxygen atom, in addition to a nitrogen atom. The preferable example includes an aziridinyl group, an acetidyl group, a pyrrolidinyl group, a pyrrolinyl group, a piperidinyl group, a piperazinyl group, an imidazolinyl group, a pyrazolidinyl group, an imidazolidinyl group, a morpholinyl group, a thiomorpholinyl group, an imidazolinyl group, an oxazolinyl group and the like. Further, the non-aromatic heterocyclic group includes also a group derived from a pyridone ring, a non-aromatic condensed ring (for example, a group derived from a phthalimide ring, a succinimide ring and the like).

The substituent of "which may optionally have substituents" used in the specification of the present application includes one or more groups selected from a $C_{1-8}$ alkyl group, a $C_{2-8}$ Alkenyl group (for example, a vinyl group), a $C_{2-8}$ Alkynyl group (for example, an ethynyl group), a $C_{6-14}$ Aryl group (for example, a phenyl group and the like), 5- to 14-membered hetero aryl group (for example, a thienyl group, a furyl group, a pyridyl group, a pyridazinyl group, a pyrimidinyl group, a pyrazinyl group and the like), a hydroxyl group, a $C_{1-8}$ Alkoxy group, a $C_{1-8}$ acyl group, a $C_{2-8}$ Acyloxy group, a $C_{2-8}$ Alkenyloxycarbonyl group, a $C_{2-8}$ Alkynyloxycarbonyl group, a $C_{1-8}$ Alkoxycarbonyl group, a halogen atom, a hydroxycarbonyl group, a thiol group, a $C_{1-8}$ Alkylthio group, a $C_{1-8}$ Alkylsulfoxide group, a $C_{1-8}$ Alkylsulfonyl group, a $C_{1-8}$ Alkylsulfonyloxy group, a hydroxysulfonyl group, an nitrile group, an nitro group, an nitroso group, an amino group, an N—$C_{1-8}$ Alkylamino group, an N,N-di($C_{1-8}$ Alkyl)amino group, an N—$C_{2-8}$ Alkenylamino group, an N,N-di($C_{2-8}$ Alkenyl)amino group, an N—$C_{2-8}$ alkynylamino group, an N,N-di($C_{2-8}$ Alkynyl) amino group, an N-arylamino group (for example, a phenylamino group), an N-heteroarylamino group (for example, a 2-pyridylamino group, a 3-pyridylamino group, a 1-pyrrolylamino group, and the like), an N—$C_{1-8}$ Alkyl-N-arylamino group, an N—$C_{1-8}$ Alkyl-N-heteroarylamino group, an aralkyloxy group, a heteroaryloxy group, a $C_{1-8}$ Alkylsulfonylamino group, a $C_{2-8}$ alkenylsulfonylamino group, a $C_{2-8}$ Alkynylsulfonylamino group, an N—$C_{1-8}$ Alkylcarbamoyl group, an N—$C_{1-8}$ alkylcarbamoyl group, an N—$C_{2-8}$ Alkenylcarbamoyl group, an N,N-di($C_{2-8}$ Alkynyl) carbamoyl group, a $C_{2-8}$ Acylamino group, and the like.

There are disclosed below 1. the property of separated microorganism, 2. the fermentation method of the microorganism, 3. the purification method of an active substance, 4. the modification method of the active substance and 5. the application method of the active substance which were described in the present invention.

1. The Property of Isolated Microorganism

As raw materials of the compound of the present invention, it is expected that any one of strains belonging to the genus *Streptomyces* can be used. However, as a typical strain used in the present invention, a strain which was named as "Mer-11107 strain" by the inventors is exemplified. The taxonomical properties of this strain are as follows.

(1) *Streptomyces* sp. Mer-11107, FERM BP-7812

(1) Morphological Charcteristics

Aerial hyphae that bore spirales is extended from vegetative hypha. Spore chain consisting of about 10 to 20 of columnar spores are formed at the edge of the ripened aerial hyphae. The size of the spores are about 0.7×10 μm, the surface of the spores is smooth, and specific organs such as sporangium, scleoric granule and zoospore are not observed.

(2) Cultural Characteristics on Various Media

Cultural characteristics after incubation at 28° C. for two weeks on various media are shown below. The color tone is described by the color name and codes which are shown in the parenthesis of the Color Harmony Manual (Container Corporation of America).

1) Yeast Extract-Malt Extract Agar Medium

The strain grew well, the aerial hyphae grew up on the surface, and light gray spores (Light gray; d) were observed. The reverse side of colony was Light melon yellow (3 ea). Soluble pigment was not produced.

2) Oatmeal Agar Medium

The strain grew in the middle level, the aerial hyphae grew slightly on the surface, and gray spores (Gray; d) were observed. The reverse side of colony was Nude tan (4gc) or Putty (1½ec). Soluble pigment was not produced.

3) Inorganic Salt-Starch Agar Medium

The strain grew well, the aerial hyphae grew up on the surface, and gray spores (Gray; d) were observed. The reverse side of colony was Fawn (4ig) or Gray (g). Soluble pigment was not produced.

4) Lycerol-Asparagine Agar Medium

The strain grew well, the aerial hyphae grew up on the surface, and white spores (White; a) were observed. The reverse side of colony was Pearl pink (3ca). Soluble pigment was not produced.

5) Peptone-yeast Extract-iron Agar Medium

The strain growth was bad, and the aerial hyphae did not grow on the surface. The reverse side of colony was Light melon yellow (3ea). Soluble pigment was not produced.

6) Tyrosine Agar Medium

The strain grew well, the aerial hyphae grew up on the surface, and white spores (White; a) were observed. The reverse side of colony was Pearl pink (3ca). Soluble pigment was not produced.

(3) Utilization of Various Carbon Sources

Various carbon sources are added in Pridham-Gottlieb agar medium, growth after incubation at 28° C. for two weeks are shown below.

| 1) L-arabinose | ± |
| 2) D-xylose | ± |
| 3) D-glucose | + |
| 4) D-fructose | + |
| 5) sucrose | + |
| 6) inositol | + |
| 7) L-rhamnose | − |

-continued

| 8) D-mannitol | + |
| 9) D-raffinose | + |

(+: positive, ±: slightly positive, −: negative)

(4) Physiological Properties

The physiological properties of the strain are as shown below.

(a) Range of growth temperature (yeast extract-malt extract agar medium, incubation for 2 weeks) 12° C. to 37° C.

(b) Range of optimum temperature (yeast extract-malt extract agar medium, incubation for 2 weeks) 21° C. to 33° C.

(c) Liquefaction of gelatin (glucose-peptone-gelatin agar medium) negative (d) Coagulation of milk (skim milk agar medium) negative (e) Peptonization of milk (skim milk agar medium) negative (f) Hydrolysis of starch (inorganic salt-starch agar medium) negative (g) Formation of melanoid pigment (peptone-yeast extract-iron agar medium) negative (tyrosine medium) negative (h) Production of hydrogen sulfide (peptone-yeast extract-iron agar medium) negative (i) Reduction of nitrate (broth containing 0.1% potassium nitrate) negative (j) Sodium chloride tolerance (yeast extract-malt extract agar medium, incubation for 2 weeks) grown at a salt content of 4% or less (5) Chemotaxonomy LL-diaminopimelic acid and glycine were detected from the cell wall of the present strain. It is considered that the present strain is a strain of the genus *Streptomyces* from the above-mentioned microbial characteristics. Accordingly, the present inventors have named the present microbial strain as *Streptomyces* sp. Mer-11107.

2. Fermentation Method of Producing Microorganism

The bioactive substances 11107A to BJ of the present invention are produced by inoculating the above-mentioned microbial strain or its variant on a nutrition source medium and carrying out aerobic fermentation. The producing microorganism of the biologically active substance 11107A to BJ belongs to *Streptomyces* sp., is not limited to the above-mentioned microbial strain so far as it has an ability of producing 11107A to BJ, and all can be utilized in the present invention. Hereinafter, both of 11107A to BJ and the analogue which the above-mentioned microbial strain produces are referred to as 11107 Analogue.

The fermentation method of the above-mentioned microorganism is subjected to the general fermentation method of microorganism, but it is preferable that it is carried out under aerobic conditions such as shaking culture or aeration-agitation fermentation using liquid medium. The medium used for culture may be a medium containing a nutrition source which can be utilized by microorganism belonging the genus *Streptomyces*, therefore all of various synthetic, a semi-synthetic medium, an organic medium and the like can be utilized. As the medium composition, there can be used a single or a combination of glucose, galactose, sucrose, maltose, fructose, glycerin, dextrine, starch, molasses, soybean oil and the like. As the nitrogen source, there can be used a single or a combination of organic nitrogen sources such as pharma media, peptone, meat extract, soybean powder, fish powder, gluten meal, casein, dry yeast, amino acid, yeast extract and urea, and inorganic nitrogen sources such as sodium nitrate and ammonium sulfate. Additionally, for example, there can be added and used salts such as sodium chloride, potassium chloride, calcium carbonate, magnesium sulfate, sodium phosphate, potassium phosphate, copper sulfate, iron sulfate, manganese chloride and cobalt chloride; heavy metal salts, vitamins such as vitamin B or biotin, if necessary. Further, when foaming is remarkable during culture, various defoaming agents can be appropriately added in the medium as necessary. When the defoaming agent is added, it is required to set at a concentration for not adversely affecting the production of an objective substance, and for example, the use concentration is desirably 0.05% or less.

The culture condition can be appropriately selected within the range at which the microbial strain is grown well and can produce the above-mentioned substance. For example, the pH of a medium is about 5 to 9, and preferably nearby neutral in general. The temperature of fermentation is usually kept at 20 to 40° C., preferably 24 to 30° C. and more preferably 28 to 35° C. The fermentation period is about 2 to 8 days, and usually about 4 to 7 days or usually about 3 to 5 days. The above-mentioned fermentation conditions can be suitably changed in accordance with the kind and property of microorganism used, external conditions and the like, and it is needless to say that an optimum condition can be selected. The biologically active substance 11107 Analogue of the present invention which was accumulated in the cultured broth can be collected by usual separation procedures utilizing its property such as, for example, a solvent extraction method and an absorbing resin method.

3. Purification Method for the Bioactive Substance

General methods for separation and purification which are used for isolation of microbial metabolites from the cultured broth can be employed in order to collect the 11107 Analogue from the cultured medium after the fermentation. For example, there can be corresponded all methods such as extraction by an organic solvent using methanol, ethanol, acetone, butanol, ethyl acetate, butyl acetate and chloroform, and toluene; the treatment of adsorption and desorption using a hydrophobic adsorption resin such as DIAION HP-20; gel filtration chromatography using Sephadex LH-20; absorption chromatography by active carbon, silica gel and the like; or the treatment of adsorption and desorption by thin layer chromatography; or high performance liquid chromatography using a reverse phase column and the like, to this. Further, the purification methods for 11107 Analogue are not specifically limited to the methods shown here.

The 11107 Analogue can be isolated and purified by using these methods alone or in combination and repeatedly using them.

4. Purification Method of Biologically Active Substance

After termination of the incubation, methods of separation and purification which are usually used for isolating microorganism metabolism product from the incubation solution can be utilized in order to collect the 11107 Analogue from the incubation solution. For example, there can be corresponded all methods such as extraction by an organic solvent using methanol, ethanol, butanol, ethyl acetate and chloroform; the treatment of adsorption and desorption by various ion exchange chromatographies, gel filtration chromatography using Sephadex LH-20; absorption chromatography by active carbon, silica gel and the like; or the treatment of adsorption and desorption by thin layer chromatography; or high performance liquid chromatography using a reverse phase column and the like, to this. Further, the methods shown here are not specifically limited.

The 11107 Analogue can be isolated and purified by using these methods alone or in combination and repeatedly using them.

5. Modification of Bioactive Substance

The compound of the present invention represented by the respective formulae including the formula (I) can be synthesized from the 11107 Analogue which was isolated and purified, using general organic synthesis methods. As a typical method, it can be synthesized by, for example, a method shown below, and a combination of these methods. In production, the reaction compound may have a protective group, and the objective compound is obtained by removing its protective group.

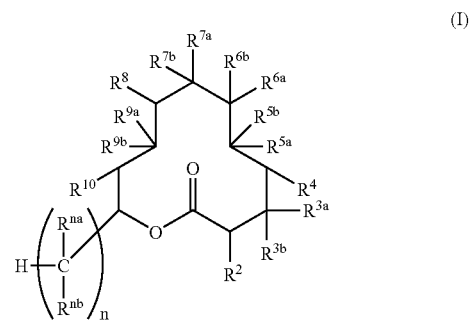

(I)

(1) Synthesis of Compound in which the Hydroxy Group of 11107 Analogue is Appropriately Protected The hydroxy group of 11107 Analogue can be protected by an appropriate protective group. It is possible to selectively protect the hydroxy group of 11107 Analogue by selecting a protecting group. All or a portion of the hydroxy group can be protected by ethoxyethyl, tetrahydropyranyl, methoxymethyl, t-butyldimethylsilyl, triethylsilyl, trimethylsilyl and the like as the protecting group.

The compound, protected by such as ethoxyethyl or tetrahydropyranyl, can be synthesized by treating ethyl vinyl ether or dihydropyran in the presence of an acid respectively. As the acid, there are mentioned usual organic acids, inorganic acids, for example, pyridinium p-toluenesulfonate, p-toluenesulfonic acid and the like. The solvent used for the reaction is not specifically limited, but the solvent which cannot easily react with a raw material substance is desirable, and for example, tetrahydrofuran, dichloromethane and the like are mentioned. The reaction time is 10 minutes to 30 hours. The reaction temperature is a temperature of −78° C. to reflux by heating.

The deprotection of the protecting group can be easily carried out by treatent with an acid. As the acid, there are mentioned usual organic acids, inorganic acids, for example, pyridinium p-toluenesulfonate, p-toluenesulfonic acid and the like. The solvent used for the reaction is not specifically limited, but a solvent which cannot easily react with a raw material substance is desirable, and for example, methanol, ethanol and the like are mentioned. The reaction time is 10 minutes to 30 hours. The reaction temperature is a temperature of −78° C. to reflux by heating.

The compound, protected by such as methoxymethyl, t-butyldimethylsilyl, triethylsilyl, or trimethylsilyl, can be synthesized by reacting with a corresponding chloro-, bromo- or trifluoromethanesulfonyl-compound respectively in the presence of a base. As the base, there are mentioned usual organic bases, inorganic bases, for example, imidazole, diisopropylethylamine, dimethylaminopyridine, triethylamine, pyridine, 2,6-rutidine, sodium hydride, 8-bis(dimethylamino)naphthalene and the like. The solvent used for the reaction is not specifically limited, but a solvent which cannot easily react with a raw material substance is desirable, and for example, tetrahydrofuran, dichloromethane, N,N-dimethylformamide and the like are mentioned. The reaction time is 10 minutes to 30 hours. The reaction temperature is a temperature of −78° C. to reflux by heating.

The deprotection of the protecting group can be carried out by treatment with a fluorine anion or an acid. As the fluorine reagent, there are mentioned tetrabutylammonium fluoride, hydrogen fluoride, potassium fluoride and the like, and as the acid, there are mentioned usual organic acids, inorganic acids, for example, acetic acid, trifluoroacetic acid, p-toluenesulfonic acid and the like. The solvent used for the reaction is not specifically limited, but a solvent which cannot easily react with a raw material substance is desirable, and for example, tetrahydrofuran, diethyl ether, water and the like are mentioned. The reaction time is 10 minutes to 30 hours. The reaction temperature is a temperature of −78° C. to reflux by heating.

Further, the neighboring hydroxy group can be protected by being treated with dimethoxyacetone in the presence of an acid catalyst. As the acid, there are mentioned usual organic acids, inorganic acids, for example, p-toluenesulfonic acid, pyridinium p-toluenesulfonate and the like. The solvent used for the reaction is not specifically limited, but a solvent which cannot easily react with a raw material substance is desirable, and for example, tetrahydrofuran, dichloromethane and the like are mentioned. The reaction time is 10 minutes to 30 hours. The reaction temperature is a temperature of −78° C. to reflux by heating.

The deprotection of the protecting group can be carrid out by treatment with an acid to convert it into a hydroxy group. As the acid, there are mentioned usual organic acids, inorganic acids, for example, acetic acid, trifluoroacetic acid, p-toluenesulfonic acid and the like. The solvent used for the reaction is not specifically limited, but a solvent which cannot easily react with a raw material substance is desirable, and for example, methanol, ethanol and the like are mentioned. The reaction time is 10 minutes to 30 hours. The reaction temperature is a temperature of −78° C. to reflux by heating.

(2) Acylation Reaction of Hydroxy Group

The hydroxy group of 11107 Analogue or a residual hydroxy group after suitable protection of the hydroxy group of 11107 Analogue can be acylated. The acylated derivative of the formula (I) can be synthesized by deprotecion of the protecting group of the product. As reagents for the acylation, an acid anhydride with a base, an acyl chloride with a base, a carboxylic acid with a condensing agent, a carboxylic acid with trimethylsilyl chloride, or reagents used for Mitsunobu reaction. As the acid anhydride, various carboxylic anhydrides are used, but for example, they are acetic anhydride, propionic anhydride, butyric anhydride and the like. As the acid chloride, various acid chlorides are used, but for example, they are acetyl chloride, propionyl chloride, benzoyl chloride and the like. As the base, there are mentioned usual organic bases, inorganic bases, for example, diisopropylethylamine, dimethylaminopyridine, triethylamine, pyridine, 2,6-rutidine, sodium hydride, and the like. As the carboxylic acid, various carboxylic acids are used, but for example, they are acetic acid and propionic acid. The condensing agent is dicyclohexylcarbodiimide, trifluoroacetic anhydride, carbonylimidazole and the like. Further, in Mitsunobu reaction, various carboxylic acids can be substituted in the presence of triphenylphosphine and diethylazodicarboxylate. The solvent used for the reaction is not specifically limited, but a solvent which cannot easily react with a raw material substance is desirable, and for example, dichloromethane, chloroform, tetrahydrofuran and the like are mentioned. The reaction time is 10 minutes to 30 hours. The reaction temperature is a temperature of −78° C. to reflux by heating.

Further, an acyloxy group having good elimination property is occasionally eliminated to form a double bond in the present reaction.

(3) Alkylation of Hydroxy Group

The hydroxy group of 11107 Analogue or a residual hydroxy group after suitable protection of the hydroxy group of 11107 Analogue can be converted into an alkoxy group. The protecting group of the product is deprotected to synthesize the alkylated derivative of the formula (I). The alkylation can be carried out by treating with $R^M$—X in the presence of a base or, in case of methylation, by treating with methyl trifluoromethanesulfonate. In the formula, various alkyls can be used for $R^M$, and for example, it is methyl, ethyl and benzyl. X represents an leaving group. For example, there can be mentioned a chloro group, a bromo group, an iodo group, or a trifluoromethanesulfonate and the like. As the base, there are mentioned usual organic bases, inorganic bases, for example, sodium hydride, lithium bis(trimethylsilyl)amide, lithium diisopropylamide, lithium dicyclohexylamide, potassium carbonate, cesium carbonate, 8-bis(dimethylamino)naphthalene and the like. The solvent used for the reaction is not specifically limited, but a solvent which cannot easily react with a raw material substance is desirable, and for example, diethyl ether, tetrahydrofuran, diethoxyethane and the like are mentioned. The reaction time is 10 minutes to 30 hours. The reaction temperature is a temperature of −78° C. to reflux by heating.

(4) Substitution of Hydroxy Group to Halogen

The hydroxy group of 11107 Analogue or a residual hydroxy group after suitable protection of the hydroxy group of 11107 Analogue can be converted into halogen such as chlorine, bromine, iodine or fluorine. The protecting group of the product can be deprotected to obtain the halogen derivative of the formula (I). For example, it is treated with diethylaminosulfate trifluorade (DAST), or it is treated with carbon tetrabromide, bromine, phosphorous tribromide, iodine and tetrachloride in the presence of triphenyl phosphine and a base. As the base, there are mentioned usual organic bases, inorganic bases, for example, diisopropylethylamine, dimethylaminopyridine, triethylamine, pyridine, 2,6-rutidine, sodium hydride and the like. The solvent used for the reaction is not specifically limited, but a solvent which cannot easily react with a raw material substance is desirable, and for example, tetrahydrofuran, dichloromethane, N,N-dimethylformamide and the like are mentioned. The reaction time is 10 minutes to 30 hours. The reaction temperature is a temperature of −78° C. to reflux by heating.

(5) Sulfonylation of Hydroxy Group

The hydroxy group of 11107 Analogue or a residual hydroxy group after suitable protection of the hydroxy group of 11107 Analogue can be sulfonylated. The protecting group of the product can be deprotected to obtain the sulfonyl derivative of the formula (I). The sulfonylation can be carried out by p-toluenesulfonyl chloride, methanesulfonyl chloride and benzenesulfonyl chloride, in the presence of an appropriate base. As the base, there are mentioned usual organic bases, inorganic bases, for example, diisopropylethylamine, dimethylaminopyridine, triethylamine, pyridine, 2,6-rutidine, sodium hydride and the like. The solvent used for the reaction is not specifically limited, but a solvent which cannot easily react with a raw material substance is desirable, and for example, tetrahydrofuran, dichloromethane, N,N-dimethylformamide and the like are mentioned. The reaction time is 10 minutes to 30 hours. The reaction temperature is a temperature of −78° C. to reflux by heating.

(6) Carbonic-esterification of Hydroxy Group

The hydroxy group of 11107 Analogue or a residual hydroxy group after suitable protection of the hydroxy group of 11107 Analogue is treated with a chloroformate derivative or carbonyldiimidazole in the presence of a base. The protecting group of the product can be eliminated to obtain the carbonic ester derivative of the formula (I). As the chloroformate derivative, 4-nitrophenylchloroformate, phenyl chloroformate and the like are mentioned. As the base, there are mentioned usual organic bases, inorganic bases, for example, diisopropylethylamine, dimethylaminopyridine, triethylamine, pyridine, 2,6-rutidine, sodium hydride and the like. The solvent used for the reaction is not specifically limited, but a solvent which cannot easily react with a raw material substance is desirable, and for example, tetrahydrofuran, dichloromethane, N,N-dimethylformamide and the like are mentioned. The reaction time is 10 minutes to 30 hours. The reaction temperature is a temperature of −78° C. to reflux by heating.

(7) Conversion of Hydroxy Group to Urethane Derivative

The hydroxy group of 11107 Analogue or a residual hydroxy group after suitable protection of the hydroxy group of 11107 Analogue is treated with an isocyanate in the presence of a base or a copper catalyst. The protecting group of the product can be eliminated to obtain the urethane derivative of the formula (I). As the isocyanate, there are mentioned usual isocyanate, for example, ethyl isocyanate, methyl isocyanate, phenyl isocyanate and the like. As the base, there are mentioned usual organic bases, inorganic bases, for example, diisopropylethylamine, dimethylaminopyridine, triethylamine, pyridine, 2,6-rutidine, sodium hydride and the like. The solvent used for the reaction is not specifically limited, but a solvent which cannot be easily reacted with a raw material substance is desirable, and for example, tetrahydrofuran, dichloromethane, N,N-dimethylformamide and the like are mentioned. The reaction time is 10 minutes to 30 hours. The reaction temperature is a temperature of 78° C. to reflux by heating.

Further, a derivative which was obtained by converting the hydroxy group of 11107 Analogue or a residual hydroxy group after suitable protection of the hydroxy group, to carbonic ester is treated with an amine in the presence of a base or with an amine alone. The protecting group of the product can be deprotected to obtain the urethane derivative of the formula (I). As the amine, various amines can be used and for example, methylamine, ethylamine, aniline and the like are mentioned. As the base, there are mentioned usual organic bases, inorganic bases, for example, diisopropylethylamine, dimethylaminopyridine, triethylamine, pyridine, 2,6-rutidine, sodium hydride and the like. The solvent used for the reaction is not specifically limited, but a solvent which cannot easily react with a raw material substance is desirable, and for example, tetrahydrofuran, dichloromethane, N,N-dimethylformamide and the like are mentioned. The reaction time is 10 minutes to 30 hours. The reaction temperature is a temperature of −78° C. to reflux by heating.

(8) Conversion of Hydroxy Group to Amino Group

Tthe hydroxy group of 11107 Analogue or a residual hydroxy group after suitable protection of the hydroxy group of 11107 Analogue is directly or indirectly converted into a good leaving group, it can be converted into an amine after introducing an azide, if necessary. The protecting group of the product can be deprotected to obtain the amine derivative of the formula (I).

When the hydroxy group or a good leaving group is converted into an azide, there can be used DPPA, diethyl azodicarboxylate and triphenylphosphine, DPPA and DBU, DPPA, TMAD, TBP or sodium azide, etc. Alternatively, it is treated with sodium azide in the presence of a palladium catalyst. As the palladium catalyst, $Pd(PPh_3)_4$ and the like are mentioned. The solvent used for the reaction is not specifically limited, but a solvent which cannot easily react with a raw material substance is desirable, and for example, tetrahydrofuran, dichloromethane, N,N-dimethylformamide and the like are mentioned. The reaction time is 10 minutes to 30 hours. The reaction temperature is a temperature of −78° C. to reflux by heating.

(9) Oxidation

11107 Analogue or 11107 derivative whose hydroxy groups are appropriately protected is treated with an oxidizing agent, and a double bond can be converted into an oxylane ring, or an allyl position can be oxidized. The protecting group of the product can be deprotected to obtain the oxidized product of the formula (I). As the oxidizing agent, m-chloro-perbenzoic acid, t-butylhydroperoxide and the like are mentioned. The solvent used for the reaction is not specifically limited, but a solvent which cannot easily react with a raw material substance is desirable, and for example, tetrahydrofuran, dichloromethane, N,N-dimethylformamide and the like are mentioned. The reaction time is 10 minutes to 30 hours. The reaction temperature is a temperature of −78° C. to reflux by heating.

(10) Reduction

The double bond of 11107 Analogue or the 11107 derivative whose hydroxy group was appropriately protected can be reduced. The protecting group of the product can be deprotected to obtain the reduced product of the formula (I). As the reducing agent, hydrogen in the presence of a catalyst, zinc and lithium are mentioned. As the catalyst, there are mentioned palladium-carbon, palladium hydroxide, platinum oxide, rhodium-carbon, and the like. The solvent used for the reaction is not specifically limited, but a solvent which cannot easily react with a raw material substance is desirable, and for example, methanol, ethanol, tetrahydrofuran, and the like are mentioned. The reaction time is 10 minutes to 30 hours. The reaction temperature is a temperature of −78° C. to reflux by heating.

(11) Oxidation of Hydroxy Group

The hydroxy group of 11107 Analogue or a residual hydroxy group after suitable protection of the hydroxy group of 11107 Analogue is treated with an oxidizing agent. The protecting group of the product can be deprotected to obtain the ketone body of the formula (I). As the oxidizing agent, there can be used manganese dioxide, pyridinium chlorochromate, pyridinium dichromate, Dess-Martin reagent, a reagent of Swern oxidation condition, and the like. The solvent used for the reaction is not specifically limited, but a solvent which cannot easily react with a raw material substance is desirable, and for example, tetrahydrofuran, dichloromethane, chloroform and the like are mentioned. The reaction time is 10 minutes to 30 hours. The reaction temperature is a temperature of 78° C. to reflux by heating.

(12) Synthesis of Oxime from Ketone Body

Among the compound of the formula (I), an oxime derivative can be synthesized by treating a corresponding ketone compound with an amine. As the amine, for example, hydroxylamine, methoxyamine, and the like are mentioned. As the solvent used for the reaction is not specifically limited, but a solvent which cannot easily react with a raw material substance is desirable, and for example, tetrahydrofuran, dichloromethane and the like are mentioned. The reaction time is 10 minutes to 30 hours. The reaction temperature is a temperature of −78° C. to reflux by heating.

(13) Synthesis of Amine from Ketone Compound

An amine derivative among the compound of the formula (I) can be synthesized by treating a corresponding ketone compound with an amine and further reducing it. The amine is not limited, and for example, methylamine, ethylamine and the like are mentioned. As the reducing agent, there can be mentioned sodium cyanoboronohydride, sodium borohydride, diisobutylaluminum hydride and the like. The solvent used for the reaction is not specifically limited, but a solvent which cannot easily react with a raw material substance is desirable, and for example, tetrahydrofuran, dichloromethane and the like are mentioned. The reaction time is 10 minutes to 30 hours. The reaction temperature is a temperature of −78° C. to reflux by heating.

(14) Modification of Amino Group

Using the amino compound obtained by the above-mentioned reaction, amino group can be modified in a similar manner as described for the acylation, sulfonylation and alkylation of a hydroxy group.

(15) Synthesis of Halohydrin

The the oxylane ring of 11107 Analogue or 11107 derivative whose hydroxy group was appropriately protected can be converted into a compound in which either of A or B is hydroxy and another is halogen, by being treated with HX. The protecting group can be deprotected to obtain the halohydrin derivative of the formula (I).

HX is, for example, hydrogen chloride or hydrogen bromide. Alternatively, it can be synthesized by treating with chlorotrimethylsilane and then treating with sodium iodide. The solvent used for the reaction is not specifically limited, but a solvent which cannot easily react with a raw material substance is desirable, and for example, diethyl ether, 1,2-diethoxyethane, water and the like are mentioned. The reaction time is 10 minutes to 30 hours. The reaction temperature is a temperature of −78° C. to reflux by heating.

Various conversions which were described in the modification of a hydroxy group can be also carried out to the hydroxy group of halohydrin.

(16) Oxidative Cleavage of Double Bond and Olefination

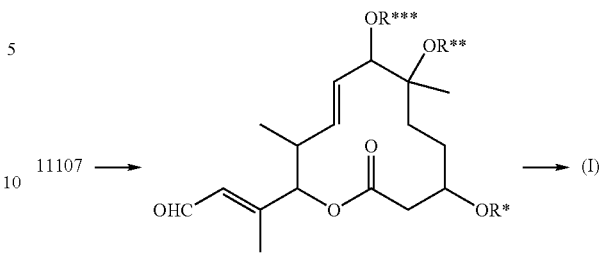

The compound of the formula (1) can be synthesized by carrying out the oxidative cleavage of the double bond of 11107 Analogue or 11107 derivatives whose hydroxy groupw are appropriately protected, and carrying out the olefination of the resulting aldehyde, and then removing the protecting group.

For example, as the oxidizing agent, osmium tetraoxide, ruthenium oxide and potassium permanganate can be used, and sodium periodate, lead tetraacetate and the like can be used for the cleavage of the resulting diol. The solvent used for the reaction is not specifically limited, but a solvent which cannot easily react with a raw material substance is desirable, and for example, tetrahydrofuran, dichloromethane and the like are mentioned. The reaction time is 10 minutes to 30 hours. The reaction temperature is a temperature of −78° C. to reflux by heating.

Further, an aldehyde compound can be directly obtained by carrying out the ozone oxidation or by simultaneously treating the double bond with osmium tetraoxide and sodium periodate. The solvent used for the reaction is not specifically limited, but a solvent which cannot be easily reacted with a raw material substance is desirable, and for example, tetrahydrofuran, dichloromethane and the like are mentioned. The reaction time is 10 minutes to 30 hours. The reaction temperature is a temperature of −78° C. to reflux by heating.

A double bond formation can be carried out by the Julia olefination of the aldehyde, with a sulfonate having a suitable substituent and a base, or by Wittig reaction of the aldehyde with a phosphate having a suitable substituent and a base, and thus, the compound represented by the formula (I) can be synthesized. As the base, there are used usual organic bases, inorganic bases, for example, lithium diisopropylamide, lithium bis(trimethylsilyl)amide, lithium hydride, butyl lithium, lithium dicyclohexylamide and the like. The solvent used for the reaction is not specifically limited, but a solvent which cannot be easily reacted with a raw material substance is desirable, and for example, tetrahydrofuran, diethyl ether and the like are mentioned. The reaction time is 10 minutes to 30 hours. The reaction temperature is a temperature of −78° C. to reflux by heating.

6. Application Method of the Active Substance

The present compound is effective as an agent for preventing or treating a disease against which control of gene expression is efficacious, an agent for preventing or treating a disease against which VEGF production suppressing action is efficacious, an agent for preventing or treating a disease against which an antiangiogenic effect is efficacious. The "preventing or treating" indicates either of preventing or treating, or both of them. More specifically, the present compound is effective as an antitumor agent, and in particular, as an antitumor agent and a carcinoma metastasis suppressor for solid cancer. As the solid cancer, for example, pancreatic cancer, gastric cancer, colon cancer, breast cancer, prostate cancer, lung cancer, kidney cancer, brain tumor, sinciput cancer, esophageal cancer, derma cancer, liver cancer, uterus cancer, cervix uteri cancer, urinary bladder cancer, thyroid cancer, testicular cancer, choroionic carcinoma, osteosarcoma, soft tissue sarcoma, and ovarian cancer may be proposed. Further, it is also effective as an antitumor agent for leukemia. Further, it is also effective as an agent for treating hematoma. Furthermore, it is also effective as an agent for treating diabetic retinopathy, rheumatoid arthritis and hematoma, which is based on VEGF production suppressing action. Further more, it is also effective as an agent for treating inflammatory diseases consisting of osteoarthritis, psoriasis and prolonged hypersensitivity reaction, and atherosclerosis.

When the compound is prepared as an injection, a pH regulator, a buffer, a stabilizer, a solubilizer and the like are added to the main drug, if necessary, to prepare an intramuscular, intra-articular or intravenous injection according to a conventional method.

When the compound is administered as a preventive or therapeutic agent for various diseases, it may be orally administered as tablets, powders, granules, capsules, syrups and the like, and may be parenterally administered as a spray, a suppository, an injection, an external preparation and a drip. The dose is remarkably different according to the extent of symptom, age, the kind of lever diseases etc., and approximately 1 mg to 100 mg per day for an adult is administered in general at one time or several times.

Conventional preparation carriers are used at preparation, and the preparations are produced by a conventional method. Namely, when a solid preparation for oral use is prepared, a filler is added to the main drug, and if necessary, a binder, a disintegrant, a lubricant, a colorant, a flavoring agent and the like are added thereto, and then tablets, coated tablets, granules, powders, capsules and the like are prepared. It is needless to say that sugar coating, gelatin coating or suitable coating may conducted on the tablet and granule, if necessary.

In the present invention, antitumor drugs effective for solid cancer and the like have been found from the cultured broth of a strain of genus Streptomyces or its variant, and a derivative of the fermentation products.

EXAMPLES

Examples below illustrate the following subjects in detail.

The cultured broth of strain Mer-11107 was obtained in Example A1 or A1-1. From the broth, 11107A–G were obtained in Examples A2 to A9. Similarly, H–Z, aA-AZ and BA-BG were obtained in Examples A10 to A67.

Cultured broth of Mer-11107 mutants EM07.015N13, EM07.015N54 and EM07.031N58 (synonymous with Streptomyces sp. A-1532, Streptomyces sp. A-1532, Streptomyces sp. A1532, respectively) and the isolated compounds from the broth were obtained in Example A-68 to A77. Namely, 11107BH, 11107BI and 11107BJ were obtained.

Further, Example B1 to B82 shows the chemical synthesis of other compounds using any one of the above-mentioned fermentation products, which were respectively specified, as a starting material. C1 to C7 are the pharmacological experimental data.

The present invention will be more specifically illustrated according to Examples below, but the present invention is not limited to these.

Example A1

200 L Tank Fermentation of Mer-11107

One loopful of the the slant culture of Mer-11107 strain (ISP-2 medium) was inoculated into a 500 ml Erlenmeyer flask containing 50 ml of seed medium (2% of glucose, 1% of ESSANMEAT (manufactured by Ajinomoto Co. Ltd.), 0.5% of yeast extract, 0.25% of sodium chloride, 0.32% of calcium carbonate, pH 6.8 before sterilization), and it was cultured at 28° C. for 2 days to give the first seed culture. 0.1 ml of the culture was inoculated into a 500 ml Erlenmeyer flask containing 100 ml of the seed medium as same as the medium mentioned above, and it was cultured at 28° C. for 1 day to give the second seed culture. 800 mL of the second culture was inoculated into a 200 L tank containing 100 L of production medium (5% of potato starch, 0.8% of pharmamedia, 0.8% of gluten meal, 0.5% of yeast extract, 0.1% of calcium carbonate, pH 6.8 before sterilization), and it was fermented at 28° C. for 5 days with an agitation at 90 rpm, an aeration of 1.0 vvm and an inner pressure of 20 kPa to give cultured broth.

Example A1-1

Fermentation of Mer-11107 and Purification

One loopful of the slant culture of Mer-11107 strain (ISP-2) was inoculated into a 500 ml Erlenmeyer flask containing 50 ml of seed medium (2% of glycerin, 2% of glucose, 2% of soybean meal (ESSANMEAT manufactured by Ajinomoto Co. Ltd.), 0.5% of yeast extract, 0.25% of sodium chloride, 0.32% of calcium carbonate, 0.0005% of copper sulfate, 0.0005% of manganese chloride, 0.0005% of zinc sulfate, and pH 7.4), and it was cultured at 28° C. for 3 days on a shaker to give the first seed culture. 0.6 ml of the seed culture was inoculated into a 500 ml Erlenmeyer flask containing 60 ml of the producing medium (5% of soluble starch, 0.5% of corn steep liquor, 0.5% of dry yeast, 0.5% of gluten meal, 0.1% of calcium carbonate) and it was fermented at 28° C. for 4 days on a rotary shaker to give a fermentation culture broth.

Example A2

Purification of 11107A, B, C, D, E, F and G

The cultured broth (10 L) obtained in Example A1 or A1-1 was extracted with 1-butanol (10 L), then thus acquired 1-butanol layer was evaporated to dryness to give 100 g of crude active fraction. The crude active fraction was applied on Sephadex LH-20 (1500 ml; manufactured by Pharmacia Co. Ltd.), and eluted with tetrahydrofuran-methanol (1:1) as a solvent. The eluted crude active fraction was concentrated to dryness, and subject to silica gel column chromatography (WAKO GEL C-200). The column was eluted with a mix solution (2 L) consisting of n-hexane and ethyl acetate (1:9, v/v) to obtain a crude active fraction which contains 11107A, 11107B and 11107C, and to obtain a crude active fraction which contains 11107D, 11107E, 11107F and 11107G. The crude active fraction which contains 11107A, 11107B and 11107C was subjected to preparative high performance liquid chromatography (HPLC) under the following preparative HPLC condition (A1), and the eluted active fractions were collected separately. After removing the acetonitrile, the respective fractions were desalted by HPLC under the following preparative HPLC condition (A2) to give 11107A (1.2 mg), 11107B (6 mg) and 11107C (0.3 mg). Similarly, the crude active fraction which contains 11107D, 11107E, 11107F and 11107G was also subjected to HPLC under the following preparative HPLC condition (A1), and the eluted active fractions were collected separately. After removing acetonitrile, the respective fractions were desalted by HPLC under the following preparative condition (A2) to obtain 11107D (1.8 mg), 11107E (1 mg), 11107F (0.1 mg) and 11107G (0.2 mg).

Example A2-1

Purification of 11107A, B, C, D, E, F and G

The cultured broth (10 L) was extracted with 1-butanol (10 L), then thus acquired 1-butanol layer was evaporated to dryness to give 100 g of crude active fraction. The crude active fraction was applied on Sephadex LH-20 (1500 ml; manufactured by Pharmacia Co. Ltd.), and eluted with tetrahydrofuran-methanol (1:1) as a solvent. An eluted fraction from 540 ml to 660 ml was concentrated to dryness under reduced pressure to give a residue (660 mg) Further, the residue was dissolved in a mix solution consisting of ethyl acetate and methanol (9:1, v/v), and subjected to silica gel column chromatography (WAKO GEL C-200, 50 g). The column was eluted with a mix solution (2 L) consisting of n-hexane and ethyl acetate (1:9, v/v), the fraction eluted from 468 ml to 1260 ml (crude active fraction A) and the fraction eluted from 1440 ml to 1566 ml (crude active fraction B) were collected separately, and crude active fraction A and B were evaporated to give 25 mg and 15 mg of residues, respectively.

The crude active fraction A was subjected to preparative high performance liquid chromatography (HPLC) under the following preparative HPLC condition (A), and the fractions eluted at the retention time of 28 min., 34 min. and 39 min. were collected respectively. After removing acetonitrile, the respective fractions were desalted by HPLC under the following preparative HPLC condition (B) to give 11107A (retention time: 36 min., 1.2 mg), 11107B (retention time: 37 min., 6 mg) and 11107C (retention time: 38 min., 0.3 mg). Similarly, the crude active fraction B was also fractionated by HPLC under the following preparative condition (A). The fractions eluted at the retention time of 17 min., 21 min., 22 min., and 26 min. to 27 min. were collected respectively. After removing acetonitrile, the respective fractions were desalted by HPLC under the following preparative condition (B) to give 11107D (retention time: 36 min., 1.8 mg), 11107E (retention time: 34 min., 1 mg), 11107F (retention time: 28 min., 0.1 mg) and 11107G (retention time: 32 min., 0.2 mg).

Preparative HPLC conditions (A-1), (A)
Column: YMC-PACK ODS-AM SH-343-5AM, φ20 mm×250 mm (manufactured by YMC Co.)
Temperature: room temperature
Flow rate: 10 ml/min.
Detection: 240 nm
Eluent: acetonitrile/0.15% aqueous potassium dihydrogenphosphorate (pH 3.5) (2:8 to 8:2, v/v, 0 to 50 min., linear gradient)

Preparative HPLC conditions (A-2), (B)
Column: YMC-PACK ODS-AM SH-343-5AM, φ20 mm×250 mm (manufactured by YMC Co.)
Temperature: room temperature
Flow rate: 10 ml/min.
Detection: 240 nm
Eluent: methanol/water (2:8 to 10:0, v/v, 0 to 40 min., linear gradient)

The retention times of the above-mentioned compounds when analysis was carried out at the under-mentioned HPLC condition, are shown as below.

Analytic HPLC condition (a)
Column: YMC J'sphere ODS-M80 JM-307, φ4.6 mm×75 mm (manufactured by YMC Co.)
Temperature: 30° C.
Flow rate: 1 ml/min.
Detection: 240 nm
Eluent: acetonitrile/0.15% aqueous potassium dihydrogenphosphorate (pH 3.5) (2:8 to 8:2, v/v, 0 to 50 min., linear gradient)

Retention time:
11107A: 13.4 min.
11107B: 15.5 min.
11107C: 17.3 min.
11107D: 11.4 min.
11107E: 12.9 min.
11107F: 9.0 min.
11107G: 10.8 min.

Example A3

Physico-chemical Properties of 11107A

The physico-chemical properties of 11107A are shown below. The structure of 11107A was determined as shown below.

1. Appearance: colorless powder
2. Molecular weight: 494, FAB-MS m/z 493 (M-H)$^-$
3. Molecular formula: $C_{2-8}H_{46}O_7$
4. Solubility: soluble in dimethylsulfoxide, pyridine, methanol and acetone, and slightly soluble in water
5. Color reaction: positive for iodine and sulfuric acid
6. Ultraviolet absorption spectrum (methanol, maximum value) nm: 239 ($\epsilon$ 28800)
7. Infrared absorption spectrum (KBr) cm$^{-1}$: 3364, 2963, 1732, 1714, 1455, 1372, 1176
8. $^1$H-NMR spectrum (CD$_3$OD, 500 MHz): δ ppm (integral, multiplicity, coupling constant J (Hz)): 0.97(3H,d,J=7.0 Hz), 0.98(3H,d,J=6.8 Hz), 1.02(3H,t,J=8.0 Hz), 1.15(3H, d,J=6.8 HZ), 1.28(1H,m), 1.33(3H,s), 1.42(2H,m), 1.50–1.73(6H,m), 1.82(3H,s), 2.54(1H,m), 2.59(2H,m), 2.64(1H, m), 2.73(1H,dd,J=2.4,8.3 Hz), 2.80(1H,dt, J=2.4,5.7 Hz), 3.58(1H,dt,J=8.3,4.4 Hz), 3.77(1H,d,J=9.8 Hz), 3.84(1H,m), 5.10(1H,d,J=9.8 Hz), 5.45(1H,dd,J=9.8, 15.2 Hz), 5.72(1H,dd,J=8.2,15.2 Hz), 5.78(1H,dd,J=9.8, 15.2 Hz), 6.15(1H,d,J=9.8 Hz), 6.36(1H,dd,J=9.8,15.2 Hz)

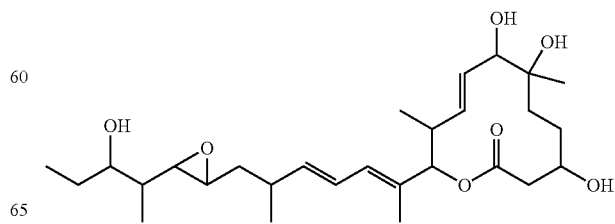

11107A

Example A4

Physico-chemical Properties of 11107B

The physico-chemical properties of 11107B are shown below. The structure of 11107B was determined as shown below.
1. Appearance: colorless powder
2. Molecular weight: 536, FAB-MS m/z 535(M−H)⁻, 559 (M+Na)⁺
3. Molecular formula: $C_{30}H_{48}O_8$
4. Solubility: soluble in dimethylsulfoxide, pyridine, methanol and acetone, and slightly soluble in water
5. Color reaction: positive for iodine and sulfuric acid
6. Ultraviolet absorption spectrum (methanol, maximum value) nm: 240 (E 31300)
7. Infrared absorption spectrum (KBr) cm⁻¹: 3443, 2968, 1732, 1715, 1456, 1371, 1244, 1176
8. ¹H-NMR spectrum (CD₃OD, 500 MHz): δ ppm (integral, multiplicity, coupling constant J (Hz)): 0.93(3H,d,J=7.0 Hz), 0.94(3H,d,J=6.8 Hz), 0.98(3H,t,J=8.0 Hz), 1.12(3H,d,J=6.8 Hz), 1.23(3H,s), 1.25(1H,m), 1.42(2H,m), 1.53–1.70(6H,m), 1.79(3H,d,J=1.0 Hz), 2.10(3H,s), 2.52 (1H,m), 2.56(2H,m), 2.60(1H,m), 2.70(1H,dd,J=2.4,8.3 Hz), 2.76(1H,dt,J=2.4,5.7 Hz), 3.56(1H,dt,J=8.3,4.4 Hz), 3.82(1H,m), 5.08(2H,d,J=9.8 Hz), 5.60(1H,dd,J=9.8,15.2 Hz), 5.70(1H,dd,J=8.3,15.2 Hz), 5.74(1H,dd,J=9.8,15.2 Hz), 6.13(1H,d,J=9.8 Hz), 6.36(1H,dd,J=9.8,15.2 Hz)
9. ¹³C-NMR spectrum (CD₃OD, 125 MHz): δ ppm (multiplicity) 10.82(q), 10.86(q), 11.91(q), 16.88(q), 21.09(q), 21.63(q), 24.21(q), 28.62(t), 30.47(t), 36.68(d), 37.53(t), 40.10(t), 40.70(t), 41.77(d), 42.77(d), 58.44(d), 62.96(d), 70.42(d), 74.10(s), 75.31(d), 80.31(d), 84.27(d), 125.83 (d), 127.06(d), 132.19(s), 132.44(d), 141.66(d), 142.36 (d), 171.78(s), 172.15(s)

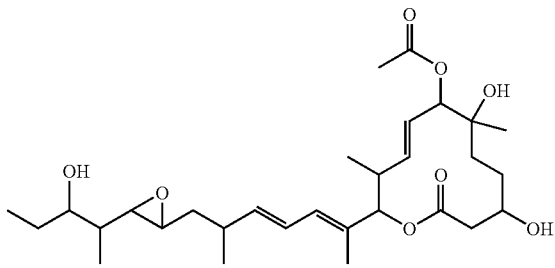

11107B

Example A5

Physico-chemical Properties of 11107C

The physico-chemical properties of 11107C are shown below. The structure of 11107C was determined as shown below.
1. Appearance: colorless powder
2. Molecular weight: 534, ESI-MS m/z 533(M−H)
3. Molecular formula: $C_{30}H_{46}O_8$
4. Solubility: soluble in dimethylsulfoxide, pyridine, methanol and acetone, and slightly soluble in water
5. Color reaction: positive for iodine and sulfuric acid
6. Ultraviolet absorption spectrum (methanol, maximum value) nm: 239 (ε 33100)
7. Infrared absorption spectrum (KBr) cm⁻¹: 3363, 2970, 1732, 1715, 1373, 1243, 1177
8. ¹H-NMR spectrum (CD₃OD, 500 MHz): δ ppm (integral, multiplicity, coupling constant J (Hz)): 0.94 (3H, d, J=7.0 Hz), 1.08 (3H, t, J=8.0 Hz), 1.13 (3H, d, J=6.8 Hz), 1.16(3H,d,J=6.8 Hz), 1.25(3H,s), 1.35–1.76(6H,m), 1.81 (3H,s), 2.12(3H,s), 2.38(1H,m), 2.50–2.67(6H,m), 2.82 (2H,m), 3.82(1H,m), 5.12(2H,d,J=9.8 Hz), 5.64(1H,dd, J=9.8,15.2 Hz), 5.72(1H,dd,J=8.3,15.2 Hz), 5.76(1H,dd, J=9.8,15.2 Hz), 6.18(1H,d,J=9.8 Hz), 6.40(1H,dd,J=9.8, 15.2 Hz)

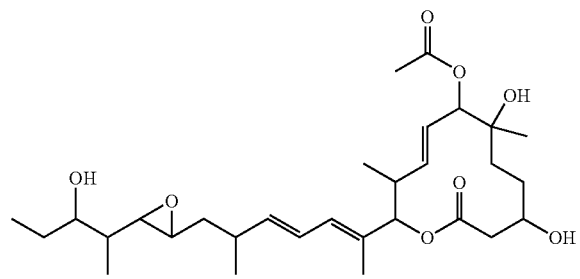

11107C

Example A6

Physico-chemical Properties of 11107D

The physico-chemical properties of 11107D are shown below. The structure of 11107D was determined as shown below.
1. Appearance: colorless powder
2. Molecular weight: 552, ESI-MS m/z 551(M−H)⁻, 575 (M+Na)
3. Molecular formula: $C_{30}H_{48}O_9$
4. Solubility: soluble in dimethylsulfoxide, pyridine, methanol and acetone, and slightly soluble in water
5. Color reaction: positive for iodine and sulfuric acid
6. Ultraviolet absorption spectrum (methanol, maximum value) nm: 239 (ε 33100)
7. Infrared absorption spectrum (KBr) cm⁻¹: 3417, 2967, 1732, 1714, 1455, 1372, 1248, 1176
8. ¹H-NMR spectrum (CD₃OD, 500 MHz): δ ppm (integral, multiplicity, coupling constant J (Hz)): 0.93(3H,d,J=7.0 Hz), 0.95(3H,d,J=6.8 Hz), 0.98(3H,t,J=8.0 Hz), 1.23(3H, s), 1.30(1H,m), 1.36–1.66(9H,m), 1.70(1H,dd,J=6.4,14.2 Hz), 1.82(3H,d,J=1.0 Hz), 1.90(1H,dd,J=6.4,14.2 Hz), 2.10(3H,s), 2.52(2H,m), 2.62(1H,m), 2.72(1H,dd,J=2.4, 8.3 Hz), 2.94(1H,dt,J=2.4,5.7 Hz), 3.55(1H,dt,J=8.3,4.4 Hz), 3.82(1H,m), 5.10(1H,d,J=9.8 Hz), 5.11(1H,d,J=10.8 Hz), 5.60(1H,dd,J=9.8,15.2 Hz), 5.74(1H,dd,J=8.3,15.2 Hz), 5.92(1H,d,J=15.2 Hz), 6.18(1H,d,J=10.8 Hz), 6.57 (1H,dd,J=10.8,15.2 Hz)
9. ¹³C-NMR spectrum (CD₃OD, 125 MHz): δ ppm (multiplicity) 10.52(q), 10.82(q), 11.98(q), 16.84(q), 21.07(q), 24.21(q), 28.62(t), 28.79(q), 30.46(t), 37.53(t), 40.10(t), 41.80(d), 42.58(d), 45.97(t), 55.99(d), 62.53(d), 70.42(d), 73.09(s), 74.11(s), 75.30(d), 80.31(d), 84.19(d), 123.64 (d), 127.10(d), 131.76(d), 133.81(s), 141.61(d), 143.22 (d), 171.75(s), 172.18(s)

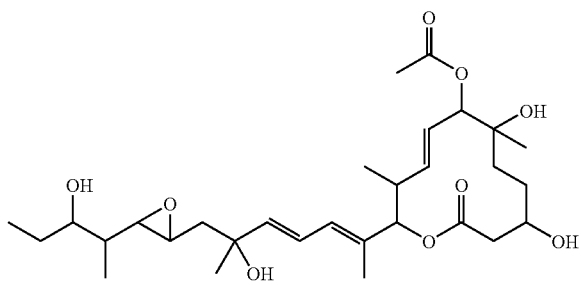

Example A7

Physico-chemical Properties of 11107E

The physico-chemical properties of 11107E are shown below. The structure of 11107E was determined as shown below.
1. Appearance: colorless powder
2. Molecular weight: 552, FAB-MS m/z 551(M-H)
3. Molecular formula: $C_{30}H_{48}O_8$
4. Solubility: soluble in dimethylsulfoxide, pyridine, methanol and acetone, and slightly soluble in water
5. Color reaction: positive for iodine and sulfuric acid
6. Ultraviolet absorption spectrum (methanol, maximum value) nm: 240 (E 26200)
7. Infrared absorption spectrum (KBr) cm$^{-1}$: 3500, 2969, 1732, 1715, 1455, 1372, 1244, 1176
8. $^1$H-NMR spectrum (CD$_3$OD, 500 MHz): δ ppm (integral, multiplicity, coupling constant J (Hz)): 0.93(3H,d,J=7.0 Hz), 1.08(3H,t,J=8.0 Hz), 1.12(3H,s), 1.16(3H,d,J=7.0 Hz), 1.25(3H,s), 1.35–1.78(8H,m), 1.81(3H,s), 2.12(3H,s), 2.55(1H,m), 2.59(2H,m), 2.63(1H,m), 2.98(1H,d,J=2.4 Hz), 3.02(1H,dt,J=2.4,5.7 Hz), 3.36(1H,m), 3.85(1H,m), 5.12(2H,d,J=9.8 Hz), 5.62(1H,dd,J=9.8,15.2 Hz), 5.74(1H,dd,J=9.8,15.2 Hz), 5.76(1H,dd,J=9.8,15.2 Hz), 6.16(1H,d,J=9.8 Hz), 6.38(1H,dd,J=9.8,15.2 Hz)

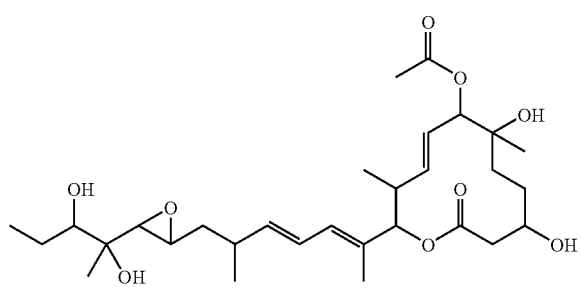

Example A8

Physico-chemical Properties of 11107F

The physico-chemical properties of 11107F are shown below. The structure of 11107F was determined as shown below.
1. Appearance: colorless powder
2. Molecular weight: 510, FAB-MS m/z 509(M-H)
3. Molecular formula: $C_{28}H_{46}O_8$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 500 MHz): δ ppm (integral, multiplicity, coupling constant J (Hz)): 0.94(3H,d,J=7.0 Hz), 0.95(3H,d,J=6.8 Hz), 0.98(3H,t,J=8.0 Hz), 1.31–1.40(7H,m), 1.50–1.60(6H,m), 1.71(1H,dd,J=6.4,14.2 Hz), 1.82(3H,s), 1.90(1H,dd,J=6.4,14.2 Hz), 2.54(2H,m), 2.62(1H,m), 2.70(1H,dd,J=2.4,8.3 Hz), 2.94(1H,dt,J=2.4,5.7 Hz), 3.56(1H,dt,J=8.3,4.4 Hz), 3.74(1H,d,J=9.8 Hz), 3.80(1H,m), 5.10(1H,d,J=9.8 Hz), 5.42(1H,dd,J=9.8,15.2 Hz), 5.78(1H,dd,J=9.8,15.2 Hz), 5.91(1H,d,J=15.2 Hz), 6.18(1H,d,J=10.8 Hz), 6.57(1H,dd,J=10.8,15.2 Hz)

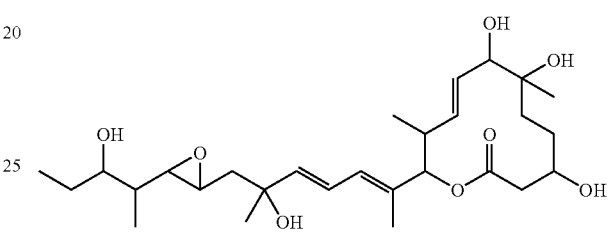

Example A9

Physico-chemical Properties of 11107G

The physico-chemical properties of 11107G are shown below. The structure of 11107G was determined as shown below.
1. Appearance: colorless powder
2. Molecular weight: 510, FAB-MS m/z 509(M-H)
3. Molecular formula: $C_{28}H_{46}O_8$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 500 MHz): δ ppm (integral, multiplicity, coupling constant J (Hz)): 0.94(3H,d,J=6.4 Hz), 1.06(3H,t,J=7.3 Hz), 1.09(3H,s), 1.13(3H,d,J=7.0 Hz), 1.31(3H,s), 1.33–1.40(3H,m), 1.55–1.78(5H,m), 1.79(3H,s), 2.52(1H,m), 2.58(2H,m), 2.60(1H,m), 2.95(1H,d,J=2.0 Hz), 3.00(1H,dt,J=2.0,5.4 Hz), 3.35(1H,m), 3.74(1H,d,J=9.8 Hz), 3.80(1H,m), 5.07(1H,d,J=10.2 Hz), 5.41(1H,dd,J=9.8,15.2 Hz), 5.70(1H,dd,J=9.8,15.2 Hz), 5.75(1H,dd,J=9.8,15.2 Hz), 6.12(1H,d,J=10.8 Hz), 6.38(1H,dd,J=10.8,15.2 Hz)

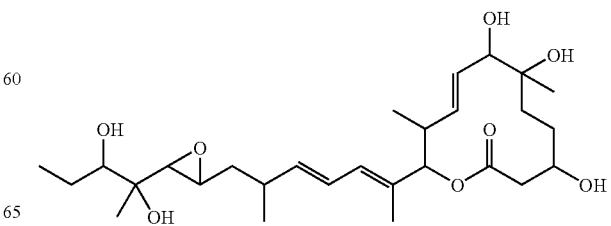

Example A10

Purification of 11107H, I, J and K

The cultured broth (20 L) was separated into the filtrate and the mycelium cake. Then the filtrate was extracted with ethyl acetate (20 L). Thus obtained ethyl acetate layer was evaporated to dryness to give 2.33 g of crude active fraction. The crude active fraction was subject to silica gel column chromatography (Wako Gel C-200), the column was eluted with a mix solution (1 L) consisting of n-hexane and ethyl acetate (9:1, v/v), and thus acquired active fractions were concentrated to give a crude active fraction which contained 11107H and 11107I and a crude active fraction which contains 11107J and 1107K. The crude active fraction which contains 11107H and 11107I was subjected to preparative high performance liquid chromatography (HPLC), under the following preparative HPLC condition (B1). Then the eluted active fractions were concentrated to give a fraction in which 11107H was a main component and a fraction in which 11107I was a main component. The respective fractions were subjected to preparative high performance liquid chromatography (HPLC), under the following preparative HPLC condition (B2) to elute active substances. They were concentrate to dryness to give 11107H (1.2 mg) and 11107I (6 mg). Similarly, the crude active fraction which contains 11107J and 11107K was also fractionated by HPLC under the following preparative HPLC condition (B3). The eluted fractions were collected separately and concentrated to give a fraction in which 11107J was a main component and a fraction in which 11107K was a main component. The respective fractions were subjected to preparative high performance liquid chromatography (HPLC), under the following preparative HPLC condition (B4) to elute corresponding active substances. They were concentrated to dryness to give 11107J (1.8 mg) and 11107K (1 mg).

Preparative HPLC condition (B1)
  Column: YMC-PACK ODS-AM SH-343-5AM, φ20 mm×250 mm (manufactured by YMC Co.)
  Temperature: room temperature
  Flow rate: 10 ml/min.
  Detection: 240 nm
  Eluent: acetonitrile/water (2:8 to 10:0, v/v, 0 to 50 min., linear gradient)

Preparative HPLC condition (B2)
  Column: YMC-PACK ODS-AM SH-343-5AM, φ20 mm×250 mm (manufactured by YMC Co.)
  Temperature: room temperature
  Flow rate: 10 ml/min.
  Detection: 240 nm
  Eluent: acetonitrile/water (4:6 to 7:3, v/v, 0 to 50 min., linear gradient)

Preparative HPLC condition (B3)
  Column: YMC J'sphere ODS-M80 JM-343, φ20 mm×250 mm (manufactured by YMC Co.)
  Flow rate: 10 ml/min.
  Detection: 240 nm
  Eluent: acetonitrile/water (3:7 to 7:3, v/v, 0 to 50 min., linear gradient)

Preparative HPLC condition (B4)
  Column: YMC J'sphere ODS-M80 JM-343, φ20 mm×250 mm (manufactured by YMC Co.)
  Flow rate: 10 ml/min.
  Detection: 240 nm
  Eluent: acetonitrile/water (2:8 to 10:0, v/v, 0 to 40 min., linear gradient)

The retention times of the above-mentioned compounds when analysis was carried out at the following HPLC analysis conditions are shown.

Analytic HPLC condition (b1):
  Column: YMC J'sphere ODS-M80 JM-307, φ4.6 mm×75 mm (manufactured by YMC Co.)
  Temperature: 30° C.
  Flow rate: 1 ml/min.
  Detection: 240 nm
  Eluent: acetonitrile/0.15% potassium dihydrogenphosphate (pH 3.5) (2:8 to 8:2, v/v, 0 to 50 min., linear gradient)
  Retention time:
  11107H: 16.2 min.
  11107I: 16.9 min.

Analytic HPLC condition (b2):
  Column: CAPCELL PAK C18 SG120 φ4.6 mm×250 mm (manufactured by SHISEIDO Co.)
  Temperature: 40° C. Flow rate: 1 ml/min.
  Detection: 240 nm
  Eluent: acetonitrile/water (4:6, v/v) isocratic
  Retention time:
  11107J: 11.2 min.
  11107K: 11.9 min.

Example A11

Physico-chemical Properties of 11107H

The physico-chemical properties of 11107H are shown below. The structure of 11107H was determined as shown below.
1. Appearance: colorless powder
2. Molecular weight: 534, ESI-MS m/z 533(M-H)$^-$, 557(M+Na)$^+$
3. Molecular formula: $C_{30}H_{46}O_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3478, 2968, 1732, 1718, 1455, 1370, 1243, 1173
7. $^1$H-NMR spectrum ($C_5D_5N$, 500 MHz): δ ppm (integral, multiplicity, coupling constant J (Hz)): 0.85(3H,d,J=6.9 Hz), 1.07(3H,t,J=7.3 Hz), 1.09(3H,d,J=6.4 Hz), 1.15(3H,d,J=7.3 Hz), 1.45(1H,m), 1.55(1H,m), 1.57(3H,s), 1.65–1.79(3H,m), 1.82(3H,s), 2.00(3H,s), 2.54(1H,m), 2.64(1H,m), 2.72(1H,dd,J=2.5,12.7 Hz), 2.90(2H,m), 3.02(1H,dd,J=2.1,8.3 Hz), 3.98(1H,m), 4.86(1H,m), 5.34(1H,d,J=10.7 Hz), 5.53(1H,d,J=9.8 Hz), 5.59(1H,dd,J=9.8,15.2 Hz), 5.72(1H,dd,J=8.3,15.2 Hz), 6.18(1H,dd,J=9.8,15.2 Hz), 6.22(1H,d,J=15.2 Hz), 6.32(1H,d,J=10.8 Hz), 6.42(1H,dd,J=2.4,15.2 Hz), 6.46(1H,dd,J=10.8,15.2 Hz)

11107H

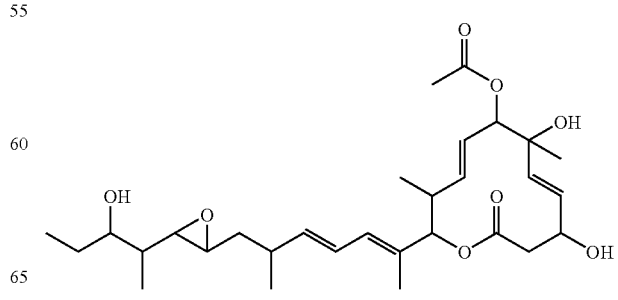

Example A12

Physico-chemical Properties of 11107I

The physico-chemical properties of 11107I are shown below. The structure of 11107I was determined as shown below.
1. Appearance: colorless powder
2. Molecular weight: 550, ESI-MS m/z 549(M-H)$^-$
3. Molecular formula: $C_{31}H_{50}O_8$
4. Solubility: soluble in dimethylsulfoxide, pyridine, methanol and acetone, and slightly soluble in water
5. Color reaction: positive for iodine and sulfuric acid
6. $^1$H-NMR spectrum ($C_5D_5N$, 500 MHz): δ ppm (integral, multiplicity, coupling constant J (Hz)): 0.87(3H,d,J=6.8 Hz), 1.04–1.10(9H,m), 1.15(3H,d,J=6.8 Hz), 1.45(1H,m), 1.47(3H,s), 1.56(1H,m), 1.65–1.79(4H,m), 1.80(3H,s), 1.82(1H,m), 1,95(1H,m), 2.11(1H,m), 2.30(2H,m), 2.55 (1H,m), 2.66(1H,m), 2.71(1H,dd,J=3.4,14.1 Hz), 2.77 (1H,dd,J=4.2,14.1 Hz), 2.89(1H,dd,J=2.0,8.3 Hz), 3.01 (1H,dd,J=2.0,8.3 Hz), 3.97(1H,m), 4.10(1H,m), 5.33(1H, d,J=10.7 Hz), 5.56(1H,d,J=9.8 Hz), 5.73(1H,dd,J=7.8, 14.6 Hz), 5.82(1H,dd,J=10.3,15.2 Hz), 6.28(1H,dd,J=9.8, 15.2 Hz), 6.34(1H,d,J=11.2 Hz), 6.46(1H,dd,J=10.8,15.2 Hz)

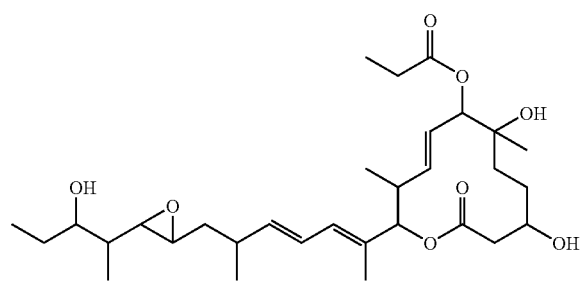

11107I

Example A13

Physico-chemical Properties of 11107J

The physico-chemical properties of 11107J are shown below. The structure of 11107J was determined as shown below.
1. Appearance: colorless powder
2. Molecular weight: 522, FAB-MS m/z 523(M+H)$^+$
3. Molecular formula: $C_{29}H_{46}O_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3386, 2969, 1731, 1714, 1455, 1371, 1249, 1174
7. $^1$H-NMR spectrum (CD$_3$OD, 500 MHz): δ ppm (integral, multiplicity, coupling constant J (Hz)): 0.88(3H,d,J=6.9 Hz), 0.92(3H,d,J=7.3 Hz), 1.08(3H,d,J=6.4 Hz), 1.15(1H, m), 1.18(3H,d,J=6.4 Hz), 1.19(3H,s), 1.35–1.68(6H,m), 1.75(3H,d,J=1.0 Hz), 2.06(3H,s), 2.43–2.60(4H,m), 2.62 (1H,dd,J=2.5,8.3 Hz), 2.71(1H,dt,J=2.5,5.9 Hz), 3.74–3.81(2H,m), 5.04(2H,d,J=9.8 Hz), 5.56(1H,dd, J=9.8,15.2 Hz), 5.66(1H,dd,J=8.3,15.1 Hz), 5.70(1H,dd, J=9.8,15.1 Hz), 6.10(1H,dd,J=1.0,10.7 Hz), 6.32(1H,dd, J=10.7,15.1 Hz)

11107J

Example A14

Physico-chemical Properties of 11107K

The physico-chemical properties of 11107K are shown below. The structure of 11107K was determined as shown below.
1. Appearance: colorless powder
2. Molecular weight: 552, FAB-MS m/z 553(M+H)$^+$
3. Molecular formula: $C_{30}H_{48}O_9$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3461, 2965, 1735, 1712, 1455, 1372, 1242, 1169
7. $^1$H-NMR spectrum (CD$_3$OD, 500 MHz): δ ppm (integral, multiplicity, coupling constant J (Hz)): 0.87(3H,d,J=6.8 Hz), 0.91(3H,d,J=7.3 Hz), 0.94(3H,t,J=7.6 Hz), 1.09(3H, d,J=6.9 Hz), 1.11(3H,s), 1.21(1H,m), 1.42–1.66(6H,m), 1.76(3H,d,J=1.0 Hz), 2.06(3H,s), 2.44–2.58(3H,m), 2.61 (1H,dd,J=3.7,12.9 Hz), 2.66(1H,dd,J=2.2,8.1 Hz), 2.73 (1H,dt,J=2.2,6.0 Hz), 3.50–3.57(2H,m), 4.15(1H,m), 5.05 (1H,d,J=9.8 Hz), 5.09(1H,d,J=10.3 Hz), 5.53(1H,dd, J=10.3,15.1 Hz), 5.64–5.70(2H,m), 6.09(1H,d,J=10.7 Hz), 6.33(1H,dd,J=10.7,15.1 Hz).

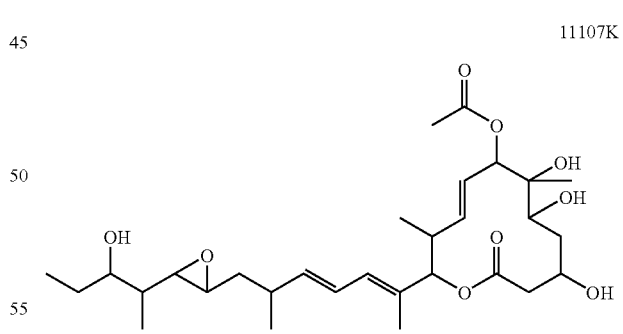

11107K

Example A15

The cultured broth (86 L) was filtrated using a small size filter press (washed with water: 10 L), and separated into the filtrate, the washed solution (94 L) and the mycelium cake (wet weight 14.5 kg). The filtrate and the washed solution were extracted with toluene (50 L). The mycelium cake was extracted with methanol (50 L), then the methanol extract was filtrated (wash with methanol: 10 L). This methanol extract was evaporated under reduced pressure to remove the methanol, then extracted with toluene (10 L). After the respective toluene layers were washed with water, they were combined and concentrated to give 69.4 g of extract containing active compound. Thus acquired extract was dissolved in methanol (400 ml), combined with 10% aqueous sodium chloride (400 ml) and washed with n-hexane (400 ml '2). Then it was extracted with ethyl acetate (400 ml '2), washed with water and concentrated under reduced pressure to give 12.1 g of crude active fraction. The crude active fraction was dissolved in a mix solution consisting of ethyl acetate and n-hexane (1:1, v/v), and subjected to silica gel chromatography (Kiesel gel 60, 120 g). The column was washed with a mix solution (1000 ml) consisting of ethyl acetate and n-hexane (1:1, v/v), developed with a mix solution (600 ml) consisting of ethyl acetate and n-hexane (2:1, v/v), a mix solution (1000 ml) consisting of ethyl acetate and n-hexane (8:2, v/v) and ethyl acetate (500 ml). A fraction eluted to 300 ml (crude active fraction A), a fraction eluted from 300 ml to 1080 ml (11107B fraction) and a fraction eluted from 1080 ml to 2010 ml (crude active fraction B) were collected separately and evaporated under reduced pressure to give 519 mg of crude active fraction A, 5.96 g of 11107B fraction and 681 mg of crude active fraction B, respectively.

Example A16

The cultured broth (86 L) was combined with acetone (18 L), stirred and extracted, and then the mixture was filtered by a continuous centrifugal filtering machine. The resulting acetone extract (106 L) was adsorbed on DIAION HP-20 column (11 L), and eluted with 5% aqueous acetone (10 L), 40% aqueous acetone (30 L), 60% aqueous acetone (60 L) and 80% aqueous acetone (80 L). The 60% aqueous acetone fraction (30 L) was concentrated, then extracted with toluene (10 L). Thus obtained toluene layer was evaporated to give 17.6 g of crude active fraction. 5.0 g of this crude active fraction was dissolved in toluene and subjected to a silica gel column chromatography (Kiesel gel 60, 350 g). The column was washed with toluene (350 ml), developed with a mix solution (4000 ml) consisting of toluene and acetone (3:1, v/v), a mix solution (1000 ml) consisting of toluene and acetone (1:1, v/v). A fraction eluted from 1100 ml to 1700 ml (crude active fraction A), a fraction eluted from 1700 ml to 4000 ml (11107B fraction) and a fraction eluted from 4000 ml to 5000 ml (crude active fraction B) were collected separately and evaporated under reduced pressure to give 640 mg of crude active fraction A, 3.32 g of crude 11107B and 466 mg of crude active fraction B, respectively.

Example A17

Purification of 11107L, M, N, 0, P, Q, R, S, T, U, V, W, X, Y, Z, aA, aB, aC, aD, aE, aF, aG, aH, aI, aJ, AK, aL, aM, aN, aP, aQ and AR The resulting crude active fraction A was subjected to preparative high performance liquid chromatography (HPLC) under the following preparative conditions (C1) and (C2) to give 11107L (8.6 mg), 11107M (6.8 mg), 11107N (5.4 mg), 11107AP (3.4 mg) and 11107AR (1.8 mg). Further, the separation with preparative high performance liquid chromatography (HPLC), followed by purification with silica gel thin layer chromatography (Merk 105715, toluene:acetone (2:1, v/v)), gave 11107X (11.1 mg), 11107Y (6.5 mg), 11107AL (1.8 mg), 11107AM (2.7 mg), 11107AN (0.6 mg) and 11107AQ (6.0 mg).

The crude 11107B fraction (5.96 g) was subjected to preparative high performance liquid chromatography (HPLC) under the following preparative HPLC condition (C3) to give the crude active fraction C (100 mg) containing 11107T, 11107U, 11107W, 11107Z, 11107AA, 11107AC, 11107AH and 11107AI. 35 mg of the resulting crude active fraction C was further subjected to the preparative high performance liquid chromatography (HPLC) under the following preparative HPLC condition (C4), a fraction containing 11107T, a fraction containing 11107AA and 11107U, and a fraction containing 11107W, 11107Z and 11107AC were collected separately, and the solvent was removed. The fraction containing 11107T was further subjected to the preparative high performance liquid chromatography (HPLC) under the following preparative HPLC condition (C5) to give a 11107T solution. Then, 11107T (0.8 mg) was given by removal of the solvent. The fraction containing 11107AA and 11107U was further subjected to the preparative high performance liquid chromatography (HPLC) under the following preparative HPLC condition (C5) to give a 11107AA solution and a 11107U solution. Then, 11107AA (0.2 mg) and 11107U (1.0 mg) were given by removal of the solvent. The fraction containing 11107W, 11107Z and 11107AC was further subjected to the preparative high performance liquid chromatography (HPLC) under the following preparative HPLC condition (C5) to give a 11107W solution, a 11107Z solution and a 11107AC solution. Then, 11107W (1.3 mg), 11107Z (1.1 mg) and 11107AC (0.4 mg) were given by removal of the solvent. Further, the total amount of the residue of the resulting crude active fraction C was subjected to the preparative high performance liquid chromatography (HPLC) under the following preparative HPLC condition (C6), a fraction containing 11107AH and a fraction containing 11107AI were collected separately, and the solvent was removed. The fraction containing 11107AH was further subjected to the preparative high performance liquid chromatography (HPLC) under the following preparative HPLC conditions (C7) to give a 11107AH solution. Then, 11107AH (0.3 mg) was given by removal of the solvent. The fraction containing 11107AI was further subjected to the preparative high performance liquid chromatography (HPLC) under the following preparative HPLC condition (C8) to obtain a 11107AI solution. Then, 11107AI (0.5 mg) was given by removal of the solvent.

The resulting crude active fraction B (1.15 g) was dissolved in 20 ml of a mix solution consisting of tetrahydrofuran-50% aqueous acetonitrile (1:2, v/v), and subjected to ODS column chromatography (ODS-AM 120-S50; manufactured by YMC Co., 750 g). The column was eluted with a mix solution (5 L) consisting of acetonitrile and water (45:55, v/v), to obtain crude active fraction B1 containing 111070, 11107P, 11107Q, 11107R, 11107AF and 11107AG which was eluted from 1300 ml to 1800 ml, crude active fraction B2 containing 11107S and 11107V which was eluted from 2160 ml to 2400 ml, and crude active fraction B3 containing 11107AD, 11107AE, 11107AJ and 11107AK which was eluted from 2565 ml to 3300 ml were collected separately. The respective fractions were evaporated to dryness, to give 50 mg of crude active fraction B1, 236 mg of crude active fraction B2 and 67.5 mg of crude active fraction B3.

38.6 mg of the resulting crude active fraction B1 was subjected to the preparative high performance liquid chromatography (HPLC) under the following preparative HPLC condition (C9), whereby a fraction containing 11107AF, a fraction containing 111070, a fraction containing 11107P, a fraction containing 11107Q, a fraction containing 11107R and a fraction containing 11107AG were collected separately, and the solvent was removed. The fraction containing 11107AF was further subjected to the preparative high performance liquid chromatography (HPLC) under the following preparative HPLC condition (C10) to obtain a 11107AF solution. Then, 11107AF (0.3 mg) was given by removal of the solvent. The fraction containing 11107O was further subjected to the preparative high performance liquid chromatography (HPLC) under the following preparative HPLC condition (C11) to give a 11107O solution. Then, 11107O (0.5 mg) was given by removal of the solvent. The fraction containing 11107P was subjected to the preparative high performance liquid chromatography (HPLC) under the following preparative HPLC condition (C11) to give a 11107P solution. Then, 11107P (1.3 mg) was given by removal of the solvent. The fraction containing 11107Q was further subjected to the preparative high performance liquid chromatography (HPLC) under the following preparative HPLC condition (C6) to give a 11107Q solution. Then, 11107Q (0.6 mg) was given by removal of the solvent. The fraction containing 11107R was further subjected to the preparative high performance liquid chromatography (HPLC) under the following preparative HPLC condition (C6) to give a 11107R solution. Then, 11107R (0.6 mg) was given by removal of the solvent. The fraction containing 11107AG was further subjected to the preparative high performance liquid chromatography (HPLC) under the following preparative HPLC condition (C12) to give a 11107AG solution. Then, 11107AG (1.0 mg) was given by removal of the solvent.

200 mg of crude active fraction B2 was subjected to repeated use of preparative high performance liquid chromatography (HPLC), under the following preparative HPLC condition (C13) to give a fraction containing 11107S and a fraction containing 11107AB and 11107V (0.5 mg). The fraction containing 11107S was subjected to the preparative high performance liquid chromatography (HPLC) under the following preparative HPLC condition (C14) to give a 11107S solution. Then, 11107S (1.2 mg) was given by removal of the solvent. Similarly, the fraction containing 11107AB (20 mg) was subjected to the preparative high performance liquid chromatography (HPLC) under the following HPLC preparative condition (C15) to give a 11107AB solution. Then, 11107AB (14 mg) was given by removal of the solvent.

The resulting crude active fraction B3 (67.5 mg) was subjected to preparative high performance liquid chromatography (HPLC) under the following preparative HPLC condition (C16), a fraction containing 11107AD, a fraction containing 11107AE and a fraction containing 11107AJ and 11107AK were collected separately, and the solvent was removed. The fraction containing 11107AD was subjected to repeated use of preparative high performance liquid chromatography (HPLC), under the following preparative conditions (C17), (C18) and (C17) in turn, to give 11107AD (4.1 mg). Further, the fraction containing 11107AE was subjected to twice repeated use of preparative high performance liquid chromatography (HPLC), under the following preparative HPLC condition (C17) to give 11107AE (8.2 mg) as a mixture of tautomers, 11107AEa and 11107AEb. Further, the fraction containing 11107AJ and 11107AK was subjected to preparative high performance liquid chromatography (HPLC), under the following preparative HPLC conditions (C17), to give a fraction containing 11107AJ and a fraction containing 11107AK separately. The solvent was removed from each fraction. Then the respective fractions were subject to repeated use of preparative high performance liquid chromatography (HPLC), under the following preparative conditions (C18) and (17) in turn, to give 11107AJ (0.5 mg) and 11107AK (0.9 mg).

Preparative HPLC condition (C1)
  Column: CAPCELL PAK C18 UG120, φ30 mm×250 mm (manufactured by SHISEIDO Co.)
  Flow rate: 20 ml/min.
  Detection: 240 nm
  Eluent: acetonitrile/water (4:6, v/v) isocratic Preparative HPLC conditions (C2)
  Column: CAPCELL PAK C18 UG120, φ30 mm×250 mm (manufactured by SHISEIDO Co.)
  Flow rate: 20 ml/min.
  Detection: 240 nm
  Eluent: acetonitrile/water (5:5, v/v) isocratic Preparative HPLC conditions (C3)
  Column: Inertsil ODS-3, φ50 mm×250 mm (manufactured by GL Science)
  Temperature: room temperature
  Flow rate: 40 ml/min.
  Detection: 240 nm
  Eluent: acetonitrile/water (45:55, v/v) isocratic Preparative HPLC condition (C4)
  Column: CAPCELL PAK C18 SG120, φ20 mm×250 mm (manufactured by SHISEIDO Co.)
  Temperature: 40° C.
  Flow rate: 5 ml/min.
  Detection: 200 nm
  Eluent: acetonitrile/water (4:6, v/v) isocratic Preparative HPLC condition (C5)
  Column: CAPCELL PAK C18 SG120, φ20 mm×250 mm (manufactured by SHISEIDO Co.)
  Temperature: 40° C.
  Flow rate: 10 ml/min.
  Detection: 240 nm
  Eluent: methanol/water (6:4, v/v) isocratic Preparative HPLC condition (C6)
  Column: CAPCELL PAK C18 SG120, φ20 mm×250 mm (manufactured by SHISEIDO Co.)
  Temperature: 40° C.
  Flow rate: 5 ml/min.
  Detection: 240 nm
  Eluent: acetonitrile/water (4:6, v/v) isocratic Preparative HPLC condition (C7)
  Column: CAPCELL PAK C18 SG120, φ20 mm×250 mm (manufactured by SHISEIDO Co.)
  Temperature: 40° C.
  Flow rate: 5 ml/min.
  Detection: 200 nm
  Eluent: methanol/water (6:4, v/v) isocratic Preparative HPLC condition (C8)
  Column: CAPCELL PAK C18 SG120, φ20 mm×250 mm (manufactured by SHISEIDO Co.)
  Temperature: 40° C.
  Flow rate: 5 ml/min.
  Detection: 240 nm
  Eluent: methanol/water (6:4, v/v) isocratic Preparative HPLC condition (C9)
  Column: YMC J'sphere ODS-M80 JM-343, φ20 mm×250 mm (manufactured by YMC Co.)
  Temperature: 40° C.

Flow rate: 5 ml/min.
Detection: 200 nm
Eluent: acetonitrile/water (3:7, v/v) isocratic Preparative HPLC condition (C10)
Column: CAPCELL PAK C18 SG120, φ20 mm×250 mm (manufactured by SHISEIDO Co.)
Temperature: 40° C.
Flow rate: 5 ml/min.
Detection: 240 nm
Eluent: methanol/water (5:5, v/v) isocratic Preparative HPLC condition (C11)
Column: YMC J'sphere ODS-M80 JM-343, φ20 mm×250 mm (manufactured by YMC Co.)
Temperature: 40° C.
Flow rate: 5 ml/min.
Detection: 240 nm
Eluent: acetonitrile/water (3:7, v/v) isocratic Preparative HPLC condition (C12)
Column: YMC J'sphere ODS-M80 JM-343, φ20 mm×250 mm (manufactured by YMC Co.)
Temperature: 40° C.
Flow rate: 5 ml/min.
Detection: 200 nm
Eluent: methanol/water (6:4, v/v) isocratic Preparative HPLC condition (C13)
Column: YMC J'sphere ODS-H80 JH-343, φ20 mm×250 mm (manufactured by YMC Co.)
Temperature: 40° C.
Flow rate: 20 ml/min.
Detection: 215 nm
Eluent: acetonitrile/water (32:68, v/v) isocratic Preparative HPLC condition (C14)
Column: YMC J'sphere ODS-H80 JH-323, φ10 mm×250 mm (manufactured by YMC Co.)
Temperature: 40° C.
Flow rate: 5 ml/min.
Detection: 215 nm
Eluent: acetonitrile/water (4:6, v/v) isocratic Preparative HPLC condition (C15)
Column: YMC J'sphere ODS-H80 JH-343, φ20 mm×250 mm (manufactured by YMC Co.)
Temperature: 40° C.
Flow rate: 20 ml/min.
Detection: 215 nm
Eluent: acetonitrile/water (4:6, v/v) isocratic Preparative HPLC condition (C16)
Column: YMC J'sphere ODS-M80 JM-343, φ20 mm×250 mm (manufactured by YMC Co.)
Temperature: room temperature
Flow rate: 10 ml/min.
Detection: 240 nm
Eluent: acetonitrile/water (35:65–4:6, v/v, 0–50 minutes, linear gradient), acetonitrile/water (4:6, v/v, 50–70 minutes, isocratic)

Preparative HPLC condition (C17)
Column: YMC J'sphere ODS-M80 JM-343, φ20 mm×250 mm (manufactured by YMC Co.)
Temperature: room temperature
Flow rate: 10 ml/min.
Detection: 240 nm
Eluent: methanol/water (65:35–7:3, v/v, 0–40 minutes, linear gradient)

Preparative HPLC condition (C18)
Column: CAPCELL PAK C18 SG120, φ20 mm×250 mm (manufactured by SHISEIDO Co.)
Temperature: room temperature
Flow rate: 5 ml/min.
Detection: 240 nm
Eluent: acetonitirle/water (4:6, v/v) isocratic The retention times of 11107B and the above-mentioned compounds when analysis was carried out at the following Analytic HPLC conditions are shown below.

Analytic HPLC condition (c1)
Column: CAPCELL PAK C18 SG120, φ4.6 mm×250 mm (manufactured by SHISEIDO Co.)
Temperature: 40° C.
Flow rate: 1 ml/min.
Detection: 240 nm
Eluent: acetonitirle/water (4:6, v/v) isocratic
Retention time:
11107B: 16.4 min.
11107L: 22.2 min.
11107M: 36.0 min.
11107N: 18.1 min.
11107R: 7.6 min.
11107X: 23.8 min.
11107Y: 23.6 min.
11107AL: 32.0 min.
11107AM: 30.3 min.
11107AN: 38.7 min.
11107AP: 60.4 min.
11107AQ: 64.7 min.
11107AR: 15.2 min.

Analytic HPLC condition (c2)
Column: CAPCELL PAK C18 SG120, φ4.6 mm 250 mm (manufactured by SHISEIDO Co.)
Temperature: 40° C.
Flow rate: 1 ml/min.
Detection: 240 nm
Eluent: methanol/water (6:4, v/v) isocratic
Retention time:
11107T: 13.0 min.
11107U: 14.4 min.
11107W: 15.4 min.
11107Z: 15.9 min.
11107AA: 12.4 min.
11107AC: 12.7 min.
11107AI: 18.3 min.

Analytic HPLC condition (c3)
Column: CAPCELL PAK C18 SG120, φ4.6 mm×250 mm (manufactured by SHISEIDO Co.)
Temperature: 40° C.
Flow rate: 1 ml/min.
Detection: 200 nm
Eluent: methanol/water (6:4, v/v) isocratic
Retention time:
11107AH: 10.3 min.

Analytic HPLC condition (c4)
Column: CAPCELL PAK C18 SG120, φ4.6 mm×250 mm (manufactured by SHISEIDO Co.)
Temperature: 40° C.
Flow rate: 1 ml/min.
Detection: 240 nm
Eluent: methanol/water (5:5, v/v) isocratic
Retention time:
11107O: 20.2 min.
11107Q: 25.2 min.

11107AF: 17.7 min.

Analytic HPLC condition (c5)
  Column: YMC J'sphere ODS-M80 JM-307, ϕ4.6 mm×75 mm (manufactured by YMC Co.)
  Temperature: 40° C.
  Flow rate: 1.5 ml/min.
  Detection: 240 nm
  Eluent: acetonitrile/water (3:7, v/v) isocratic
  Retention time:
  11107P: 5.8 min.

Analytic HPLC condition (c6)
  Column: YMC Pack Ph A407, ϕ4.6 mm×75 mm (manufactured by YMC Co.)
  Temperature: 40° C.
  Flow rate: 1 ml/min.
  Detection: 200 nm
  Eluent: methanol/water (5:5, v/v) isocratic
  Retention time:
  11107AG: 6.5 min.

Analytic HPLC condition (c7)
  Column: CAPCELL PAK C18 SG120, ϕ4.6 mm×250 mm (manufactured by SHISEIDO Co.)
  Temperature: 40° C.
  Flow rate: 1 ml/min.
  Detection: 254 nm
  Eluent: acetonitrile/water (4:6, v/v) isocratic
  Retention time:
  11107V: 9.6 min.
  11107AB: 10.8 min.

Analytic HPLC condition (c8)
  Column: CAPCELL PAK C18 SG120, ϕ4.6 mm×250 mm (manufactured by SHISEIDO Co.)
  Temperature: 40° C.
  Flow rate: 1.5 ml/min.
  Detection: 240 nm
  Eluent: acetonitrile/water (4:6, v/v) isocratic
  11107S: 6.6 min.

Analytic HPLC condition (c9)
  Column: CAPCELL PAK C18 SG120, ϕ4.6 mm×250 mm (manufactured by SHISEIDO Co.)
  Temperature: room temperature
  Flow rate: 1 ml/min.
  Detection: 240 nm
  Eluent: acetonitrile/water (4:6, v/v) isocratic
  Retention time:
  11107AD: 15.6 min.
  11107AE: 14.7 min. (11107AEa), 15.4 min. (11107AEb)
  11107AJ: 12.9 min.
  11107AK: 13.4 min.

Example A18

Physico-chemical Properties of 11107L

The physico-chemical properties of 11107L are shown below. The structure of 11107L was determined as shown below.
1. Appearance: colorless powder
2. Molecular weight: 594, FAB-MS m/z 617(M+Na)$^+$, 593 (M−H)$^−$
3. Molecular formula: $C_{32}H_{50}O_{10}$
4. Solubility: soluble in dimethylsulfoxide, pyridine, methanol and acetone, and slightly soluble in water
5. Color reaction: positive for iodine and sulfuric acid
6. Infrared absorption spectrum: 3470, 2970, 1735, 1718, 1456, 1373, 1236, 1175
7. $^1$H-NMR spectrum (CD$_3$OD, 400 MHz): δ ppm (integral, multiplicity, coupling constant J (Hz)): 0.87(3H,d,J=6.6 Hz), 0.90(3H,d,J=7.0 Hz), 0.94(3H,t,J=7.3 Hz), 1.08(3H, d,J=7.0 Hz), 1.18–1.22(4H,m), 1.42–1.52(3H,m), 1.65–1.69(1H,m), 1.70–1.74(2H,m), 1.77(3H,d,J=0.7 Hz), 2.06(3H,s), 2.08(3H,s), 2.46–2.50(1H,m), 2.52(1H, dd,J=4.4,15.0 Hz), 2.55–2.62(1H,m), 2.65(1H,dd,J=2.2, 8.4 Hz), 2.72(1H,dt,J=2.2,5.9 Hz), 2.77(1H,dd,J=3.3,15.0 Hz), 3.51(1H,dt,J=8.4,4.4 Hz), 3.73–3.75(1H,m), 4.98 (1H,dd,J=3.1,10.7 Hz), 5.08(1H,d,J=9.9 Hz), 5.11(1H, d,J=11.0 Hz), 5.60(1H,dd,J=9.9,15.0 Hz), 5.66(1H,dd, J=8.4,15.0 Hz), 5.74(1H,dd,J=9.9,15.0 Hz), 6.09(1H,d, J=11.0 Hz), 6.33(1H,dd,J=11.0,15.0 Hz)

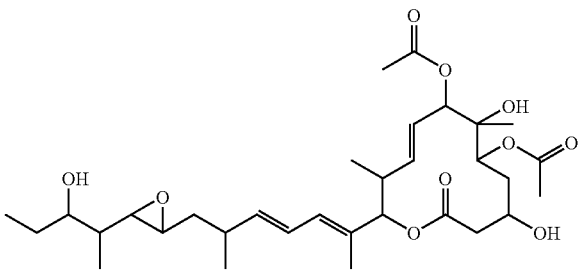

11107L

Example A19

Physico-chemical Properties of 11107M

The physico-chemical properties of 11107M are shown below. The structure of 11107M was determined as shown below.
1. Appearance: colorless powder
2. Molecular weight: 578, FAB-MS m/z 577(M−H)$^−$
3. Molecular formula: $C_{32}H_{50}O_9$
4. Solubility: soluble in dimethylsulfoxide, pyridine, methanol and acetone, and slightly soluble in water
5. Color reaction: positive for iodine and sulfuric acid
6. Infrared absorption spectrum: 3498, 2970, 1731, 1719, 1456, 1374, 1254, 1174
7. $^1$H-NMR spectrum (CD$_3$OD, 400 MHz): δ ppm (integral, multiplicity, coupling constant J (Hz)): 0.89(3H,d,J=6.6 Hz), 0.90(3H,d,J=7.0 Hz), 0.93(3H,t,J=7.3 Hz), 1.08(3H, d,J=7.0 Hz), 1.17–1.20(4H,m), 1.42–1.55(5H,m), 1.60–1.66(3H,m), 1.74(3H,d,J=1.1 Hz), 2.04(3H,s), 2.06 (3H,s), 2.44–2.52(1H,m), 2.54–2.58(1H,m), 2.60(1H,dd, J=3.7,14.8 Hz), 2.62(1H,dd,J=5.9,14.8 Hz), 2.64(1H,dd, J=2.2,8.1 Hz), 2.72(1H,dt,J=2.2,5.9 Hz), 3.51(1H,dt, J=8.4,4.8 Hz), 4.82–4.84(1H,m), 4.98(1H,d,J=10.6 Hz), 5.02(1H,d,J=9.6 Hz), 5.57(1H,dd,J=9.9,15.0 Hz), 5.66 (1H,dd,J=9.4,15.0 Hz), 5.71(1H,dd,J=9.6,15.0 Hz), 6.09 (1H,d,J=11.0 Hz), 6.32(1H,dd,J=11.0,15.0 Hz)

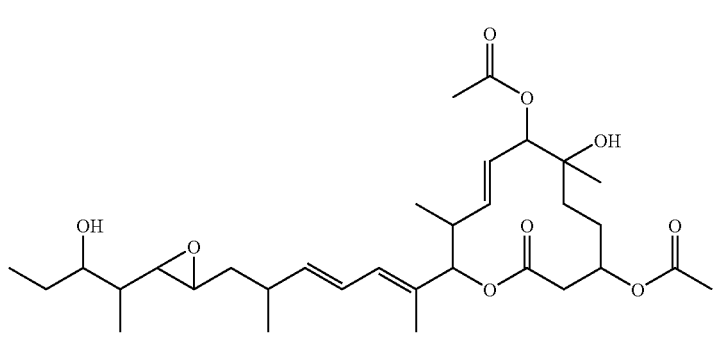

11107M

Example A20

Physico-chemical Properties of 11107N

The physico-chemical properties of 11107N are shown below. The structure of 11107N was determined as shown below.

1. Appearance: colorless powder
2. Molecular weight: 594, FAB-MS m/z 595(M+H)$^+$, 617 (M+Na)$^+$
3. Molecular formula: $C_{32}H_{50}O_{10}$
4. Solubility: soluble in dimethylsulfoxide, pyridine, methanol and acetone, and slightly soluble in water
5. Color reaction: positive for iodine and sulfuric acid
6. Infrared absorption spectrum: 3480, 2964, 1740, 1719, 1456, 1371, 1244, 1174
7. $^1$H-NMR spectrum (CD$_3$OD, 400 MHz): δ ppm (integral, multiplicity, coupling constant J (Hz)): 0.88(3H,d,J=6.2 Hz), 0.90(3H,d,J=6.6 Hz), 0.94(3H,t,J=7.3 Hz), 1.08(3H, d,J=7.0 Hz), 1.17–1.22(1H,m), 1.42–1.52(5H,m), 1.55–1.65(3H,m), 1.75(3H,d,J=0.7 Hz), 2.04(3H,s), 2.05 (3H,s), 2.45–2.50(1H,m), 2.51(1H,d,J=4.4 Hz), 2.53(1H, d,J=3.3 Hz), 2.54–2.62(1H,m), 2.65(1H,dd,J=2.6,8.4 Hz), 2.72(1H,dt,J=2.6,6.2 Hz), 3.51(1H,dt,J=8.8,4.8 Hz), 3.75–3.81(1H,m), 4.00(1H,d,J=11.4 Hz), 4,14(1H,d, J=11.4 Hz), 5.05(1H,d,J=10.6 Hz), 5.21(1H,d,J=9.5 Hz), 5.63(1H,dd,J=9.5,15.0 Hz), 5.65(1H,dd,J=9.5,15.0 Hz), 5.72(1H,dd,J=9.5,15.0 Hz), 6.09(1H,d,J=11.0 Hz), 6.32 (1H,dd,J=11.0,15.0 Hz)

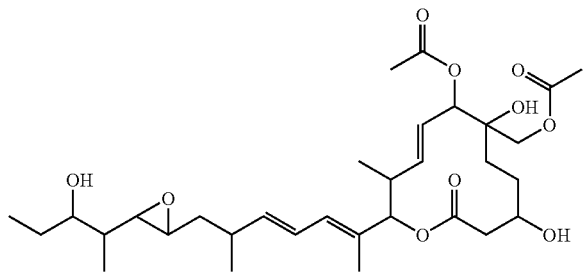

11107N

Example A21

Physico-chemical Properties of 111070

The physico-chemical properties of 111070 are shown below. The structure of 111070 was determined as shown below.

1. Appearance: colorless powder
2. Molecular weight: 554, FAB-MS m/z 555(M+H)$^+$, 577 (M+Na)$^+$
3. Molecular formula: $C_{30}H_{50}O_9$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3419, 2966, 1733, 1716, 1457, 1374, 1258, 1176
7. $^1$H-NMR spectrum (CD$_3$OD, 500 MHz): δ ppm (integral, multiplicity, coupling constant J (Hz)): 0.88(3H,d,J=6.8 Hz), 0.90(3H,d,J=7.3 Hz), 0.93(3H,t,J=7.3 Hz), 1.06(3H, d,J=6.8 Hz), 1.19(3H,s), 1.34–1.44(3H,m), 1.51(2H,m), 1.54–1.71(3H,m), 1.75(3H,s), 1.90(1H,m), 2.06(3H,s), 2.53(2H,m), 2.56(2H,m), 3.43–3.50(2H,m), 3.57(1H,m), 3.78(1H,m), 5.05(2H,d,J=10.3 Hz), 5.57(1H,dd,J=10.3, 15.1 Hz), 5.61(1H,dd,J=8.3,15.1 Hz), 5.70(1H,dd,J=9.8, 15.1 Hz), 6.10(1H,d,J=10.7 Hz), 6.33(1H,dd,J=10.7,15.1 Hz)

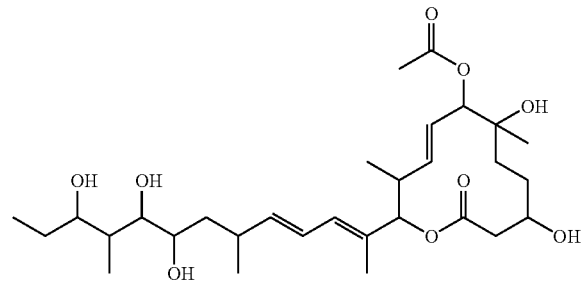

111070

Example A22

Physico-chemical Properties of 11107P

The physico-chemical properties of 11107P are shown below. The structure of 11107P was determined as shown below.

1. Appearance: colorless powder
2. Molecular weight: 552, FAB-MS m/z 553(M+H)$^+$, 575 (M+Na)$^+$
3. Molecular formula: $C_{30}H_{48}O_9$ 4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3290, 2969, 1734, 1716, 1457, 1374, 1247, 1177
7. $^1$H-NMR spectrum (CD$_3$OD, 500 MHz): δ ppm (integral, multiplicity, coupling constant J (Hz)): 0.88(3H,d,J=6.8 Hz), 0.90(3H,d,J=7.3 Hz), 0.94(3H,t,J=7.3 Hz), 1.13(3H,d,J=6.8 Hz), 1.19(3H,s), 1.22(1H,m), 1.28–1.67(6H,m), 1.75(3H,d,J=1.0 Hz), 2.06(3H,s), 2.44(1H,m), 2.53–2.57 (3H,m), 2.74(1H,dd,J=2.4,6.8 Hz), 2.83(1H,dd,J=2.0,8.3 Hz), 3.09(1H,dd,J=6.8,7.3 Hz), 3.52(1H,m), 3.78(1H,m), 5.04(1H,d,J=10.7 Hz), 5.05(1H,d,J=9.8 Hz), 5.56(1H,dd,J=9.8,15.1 Hz), 5.701(1H,dd,J=9.8,15.1 Hz), 5.703(1H,dd,J=7.3,15.1 Hz), 6.10(1H,d,J=10.7 Hz), 6.37(1H,dd,J=10.7,15.1 Hz)

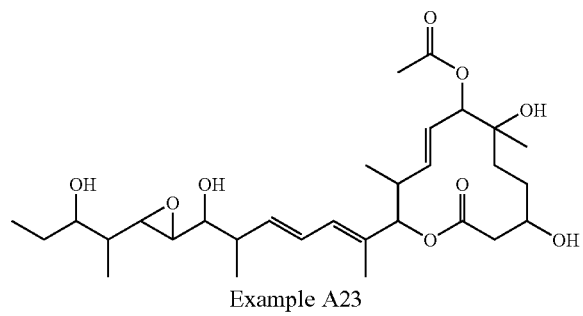

11107P

Example A23

Physico-chemical Properties of 11107Q

The physico-chemical properties of 11107Q are shown below. The structure of 11107Q was determined as shown below.
1. Appearance: colorless powder
2. Molecular weight: 550, FAB-MS m/z 551(M+H)$^+$, 573 (M+Na)$^+$
3. Molecular formula: C$_{30}$H$_{46}$O$_9$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3384, 2970, 1732, 1716, 1670, 1456, 1374, 1258, 1174
7. $^1$H-NMR spectrum (CD$_3$OD, 500 MHz): δ ppm (integral, multiplicity, coupling constant J (Hz)): 0.88(3H,d,J=6.4 Hz), 1.07(3H,d,J=6.8 Hz), 1.19(3H,s), 1.31(3H,d,J=6.8 Hz), 1.34–1.46(3H,m), 1.53–1.71(3H,m), 1.75(3H,s), 1.77(3H,s), 2.06(3H,s), 2.50–2.57(4H,m), 3.79(1H,m), 4.48(1H,m), 4.94(1H,q,J=6.8 Hz), 5.045(1H,d,J=11.2 Hz), 5.047(1H,d,J=9.3 Hz), 5.57(1H,dd,J=9.3,15.1 Hz), 5.63(1H,dd,J=8.8,15.1 Hz), 5.70(1H,dd,J=9.8,15.1 Hz), 6.10(1H,d,J=10.7 Hz), 6.35(1H,dd,J=10.7,15.1 Hz), 6.54 (1H,d,J=8.3 Hz)

11107Q

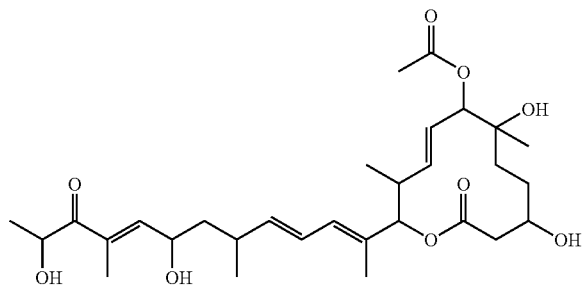

Example A24

Physico-chemical Properties of 11107R

The physico-chemical properties of 11107R are shown below. The structure of 11107R was determined as shown below.
1. Appearance: colorless powder
2. Molecular weight: 494, FAB-MS m/z 495(M+H)$^+$, 517 (M+Na)$^+$
3. Molecular formula: C$_{27}$H$_{42}$O$_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3385, 2968, 1734, 1716, 1457, 1373, 1245, 1174
7. $^1$H-NMR spectrum (CD$_3$OD, 500 MHz): δ ppm (integral, multiplicity, coupling constant J (Hz)): 0.88(3H,d,J=6.8 Hz), 1.08(3H,d,J=6.8 Hz), 1.17(3H,d,J=6.8 Hz), 1.19(3H,s), 1.34–1.52(3H,m), 1.52–1.68(3H,m), 1.74(3H,s), 2.06 (3H,s), 2.47–2.53(4H,m), 2.64(1H,dd,J=2.4,6.4 Hz), 2.83 (1H,dt,J=2.5,6.1 Hz), 3.45(1H,dq,J=6.4,6.8 Hz), 3.78(1H,m), 5.05(2H,d,J=9.8 Hz), 5.57(1H,dd,J=9.8,15.1 Hz), 5.66(1H,dd,J=8.8,15.1 Hz), 5.70(1H,dd,J=9.8,15.1 Hz), 6.09(1H,d,J=10.8 Hz), 6.32(1H,dd,J=10.8,15.1 Hz)

11107R

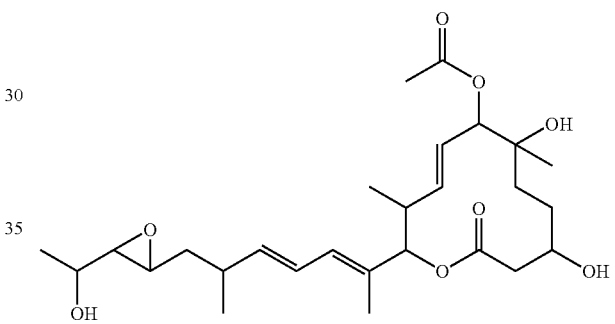

Example A25

Physico-chemical Properties of 11107S

The physico-chemical properties of 11107S are shown below. The structure of 11107S was determined as shown below.
1. Appearance: colorless powder
2. Molecular weight: 492, ESI-MS m/z 515(M+Na)$^+$, 493 (M+H)$^+$
3. Molecular formula: C$_{2-8}$H$_{44}$O$_7$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 600 MHz): δ ppm (integral, multiplicity, coupling constant J (Hz)): 0.88(3H,d,J=6.9 Hz), 0.94(3H,d,J=7.1 Hz), 0.98(3H,t,J=7.4 Hz), 1.12(3H,d,J=6.7 Hz), 1.25(1H,m), 1.38(3H,s), 1.45–1.60(3H,m), 1.67(1H,dt,J=13.7,5.8 Hz), 1.77(3H,s), 2.40–2.55(2H,m), 2.57(1H,dd,J=2.7,13.4 Hz), 2.67(1H,dd,J=6.1,13.4 Hz), 2.70(1H,dd,J=2.2,8.2 Hz), 2.76(1H,dt,J=2.2,5.8 Hz), 3.55 (1H,dt,J=8.8,4.4 Hz), 3.71(1H,d,J=9.4 Hz), 4.54(1H,m), 5.01(1H,d,J=10.5 HZ), 5.18(1H,dd,J=9.3,15.2 Hz), 5.59 (1H,dd,J=9.4,15.2 Hz), 5.61(1H,dd,J=1.8,15.4 Hz), 5.68 (1H,dd,J=8.3,15.0 Hz), 5.74(1H,dd,J=3.2,15.4 Hz), 6.07 (1H,d,J=10.7 Hz), 6.35(1H,dd,J=10.7,15.0 Hz)

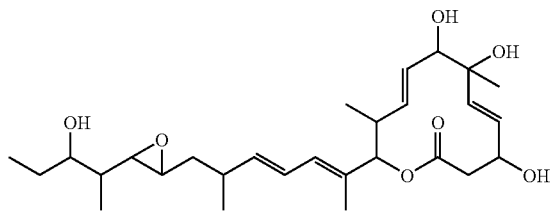

Example A26

Physico-chemical Properties of 11107T

The physico-chemical properties of 11107T are shown below. The structure of 11107T was determined as shown below.
1. Appearance: colorless powder
2. Molecular weight: 522, FAB-MS m/z 545(M+Na)$^+$
3. Molecular formula: $C_{29}H_{46}O_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3421, 2965, 1734, 1718, 1457, 1370, 1244, 1175
7. $^1$H-NMR spectrum (CD$_3$OD, 500 MHz): δ ppm (integral, multiplicity, coupling constant J (Hz)): 0.89(3H,d,J=6.8 Hz), 0.93(3H,t,J=7.3 Hz), 1.09(3H,d,J=6.8 Hz), 1.19(3H, s), 1.28–1.42(2H,m), 1.42–1.68(8H,m), 1.75(3H,s), 2.06 (3H,s), 2.48–2.57(4H,m), 2.74(1H,ddd,J=2.4,4.9,5.9 Hz), 2.85(1H,ddd,J=2.4,4.4,7.3 Hz), 3.64(1H,m), 3.78(1H,m), 5.047(1H,d,J=9.8 Hz), 5.052(1H,d,J=10.8 Hz), 5.57(1H, dd,J=9.8,15.1 Hz), 5.69(1H,dd,J=8.3,15.1 Hz), 5.70(1H, dd,J=9.8,15.1 Hz), 6.10(1H,d,J=10.7 Hz), 6.32(1H,dd, J=10.7,15.1 Hz)

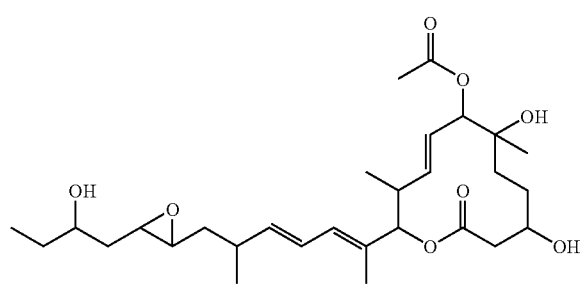

Example A27

Physico-chemical Properties of 11107U

The physico-chemical properties of 11107U are shown below. The structure of 11107U was determined as shown below.
1. Appearance: colorless powder
2. Molecular weight: 522, FAB-MS m/z 545(M+Na)$^+$
3. Molecular formula: $C_{29}H_{46}O_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3461, 2967, 1732, 1715, 1455, 1372, 1247, 1174
7. $^1$H-NMR spectrum (CD$_3$OD, 500 MHz): δ ppm (integral, multiplicity, coupling constant J (Hz)): 0.88(3H,d,J=6.8 Hz), 0.93(3H,d,J=6.8 Hz), 0.95(3H,t,J=7.8 Hz), 1.19(3H, s), 1.26(1H,m), 1.34–1.42(2H,m), 1.42–1.56(2H,m), 1.56–1.72(4H,m), 1.74(3H,s), 2.06(3H,s), 2.29(2H,m), 2.52–2.56(3H,m), 2.70(1H,dd,J=2.4,8.3 Hz), 2.76(1H,dt, J=2.4,5.9 Hz), 3.53(1H,m), 3.78(1H,m), 5.05(2H,d, J=10.3 Hz), 5.56(1H,dd,J=9.8,15.1 Hz), 5.70(1H,dd, J=9.8,15.1 Hz), 5.79(1H,dt,J=15.1,7.1 Hz), 6.09(1H,d, J=10.7 Hz), 6.34(1H,dd,J=10.7,15.1 Hz)

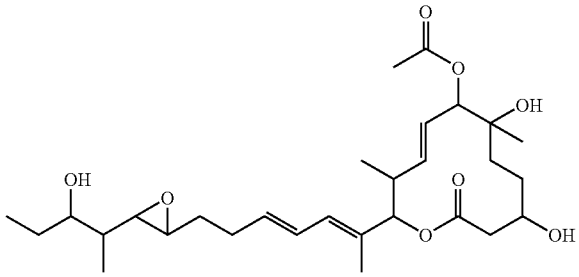

Example A28

Physico-chemical Properties of 11107V

The physico-chemical properties of 11107V are shown below. The structure of 11107V was determined as shown below.
1. Appearance: colorless powder
2. Molecular weight: 494, ESI-MS m/z 517(M+Na)$^+$, 495 (M+H)$^+$
3. Molecular formula: $C_{28}H_{46}O_7$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 500 MHz): δ ppm (integral, multiplicity, coupling constant J (Hz)): 0.93(3H,d,J=6.9 Hz), 0.94(3H,d,J=7.1 Hz), 0.98(3H,t,J=7.4 Hz), 1.13(3H, d,J=6.9 Hz), 09(1H,m), 1.23(1H,m), 1.26(3H,s), 1.30(1H, m), 1.44–1.70(6H,m), 1.68(1H,dt,J=13.7,5.7 Hz), 1.79 (3H,s), 2.27(1H,m), 2.45(1H,dd,J=5.3,13.6 Hz), 2.50–2.56(2H,m), 2.59(1H,dd,J=3.2,13.6 Hz), 2.70(1H, dd,J=2.1,8.2 Hz), 2.76(1H,dt,J=2.1,5.7 Hz), 3.02(1H,m), 3.25(H,dq,J=10.9,7.0 Hz), 3.55(1H,dt,J=8.7,4.5 Hz), 3.82–3.88(1H,m), 5.31(1H,d,J=10.9 Hz), 5.74(1H,dd, J=8.4,15.1 Hz), 6.18(1H,d,J=10.8 Hz), 6.36(1H,dd, J=10.8,15.1 Hz)

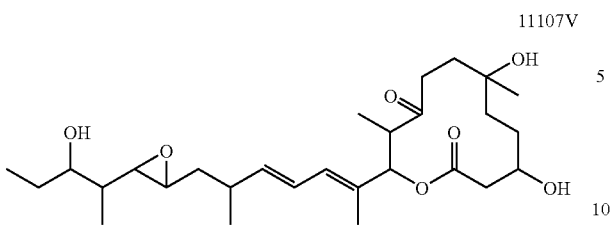

Example A29

Physico-chemical Properties of 11107W

The physico-chemical properties of 11107W are shown below. The structure of 11107W was determined as shown below.
1. Appearance: colorless powder
2. Molecular weight: 522, FAB-MS m/z 523(M+H)$^+$, 545 (M+Na)$^+$
3. Molecular formula: $C_{29}H_{46}O_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3463, 2967, 1734, 1715, 1456, 1373, 1245, 1174
7. $^1$H-NMR spectrum (CD$_3$OD, 500 MHz): δ ppm (integral, multiplicity, coupling constant J (Hz)): 0.91(3H,d,J=7.3 Hz), 0.94(3H,t,J=7.3 Hz), 1.00(3H,d,J=6.8 Hz), 1.08(3H, d,J=6.8 Hz), 1.19(3H,s), 1.20(1H,m), 1.32–1.42(2H,m), 1.42–1.54(3H,m), 1.54–1.67(3H,m), 2.06(3H,s), 2.37–2.53(4H,m), 2.66(1H,dd,J=2.4,8.3 Hz), 2.72(1H,dt, J=2.4,5.9 Hz), 3.52(1H,m), 3.79(1H,m), 5.04(1H,d,J=9.8 Hz), 5.09(1H,dd,J=8.3,10.7 Hz), 5.52(1H,dd,J=8.3,15.1 Hz), 5.56(1H,dd,J=10.3,15.1 Hz), 5.67(1H,dd,J=9.8,15.1 Hz), 5.69(1H,dd,J=8.3,15.1 Hz), 6.10(1H,dd,J=10.3,15.1 Hz), 6.29(1H,dd,J=10.3,15.1 Hz)

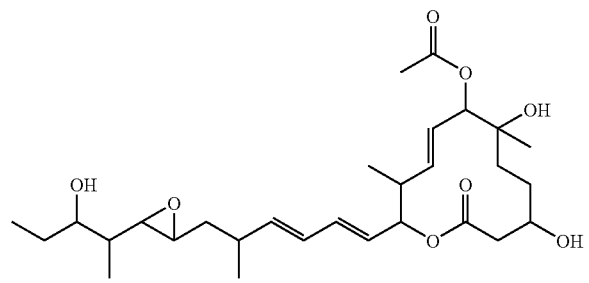

Example A30

Physico-chemical Properties of 11107X

The physico-chemical properties of 11107X are shown below. The structure of 11107X was determined as shown below.
1. Appearance: colorless powder
2. Molecular weight: 550, FAB-MS m/z 573(M+Na)$^+$, 549 (M-H)$^-$
3. Molecular formula: $C_{31}H_{50}O_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3479, 2967, 1733, 1716, 1457, 1374, 1243, 1178
7. $^1$H-NMR spectrum (CD$_3$OD, 400 MHz): δ ppm (integral, multiplicity, coupling constant J (Hz)): 0.87(3H,d,J=7.0 Hz), 0.90(3H,d,J=7.0 Hz), 0.94(3H,t,J=7.3 Hz), 1.08(3H, d,J=6.6 Hz), 1.18–1.22(7H,m), 1.33–1.35(2H,m), 1.43–1.52(3H,m), 1.59–1.63(1H,m), 1.59–1.70(2H,m), 1.73(3H,d,J=0.7 Hz), 2.06(3H,s), 2.45–2.50(1H,m), 2.53–2.60(1H,m), 2.60–2.64(1H,m), 2.65(1H,dd,J=2.2, 8.1 Hz), 2.72(1H,dt,J=2.2,5.9 Hz), 3.48–3.53(2H,m), 5.00 (1H,d,J=11.0 Hz), 5.02(1H,d,J=9.9 Hz), 5.55(1H,dd, J=9.9,15.0 Hz), 5.66(1H,dd,J=9.4,15.0 Hz), 5.70(1H,dd, J=9.9,15.0 Hz), 6.09(1H,d,J=11.0 Hz), 6.32(1H,dd, J=11.0,15.0 Hz)

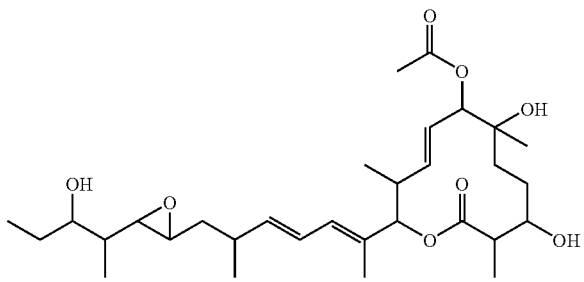

Example A31

Physico-chemical Properties of 11107Y

The physico-chemical properties of 11107Y are shown below. The structure of 11107Y was determined as shown below.
1. Appearance: colorless powder
2. Molecular weight: 536, FAB-MS m/z 559(M+Na)$^+$, 535 (M-H)$^-$
3. Molecular formula: $C_{30}H_{48}O_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3442, 2965, 1733, 1716, 1457, 1373, 1241, 1167
7. $^1$H-NMR spectrum (CD$_3$OD, 400 MHz): δ ppm (integral, multiplicity, coupling constant J (Hz)): 0.86(3H,d,J=7.0 Hz), 0.90(3H,d,J=7.3 Hz), 0.93(3H,t,J=7.3 Hz), 0.95(3H, d,J=6.6 Hz), 1.08(3H,d,J=7.0 Hz), 1.17–1.20(1H,m), 1.43–1.52(5H,m), 1.60–1.64(1H,m), 1.75(3H,d,J=1.1 Hz), 2.00(3H,s), 2.01–2.04(1H,m), 2.47–2.52(1H,m), 2.53–2.55(1H,m), 2.56(1H,d,J=4.0 Hz), 2.61(1H,d,J=3.3 Hz), 2.65(1H,dd,J=2.2,8.1 Hz), 2.72(1H,dt,J=2.2,5.9 Hz), 3.51(1H,dt,J=8.1,4.8 Hz), 3.76(1H,dt,J=3.6,12.5 Hz), 4.09–4.12(1H,m), 4.88(1H,d,J=9.2 Hz), 5.05(1H,d, J=10.6 Hz), 5.42(1H,dd,J=9.2,15.0 Hz), 5.50(1H,dd, J=9.5,15.0 Hz), 5.66(1H,dd,J=8.4,15.0 Hz), 6.08(1H,d, J=10.3 Hz), 6.32(1H,dd,J=10.3,15.0 Hz)

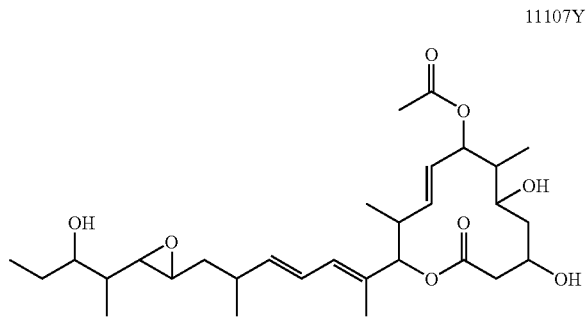

Example A32

Physico-chemical Properties of 11107Z

The physico-chemical properties of 11107Z are shown below. The structure of 11107Z was determined as shown below.
1. Appearance: colorless powder
2. Molecular weight: 522, FAB-MS m/z 523(M+H)$^+$, 545 (M+Na)$^+$
3. Molecular formula: $C_{29}H_{46}O_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3423, 2965, 1733, 1716, 1457, 1373, 1242, 1174
7. $^1$H-NMR spectrum (CD$_3$OD, 500 MHz): δ ppm (integral, multiplicity, coupling constant J (Hz)): 0.90(3H,d,J=6.8 Hz), 0.94(3H,t,J=7.3 Hz), 1.08(3H,d,J=6.8 Hz), 1.20(3H, s), 1.21(1H,m), 1.36–1.42(2H,m), 1.42–1.54(3H,m), 1.54–1.66(3H,m), 1.79(3H,s), 2.07(3H,s), 2.40(2H,m), 2.46(1H,m), 2.57(2H,m), 2.66(1H,dd,J=2.4,8.3 Hz), 2.73 (1H,dt,J=2.4,5.9 Hz), 3.52(1H,m), 3.79(1H,m), 5.05(1H, d,J=9.3 Hz), 5.47(1H,dd,J=3.4,11.2 Hz), 5.63(1H,dd, J=8.8,15.1 Hz), 5.69(1H,dd,J=9.3,15.1 Hz), 5.74(1H,ddd, J=3.4,9.8,15.1 Hz), 6.07(1H,d,J=10.8 Hz), 6.31(1H,dd, J=10.8,15.1 Hz)

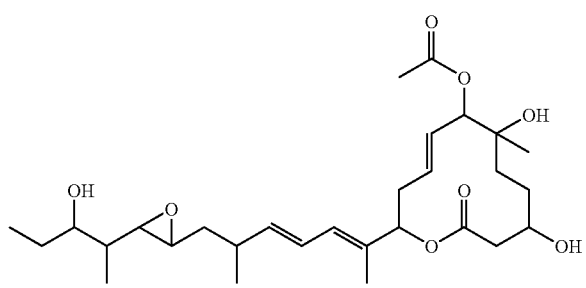

Example A33

Physico-chemical Properties of 11107AA

The physico-chemical properties of 11107AA are shown below. The structure of 11107AA was determined as shown below.
1. Appearance: colorless powder
2. Molecular weight: 534, FAB-MS m/z 535(M+H)$^+$, 557 (M+Na)$^+$
3. Molecular formula: $C_{30}H_{46}O_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3414, 2971, 1733, 1716, 1457, 1374, 1257, 1175
7. $^1$H-NMR spectrum (CD$_3$OD, 500 MHz): δ ppm (integral, multiplicity, coupling constant J (Hz)): 0.87(3H,d,J=6.3 Hz), 1.059(3H,t,J=7.3 Hz), 1.060(3H,d,J=6.3 Hz), 1.19 (3H,s), 1.32–1.44(3H,m), 1.52–1.68(3H,m), 1.72(3H,d, J=1.5 Hz), 1.75(3H,d,J=1.0 Hz), 2.06(3H,s), 2.49–2.57 (4H,m), 2.72(2H,m), 3.78(1H,m), 4.47(1H,m), 5.046(1H, d,J=10.7 Hz), 5.047(1H,d,J=9.3 Hz), 5.57(1H,dd,J=9.9, 15.1 Hz), 5.63(1H,dd,J=8.8,15.1 Hz), 5.70(1H,dd,J=9.3, 15.1 Hz), 6.10(1H,d,J=11.2 Hz), 6.33(1H,dd,J=11.2,15.1 Hz), 6.56(1H,dd,J=1.0,8.3 Hz)

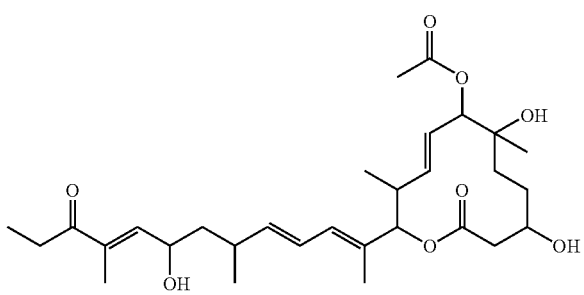

Example A34

Physico-chemical Properties of 11107AB

The physico-chemical properties of 11107AB are shown below. The structure of 11107AB was determined as shown below.
1. Appearance: colorless powder
2. Molecular weight: 552, FAB-MS m/z 551(M-H)$^-$
3. Molecular formula: $C_{30}H_{48}O_9$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3460, 2964, 1732, 1716, 1456, 1374, 1174
7. $^1$H-NMR spectrum (CD$_3$OD, 500 MHz): δ ppm (integral, multiplicity, coupling constant J (Hz)): 0.91(3H,d,J=6.8 Hz), 0.92(3H,d,J=6.8 Hz), 0.94(3H,t,J=7.6 Hz), 1.08(3H, d,J=6.4 Hz), 1.21(1H,m), 1.30–1.70(8H,m), 1.75(3H,d, J=1.0 Hz), 2.08(3H,s), 2.45–2.65(4H,m), 2.66(1H,dd, J=2.0,8.3 Hz), 2.72(1H,dt,J=2.4,5.9 Hz), 3.51(1H,m), 3.75(1H,m), 3.86(1H,d,J=9.8 Hz), 4.07(1H,d,J=11.7 Hz), 4.34(1H,d,J=11.7 Hz), 5.04(1H,d,J=10.7 Hz), 5.44(1H, dd,J=9.7,15.1 Hz), 5.66(1H,dd,J=8.3,15.1 Hz), 5.74(1H, dd,J=9.8,15.4 Hz), 6.09(1H,d,J=10.7 Hz), 6.33(1H,dd, J=10.7,15.1 Hz).

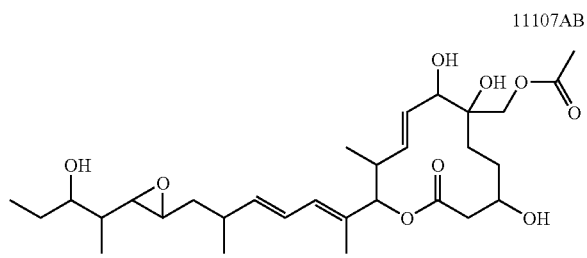

Example A35

Physico-chemical Properties of 11107AC

The physico-chemical properties of 11107AC are shown below. The structure of 11107AC was determined as shown below.
1. Appearance: colorless powder
2. Molecular weight: 492, FAB-MS m/z 493(M+H)$^+$, 515 (M+Na)$^+$
3. Molecular formula: $C_{2-8}H_{44}O_7$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 500 MHz): δ ppm (integral, multiplicity, coupling constant J (Hz)): 0.91(3H,d,J=6.8 Hz), 1.01(3H,t,J=7.1 Hz), 1.07(3H,d,J=6.8 Hz), 1.09(3H,d,J=7.3 Hz), 1.27(3H,s), 1.32–1.38(2H,m), 1.44(1H,m), 1.52–1.62(2H,m), 1.67(1H,m), 1.75(3H,d,J=2.0 Hz), 2.32 (1H,dq,J=8.3,6.8 Hz), 2.48(1H,m), 2.51(2H,m), 2.54–2.61(3H,m), 2.73–2.78(2H,m), 3.70(1H,d,J=9.8 Hz), 3.76(1H,m), 5.03(1H,d,J=10.7 Hz), 5.38(1H,dd,J=9.8,15.1 Hz), 5.66(1H,dd,J=8.8,15.1 Hz), 5.72(1H,dd,J=9.8,15.1 Hz), 6.09(1H,d,J=11.2 Hz), 6.33(1H,dd,J=10.7,15.1 Hz)

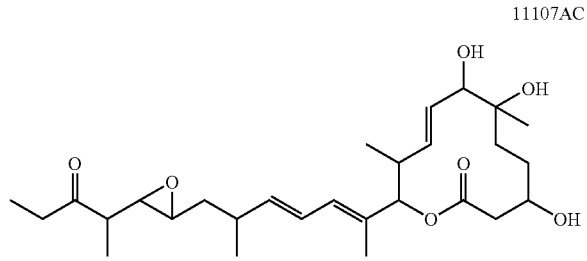

Example A36

Physico-chemical Properties of 11107AD

The physico-chemical properties of 11107AD are shown below. The structure of 11107AD was determined as shown below. Further, the present compound is the stereoisomer of 3-position hydroxy group of 11107B.
1. Appearance: colorless powder
2. Molecular weight: 536, FAB-MS m/z 559(M+Na)$^+$
3. Molecular formula: $C_{30}H_{48}O_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3420, 2960, 1730, 1460, 1380, 1240, 1140
7. $^1$H-NMR spectrum (CD$_3$OD, 500 MHz): δ ppm (integral, multiplicity, coupling constant J (Hz)): 0.86(3H,d,J=6.8 Hz), 0.90(3H,d,J=7.3 Hz), 0.94(3H,t,J=7.3 Hz), 1.08(3H,d,J=6.8 Hz), 1.16(3H,s),1.20(1H,m), 1.36–1.72(8H,m), 1.75(3H,s), 2.06(3H,s), 2.42–2.63(4H,m), 2.66(1H,dd,J=2.4,7.8 Hz), 2.73(1H,dt,J=2.4,5.9 Hz), 3.51(1H,dt,J=8.8,4.4 Hz), 4.23(1H,m), 5.01(1H,d,J=9.8 Hz), 5.04(1H,d,J=10.7 Hz), 5.49(1H,dd,J=10.0,15.1 Hz), 5.67(1H,dd,J=8.3,15.1 Hz), 5.71(1H,dd,J=9.8,15.1 Hz), 6.08(1H,d,J=10.7 Hz), 6.34(1H,dd,J=10.7,15.1 Hz)

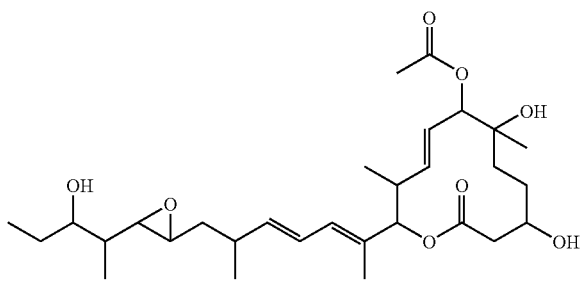

Example A37

Physico-chemical Properties of 11107AE

The physico-chemical properties of 11107AE are shown below. 11107AE was determined to be a mixture of two tautomers, 11107AEa and 11107AEb (1:1) of which structures are shown below.
1. Appearance: colorless powder
2. Molecular weight: 522, FAB-MS m/z 545(M+Na)$^+$
3. Molecular formula: $C_{29}H_{46}O_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3420, 2960, 1735, 1720, 1460, 1375, 1245, 1170
7. $^1$H-NMR spectrum (CD$_3$OD, 500 MHz): δ ppm (integral, multiplicity, coupling constant J (Hz)): 11107AEa: 0.90 (3H,d,J=6.6 Hz), 0.91(3H,d,J=7.0 Hz), 0.94(3H,t,J=7.3 Hz), 1.09(3H,d,J=6.6 Hz), 1.20(1H,m), 1.36–1.68(8H,m), 1.75(3H,s), 2.05(3H,s), 2.47(1H,m), 2.48(1H,dd,J=4.6,14.1 Hz), 2.58(1H,dd,J=3.5,14.1 Hz), 2.62(1H,m), 2.66(1H,dd,J=2.2,8.1 Hz), 2.73(1H,dt,J=2.2,5.9 Hz), 3.51(1H,dt,J=8.1,4.8 Hz), 3.84(1H,m), 3.88(1H,m), 5.04(1H,d,J=10.6 Hz), 5.13(1H,dd,J=2.9,9.9 Hz), 5.59(1H,dd,J=9.7,15.2 Hz), 5.66(1H,dd,J=8.4,15.1 Hz), 5.71(1H,dd,J=9.7,15.2 Hz), 6.10(1H,d,J=10.6 Hz), 6.33(1H,dd,J=10.6,15.1 Hz) 11107AEb: 0.91(3H,d,J=7.0 Hz), 0.92(3H,d,J=7.7 Hz), 0.94(3H,t,J=7.3 Hz), 1.09(3H,d,J=6.6 Hz), 1.20(1H,m), 1.42–1.68(8H,m), 1.76(3H,s), 2.09(3H,s), 2.40(1H,dd,J=5.5,13.9 Hz), 2.47(1H,m), 2.59(1H,dd,J=3.7,13.9 Hz), 2.62(1H,m), 2.66(1H,dd,J=2.2,8.1 Hz), 2.73(1H,dt,J=2.2,5.9 Hz), 3.51(1H,dt,J=8.1,4.8 Hz), 3.87(1H,m), 4.12(1H,dd,J=3.1,9.7 Hz), 5.01(1H,d,J=10.6 Hz), 5.02

(1H,m), 5.47(1H,dd,J=9.7,15.2 Hz), 5.66(1H,dd,J=8.4, 15.1 Hz), 5.72(1H,dd,J=9.7,15.2 Hz), 6.10(1H,d,J=10.6 Hz), 6.33(1H,dd,J=10.6,15.1 Hz)

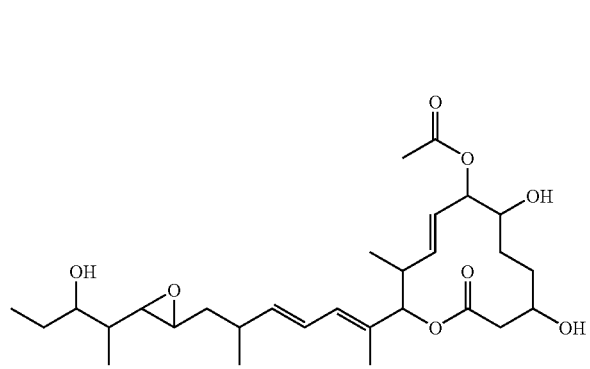

11107AEa

⇅

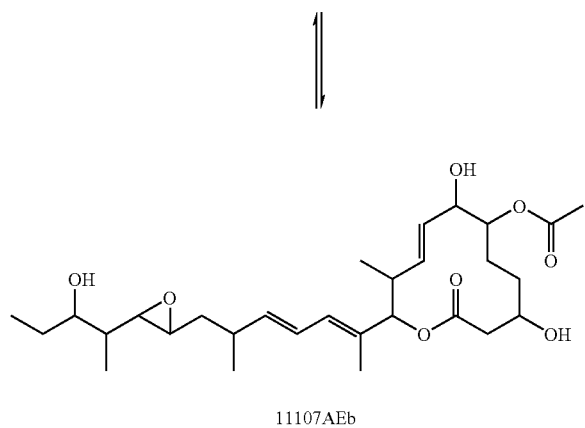

11107AEb

Example A38

Physico-chemical Properties of 11107AF

The physico-chemical properties of 11107AF are shown below. The structure of 11107AF was determined as shown below.

1. Appearance: colorless powder
2. Molecular weight: 496, FAB-MS m/z 497(M+H)$^+$, 519 (M+Na)$^+$
3. Molecular formula: $C_{27}H_{44}O_8$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 500 MHz): δ ppm (integral, multiplicity, coupling constant J (Hz)): 0.87(3H,d,J=6.8 Hz), 0.96(3H,t,J=7.6 Hz), 1.06(3H,d,J=6.8 Hz), 1.19(3H, s), 1.28–1.44(4H,m), 1.52–1.66(4H,m), 1.74(3H,d,J=1.0 Hz), 2.06(3H,s), 2.51–2.60(4H,m), 3.25(1H,m), 3.37(1H, dt,J=2.0,4.9 Hz), 3.78(1H,m), 5.04(1H,d,J=11.7 Hz), 5.05 (1H,d,J=9.8 Hz), 5.56(1H,dd,J=9.8,15.1 Hz), 5.70(1H,dd, J=9.8,15.1 Hz), 5.78(1H,dd,J=8.8,15.1 Hz), 6.09(1H,d, J=10.7 Hz), 6.32(1H,dd,J=10.7,15.1 Hz)

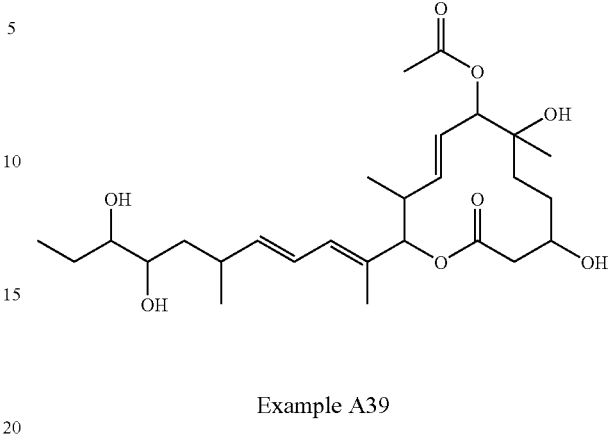

Example A39

Physico-chemical Properties of 11107AG

The physico-chemical properties of 11107AG are shown below. The structure of 11107AG was determined as shown below.

1. Appearance: colorless powder
2. Molecular weight: 556, FAB-MS m/z 579(M+Na)$^+$, 557 (M+H)$^+$, 555(M-H)$^-$
3. Molecular formula: $C_{30}H_{52}O_9$
4. Solubility: soluble in dimethylsulfoxide, pyridine, methanol and acetone, and slightly soluble in water
5. Color reaction: positive for iodine and sulfuric acid
6. Ultraviolet absorption spectrum (methanol): terminal adsorption
7. Infrared absorption spectrum (KBr) cm$^{-1}$: 3270, 2965, 1731, 1714, 1457, 1384, 1255, 1178
8. $^1$H-NMR spectrum (CD$_3$OD, 500 MHz): δ ppm (integral, multiplicity, coupling constant J (Hz)): 0.89(3H,d,J=6.4 Hz), 0.935(3H,d,J=6.8 Hz), 0.939(3H,t,J=7.3 Hz), 0.97 (3H,d,J=6.8 Hz), 1.18(3H,s), 1.24(1H,m), 1.30–1.70(10H,m), 1.64(3H,s), 1.76(1H,m), 1.93(1H,m), 2.06(3H,s), 2.13(1H,m), 2.52(2H,m), 2.54(1H,m), 3.45 (1H,dd,J=2.9,7.8 Hz), 3.56(1H,m), 3.60(1H,m), 3.78(1H, m), 5.04(1H,d,J=10.7 Hz), 5.05(1H,d,J=9.8 Hz), 5.52–5.58(2H,m), 5.69(1H,dd,J=9.8,15.1 Hz)

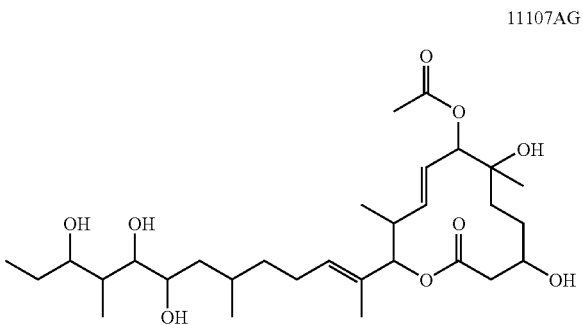

Example A40

Physico-chemical Properties of 11107AH

The physico-chemical properties of 11107AH are shown below. The structure of 11107AH was determined as shown below.
1. Appearance: colorless powder
2. Molecular weight: 494, FAB-MS m/z 495(M+H)$^+$, 517 (M+Na)$^+$, 493(M-H)$^-$
3. Molecular formula: $C_{27}H_{42}O_8$
4. Solubility: soluble in dimethylsulfoxide, pyridine, methanol and acetone, and slightly soluble in water
5. Color reaction: positive for iodine and sulfuric acid
6. Ultraviolet absorption spectrum (methanol): terminal adsorption
7. Infrared absorption spectrum (KBr) cm$^{-1}$: 3367, 2973, 1733, 1716, 1456, 1374, 1257, 1175
8. $^1$H-NMR spectrum (CD$_3$OD, 500 MHz): δ ppm (integral, multiplicity, coupling constant J (Hz)): 0.96(3H,d,J=6.8 Hz), 0.99(3H,d,J=6.8 Hz), 1.00(3H,t,J=7.3 Hz), 1.18(3H, s), 1.28–1.42(5H,m), 1.60(2H,m), 2.06(3H,s), 2.08(2H, m), 2.25(1H,m), 2.33(1H,m), 2.53(2H,m), 2.63(2H,m), 3.78(1H,m), 5.02–5.07(2H,m), 5.36(1H,dd,J=8.3,15.1 Hz), 5.55(1H,dd,J=9.8,15.1 Hz), 5.56(1H,d,J=15.1 Hz), 5.66(1H,dd,J=9.8,15.1 Hz), 5.71(1H,dd,J=7.3,15.1 Hz), 5.76(1H,ddd,J=7.3,7.8,15.1 Hz)

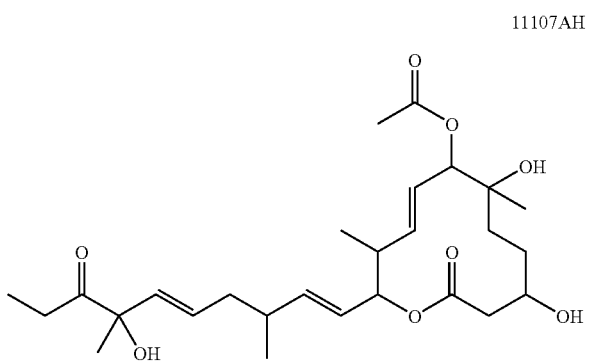

11107AH

Example A41

Physico-chemical Properties of 11107AI

The physico-chemical properties of 11107AI are shown below. The structure of 11107AI was determined as shown below.
1. Appearance: colorless powder
2. Molecular weight: 508, FAB-MS m/z 531(M+Na)$^+$
3. Molecular formula: $C_{29}H_{48}O_7$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 500 MHz): δ ppm (integral, multiplicity, coupling constant J (Hz)): 0.91(6H,s), 0.94 (3H,t,J=7.3 Hz), 1.09(3H,d,J=6.8 Hz), 1.19(3H,d,J=6.8 Hz), 1.21(1H,m), 1.26(3H,s), 1.28–1.38(2H,m), 1.42–1.58(4H,m), 1.60–1.68(2H,m), 1.74(3H,s), 2.48(1H,m), 2.54–2.63(2H,m), 2.66(1H,dd,J=2.4,8.3 Hz), 2.73(1H,dt,J=2.4,5.9 Hz), 3.46–3.54(2H,m), 3.68(1H,d, J=9.8 Hz), 4.99(1H,d,J=10.7 Hz), 5.37(1H,dd,J=9.8,15.1 Hz), 5.66(1H,dd,J=8.3,15.1 Hz), 5.71(1H,dd,J=9.8,15.1 Hz), 6.08(1H,d,J=10.7 Hz), 6.33(1H,dd,J=10.7,15.1 Hz)

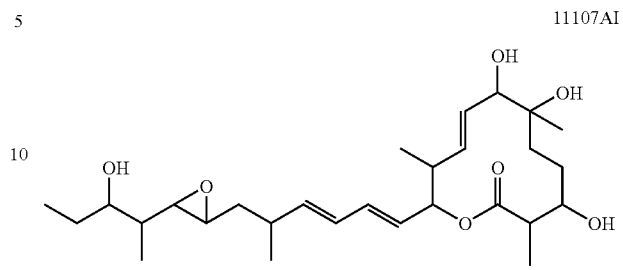

11107AI

Example A42

Physico-chemical Properties of 11107AJ

The physico-chemical properties of 11107AJ were shown below. The structure of 11107AJ was determined as shown below.
1. Appearance: colorless powder
2. Molecular weight: 536, FAB-MS m/z 559(M+Na)$^+$
3. Molecular formula: $C_{30}H_{48}O_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3420, 2960, 1735, 1460, 1375, 1255, 1180
7. $^1$H-NMR spectrum (CD$_3$OD, 500 MHz): δ ppm (integral, multiplicity, coupling constant J (Hz)): 0.88(3H,d,J=6.8 Hz), 1.01(3H,d,J=6.3 Hz), 1.02(3H,d,J=6.8 Hz), 1.11(3H, d,J=6.3 Hz), 1.19(3H,s), 1.36–1.42(2H,m), 1.54–1.68(2H, m), 1.73(3H,s), 2.00–2.08(5H,m), 2.25(2H,m), 2.53–2.60 (3H,m), 3.27(1H,dd,J=4.9,7.3 Hz), 3.70(1H,dq,J=4.9,6.3 Hz), 3.78(1H,m), 5.04(1H,d,J=9.8 Hz), 5.05(1H,d,J=9.8 Hz), 5.34(1H,dd,J=8.3,15.1 Hz), 5.41(1H,dt,J=15.1,7.3 Hz), 5.57(1H,dd,J=9.8,15.1 Hz), 5.65(1H,dd,J=7.3,15.1 Hz), 5.70(1H,dd,J=9.8,15.1 Hz), 6.07(1H,d,J=11.2 Hz), 6.33(1H,dd,J=11.2,15.1 Hz)

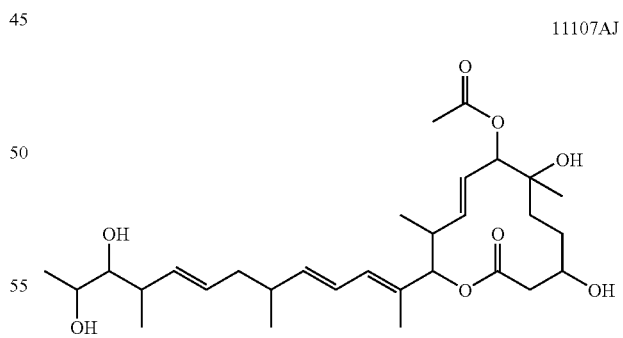

11107AJ

Example A43

Physico-chemical Properties of 11107AK

The physico-chemical properties of 11107AK are shown below. The structure of 11107AK was determined as shown below.
1. Appearance: colorless powder 2. Molecular weight: 464, FAB-MS m/z 487(M+Na)$^+$
3. Molecular formula: $C_{27}H_{44}O_6$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3300, 2960, 1725, 1715, 1455, 1370, 1255, 1020
7. $^1$H-NMR spectrum (CD$_3$OD, 500 MHz): δ ppm (integral, multiplicity, coupling constant J (Hz)): 0.89(3H,d,J=6.8 Hz), 0.90(3H,d,J=6.8 Hz), 0.94(3H,t,J=7.6 Hz), 1.08(3H, d,J=6.8 Hz), 1.10–1.74(11H,m), 1.75(3H,s), 2.32(1H,dd, J=6.8,13.7 Hz), 2.48(1H,m), 2.56(1H,m), 2.63(1H,dd, J=4.1,13.7 Hz), 2.66(1H,dd,J=2.4,8.3 Hz), 2.73(1H,dt, J=2.4,6.3 Hz), 3.51(1H,m), 3.89(1H,m), 3.98(1H,dt, J=3.9,9.8 Hz), 4.95(1H,d,J=10.7 Hz), 5.32(1H,dd,J=9.5, 15.1 Hz), 5.43(1H,dd,J=9.3,15.1 Hz), 5.66(1H,dd,J=8.3, 14.9 Hz), 6.08(1H,d,J=11.0 Hz), 6.32(1H,dd,J=11.0,14.9 Hz)

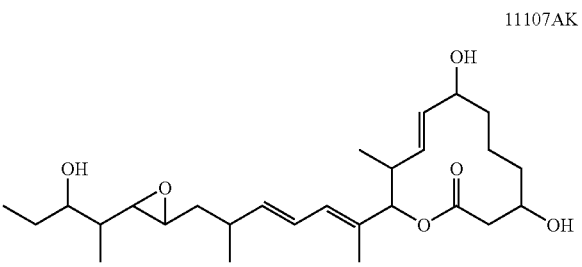

Example A44

Physico-chemical Properties of 11107AL

The physico-chemical properties of 11107AL are shown below. The structure of 11107AL was determined as shown below.

1. Appearance: colorless powder
2. Molecular weight: 532, FAB-MS m/z 555(M+Na)$^+$, 531 (M-H)$^-$
3. Molecular formula: $C_{30}H_{44}O_8$
4. Solubility: soluble in dimethylsulfoxide, pyridine, methanol and acetone, and slightly soluble in water
5. Color reaction: positive for iodine and sulfuric acid
6. Infrared absorption spectrum: 3497, 2973, 1733, 1715, 1457, 1373, 1242, 1173
8. $^1$H-NMR spectrum (CD$_3$OD, 400 MHz): δ ppm (integral, multiplicity, coupling constant J (Hz)): 0.81(3H,d,J=7.2 Hz), 1.00(3H,t,J=7.3 HZ), 1.05(3H,d,J=7.0 Hz), 1.07(3H, d,J=7.3 Hz), 1.25(3H,s), 1.39–1.43(1H,m), 1.63–1.68(1H, m), 1.71(3H,d,J=1.1 Hz), 2.07(3H,s), 2.28–2.32(1H,m), 2.42–2.52(2H,m), 2.53–2.65(4H,m), 2.72–2.76(2H,m), 4.50–4.53(1H,m), 4.95(1H,d,J=10.6 Hz), 4.99(1H, d,J=9.5 Hz), 5.29(1H,dd,J=9.9,15.0 Hz), 5.52(1H,dd,J=9.5, 15.0 Hz), 5.58(1H,dd,J=1.8,15.4 Hz), 5.63(1H,dd,J=8.4, 15.0 Hz), 5.67(1H,dd,J=2.9,15.4 Hz), 6.03(1H,d,J=11.0 Hz), 6.31(1H,dd,J=11.0,15.0 Hz)

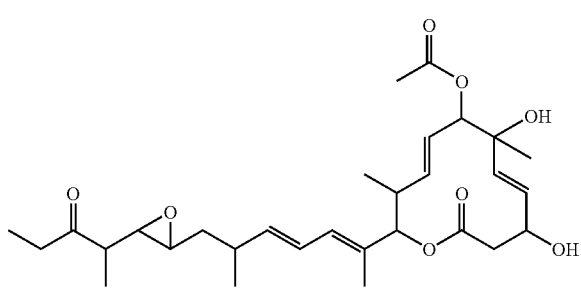

Example A45

Physico-chemical Properties of 11107AM

The physico-chemical properties of 11107AM are shown below. The structure of 11107AM was determined as shown below.

1. Appearamce: colorless powder
2. Molecular weight: 534, FAB-MS m/z 557(M+Na)$^+$, 533 (M-H)$^-$
3. Molecular formula: $C_{30}H_{46}O_8$
4. Solubility: soluble in dimethylsulfoxide, pyridine, methanol and acetone, and slightly soluble in water
5. Color reaction: positive for iodine and sulfuric acid
6. Infrared absorption spectrum: 3461, 2965, 1733, 1716, 1457, 1374, 1242, 1174
7. $^1$H-NMR spectrum (CD$_3$OD, 400 MHz): δ ppm (integral, multiplicity, coupling constant J (Hz)): 0.87(3H,d,J=7.0 Hz), 0.89(3H,d,J=7.0 Hz), 0.94(3H,t,J=7.3 Hz), 1.08(3H, d,J=6.6 Hz), 1.17–1.21(1H,m), 1.42–1.55(6H,m), 1.61–1.67(2H,m), 1.76(3H,d,J=1.1 Hz), 2.00(3H,s), 2.19 (1H,dd,J=9.2,12.8 Hz), 2.45–2.50(1H,m), 2.54(1H,d, J=4.8 Hz), 2.56–2.61(1H,m), 2.65(1H,dd,J=2.2,8.0 Hz), 2.70(1H,dd,J=4.0,12.8 Hz), 2.72(1H,dt,J=2.2,5.9 Hz), 2.82(1H,d,J=4.8 Hz), 3.51(1H,dt,J=8.4,4.4 Hz), 4.06–4.12(1H,m), 4.99(1H,d,J=10.6 Hz), 5.36(1H,d, J=9.5 Hz), 5.62–5.69(3H,m), 6.10(1H,d,J=11.0 Hz), 6.33 (1H,dd,J=11.0,15.0 Hz)

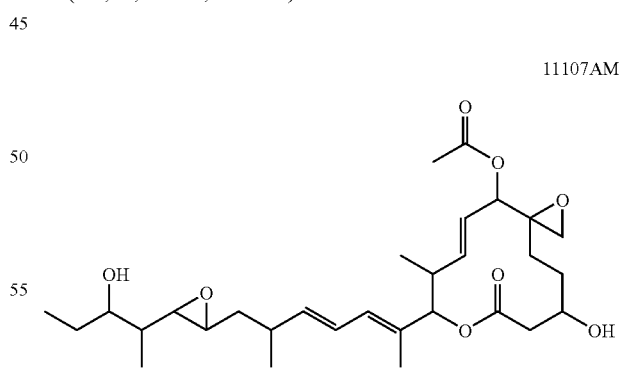

Example A46

Physico-chemical Properties of 11107AN

The physico-chemical properties of 11107AN are shown below. The structure of 11107AN was determined as shown below.

1. Appearance: colorless powder
2. Molecular weight: 532, FAB-MS m/z 531(M-H)⁻
3. Molecular formula: $C_{30}H_{44}O_8$
4. Solubility: soluble in dimethylsulfoxide, pyridine, methanol and acetone, and slightly soluble in water
5. Color reaction: positive for iodine and sulfuric acid
6. ¹H-NMR spectrum (CD₃OD, 400 MHz): δ ppm (integral, multiplicity, coupling constant J (Hz)): 0.84(3H,d,J=7.0 Hz), 0.89(3H,d,J=7.0 Hz), 0.93(3H,t,J=7.3 Hz), 1.08(3H, d,J=7.0 Hz), 1.16–1.18(1H,m), 1.42–1.51(3H,m), 1.60–1.65(1H,m), 1.73(3H,d,J=0.7 Hz), 2.02(3H,s), 2.45–2.53(3H,m), 2.62(1H,d,J=5.5 Hz), 2.65(1H,dd, J=2.2,8.1 Hz), 2.71(1H,dt,J=2.2,5.8 Hz), 2.72(1H,dd, J=5.5,13.2 Hz), 2.96(1H,d,J=5.5 Hz), 3.51(1H,dt,J=8.4, 4.4 Hz), 4.47(1H,m), 4.97(1H,d,J=10.6 Hz), 5.39(1H,dd, J=8.4,15.0 Hz), 5.43(1H,d,J=9.9 Hz), 5.47(1H,dd,J=9.1, 15.0 Hz), 5.64(1H,dd,J=8.8,14.7 Hz), 5.78(1H,dd,J=1.8, 15.4 Hz), 5.86(1H,dd,J=3.2,15.4 Hz), 6.06(1H,d,J=10.6 Hz), 6.31(1H,dd,J=10.6,14.7 Hz)

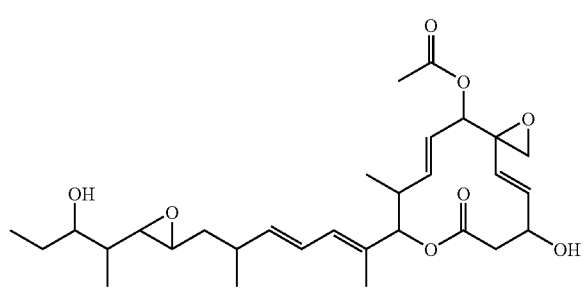

Example A47

Physico-chemical Properties of 11107AP

The physico-chemical properties of 11107AP are shown below. The structure of 11107AP was determined as shown below.
1. Appearance: colorless powder
2. Molecular weight: 576, FAB-MS m/z 575(M-H)⁻
3. Molecular formula: $C_{32}H_{48}O_9$
4. Solubility: soluble in dimethylsulfoxide, pyridine, methanol and acetone, and slightly soluble in water
5. Color reaction: positive for iodine and sulfuric acid
6. ¹H-NMR spectrum (CD₃OD, 400 MHz): δ ppm (integral, multiplicity, coupling constant J (Hz)): 0.83(3H,d,J=7.0 Hz), 0.89(3H,d,J=7.0 Hz), 0.93(3H,t,J=7.3 Hz), 1.08(3H, d,J=7.0 Hz), 1.16–1.21(1H,m), 1.42–1.51(3H,m), 1.60–1.63(1H,m), 1.61(3H,s), 1.74(3H,d,J=1.1 Hz), 2.06 (3H,s), 2.10(3H,s), 2.45–2.52(2H,m), 2.58(2H,m), 2.65 (1H,dd,J=2.2,8.1 Hz), 2.72(1H,dt,J=2.2,5.9 Hz), 3.51(1H, dt,J=8.4,4.4 Hz), 4.47–4.52(1H,m), 4.97(1H,d,J=10.6 Hz), 4.98(1H,d,J=9.5 Hz), 5.37(1H,dd,J=10.0,15.4 Hz), 5.45(1H,dd,J=2.6,15.8 Hz), 5.57(1H,dd,J=9.5,15.4 Hz), 5.58(1H,dd,J=2.2,15.8 Hz), 5.64(1H,dd,J=8.4,15.0 Hz), 6.04(1H,d,J=10.2 Hz), 6.31(1H,dd,J=10.2,15.0 Hz)

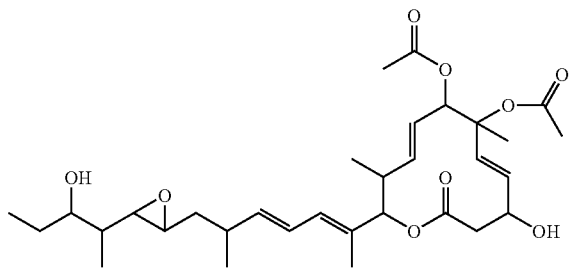

Example A48

Physico-chemical Properties of 11107AQ

The physico-chemical properties of 11107AQ are shown below. The structure of 11107AQ was determined as shown below.
1. Appearance: colorless powder
2. Molecular weight: 578, FAB-MS m/z 577(M-H)⁻
3. Molecular formula: $C_{32}H_{50}O_9$
4. Solubility: soluble in dimethylsulfoxide, pyridine, methanol and acetone, and slightly soluble in water
5. Color reaction: positive for iodine and sulfuric acid
6. Infrared absorption spectrum: 3461, 2968, 1733, 1716, 1457, 1373, 1230, 1175
7. ¹H-NMR spectrum (CD₃OD, 400 MHz): δ ppm (integral, multiplicity, coupling constant J (Hz)): 0.89(3H,d,J=6.6 Hz), 0.90(3H,d,J=7.0 Hz), 0.94(3H,t,J=7.3 Hz), 1.08(3H, d,J=7.0 Hz), 1.17–1.22(1H,m), 1.42–1.52(5H,m), 1.55 (3H,s), 1.56–1.66(3H,m), 1.75(3H,d,J=1.1 Hz), 2.04(3H, s), 2.05(3H,s), 2.45–2.50(1H,m), 2.49(2H,d,J=3.7 Hz), 2.57–2.64(1H,m), 2.65(1H,dd,J=2.2,8.0 Hz), 2.72(1H,dt, J=2.2,5.9 Hz), 3.51(1H,dt,J=8.4,4.6 Hz), 3.78–3.81(1H, m), 5.05(1H,d,J=10.6 Hz), 5.13(1H,d,J=9.5 Hz), 5.62(1H, dd,J=9.5,15.0 Hz), 5.68(1H,dd,J=6.9,15.0 Hz), 5.74(1H, dd,J=9.5,15.0 Hz), 6.10(1H,d,J=11.0 Hz), 6.32(1H,dd, J=11.0,15.0 Hz)

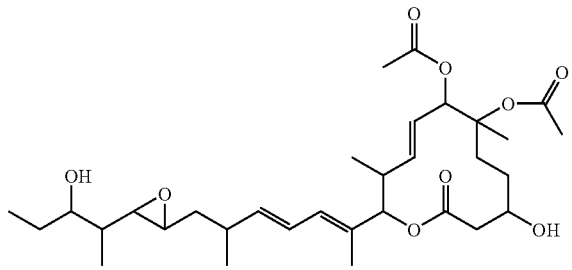

Example A49

Physico-chemical Properties of 11107AR

The physico-chemical properties of 11107AR are shown below. The structure of 11107AR was determined as shown below.
1. Appearance: colorless powder 2. Molecular weight: 394, ESI-MS m/z 811(2M+Na)$^+$
3. Molecular formula: $C_{22}H_{34}O_6$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 400 MHz): δ ppm (integral, multiplicity, coupling constant J (Hz)): 0.87(3H,d,J=7.0 Hz), 0.97(3H,d,J=7.0 Hz), 1.24(3H,d,J=6.6 Hz), 1.29–1.36(2H,m), 1.59–1.61(2H,m), 1.75(3H,d,J=1.1 Hz), 1.89–1.93(1H,m), 2.00(3H,s), 2.43(1H,dd,J=5.5, 14.2 Hz), 2.51–2.58(2H,m), 3.75–3.81(1H,m), 4.27–4.33 (1H,m), 4.91(1H,dd,J=8.8,10.3 Hz), 5.01(1H,d,J=10.6 Hz), 5.42(1H,dd,J=8.8,15.0 Hz), 5.50(1H,dd,J=9.2,15.0 Hz), 5.77(1H,dd,J=6.2,15.0 Hz), 6.11(1H,d,J=11.0 Hz), 6.45(1H,ddd,J=1.1,11.0,15.0 Hz)

11107AR

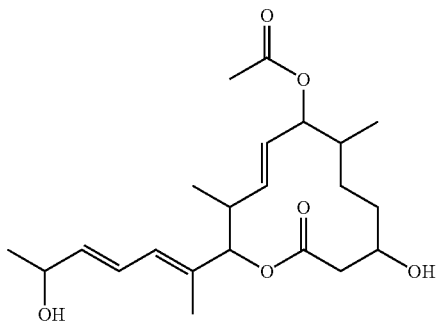

Example A50

Purification of 11107AO, aS, aT, aU and BC

The crude active fraction B (970 mg) was dissolved in 20 ml of a mix solution consisting of tetrahydrofuran-50% aqueous acetonitrile (1:2; v/v), and subjected to ODS column chromatography (ODS-AM 120-S50, manufactured by YMC Co., 750 g). The column was eluted with a mix solution (5 L) consisting of acetonitrile and water (45:55; v/v), crude active fraction B4 containing 11107AS, 11107AT, 11107AU and 11107BC which was eluted from 825 ml to 1650 ml and crude active fraction B5 containing 11107AO which was eluted from 2400 ml to 2565 ml were collected, and the respective fractions were concentrated to dryness under reduced pressure, to give 54 mg of crude active fraction B4 and 25 mg of crude active fraction B5.

The resulting active fraction B4 (34.7 mg) was subjected to preparative high performance liquid chromatography (HPLC) under the following preparative HPLC condition (D1). A fraction containing 11107AT, a fraction containing 11107AS and a fraction containing 11107 AU and 11107BC were collected, and the solvent was removed. The fraction containing 11107AT was further subjected to the preparative high performance liquid chromatography (HPLC) under the following preparative HPLC conditions (D2) to give a 11107AT solution. Then, the solvent was removed to give 11107AT (2.8 mg). Similarly, the fraction containing 11107AS was also subjected to preparative high performance liquid chromatography (HPLC) under the following preparative HPLC condition (D2) to give 11107AS (1.8 mg). The fraction containing 11107 AU and 11107BC was subjected to preparative high performance liquid chromatography (HPLC) under the following preparative HPLC condition (D3) to give a 11107AU solution and a 11107BC solution. Then, the each solvent was removed to give 11107AU (1.1 mg) and 11107BC (0.5 mg). Further, the resulting crude active fraction B5 (24 mg) was subjected to preparative high performance liquid chromatography (HPLC) under the following preparative HPLC condition (D4) to give a 11107AO solution. Then, the solvent was removed to give 11107AO (0.9 mg).

Preparative HPLC condition (D1)
  Column: YMC J'sphere ODS-M80 JM-343, φ20 mm×250 mm (manufactured by YMC Co.)
  Temperature: 40° C.
  Flow rate: 5 ml/min.
  Detection: 200 nm
  Eluent: acetonitrile/water (3:7, v/v) isocratic Preparative HPLC condition (D2)
  Column: CAPCELL PAK C18 SG120, φ420 mm×250 mm (manufactured by SHISEIDO Co.)
  Temperature: 40° C.
  Flow rate: 5 ml/min.
  Detection: 240 nm
  Eluent: methanol/water (5:5, v/v) isocratic Preparative HPLC condition (D3)
  Column: CAPCELL PAK C18 SG120, φ20 mm×250 mm (manufactured by SHISEIDO Co.)
  Temperature: 40° C.
  Flow rate: 5 ml/min.
  Detection: 200 nm
  Eluent: methanol/water (5:5, v/v) isocratic Preparative HPLC condition (D4)
  Column: CAPCELL PAK C18 SG120, φ20 mm×250 mm (manufactured by SHISEIDO Co.)
  Temperature: 40° C.
  Flow rate: 5 ml/min.
  Detection: 200 nm
  Eluent: methanol/water (6:4, v/v) isocratic The retention time of the above-mentioned compounds when analysis was carried out under the following analytic HPLC conditions are shown below.

Analytic HPLC condition (d1)
  Column: YMC J'sphere ODS-M80 JM-307, φ4.6 mm×75 mm (manufactured by YMC Co.)
  Temperature: 40° C.
  Flow rate: 1 ml/min.
  Detection: 240 nm
  Eluent: acetonitrile/water (3:7, v/v) isocratic
  Retention time:
  11107AT: 6.9 min.

Analytic HPLC condition (d2)
  Column: CAPCELL PAK C18 SG120, φ4.6 mm×250 mm (manufactured by SHISEIDO Co.)
  Temperature: 40° C.
  Flow rate: 1 ml/min.
  Detection: 240 nm
  Eluent: methanol/water (5:5, v/v) isocratic
  Retention time:
  11107AS: 19.4 min.
  11107AU: 34.3 min.

Analytic HPLC condition (d3)
  Column: CAPCELL PAK C18 SG120, φ4.6 mm×250 mm (manufactured by SHISEIDO Co.)
  Temperature: 40° C.
  Flow rate: 1 ml/min.

Detection: 200 nm
Eluent: methanol/water (5:5, v/v) isocratic
Retention time:
11107BC: 31.0 min.

Analytic HPLC condition (d4)
Column: CAPCELL PAK C18 SG120, φ4.6 mm×250 mm (manufactured by SHISEIDO Co.)
Temperature: 40° C.
Flow rate: 1 ml/min.
Detection: 240 nm
Eluent: acetonitrile/water (4:6, v/v) isocratic
Retention time:
11107AO: 11.6 min.

Example A51

Physico-chemical Properties of 11107AO

The physico-chemical properties of 11107AO are shown below. The structure of 11107AO was determined as shown below.
1. Appearance: colorless powder
2. Molecular weight: 492, FAB-MS m/z 515(M+Na)$^+$
3. Molecular formula: $C_{28}H_{44}O_7$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3407, 2965, 1731, 1716, 1456, 1384, 1249, 1178
7. $^1$H-NMR spectrum (CD$_3$OD, 500 MHz): δ ppm (integral, multiplicity, coupling constant J (Hz)): 0.907(3H,d,J=6.8 Hz), 0.912(3H,d,J=6.8 Hz), 0.94(3H,t,J=7.6 Hz), 1.09 (3H,d,J=6.8 Hz), 1.21(1H,m), 1.44–1.55(5H,m), 1.61–1.72(2H,m), 1.76(3H,d,J=1.0 Hz), 1.86(1H,m), 2.31 (1H,dd,J=7.3,13.7 Hz), 2.48(1H,m), 2.53(1H,d,J=5.9 Hz), 2.60(1H,ddq,J=9.3,10.7,6.8 Hz), 2.64(1H,dd,J=3.4,13.7 Hz), 2.66(1H,dd,J=2.4,8.3 Hz), 2.73(1H,dt,J=2.4,5.9 Hz), 3.02(1H,d,J=5.9 Hz), 3.52(1H,dt,J=8.8,4.9 Hz), 3.97(1H, m), 4.20(1H,d,J=9.3 Hz), 5.00(1H,d,J=10.7 Hz), 5.49(1H, dd,J=9.3,15.1 Hz), 5.62(1H,dd,J=9.3,15.1 Hz), 5.67(1H, dd,J=8.3,15.1 Hz), 6.10(1H,d,J=10.7 Hz), 6.33(1H,dd, J=10.7,15.1 Hz)

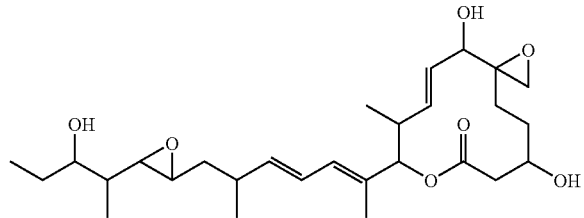

11107AO

Example A52

Physico-chemical Properties of 11107AS

The physico-chemical properties of 11107AS are shown below. The structure of 11107AS was determined as shown below.
1. Appearance: colorless powder
2. Molecular weight: 552, FAB-MS m/z 553(M+H)$^+$, 575 (M+Na)$^+$
3. Molecular formula: $C_{30}H_{48}O_9$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3403, 2968, 1732, 1715, 1457, 1373, 1256, 1177
7. $^1$H-NMR spectrum (CD$_3$OD, 500 MHz): δ ppm (integral, multiplicity, coupling constant J (Hz)): 0.88(3H,d,J=6.8 Hz), 1.00(3H,d,J=7.3 Hz), 1.05(3H,d,J=6.8 Hz), 1.19(3H, s), 1.25(3H,d,J=6.4 Hz), 1.34–1.44(3H,m), 1.54–1.68(2H, m), 1.72(1H,m), 1.75(3H,d,J=1.0 Hz), 2.06(3H,s), 2.14 (1H,ddq,J=2.9,5.4,7.3 Hz), 2.53(2H,m), 2.56(2H,m), 3.42 (1H,dd,J=2.9,4.4 Hz), 3.53(1H,m), 3.65(1H,dq,J=4.4,6.4 Hz), 3.72(1H,dd,J=5.4,8.3 Hz), 3.78(1H,m), 5.05(1H,d, J=9.8 Hz), 5.06(1H,d,J=10.7 Hz), 5.57(1H,dd,J=9.8,15 Hz), 5.61(1H,dd,J=8.3,15.1 Hz), 5.70(1H,dd,J=9.8,15.1 Hz), 6.10(1H,d,J=10.7 Hz), 6.33(1H,dd,J=10.7,15.1 Hz)

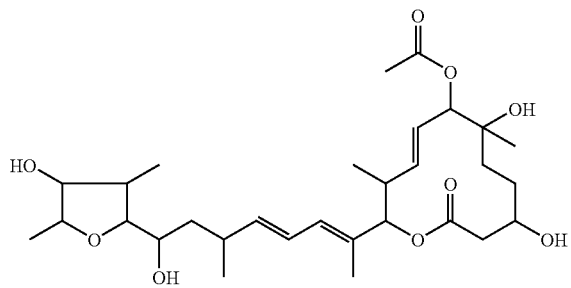

11107AS

Example A53

Physico-chemical Properties of 11107AT

The physico-chemical properties of 11107AT are shown below. The structure of 11107AT was determined as shown below. Further, the present compound is the stereoisomer of 5-position methyl group of a furan ring of 11107AS.
1. Appearance: colorless powder
2. Molecular weight: 552, FAB-MS m/z 553(M+H)$^+$, 575 (M+Na)$^+$
3. Molecular formula: $C_{30}H_{48}O_9$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3353, 2967, 1732, 1715, 1456, 1373, 1256, 1177
7. $^1$H-NMR spectrum (CD$_3$OD, 500 MHz): δ ppm (integral, multiplicity, coupling constant J (Hz)): 0.87(3H,d,J=6.4 Hz), 0.96(3H,d,J=7.3 Hz), 1.05(3H,d,J=6.8 Hz), 1.16(3H, d,J=6.4 Hz), 1.19(3H,s), 1.34–1.44(3H,m), 1.54–1.67(2H, m), 1.73(1H,m), 1.74(3H,s), 2.06(3H,s), 2.29(1H,m), 2.52 (2H,m), 2.56(2H,m), 3.49(1H,m), 3.75–3.81(2H,m), 3.86 (1H,dd,J=4.9,9.3 Hz), 4.15(1H,dq,J=3.9,6.3 Hz), 5.047 (1H,d,J=9.8 Hz), 5.052(1H,d,J=10.7 Hz), 5.57(1H,dd, J=9.8,15.1 Hz), 5.61(1H,dd,J=8.3,15.1 Hz), 5.70(1H,dd, J=9.8,15.1 Hz), 6.10(1H,d,J=10.7 Hz), 6.33(1H,dd, J=10.7,15.1 Hz)

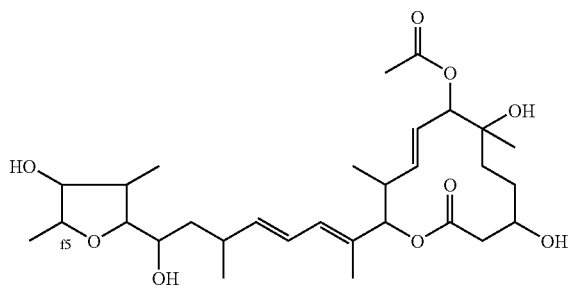

11107AT

Example A54

Physico-chemical Properties of 11107AU

The physico-chemical properties of 11107AU are shown below. The structure of 11107AU was determined as shown below.

1. Appearance: colorless powder
2. Molecular weight: 552, FAB-MS m/z 553(M+H)+, 575 (M+Na)+
3. Molecular formula: $C_{30}H_{48}O_9$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3402, 2968, 1733, 1717, 1457, 1373, 1256, 1178
7. $^1$H-NMR spectrum (CD$_3$OD, 500 MHz): δ ppm (integral, multiplicity, coupling constant J (Hz)): 0.88(3H,d,J=6.8 Hz), 0.97(3H,t,J=7.3 Hz), 1.06(3H,d,J=6.8 Hz), 1.12(3H, s), 1.19(3H,s), 1.28–1.42(2H,m), 1.42–1.56(2H,m), 1.56–1.65(3H,m), 1.70(1H,m), 1.74(3H,s), 2.06(3H,s), 2.47(1H,m), 2.53(2H,m), 2.57(1H,tq,9.8,6.8 Hz), 3.57 (1H,dd,J=3.9,9.8 Hz), 3.62(1H,ddd,J=4.4,6.8,8.6 Hz), 3.70(1H,d,J=6.8 Hz), 3.78(1H,m), 5.05(2H,d,J=9.8 Hz), 5.57(1H,dd,J=9.8,15.1 Hz), 5.70(1H,dd,J=9.8,15.1 Hz), 5.73(1H,dd,J=7.8,15.1 Hz), 6.08(1H,d,J=10.7 Hz), 6.28 (1H,dd,J=10.7,15.1 Hz)

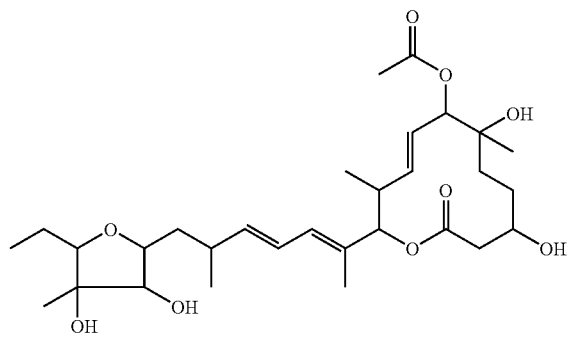

11107AU

Example A55

Physico-chemical Properties of 11107BC

The physico-chemical properties of 11107BC are shown below. The structure of 11107BC was determined as shown below.

1. Appearance: colorless powder
2. Molecular weight: 496, FAB-MS m/z 519(M+Na)+, 495 (M-H)−
3. Molecular formula: $C_{27}H_{44}O_8$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3361, 2965, 1723, 1458, 1383, 1249, 1174
7. $^1$H-NMR spectrum (CD$_3$OD, 500 MHz): δ ppm (integral, multiplicity, coupling constant J (Hz)): 0.97(3H,d,J=6.8 Hz), 0.98(3H,t,J=7.3 Hz), 1.01(3H,d,J=6.8 Hz), 1.18(3H, s), 1.20(3H,s), 1.24–1.44(3H,m), 1.52–1.66(3H,m), 2.06 (3H,s), 2.08(2H,m), 2.26(1H,m), 2.34(1H,m), 2.53(2H, m), 3.18(1H,dd,J=2.2,10.8 Hz), 3.78(1H,m), 5.04(1H,d, J=9.8 Hz), 5.05(1H,m), 5.37(1H,dd,J=8.3,15.1 Hz), 5.54–5.68(3H,m), 5.66(1H,dd,J=9.8,15.1 Hz), 5.74(1H, dd,J=7.3,15.1 Hz)

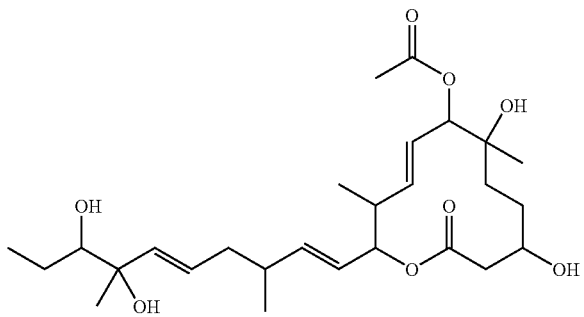

11107BC

Example A56

Purification of 11107AV, aW, aX, aY, aZ, BA, BB, BD, BE, BF and BG

The crude active fraction B (1.47 g) was dissolved in a mix solution (20 ml) consisting of tetrahydrofuran-50% aqueous acetonitrile (1:2; v/v), and subjected to an ODS column chromatography (ODS-AM 120-S50, manufactured by YMC co., 750 g). The column was eluted with a mix solution (5 L) consisting of acetonitrile and water (45:55; v/v). The crude active fraction B6 containing 11107AV, 11107AW, 11107AX, 11107AY, 11107AZ, 11107BA, 11107BB, 11107BD, 11107BE, 11107BF and 11107BG which was eluted from 1140 ml to 1650 ml was collected, and concentrated to dryness under reduced pressure to give 87 mg of the crude active fraction B6.

The resulting crude active fraction B6 (81.7 mg) was subjected to the preparative high performance liquid chromatography (HPLC) under the following preparative HPLC condition (E1), a fraction containing 11107BB, a fraction containing 11107BA, a fraction containing 11107AW, 11107AX, 11107AY, 11107BG and 11107BE, a fraction containing 11107AV, a fraction containing 11107BD and 11107BF, and a fraction containing 11107AZ were collected separately, and the solvent was removed. The fraction containing 11107BB was subjected to repeated use of a high performance liquid chromatography (HPLC) under the following preparative HPLC conditions (E2) and (E3) in turn, to give 11107BB (0.1 mg). The fraction containing 11107BA was subjected further to preparative high performance liquid chromatography (HPLC), under the following preparative HPLC conditions (E3) to give 11107BA (0.3 mg). The fraction containing 11107AW, 11107AX, 11107AY, 11107BG and 11107BE was subjected further to preparative high performance liquid chromatography (HPLC), under the following preparative HPLC condition (E4), and a 11107AW solution, a fraction containing 11107AX, a fraction containing 11107AY, a fraction containing 11107BG and a fraction containing 11107BE were collected separately. As for 11107AW, 11107AW (0.6 mg) was given by removal of the solvent. After removing the solvent of the fraction containing 11107AY, it was subjected further to preparative high performance liquid chromatography (HPLC) under the following preparative HPLC condition (E2) to give 11107AY (0.2 mg). With respect to the fraction containing 11107AX, after removing the solvent, it was subjected further to preparative high performance liquid chromatography (HPLC) under the following preparative HPLC condition (E2) to give 11107AX (0.5 mg). Also, with respect to the fraction containing 11107BG, after removing the solvent, it was subjected further to preparative high performance liquid chromatography (HPLC) under the following preparative HPLC condition (E2) to give 11107BG (0.2 mg). After removing the solvent of the fraction containing 11107BE, it was subjected further to repeated use of a preparative high performance liquid chromatography (HPLC) under the following preparative HPLC conditions (E5), (E4) and (E6) in turn, to give 11107BE (0.2 mg). The fraction containing 11107AV was subjected to preparative high performance liquid chromatography (HPLC) under the following preparative HPLC condition (E7) to give 11107AV (0.5 mg). The fraction containing 11107BD and 11107BF was subjected further to preparative high performance liquid chromatography (HPLC) under the following preparative HPLC condition (E8) to give a fraction containing 11107BD and a fraction containing 11107BF. The fraction containing 11107BD was subjected further to preparative high performance liquid chromatography (HPLC) under the following preparative HPLC condition (E7) to give 11107BD (0.1 mg), and the fraction containing 11107BF was also subjected further to preparative high performance liquid chromatography (HPLC) under the following preparative HPLC condition (E7) to give 11107BF (0.1 mg). The fraction containing 11107AZ was subjected to preparative high performance liquid chromatography (HPLC) under the following preparative HPLC condition (E8) to give a 11107AZ solution, and then the solvent was removed to give 11107AZ (0.1 mg).

Preparative HPLC condition (E1)
  Column: YMC J'sphere ODS-M80 JM-343, φ20 mm×250 mm (manufactured by YMC Co.)
  Temperature: 40° C.
  Flow rate: 5 ml/min.
  Detection: 200 nm
  Eluent: acetonitrile/water (3:7, v/v) isocratic Preparative HPLC condition (E2)
  Column: CAPCELL PAK C18 SG120, φ20 mm×250 mm (manufactured by SHISEIDO Co.)
  Temperature: 40° C.
  Flow rate: 5 ml/min.
  Detection: 240 nm
  Eluent: acetonitirle/water (4:6, v/v) isocratic Preparative HPLC condition (E3)
  Column: CAPCELL PAK C18 SG120, φ20 mm×250 mm (manufactured by SHISEIDO Co.)
  Temperature: 40° C.
  Flow rate: 5 ml/min.
  Detection: 240 nm
  Eluent: methanol/water (5:5, v/v) isocratic Preparative HPLC condition (E4)
  Column: YMC-Pack Ph SH-443-5, φ20 mm×250 mm (manufactured by YMC Co.)
  Temperature: 40° C.
  Flow rate: 5 ml/min.
  Detection: 200 nm
  Eluent: methanol/water (5:5, v/v) isocratic Preparative HPLC condition (E5)
  Column: CAPCELL PAK C18 SG120, φ20 mm×250 mm (manufactured by SHISEIDO Co.)
  Temperature: 40° C.
  Flow rate: 5 ml/min.
  Detection: 200 nm
  Eluent: acetonitrile/water (4:6, v/v) isocratic Preparative HPLC condition (E6)
  Column: CAPCELL PAK C18 SG120, φ20 mm×250 mm (manufactured by SHISEIDO Co.)
  Temperature: 40° C.
  Flow rate: 5 ml/min.
  Detection: 200 nm
  Eluent: methanol/water (5:5, v/v) isocratic Preparative HPLC condition (E7)
  Column: YMC-Pack Ph SH-443-5, φ20 mm×250 mm (manufactured by YMC Co.)
  Temperature: 40° C.
  Flow rate: 5 ml/min.
  Detection: 240 nm
  Eluent: methanol/water (5:5, v/v) isocratic Preparative HPLC condition (E8)
  Column: CAPCELL PAK C18 SG120, φ20 mm×250 mm (manufactured by SHISEIDO Co.)
  Temperature: 40° C.
  Flow rate: 5 ml/min.
  Detection: 240 nm
  Eluent: methanol/water (6:4, v/v) isocratic The retention time of the above-mentioned compounds when analysis was carried out under the following analytic HPLC conditions are shown below.

Analytic HPLC condition (e1)
  Column: CAPCELL PAK C18 SG120, φ4.6 mm×250 mm (manufactured by SHISEIDO Co.)
  Temperature: 40° C.
  Flow rate: 1 ml/min.
  Detection: 240 nm
  Eluent: acetonitirle/water (4:6, v/v) isocratic
  Retention time:
  11107AV: 7.9 min.
  11107AW: 6.8 min.
  11107AX: 7.2 min.

11107AZ: 9.8 min.
11107BB: 6.1 min.
11107BG: 7.1 min.

Analytic HPLC condition (e2)
Column: CAPCELL PAK C18 SG120, ϕ4.6 mm×250 mm (manufactured by SHISEIDO Co.)
Temperature: 40° C.
Flow rate: 1 ml/min.
Detection: 240 nm
Eluent: methanol/water (5:5, v/v) isocratic
Retention time:
11107BA: 22.0 min.

Analytic HPLC condition (e3)
Column: CAPCELL PAK C18 SG120, ϕ4.6 mm×250 mm (manufactured by SHISEIDO Co.)
Temperature: 40° C.
Flow rate: 1 ml/min.
Detection: 200 nm
Eluent: methanol/water (5:5, v/v) isocratic
Retention time:
11107BE: 23.0 min.

Analytic HPLC condition (e4)
Column: CAPCELL PAK C18 SG120, ϕ4.6 mm×250 mm (manufactured by SHISEIDO Co.)
Temperature: 40° C.
Flow rate: 1 ml/min.
Detection: 240 nm
Eluent: methanol/water (6:4, v/v) isocratic
Retention time:
11107BD: 10.4 min.
11107BF: 9.1 min.

Analytic HPLC condition (e5)
Column: YMC Pack Ph A-402, ϕ4.6 mm×150 mm (manufactured by YMC Co.)
Temperature: 40° C.
Flow rate: 1 ml/min.
Detection: 240 nm
Eluent: methanol/water (5:5, v/v) isocratic
Retention time:
11107AY: 9.4 min.

Example A57

Physico-chemical Properties of 11107AV

The physico-chemical properties of 11107AV are shown below. The structure of 11107AV was determined as shown below.
1. Appearance: colorless powder
2. Molecular weight: 550, FAB-MS m/z 573(M+Na)$^+$
3. Molecular formula: $C_{30}H_{46}O_9$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3421, 2972, 1733, 1716, 1457, 1373, 1254, 1175
7. $^1$H-NMR spectrum (CD$_3$OD, 600 MHz): δ ppm (integral, multiplicity, coupling constant J (Hz)): 0.92(3H,d,J=6.7 Hz), 1.05(3H,t,J=7.2 Hz), 1.17(3H,d,J=7.2 Hz), 1.23(3H, s), 1.35–1.45(5H,m), 1.55–1.72(2H,m), 1.68(1H,dd, J=6.5,14.2 Hz), 1.82(3H,d,J=1.1 Hz), 1.93(1H,dd,J=5.2, 14.2 Hz), 2.10(3H,s), 2.37(1H,dq,J=8.3,7.2 Hz), 2.56(2H, m), 2.58–2.64(3H,m), 2.80(1H,dd,J=2.2,8.3 Hz), 2.96 (1H,dt,J=2.2,5.2 Hz), 3.83(1H,m), 5.09(1H,d,J=9.7 Hz), 5.10(1H,d,J=10.8 Hz), 5.61(1H,dd,J=9.9,15.3 Hz), 5.75 (1H,dd,J=9.7,15.3 Hz), 5.91(1H,d,J=15.3 Hz), 6.18(1H, d,J=11.0 Hz), 6.57(1H,dd,J=11.0,15.3 Hz)

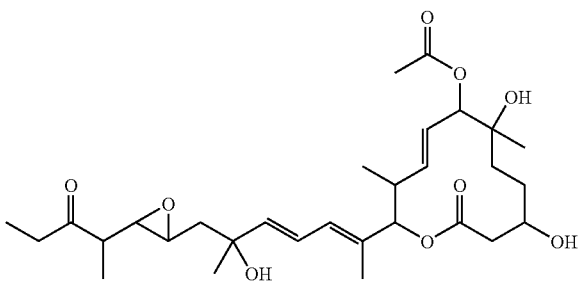

Example A58

Physico-chemical Properties of 11107AW

The physico-chemical properties of 11107AW are shown below. The structure of 11107AW was determined as shown below.
1. Appearance: colorless powder
2. Molecular weight: 552, FAB-MS m/z 575(M+Na)$^+$
3. Molecular formula: $C_{30}H_{48}O_9$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 500 MHz): δ ppm (integral, multiplicity, coupling constant J (Hz)): 0.92(3H,d,J=6.8 Hz), 0.97(3H,d,J=7.1 Hz), 1.13(3H,d,J=6.8 Hz), 1.23(3H, s), 1.24(3H,d,J=6.1 Hz), 1.38–1.46(2H,m), 1.46–1.72(5H, m), 1.79(3H,d,J=0.7 Hz), 2.10(3H,s), 2.52(1H,m), 2.57 (2H,m), 2.61(1H,m), 2.71(1H,dd,J=2.2,8.5 Hz), 2.78(1H, dt,J=2.2,5.9 Hz), 3.46(1H,dd,J=4.2,7.1 Hz), 3.72(1H,dq, J=7.1,6.1 Hz), 3.82(1H,m), 5.09(2H,d,J=10.0 Hz), 5.60 (1H,dd,J=9.8,15.2 Hz), 5.70(1H,dd,J=8.3,14.9 Hz), 5.74 (1H,dd,J=9.8,15.2 Hz), 6.13(1H,d,J=10.6 Hz), 6.36(1H, dd,J=10.7,14.9 Hz)

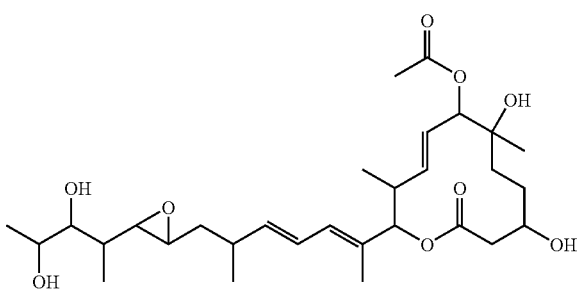

Example A59

Physico-chemical Properties of 11107AX

The physico-chemical properties of 11107AX are shown below. The structure of 11107AX was determined as shown below.
1. Appearance: colorless powder
2. Molecular weight: 550, FAB-MS m/z 551(M+H)$^+$, 573 (M+Na)$^+$
3. Molecular formula: $C_{30}H_{46}O_9$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 600 MHz): δ ppm (integral, multiplicity, coupling constant J (Hz)): 0.85(3H,d,J=6.8 Hz), 0.93(3H,d,J=7.0 Hz), 0.98(3H,t,J=7.4 Hz), 1.17(3H, d,J=6.7 Hz), 1.25(1H,m), 1.30(3H,s), 1.47–1.60(2H,m), 1.77(3H,s), 2.12(3H,s), 2.45–2.52(2H,m), 2.57(1H,dd, J=2.5,13.1 Hz), 2.67(1H,dd,J=5.8,13.1 Hz), 2.77(1H,dd, J=2.2,6.7 Hz), 2.86(1H,dd,J=2.2,8.3 Hz), 3.12(1H,t,J=7.3 Hz), 3.56(1H,dt,J=8.4,4.3 Hz), 4.56(1H,m), 5.00(1H,d, J=10.7 Hz), 5.03(1H,d,J=9.4 Hz), 5.34(1H,dd,J=9.7,15.1 Hz), 5.56(1H,dd,J=9.4,15.1 Hz), 5.63(1H,dd,J=2.0,15.7 Hz), 5.73(1H,dd,J=8.6,14.9 Hz), 5.82(1H,dd,J=3.1,15.7 Hz), 6.08(1H,d,J=10.6 Hz), 6.39(1H,dd,J=10.6,14.9 Hz)

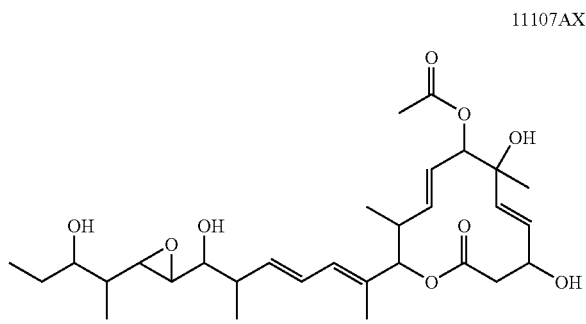

11107AX

Example A60

Physico-chemical Properties of 11107AY

The physico-chemical properties of 11107AY are shown below. The structure of 11107AY was determined as shown below.
1. Appearance: colorless powder
2. Molecular weight: 494, FAB-MS m/z 495(M+H)$^+$, 517 (M+Na)$^+$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 3405, 2973, 1733, 1716, 1457, 1374, 1257, 1176
7. $^1$H-NMR spectrum (CD$_3$OD, 600 MHz): δ ppm (integral, multiplicity, coupling constant J (Hz)): 0.92(3H,d,J=6.8 Hz), 0.97(3H,t,J=7.6 Hz), 1.16(3H,d,J=6.7 Hz), 1.23(3H, s), 1.37–1.43(2H,m), 1.50–1.59(2H,m), 1.59–1.70(2H,m), 1.79(3H,s), 2.10(3H,s), 2.46(1H,ddq, J=8.1,8.6,6.7 Hz), 2.56(2H,m), 2.61(1H,ddq,J=9.7,11.5, 6.8 Hz), 2.73(1H,dd,J=2.3,7.0 Hz), 2.81(1H,dt,J=2.3,5.4 Hz), 3.07(1H,dd,J=7.0,8.1 Hz), 3.83(1H,m), 5.085(1H,d, J=11.5 Hz), 5.086(1H,d,J=9.7 Hz), 5.61(1H,dd,J=9.7,15.3 Hz), 5.70(1H,dd,J=8.6,15.1 Hz), 5.74(1H,dd,J=9.7,15.3 Hz), 6.14(1H,d,J=10.8 Hz), 6.40(1H,dd,J=10.8,15.1 Hz)

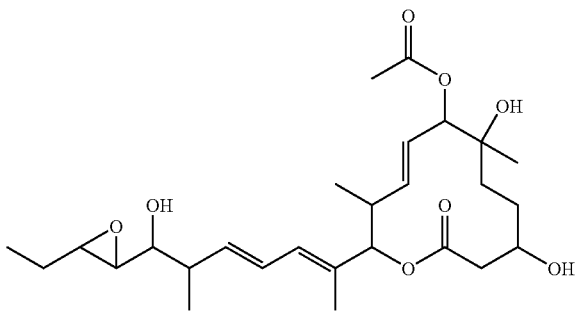

11107AY

Example A61

Physico-chemical Properties of 11107AZ

The physico-chemical properties of 11107AZ are shown below. The structure of 11107AZ was determined as shown below.
1. Appearance: colorless powder
2. Molecular weight: 568, FAB-MS m/z 569(M+H)$^+$, 591 (M+Na)$^+$
3. Molecular formula: $C_{30}H_{48}O_{10}$
4. Solubility: soluble in dimethylsulfoxide, pyridine, methanol and acetone, and slightly soluble in water
5. Color reaction: positive for iodine and sulfuric acid
6. Infrared absorption spectrum (KBr) cm$^{-1}$: 2970, 1732, 1715, 1455, 1383, 1259, 1181
7. $^1$H-NMR spectrum (CD$_3$OD, 500 MHz): δ ppm (integral, multiplicity, coupling constant J (Hz)): 0.87(3H,d,J=6.8 Hz), 0.93(3H,d,J=6.8 Hz), 1.09(3H,d,J=6.4 Hz), 1.11(3H, s), 1.20(3H,d,J=5.9 Hz), 1.42–1.68(5H,m), 1.76(3H,s), 2.06(3H,s), 2.45–2.65(4H,m), 2.67(1H,dd,J=2.4,8.3 Hz), 2.75(1H,dt,J=2.4,5.9 Hz), 3.42(1H,dd,J=4.4,7.3 Hz), 3.53 (1H,dd,J=2.0,11.7 Hz), 3.68(1H,dq,J=7.3,5.9 Hz), 4.15 (1H,m), 5.06(1H,d,J=9.8 Hz), 5.09(1H,d,J=10.8 Hz), 5.53 (1H,dd,J=10.3,15.1 Hz), 5.67(2H,m), 6.09(1H,d,J=10.7 Hz), 6.33(1H,dd,J=10.7,15.1 Hz)

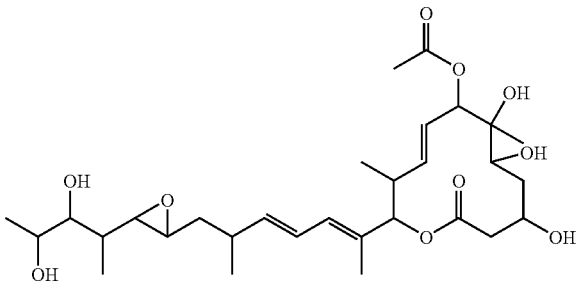

11107AZ

Example A62

Physico-chemical Properties of 11107BA

The physico-chemical properties of 11107BA are shown below. The structure of 11107BA was determined as shown below.
1. Appearance: colorless powder
2. Molecular weight: 552, FAB-MS m/z 553(M+H)$^+$, 575 (M+Na)$^+$
3. Molecular formula: $C_{30}H_{48}O_9$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 600 MHz): δ ppm (integral, multiplicity, coupling constant J (Hz)): 0.85(3H,d,J=6.7 Hz), 0.93(3H,d,J=7.0 Hz), 0.97(3H,t,J=7.4 Hz), 1.10(3H, d,J=6.8 Hz), 1.30(3H,s), 1.37(1H,m), 1.50–1.60(2H,m), 1.75(1H,m), 1.77(3H,s), 1.94(1H,m), 2.12(3H,s), 2.48 (1H,m), 2.55–2.64(2H,m), 2.68(1H,dd,J=5.9,13.5 Hz), 3.50(2H,m), 3.61(1H,m), 4.58(1H,m), 5.01(1H,d,J=10.4 Hz), 5.03(1H,d,J=9.7 Hz), 5.34(1H,dd,J=9.9,15.1 Hz), 5.56(1H,dd,J=9.4,15.3 Hz), 5.63(2H,m), 5.82(1H,dd, J=2.9,15.5 Hz), 6.08(1H,d,J=10.6 Hz), 6.36(1H,dd, J=10.6,14.7 Hz)

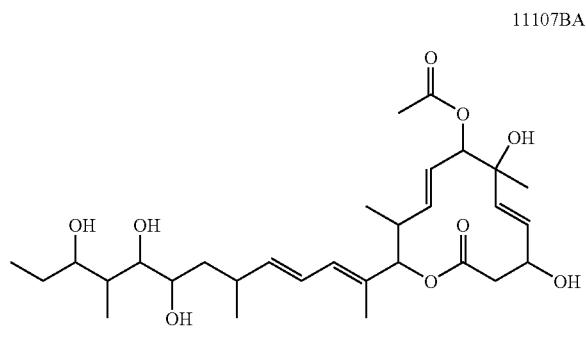

11107BA

Example A63

Physico-chemical Properties of 11107BB

The physico-chemical properties of 11107BB are shown below. The structure of 11107BB was determined as shown below.
1. Appearance: colorless powder
2. Molecular weight: 494, FAB-MS m/z 517(M+Na)$^+$
3. Molecular formula: $C_{27}H_{42}O_8$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 600 MHz): δ ppm (integral, multiplicity, coupling constant J (Hz)): 0.92(3H,d,J=6.8 Hz), 0.99(3H,t,J=7.6 Hz), 1.23(3H,s), 1.32–1.50(5H,m), 1.52–1.58(2H,m), 1.58–1.72(3H,m), 1.82(3H,d,J=0.9 Hz), 1.87(1H,dd,J=5.8,14.0 Hz), 2.10(3H,s), 2.57(2H,m), 2.62(1H,m), 2.69(1H,dt,J=2.3,5.6 Hz), 2.90(1H,dt,J=2.3, 5.8 Hz), 3.83(1H,m), 5.09(1H,d,J=9.7 Hz), 5.10(1H,d, J=9.9 Hz), 5.61(1H,dd,J=9.7,15.3 Hz), 5.75(1H,dd,J=9.7, 15.3 Hz), 5.91(1H,d,J=15.3 Hz), 6.18(1H,d,J=11.0 Hz), 6.57(1H,dd,J=11.0,15.3 Hz)

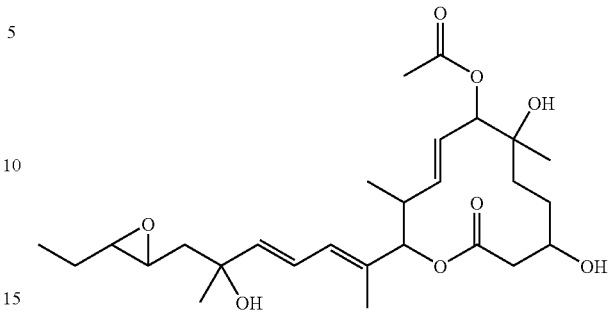

11107BB

Example A64

Physico-chemical Properties of 11107BD

The physico-chemical properties of 11107BD are shown below. The structure of 11107BD was determined as shown below.
1. Appearance: colorless powder
2. Molecular weight: 480, FAB-MS m/z 503(M+Na)$^+$
3. Molecular formula: $C_{27}H_{44}O_7$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 500 MHz): δ ppm (integral, multiplicity, coupling constant J (Hz)): 0.91(3H,d,J=6.8 Hz), 0.94(3H,t,J=7.3 Hz), 0.98(3H,d,J=6.8 Hz), 1.08(3H, d,J=6.8 Hz), 1.22(1H,m), 1.26(3H,s), 1.30–1.40(2H,m), 1.43–1.65(6H,m), 2.37(1H,m), 2.44(1H,m), 2.52(2H,m), 2.66(1H,dd,J=2.4,8.3 Hz), 2.72(1H,dt,J=2.4,5.9 Hz), 3.52 (1H,m), 3.70(1H,d,J=9.8 Hz), 3.77(1H,m), 5.08(1H,dd, J=8.8,10.3 Hz), 5.38(1H,dd,J=9.8,15.1 Hz), 5.53(1H,dd, J=8.3,15.1 Hz), 5.69(2H,m), 6.10(1H,dd,J=10.3,15.1 Hz), 6.28(1H,dd,J=10.3,15.1 Hz)

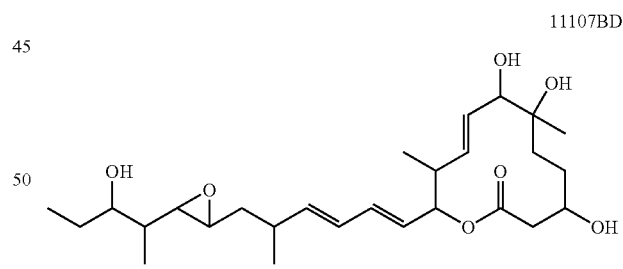

11107BD

Example A65

Physico-chemical Properties of 11107BE

The physico-chemical properties of 11107BE are shown below. The structure of 11107BE was determined as shown below.
1. Appearance: colorless powder
2. Molecular weight: 438, FAB-MS m/z 461(M+Na)$^+$, 439 (M+H)$^+$, 437(M-H)$^-$
3. Molecular formula: $C_{24}H_{38}O_7$ 4. Solubility: soluble in dimethylsulfoxide, pyridine, methanol and acetone, and slightly soluble in water
5. Color reaction: positive for iodine and sulfuric acid
6. Ultraviolet absorption spectrum (methanol): terminal adsorption
7. Infrared absorption spectrum (KBr) cm$^{-1}$: 3447, 2970, 1734, 1717, 1457, 1374, 1259, 1174
8. $^1$H-NMR spectrum (CD$_3$OD, 500 MHz): δ ppm (integral, multiplicity, coupling constant J (Hz)): 0.96(3H,d,J=6.8 Hz), 1.00(3H,d,J=6.8 Hz), 1.18(3H,s), 1.19(3H,d,J=7.3 Hz), 1.28–1.44(2H,m), 1.53–1.66(2H,m), 2.03–2.07(5H, m), 2.24(1H,m), 2.33(1H,m), 2.52(2H,d,J=3.9 Hz), 3.78 (1H,m), 4.17(1H,m), 5.037(1H,d,J=9.8 Hz), 5.042(1H,dd, J=8.3,10.3 Hz), 5.35(1H,dd,J=7.8,15.1 Hz), 5.48(1H,dd, J=6.4,15.6 Hz), 5.56(2H,m), 5.66(1H,dd,J=9.8,15.1 Hz), 5.70(1H,dd,J=7.3,15.1 Hz)

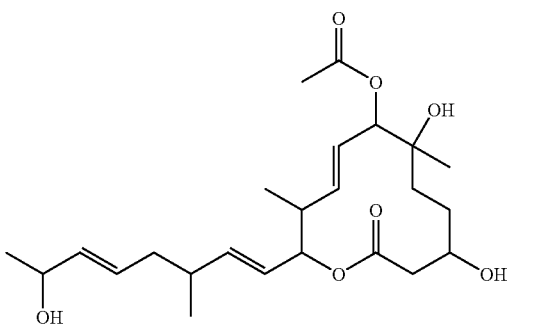

Example A66

Physico-chemical Properties of 11107BF

The physico-chemical properties of 11107BF were shown below. The structure of 11107BF was determined as shown below. Further, the present compound is the stereoisomer of 17-position hydroxy group of 11107P.
1. Apperance: colorless powder
2. Molecular weight: 552, FAB-MS m/z 553(M+H)$^+$, 575 (M+Na)$^+$
3. Molecular formula: C$_{30}$H$_{48}$O$_9$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 500 MHz): δ ppm (integral, multiplicity, coupling constant J (Hz)): 0.88(3H,d,J=6.8 Hz), 0.93(3H,d,J=6.8 Hz), 0.95(3H,t,J=7.3 Hz), 1.14(3H, d,J=6.8 Hz), 1.19(3H,s), 1.24(1H,m), 1.34–1.44(2H,m), 1.44–1.66(4H,m), 1.75(3H,s), 2.06(3H,s), 2.47–2.60(4H, m), 2.73(1H,dd,J=2.4,4.9 Hz), 2.92(1H,dd,J=2.0,8.3 Hz), 3.39(1H,dd,J=4.4,4.9 Hz), 3.53(1H,dt,J=8.8,4.4 Hz), 3.78 (1H,m), 5.05(2H,d,J=10.3 Hz), 5.57(1H,dd,J=9.8,15.1 Hz), 5.70(1H,dd,J=9.8,15.1 Hz), 5.81(1H,dd,J=8.1,15.1 Hz), 6.11(1H,d,J=11.2 Hz), 6.36(1H,dd,J=11.2,15.1 Hz)

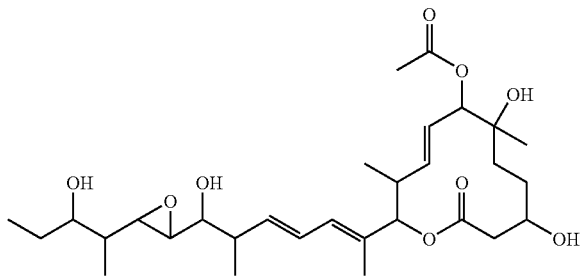

Example A67

Physico-chemical Properties of 11107BG

The physico-chemical properties of 11107BG are shown below. The structure of 11107BG was determined as shown below.
1. Appearance: colorless powder
2. Molecular weight: 508, FAB-MS m/z 509(M+H)$^+$, 531 (M+Na)$^+$
3. Molecular formula: C$_{28}$H$_{44}$O$_8$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 600 MHz): δ ppm (integral, multiplicity, coupling constant J (Hz)): 0.91(3H,d,J=6.7 Hz), 0.96(3H,t,J=7.6 Hz), 1.15(3H,d,J=6.7 Hz), 1.23(3H, s), 1.27(3H,s), 1.37–1.47(3H,m), 1.53–1.70(3H,m), 1.79 (3H,s), 2.06(3H,s), 2.39(1H,ddq,J=9.5,9.9,6.7 Hz), 2.56 (2H,m), 2.61(1H,ddq,J=9.7,10.3,6.7 Hz), 2.73(1H,t,J=6.3 Hz), 2.84(1H,d,J=9.9 Hz), 3.83(1H,m), 5.07(1H,d,J=10.3 Hz), 5.09(1H,d,J=9.7 Hz), 5.60(2H,m), 5.74(1H,dd,J=9.7, 15.3 Hz), 6.11(1H,d,J=10.8 Hz), 6.36(1H,dd,J=10.8,15.1 Hz)

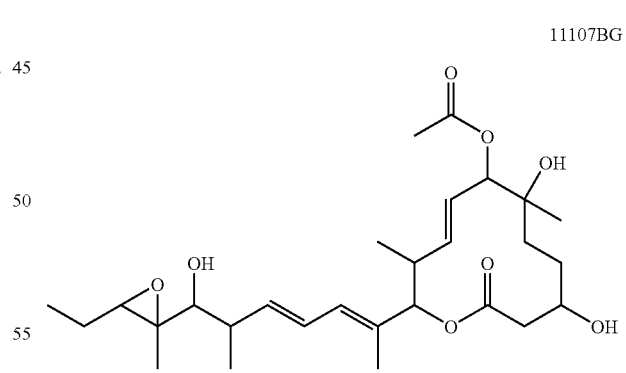

Example A68

Acquisition of mutant of Mer-11107

The present inventors carried out the mutation treatment (100 μg/ml, 28° C., 1 hour) of *Streptomyces* sp. Mer-11107 (Deposit No. FERM BP-7812) by N-methyl-N'-nitro-N-nitrosoguanidine in a tris-maleate buffer (pH 6.0), then spread it on an yeast-malt agar medium to form spores. The spores obtained were collected, the portion was diluted and spread on an yeast-malt agar medium to form colonies. Mycerial cell was collected from the respective colonies, inoculated in a 15 ml of test tube containing 2 ml of seed medium (2% of glucose, 1% of soybean meal (ESUSAN-MEAT manufactured by Ajinomoto Co., Ltd.), 0.5% of yeast extract (manufactured by Oriental Yeast Co., Ltd.), 0.25% of sodium chloride, 0.32% of calcium carbonate, pH 6.8), and cultured by shaking at 25° C. for 3 days. Further, the portion of the cultured broth was transferred to 2 ml of a producing medium (7% of soluble starch, 0.8% of gluten meal, 0.8% of PHARMAMEDIA, 0.1% of calcium carbonate, pH 6.8), and cultured at 25° C. for 4 days (the residual seed culture were stored in a frozen state). The cultured broth was extracted with ethyl acetate, analyzed by TLC (Merck 5717, acetone:toluene=1:1, coloration by phosphomolybdic acid), and 3 strains, that is A-1532, a-1533 and A-1534 strains in which spots other than 11107B substance (Rf: about 0.5) appear were selected. These strains are deposited as FERM BP-7849, FERM BP-7850 and FERM BP-7851, respectively, at the above-mentioned International Deposit Organization.

Example A69

Fermentation of A-1532

The frozen seed culture of A-1532 was melted, 0.2 ml of the seed culture was inoculated into a 250 ml Erlenmeyer flask containing 20 ml of the seed medium (2% of glucose, 1% of soybean meal (ESSAN-MEAT manufactured by Ajinomoto Co. Ltd.), 0.5% of yeast extract (manufactured by Oriental Yeast Co. Ltd.), 0.25% of sodium chloride, 0.32% of calcium carbonate, pH 6.8), and it was cultured on a shaker at 25° C. for 3 days to obtain a seed culture broth. 0.6 ml of the seed culture broth was inoculated into a 500 ml Erlenmeyer flask containing 60 ml of a producing medium (5% of soluble starch, 1% of glucose, 1% of gluten meal, 2% of PHARMAMEDIA, 0.1% of calcium carbonate, pH 6.8), and it was cultured at 25° C. for 4 days on a shaker to obtain a cultured broth.

Example A70

Purification of 11107BH

The culturer broth (100 ml) was extracted with ethyl acetate (100 ml), and then the ethyl acetate layer was concentrated to dryness to obtain 80 mg of a crude active fraction. The resulting crude active fraction was subjected to the preparative high performance liquid chromatography (HPLC) under the above-mentioned preparative HPLC condition (G) to obtain a 11107BH solution. Then, the solvent was removed to otbain 11107BH (10.7 mg).

Preparative HPLC condition (G)
　Column: CAPCELL PAK C18 UG120, ϕ30 mm×250 mm (manufactured by SHISEIDO Co.)
　Flow rate: 20 ml/min.
　Detection: 240 nm
　Eluent: acetonitrile/water (4:6, v/v) isocratic The retention time of the above-mentioned compound when analysis was carried out at the following analytic HPLC conditions is shown below.

Analytic HPLC condition (g)
　Column: CAPCELL PAK C18 SG120, ϕ4.6 mm×250 mm (manufactured by SHISEIDO Co.)
　Temperature: 40° C.
　Flow rate: 1 ml/min.
　Detection: 240 nm
　Eluent: acetonitrile/water (4:6, v/v) isocratic
　Retention time:
　11107BH: 19.6 min.

Example A71

Physico-chemical Properties of 11107BH

The physico-chemical properties of 11107BH are shown below. The structure of 11107BH was determined as shown below.
1. Appearance: colorless powder
2. Molecular weight: 550, FAB-MS m/z 573(M+Na)$^+$, 549 (M-H)$^-$
3. Molecular formula: $C_{30}H_{46}O_9$
4. Solubility: soluble in dimethylsulfoxide, pyridine, methanol and acetone, and slightly soluble in water
5. Color reaction: positive for iodine and sulfuric acid
7. Infrared absorption spectrum: 3470, 2966, 1733, 1716, 1457, 1373, 1242, 1187
8. $^1$H-NMR spectrum (CD$_3$OD, 400 MHz): δ ppm (integral, multiplicity, coupling constant J (Hz)): 0.83(3H,d,J=6.6 Hz), 0.89(3H,d,J=7.0 Hz), 0.93(3H,t,J=7.3 Hz), 1.07(3H, d,J=6.6 Hz), 1.16–1.21(1H,m), 1.32(3H,s), 1.42–1.66(4H, m), 1.71(3H,d,J=1.1 Hz), 2.08(3H,s), 2.39–2.46(2H,m), 2.60(1H,dd,J=5.4,15.0 Hz), 2.65(1H,dd,J=2.2,8.1 Hz), 2.71(1H,dt,J=2.2,5.9 Hz), 2.75(1H,dd,J=9.2,18.0 Hz), 2.76(1H,dd,J=3.3,15.10 Hz), 3.08(1H,dd,J=3.3,18.0 Hz), 3.51(1H,dt,J=8.8,4.8 Hz), 4.26–4.33(1H,m), 5.02(1H,d, J=10.6 Hz), 5.47(1H,d,J=9.5 Hz), 5.49(1H,dd,J=9.5,15.0 Hz), 5.60–5.68(2H,m), 6.06(1H,d,J=11.0 Hz), 6.31(1H, dd,J=11.0,15.0 Hz)

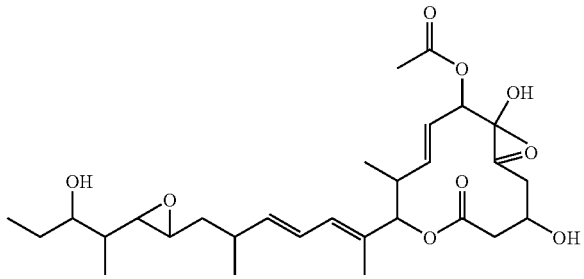

11107BH

Example A72

Fermentation of A-1533 strain 0.2 ml of the frozen seed culture of A-1533 was inoculated into a 250 ml Erlenmeyer flask containing 20 ml of a seed medium (2% of glucose, 1% of soybean meal (ESUSAN-MEAT manufactured by Ajinomoto Co. Ltd.), 0.5% of yeast extract (manufactured by Oriental Yeast Co. Ltd.), 0.25% of sodium chloride, 0.32% of calcium carbonate, pH 6.8), and it was cultured on a shaker at 25° C. for 3 days to obtain a seed culture broth. 0.6 ml of the seed culture broth was inoculated into a 500 ml Erlenmeyer flask containing 60 ml of a producing medium (5% of soluble starch, 1% of glucose, 1% of gluten meal, 2% of PHARMAMEDIA, 0.1% of calcium carbonate, pH 6.8), and it was cultured at 25° C. for 4 days on a shaker to obtain a cultured broth.

Example A73

Purification of 11107BI

The cultured broth (100 ml) was extracted with ethyl acetate (100 ml), and then the ethyl acetate layer was concentrated to dryness to obtain 60 mg of a crude active fraction. The resulting crude active fraction was subjected to the preparative high performance liquid chromatography (HPLC) under the above-mentioned preparative HPLC condition (H) to obtain a 11107BI solution. Then, the solvent was removed to obtain 11107BI (7.1 mg).

Preparative HPLC condition (H)
Column: CAPCELL PAK C18 UG120, φ30 mm×250 mm (manufactured by SHISEIDO Co.)
Temperature: room temperature
Flow rate: 20 ml/min.
Detection: 240 nm
Eluent: acetonitrile/water (5:5, v/v) isocratic
The retention time of the above-mentioned compound when analysis was carried out at the following analytic HPLC condition is shown.

Analytic HPLC condition (h)
Column: CAPCELL PAK C18 SG120, φ4.6 mm×250 mm (manufactured by SHISEIDO Co.)
Temperature: 40° C.
Flow rate: 1 ml/min.
Detection: 240 nm
Eluent: acetonitrile/water (4:6, v/v) isocratic
Retention time:
11107BI: 56.7 min.

Example A74

Physico-chemical Properties of 11107BI

The physico-chemical properties of 11107BI are shown below. The structure of 11107BI was determined as shown below.
1. Appearance: colorless powder
2. Molecular weight: 520, FAB-MS m/z 543(M+Na)$^+$, 519 (M-H)$^-$
3. Molecular formula: $C_{30}H_{48}O_7$
4. Solubility: soluble in dimethylsulfoxide, pyridine, methanol and acetone, and slightly soluble in water
5. Color reaction: positive for iodine and sulfuric acid
6. Infrared absorption spectrum: 3470, 2962, 1733, 1716, 1457, 1373, 1244, 1176
7. $^1$H-NMR spectrum (CD$_3$OD, 400 MHz): δ ppm (integral, multiplicity, coupling constant J (Hz)): 0.87(3H,d,J=6.6 Hz), 0.92(3H,t,J=7.3 Hz), 0.98(3H,d,J=6.6 Hz), 1.01(3H, d,J=6.6 Hz), 1.18(3H,s), 1.26–1.39(3H,m), 1.50–1.62(3H, m), 1.73(3H,d,J=1.1 Hz), 2.00–2.06(2H,m), 2.06(3H,s), 2.08–2.13(1H,m), 2.24–2.30(1H,m), 2.52(2H,d,J=3.7 Hz), 2.54–2.57(1H,m), 3.19(1H,dt,J=3.3,8.4 Hz), 3.75–3.80(1H,m), 5.04(2H,d,J=9.9 Hz), 5.32(1H,dd, J=7.7,15.4 Hz), 5.39(1H,dd,J=6.2,15.4 Hz), 5.56(1H,dd, J=9.9,15.0 Hz), 5.64(1H,dd,J=8.0,15.0 Hz), 5.69(1H,dd, J=9.9,15.0 Hz), 6.06(1H,d,J=11.0 Hz), 6.21(1H,dd, J=11.0,15.0 Hz)

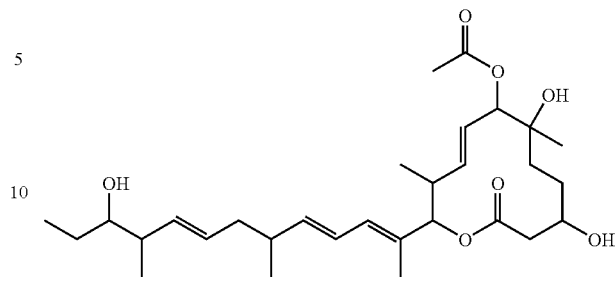

Example A75

Fermentaion of A-1534 strain

The frozen seed culture of A-1534 was melted, 0.2 ml of the seed culture was inoculated into a 250 ml Erlenmeyer flask containing 20 ml of a seed medium (2% of glucose, 1% of soybean meal (ESUSAN-MEAT manufactured by Ajinomoto Co. Ltd.), 0.5% of yeast extract (manufactured by Oriental Yeast Co. Ltd.), 0.25% of sodium chloride, 0.32% of calcium carbonate, pH 6.8), and it was cultured at 25° C. for 3 days on a shaker to obtain a seed culture broth. 0.6 ml of the seed culture broth was inoculated into a 500 ml Erlenmeyer flask containing 60 ml of a producing medium (5% of soluble starch, 1% of glucose, 1% of gluten meal, 2% of PHARMAMEDIA, 0.1% of calcium carbonate, pH 6.8), and it was cultured at 25° C. for 4 days on a shaker to obtain a culture broth.

Example A76

Purification of 11107BJ

The cultured broth (100 ml) was extracted with ethyl acetate (100 ml), and then the ethyl acetate layer was concentrated to dryness to obtain 86 mg of a crude active fraction. The resulting crude active fraction was subjected to the preparative high performance liquid chromatography (HPLC) under the following preparative HPLC condition (I) to obtain a 11107BJ solution. Then, the solvent was removed to obtain 11107BJ (3.0 mg).

Preparative HPLC condition (I)
Column: CAPCELL PAK C18 UG120, φ30 mm×250 mm (manufactured by SHISEIDO Co.)
Flow rate: 20 ml/min.
Detection: 240 nm
Eluent: acetonitrile/water (5:5, v/v) isocratic
The retention time of the above-mentioned compound when analysis was carried out at the following analytic HPLC condition is shown below.

Analytic HPLC condition (i)
Column: CAPCELL PAK C18 SG120, φ4.6 mm×250 mm (manufactured by SHISEIDO Co.)
Temperature: 40° C.
Flow rate: 1 ml/min.
Detection: 240 nm
Eluent: acetonitrile/water (4:6, v/v) isocratic
Retention time:
11107BJ: 54.9 min.

Example A77

Physico-chemical Properties of 11107BJ

The physico-chemical properties of 11107BJ are shown below. The structure of 11107BJ was determined as shown below.
1. Appearance: colorless powder
2. Molecular weight: 436, FAB-MS m/z 459(M+Na)$^+$, 435 (M-H)$^-$
3. Molecular formula: $C_{25}H_{40}O_6$
4. Solubility: soluble in dimethylsulfoxide, pyridine, methanol and acetone, and slightly soluble in water
5. Color reaction: positive for iodine and sulfuric acid
6. $^1$H-NMR spectrum (CD$_3$OD, 400 MHz): δ ppm (integral, multiplicity, coupling constant J (Hz)): 0.87(3H,d,J=7.0 Hz), 0.94(3H,t,J=7.4 Hz), 0.97(3H,d,J=7.0 Hz), 1.04(3H, d,J=7.0 Hz), 1.26–1.38(3H,m), 1.49–1.66(3H,m), 1.73 (3H,d,J=1.1 Hz), 1.89–1.92(1H,m), 2.00(3H,s), 2.23–2.28 (1H,m), 2.43(1H,dd,J=5.1,13.8 Hz), 2.51–2.56(1H,m), 2.56(1H,dd,J=3.3,13.8 Hz), 3.25–3.29(1H,m), 3.75–3.80 (1H,m), 4.91(1H,t,J=9.2 Hz), 5.02(1H,d,J=10.6 Hz), 5.42 (1H,dd,J=9.2,15.0 Hz), 5.49(1H,dd,J=9.2,15.0 Hz), 5.69 (1H,dd,J=8.4,15.0 Hz), 6.08(1H,d,J=11.0 Hz), 6.28(1H, dd,J=11.0,15.0 Hz)

11107BJ

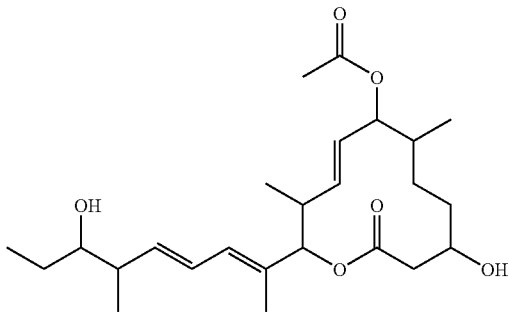

Example B1

(8E,12E,14E)-7-Acetoxy-19-chloro-3,6,18,21-tetrahydroxy-6,10,12,16,20-pentamethyltricosa-8,12,14-trien-11-olide (Compound B1-1) and (8E,12E,14E)-7-acetoxy-18-chloro-3,6,19,21-tetrahydroxy-6,10,12,16,20-pentamethyltricosa-8,12,14-trien-11-olide (Compound B1-2)

Compound B1-1

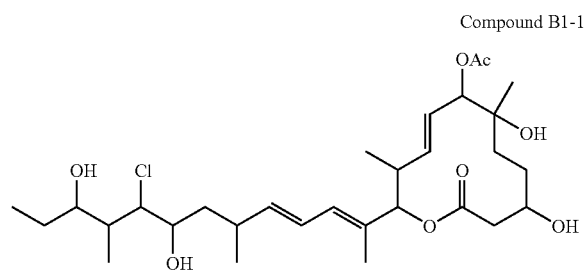

Compound B1-2

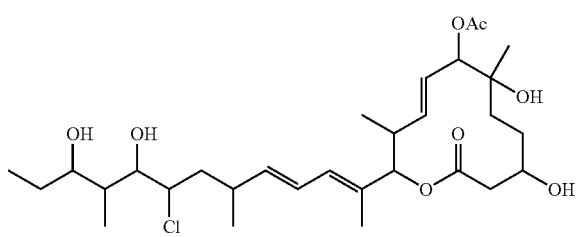

(8E,12E,14E)-7-Acetoxy-3,6,21-trihydroxy-6,10,12,16,20-pentamethyl-18,19-epoxytricosa-8,12,14-trien 11-olide (18.0 mg, 33.5 μmol) was dissolved in DME (0.2 mL). After cooling to −20° C., 4M HCl in dioxane (17.0 μL, 68.0 μmol) was added thereto and the mixture was stirred for 4 hours. Potassium carbonate (10.5 mg, 76.0 μmol) and toluene (1 mL) were added to the reaction solution, and the temperature was raised to room temperature. The reaction solution was concentrated, and the resulting crude product was purified by preparative HPLC (SHISEIDO Capcell pak C18, 10 mm I.D.×250 mm, acetonitrile:water=40:60, 4.0 mL/min.) to obtain the title Compound B1-1 (3.0 mg, 5.2 μmol, 15.6%) and Compound B1-2 (10.8 mg, 18.8 μmol, 56.2%) as colorless oils, respectively.

Compound B1-1

$^1$H-NMR spectrum (CD$_3$OD, 400 MHz) δ (ppm): 0.88 (3H,d,J=7 Hz), 0.95(3H,t,J=7 Hz), 1.02(3H,d,J=7 Hz), 1.05 (3H,d,J=7 Hz), 1.18(3H,s), 1.30–1.46(4H,m), 1.52–1.66(3H,m), 1.74(3H,s), 1.80(1H,brt,J=11 Hz), 2.05 (3H,s), 2.05–2.11(1H,m), 2.52(2H,d,J=4 Hz), 2.48–2.61(2H,m), 3.35–3.42(1H,m), 3.65(1H,brt,J=8 Hz), 3.74–3,80(1H,m), 3.84(1H,dd,J=4,8 Hz), 5.04(1H,d,J=10 Hz), 5.05(1H,d,J=11 Hz), 5.56(1H,dd,J=10,15 Hz), 5.58 (1H,dd,J=9,15 Hz), 5.69(1H,dd,J=10,15 Hz), 6.09(1H,d, J=10 Hz), 6.33(1H,dd,J=11,15 Hz); FAB-MS m/z 573(M+ H)$^+$.

Compound B1-2

$^1$H-NMR spectrum (CD$_3$OD, 400 MHz) δ (ppm): 0.87 (3H,d,J=7 Hz), 0.91(3H,d,J=7 Hz), 0.93(3H,t,J=7 Hz), 1.05 (3H,d,J=7 Hz), 1.18(3H,s), 1.32–1.47(3H,m), 1.49–1.65(3H,m), 1.74(3H,s), 1.76–1.81(2H,m), 1.82–1.90 (1H,m), 2.05(3H,s), 2.52(2H,d,J=4 Hz), 2.52–2.63(2H,m), 3.68(1H,dd,J=6,6 Hz), 3.74–3.80(1H,m), 3.89(1H,dq,J=2,6 Hz), 4.12(1H,dt,J=5,9 Hz), 5.037(1H,d,J=10 Hz), 5.039(1H, d,J=11 Hz), 5.56(1H,dd,J=10,15 Hz), 5,69(1H,dd,J=10,15 Hz), 5.74(1H,dd,J=7,15 Hz), 6.08(1H,d,J=11 Hz), 6.29(1H, dd,J=11,15 Hz); FAB-MS m/z 573(M+H)$^+$.

Example B2

(8E,12E,14E)-7-Acetoxy-18-bromo-3,6,19,21-tetrahydroxy-6,10,12,16,20-pentamethyltricosa-8,12,14-trien-11-olide (Compound B2-1) and (8E,12E,14E)-7-acetoxy-19-bromo-3,6,18,21-tetrahydroxy-6,10,12,16,20-pentamethyltricosa-8,12,14-trien-11-olide (Compound B2-2)

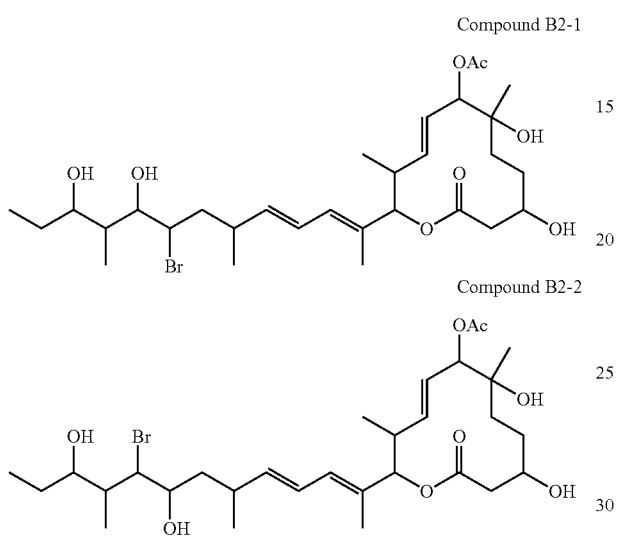

(8E,12E,14E)-7-Acetoxy-3,6,21-trihydroxy-6,10,12,16,20-pentamethyl-18,19-epoxytricosa-8,12,14-trien 11-olide (18.6 mg, 34.7 μmol) was dissolved in DME (0.2 mL). After cooling to −20° C., 47% HBr (13 μL, 75.5 μmol) was added thereto and the mixture was stirred for 20 hours. Potassium carbonate (10.5 mg, 76.0 μmol) and toluene (1 mL) were added to the reaction solution and the temperature was raised to room temperature. The reaction solution was concentrated, and the resulting crude product was purified by thin layer chromatography (MERCK Silicagel 60 F254, 0.5 mm, developing solution; chloroform:methanol=20:1) to obtain the title Compound B2-1 (8.8 mg, 14.3 μmol, 41.1%) and Compound B2-2 (4.8 mg, 7.8 μmol, 22.4%) as colorless oils, respectively.

Compound B2-1

$^1$H-NMR spectrum (CD$_3$OD, 400 MHz) δ (ppm): 0.87 (3H,d,J=7 Hz), 0.90(3H,d,J=7 Hz), 0.94(3H,t,J=7 Hz), 1.04 (3H,d,J=7 Hz), 1.18(3H,s), 1.33–1.45(3H,m), 1.48–1.64(3H,m), 1.74(3H,s), 1.75–1.83(1H,m), 1.87–1.96 (2H,m), 2.05(3H,s), 2.50–2.63(2H,m), 2.52(2H,d,J=4 Hz), 3.74–3.82(1H,m), 3.79(1H,dd,J=5,7 Hz), 3.88(1H,ddd,J=2, 6,8 Hz), 4.27(1H,ddd,J=3,5,11 Hz), 5.04(2H,d,J=10 Hz), 5.56(1H,dd,J=10,15 Hz), 5.69(1H,dd,J=10,15 Hz), 5.75(1H, dd,J=8,15 Hz), 6.08(1H,d,J=11 Hz), 6.29(1H,dd,J=11,15 Hz); FAB-MS m/z 616(M)$^+$.

Compound B2-2

$^1$H-NMR spectrum (CD$_3$OD, 400 MHz) δ (ppm): 0.88 (3H,d,J=7 Hz)$_1$ 0.95(3H,t,J=7 Hz), 1.05(6H,d,J=7 Hz), 1.18 (3H,s), 1.30–1.47(4H,m), 1.55–1.66(3H,m), 1.74(3H,d, J=0.7 Hz), 1.82–1.96(1H,m), 1.95–2.03(1H,m), 2.05(3H,s), 2.52(2H,d,J=4 Hz), 2.45–2.62(2H,m), 3.38(1H,dt,J=3,8 Hz), 3.68(1H,brt,J=8 Hz), 3.74–3.80(1H,m), 3.96(1H,dd, J=4,8 Hz), 5.04(1H,d,J=10 Hz), 5.05(1H,d,J=11 Hz), 5.56 (1H,dd,J=10,15 Hz), 5.59(1H,dd,J=9,15 Hz), 5.69(1H,dd, J=10,15 Hz), 6.09(1H,d,J=11 Hz), 6.33(1H,dd,J=11,15 Hz); FAB-MS m/z 617(M+H)$^+$.

Example B3

(8E,12E,14E)-7-Acetoxy-3,6,18,21-tetrahydroxy-19-iodo-6,10,12,16,20-pentamethyltricosa-8,12,14-trien-11-olide (Compound B3-1) and (8E,12E,14E)-7-acetoxy-3,6,19,21-tetrahydroxy-18-iodo-6,10,12,16,20-pentamethyltricosa-8,12,14-trien-11-olide (Compound B3-2)

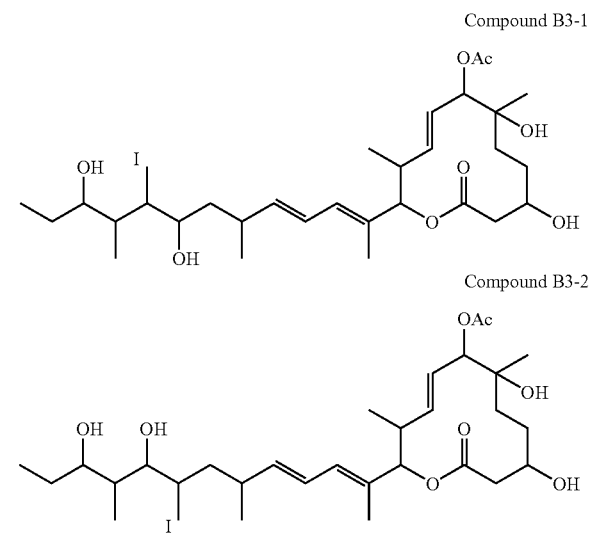

To a suspension of NaI (15.3 mg, 102.1 μmol) in acetonitrile (0.2 mL) was added dropwise TMS-Cl (7.0 μL, 55.2 μmol), followed by stirring at room temperature for 10 min. To the reaction mixture was slowly added dropwise a solution of (8E,12E,14E)-7-acetoxy-3,6,21-trihydroxy-6,10,12,16,20-pentamethyl-18,19-epoxytricosa-8,12,14-trien-11-olide (17.5 mg, 32.6 μmol) in acetonitrile (0.1 mL), followed by stirring for 40 min. To the reaction suspension was added a 10% aqueous sodium thiosulfate solution (1 mL), followed by extracting with chloroform (2 mL) for two times. The resulting organic layers were dried over anhydrous sodium sulfate, filtered and then evaporated. The resulting crude product was purified by thin layer chromatography (MERCK Silicagel 60 F254, 0.5 mm, developing solution; chloroform:methanol=20:1) to obtain the title Compound B3-1 (1.8 mg, 2.7 μmol, 8.3%) and Compound B3-2 (4.6 mg, 6.9 μmol, 21.2%) as colorless oils, respectively.

Compound B3-1

$^1$H-NMR spectrum (CD$_3$OD, 400 MHz) δ (ppm): 0.88 (3H,d,J=7 Hz), 0.95(3H,t,J=7 Hz), 1.03(3H,d,J=6 Hz), 1.04 (3H,d,J=7 Hz), 1.18(3H,s), 1.26–1.45(5H,m), 1.54–1.65(3H,m), 1.74(3H,d,J=0.7 Hz), 1.98–2.07(1H,m), 2.05(3H,s), 2.52(2H,d,J=4 Hz), 2.50–2.60(2H,m), 3.56(1H, brt,J=9 Hz), 3.73–3.80(1H,m), 4.06(1H,dd,J=4,8 Hz), 5.04 (1H,d,J=10 Hz), 5.05(1H,d,J=11 Hz), 5,56(1H,dd,J=10,15 Hz), 5.59(1H,dd,J=9,15 Hz), 5.69(1H,dd,J=10,15 Hz), 6.09 (1H,d,J=11 Hz), 6.33(1H,dd,J=11,15 Hz); FAB-MS m/z 665(M+H)$^+$.

Compound B3-2

¹H-NMR spectrum (CD₃OD, 400 MHz) δ (ppm): 0.87 (3H,d,J=6 Hz), 0.89(3H,d,J=7 Hz), 0.94(3H,t,J=7 Hz), 1.00 (3H,d,J=7 Hz), 1.18(3H,s), 1.35–1.45(3H,m), 1.48–1.64(4H,m), 1.74(3H,d,J=1.1 Hz), 1.90–2.02(2H,m), 2.05(3H,s), 2.52(2H,d,J=4 Hz), 2.45–2.58(2H,m), 3.74–3.80 (1H,m), 3.82–3.88(2H,m), 4.40(1H,ddd,J=3,5,11 Hz), 5.04 (1H,d,J=10 Hz), 5.56(1H,dd,J=10,15 Hz), 5,69(1H,dd,J=10, 15 Hz), 5.77(1H,dd,J=7,15 Hz), 6.08(1H,d,J=11 Hz), 6.29 (1H,dd,J=11,15 Hz); FAB-MS m/z 665(M+H)⁺.

Example B4

(8E,12E)-7-Acetoxy-3,6,21-trihydroxy-6,10,12,16, 20-pentamethyl-14,15,18,19-diepoxytricosa-8,12-dien-11-olide and (8E,14E)-7-acetoxy-3,6,21-trihydroxy-6,10,12,16,20-pentamethyl-12,13,18,19-diepoxytricosa-8,14-dien-11-olide (Compound B4)

Compound B4

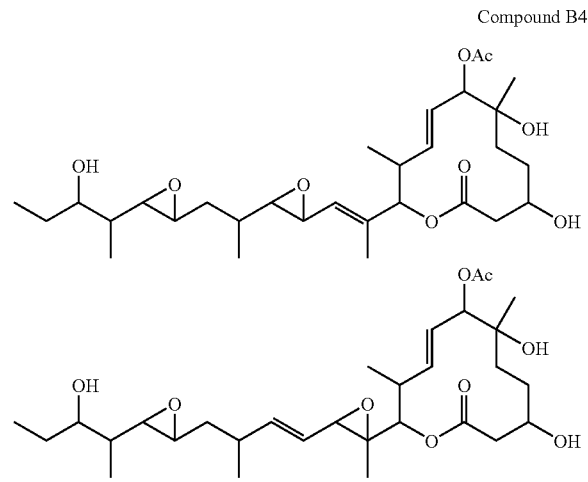

A solution of (8E,12E,14E)-7-acetoxy-3,6,21-trihydroxy-6,10,12,16,20-pentamethyl-18,19-epoxytricosa-8,12,14-trien-11-olide (21.7 mg, 40.4 μmol) in dichloromethane (0.5 mL) was cooled to −30° C. m-Chloroperbenzoic acid (26.4 mg, 76.5 μmol) was added thereto, followed by stirring for 17.5 hours. After the temperature was raised to room temperature, a saturated sodium bicarbonate aqueous solution (1.0 mL) was added thereto and the mixture was extracted with chloroform (12 mL). The resulting organic layer was dried over anhydrous sodium sulfate, filtered and then concentrated. The resulting crude product was purified by thin layer chromatography (MERCK Silicagel 60 F254, 0.5 mm, devloping solution; toluene:acetone=1:1) to obtain the title Compound B4 (9.3 mg, 16.8 μmol, 41.6%) as a colorless oil.

¹H-NMR spectrum (CD₃OD, 400 MHz) δ (ppm): 0.83–0.97(23.6H,m), 0.98–1.12(13.2H), 1.15–1.19(8.7H,m), 1.21–1.40(13.4H,m), 1.43–1.65(17.8H, m), 1.70–1.84(6.9H,m), 2.03–2.06(8.9H,m), 2.43–2.77(15.5H,m), 2.84–2.88(1.6H,m), 3.40–3.47(2.5H, m), 3.47–3.56(2.7H,m), 3.70–3.80(3.0H,m), 4.48–4.52(1.0H,m), 5.00–5.08(4.3H,m), 5.19–5.23(1.4H,m), 5.39–5.46(1.2H,m), 5.50–5.72(5.91H, m), 5.92–6.00(1.0H,m); FAB-MS m/z 553(M+H)⁺.

Example B5

(8E,12E,14E)-7-Acetoxy-3,6,16,21-tetrahydroxy-6, 10,12,16,20-pentamethyl-18,19-epoxytricosa-8,12, 14-trien-11-olide (Compound B5-1) and epi-(8E, 12E,14E)-7-acetoxy-3,6,16,21-tetrahydroxy-6,10,12, 16,20-pentamethyl-18,19 -epoxytricosa-8,12,14-trien-11-olide (Compound B5-2)

Compound B5-1 (11107D)

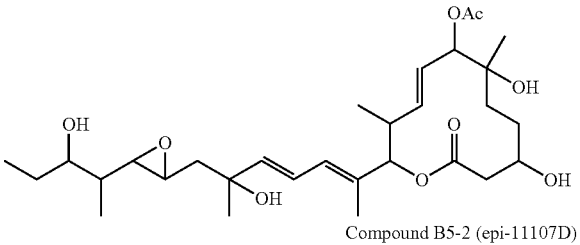

Compound B5-2 (epi-11107D)

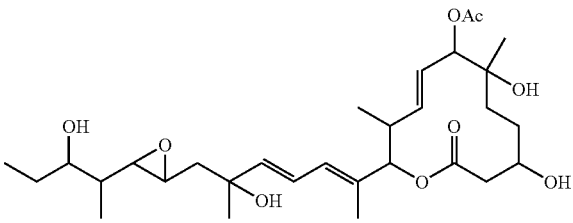

4A molecular sieves (26 mg) and V(acac)₃ (6.0 mg, 17.2 μmol) were added to a solution of (8E,12E,14E)-7-acetoxy-3,6,21-trihydroxy-6,10,12,16,20-pentamethyl-18, 19-epoxytricosa-8,12,14-trien-11-olide (18.7 mg, 34.8 μmol) in dichloromethane (0.4 mL), followed by cooling to −30° C. TBHP (20 μL, 100 μmol) was added thereto, the mixture was stirred for about 19 hours and the temperature was raised to −10° C. TBHP (50 μL, 250 μmol) was further added thereto, followed by stirring about 20 hours. Dimethylsulfoxide (51 μL, 255 μmol) was added to the reaction mixture and concentrated. The resulting crude product was purified by thin layer chromatography (MERCK Silicagel 60 F254, 0.5 mm, developing solution; toluene:acetone=1:1) and preparative HPLC (SHISEIDO Capcell pak C18, 10 mm I.D.×250 mm, acetonitrile:water=30:70, 4.0 mL/min.) to obtain the title Compound B5-1 (1.06 mg, 1.92 μmol, 5.5%) and Compound B5-2 (1.25 mg, 2.26 μmol, 6.5%) as colorless oils, respectively.

Compound B5-1

¹H-NMR spectrum (CD₃OD, 400 MHz) δ (ppm): 0.87 (1H,d,J=7 Hz), 0.88(3H,d,J=7 Hz), 0.93(3H,t,J=7 Hz), 1.18 (3H,s), 1.18–1.69(8H,m), 1.33(3H,s), 1.77(3H,d,J=1.1 Hz), 1.82–1.90(1H,m), 2.05(3H,s), 2.49–2.60(3H,m), 2.66(1H, dd,J=2,8 Hz), 2.89(1H,dt,J=2,6 Hz), 3.52(1H,dt,J=4,8 HZ), 3.73–3.82(1H,m), 5.04(1H,d,J=10 Hz), 5.05(1H,d,J=11 Hz), 5.56(1H,dd,J=10,15 Hz), 5.70(1H,dd,J=10,15 Hz), 5.86(1H, d,J=15 Hz), 6.13(1H,d,J=11 Hz), 6.52(1H,dd,J=11,15 Hz); FAB-MS m/z 551(M-H)⁻.

Compound B5-2

¹H-NMR spectrum (CD₃OD, 400 MHz) δ (ppm): 0.88 (3H,d,J=7 Hz), 0.90(3H,d,J=7 Hz), 0.94(3H,t,J=7 Hz), 1.18 (3H,s), 1.27–1.43(3H,m), 1.34(3H,s), 1.43–1.65(4H,m), 1.77(3H,d,J=1.1 Hz), 1.88(1H,dd,J=6,14 Hz), 2.05(3H,s), 2.50–2.62(3H,m), 2.70(1H,dd,J=2,7 Hz), 2.82(1H,dt,J=2,6 HZ), 3.54(1H,dt,J=5,9 Hz), 3.74–3.80(1H,m), 5.04(1H,d, J=10 Hz), 5.07(1H,d,J=11 Hz), 5.56(1H,dd,J=10,15 Hz), 5.70(1H,dd,J=10,15 Hz), 5.89(1H,d,J=15 Hz), 6.14(1H,d, J=12 Hz), 6.53(1H,dd,J=11,15 Hz); FAB-MS m/z 551(M-H)⁻.

Example B6

7-Acetoxy-3,6,21-trihydroxy-6,10,12,16,20-pentamethyl-18,19-epoxytricosa-11-olide and E-7-acetoxy-3,6,21-trihydroxy-6,10,12,16,20-pentamethyl-18,19-epoxytricosa-14-en-11-olide (Compound B6-1), and E-7-acetoxy-3,6,21-trihydroxy-6,10,12,16,20-pentamethyl-18,19-epoxytricosa-12-en-11-olide (Compound B6-2)

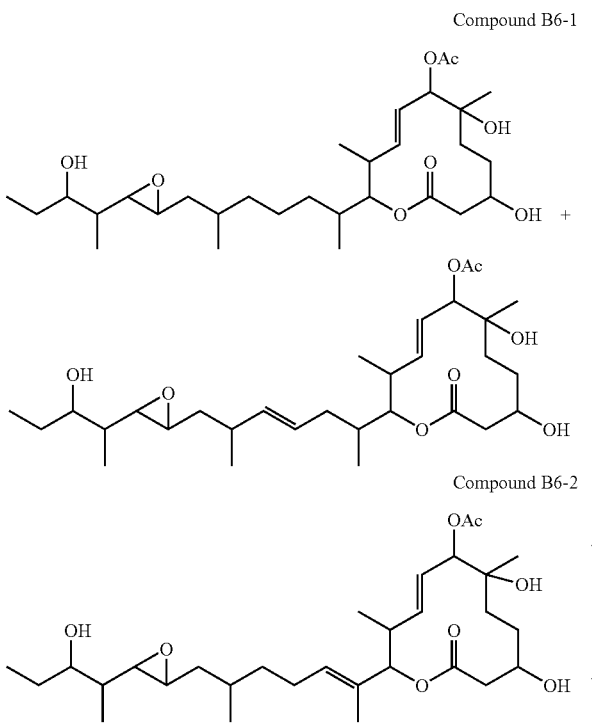

Compound B6-1

Compound B6-2

(8E,12E,14E)-7-acetoxy-3,6,21-trihydroxy-6,10,12,16, 20-pentamethyl-18,19-epoxytricosa-8,12,14-trien-11-olide (12.0 mg, 22.4 µmol) was dissolved in methanol (2.0 mL), and a 10% palladium carbon catalyst (WET, moisture 52.2%) (1.2 mg) was added. The mixture was stirred for 20 minutes under hydrogen atmosphere, was filtered (ADVANTEC DISMIC-13HP, PTFE, 0.2 µm), and was concentrated. The resulting crude product was purified by thin layer chromatography (MERCK Silicagel 60 F254, 0.5 mm, evolution solution; hexane:tetrahydrofuran=1:2) to obtain the title Compound B6-2 (2.7 mg, 5.1 µmol, 22.7%) and Compound B6-1 (3.6 mg) as colorless oils, respectively.

Compound B6-1

¹H-NMR Spectrum(CD₃OD,400 MHz) δ (ppm): 0.85–1.05(18.0H,m), 1.14–1.18(3.8H,m), 1.18–2.03(16.0H, m), 2.03–2.06(3.4H,m), 2.06–2.18(0.6H,m), 2.26–2.70(4.9H,m), 2,73–2.82(0.9H,m), 3.49–3.58(1.0H,m), 3.71–3.79(1.1H,m),
4.77–4.95(1.1H,m), 5.00–5.06(1.1H,m), 5.30–5.653.4H,m); FAB-MS m/z 539(M+H)⁺, 540M⁻, 537(M-H)⁻.

Compound B6-2

¹H-NMR Spectrum(CD₃OD,400 MHz)δ (ppm): 0.87(1H, d,J=7 Hz), 0.942(3H,d,J=7 Hz), 0.944(3H,t,J=7 Hz), 0.98 (1H,d,J=7 Hz), 1.17(3H,s), 1.20–1.70(12H,m), 1.63(3H,s), 2.05–2.13(2H,m), 2.05(3H,s), 2.49–2.57(1H,m), 2.51(2H,d, J=4 Hz), 2.63(1H,dd,J=3,8 Hz), 2.76(1H,dt,J=2,6 Hz), 3.52 (1H,dt,J=4,8 Hz), 3.73–3.80(1H,m), 5.02(1H,d,J=11 Hz), 5.03(1H,d,J=10 Hz), 5.50–5.55(1H,m), 5.54(1H,dd,J=10,15 Hz), 5.68(1H,dd,J=10,15 Hz); FAB-MS m/z 539(M+H)⁺.

Example B7

(8E,12E)-7-Acetoxy-3,6-dihydroxy-14-oxo-6,10,12-trimethyl-tetradeca-11-olide (Compound B7)

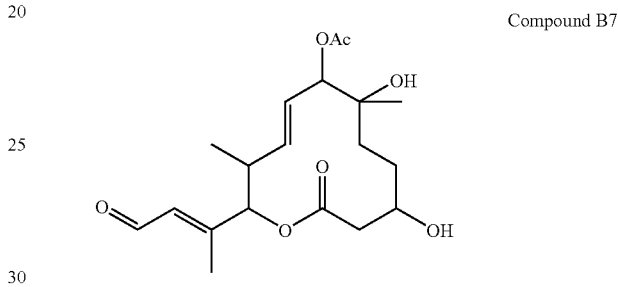

Compound B7

A 4% aqueous solution (213 µL) of osmium tetraoxide was added to a solution of (8E,12E,14E)-7-acetoxy-3,6,21-trihydroxy-6,10,12,16,20-pentamethyl-18,19-epoxytricosa-8,12,14-trien-11-olide (15 mg, 28 µmol) in 2 mL of acetone, followed by stirring for 2 hours at room temperature. An aqueous solution of sodium sulfite was added to the reaction solution and vigorously stirred for a while, and then ethyl acetate was added thereto. The organic layer was washed with brine, dried over anhydrous magnesium sulfate and evaporated. The resulting residue was dissolved in 1 mL of tetrahydrofuran and an aqueous solution of sodium periodate (7.6 mg in 0.5 ml of water) was added thereto, followed by stirring at room temperature 12 hours. After the reaction solution was diluted with ethyl acetate, the solution was washed with distilled water and brine, dried over anhydrous magnesium sulfate and evaporated. The resulting residue was purified by silica gel column chromatography (Kanto silica gel 60N spherical, neutral, 40 to 100 µm, eluate; ethyl acetate/ethyl acetate:methanol=10:1) to obtain the objective compound (1.2 mg, 11.6%) as a colorless oil.

¹H-NMR Spectrum (CD₃OD,500 MHz) δ (ppm): 0.95 (3H,d,J=7.0 Hz), 1.20(3H,s), 1.30–1.46(2H,m), 1.54–1.72 (2H,m), 2.07(3H,s), 2.20(3H,s), 2.50–2.66(4H,m), 3.76–3.86(1H,m), 5.05(1H,d,J=6.0 Hz), 5.07(1H,d,J=6.0 Hz), 5.60(1H,dd,10.0,15.0 Hz), 5.76(1H,dd,J=10.0,15.0 Hz), 6.02(1H,d,8.00 Hz), 10.03(1H,d,J=8.0 Hz); ESI-MS m/z 391(M+Na)⁺.

Example B8

(8E,12E,14E)-7-Acetoxy-3,6-dihydroxy-21-methoxy-6,10,12,16,20-pentamethyl-18,19-epoxytricosa-8,12,14-trien-11-olide (Compound B8-1), (8E,12E, 14E)-7-acetoxy-3-hydroxy-6,21-dimethoxy-6,10,12, 16,20-pentamethyl-18,19-epoxytricosa-8,12,14-trien-11-olide (Compound B8-2), (8E,12E,14E)-7- acetoxy-3,6,21-trimethoxy-6,10,12,16,20-pentamethyl-18,19-epoxytricosa-8,12,14-trien-11-olide (Compound B8-3), (8E,12E,14E)-7-acetoxy-6,21-dihydroxy-3-methoxy-6,10,12,16,20-pentamethyl-18,19-epoxytricosa-8,12,14-trien-11-olide (Compound B8-4), (8E,12E,14E)-7-acetoxy-3,21-dihydroxy-6-methoxy-6,10,12,16,20-pentamethyl-18,19-epoxytricosa-8,12,14-trien-11-olide (Compound B8-5) and (8E,12E,14E)-7-acetoxy-6-hydroxy-3,21-dimethoxy-6,10,12,16,20-pentamethyl-18,19-epoxytricosa-8,12,14-trien-11-olide (Compound B8-6)

Compound B8-1
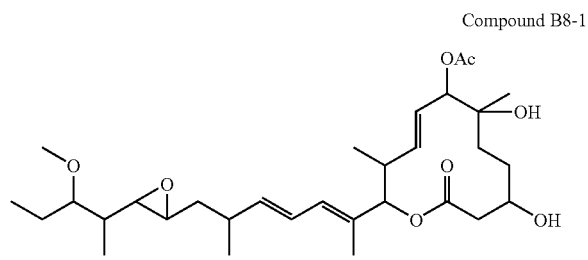

Compound B8-2
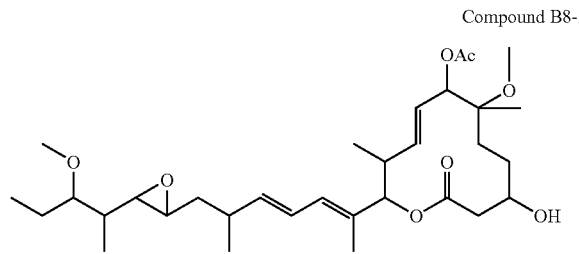

Compound B8-3
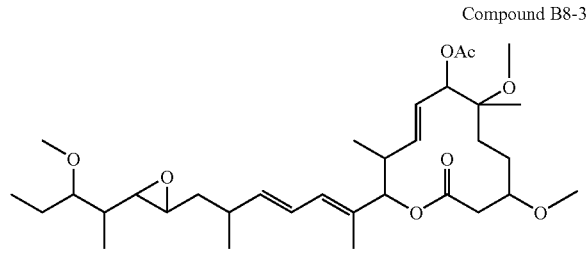

Compound B8-4
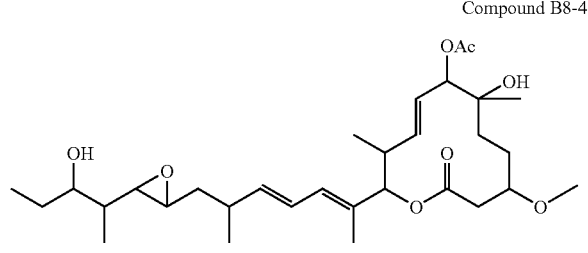

Compound B8-5
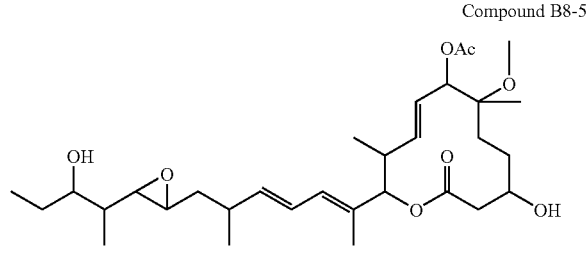

Compound B8-6
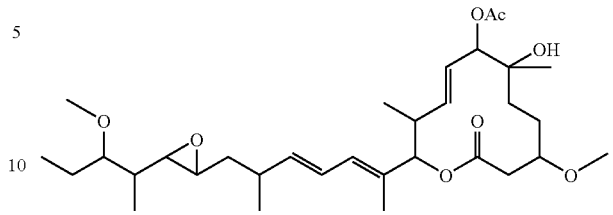

Methyl trifluoromethanesulfonate (28 mg, 168 μmol) was added to a solution of (8E,12E,14E)-7-acetoxy-3,6,21-trihydroxy-6,10,12,16,20-pentamethyl-18,19-epoxytricosa-8,12,14-trien-11-olide (30 mg, 56 μmol) and 1,8-bis(dimethylamino)naphthalene (43 mg, 202 μmol) in 1 ml toluene, followed by heating at 60° C. for 20 hours under nitrogen atmosphere. After filtering off the resulting precipitates, the filtrate was diluted with ethyl acetate, an aqueous ammonium chloride was added thereto, and the solution was vigorously stirred for 5 min. The organic layer was washed with a saturated sodium bicarbonate aqueous solution and brine, dried over anhydrous magnesium sulfate and evaporated. The resulting residue was purified by silica gel column chromatography (Kanto silica gel 60N spherical, neutral, 40 to 100 μm, eluate; hexane:ethyl acetate=1:1 to 1:4) and a preparative HPLC (YMC J'sphere ODS M-80, 20 mm I.D.×250 mm, elution solvent; acetonitrile:water=20:80 to 100:0) to obtain the respective title compounds.

Compound B8-1

$^1$H-NMR Spectrum(CD$_3$OD,500 MHz) δ (ppm): 0.92 (3H,d,J=7.0 Hz) 0.92(3H,d,J=7.0 Hz), 0.93(3H,t,J=7.0 Hz), 1.13(3H,d,J=6.5 Hz), 1.23(3H,s), 1.32–1.72(9H,m), 1.79 (3H,s), 2.10(3H,s), 2.46–2.66(4H,m), 2,68(1H,dd,J=2.0,8.0 Hz), 2.77(1H,dt,J=2.0,6.0 Hz), 3.17–3.24(1H,m), 3.42(3H,s), 3.76–3.88(1H,m), 5.09(2H,d,J=10.0 Hz), 5.61(1H,dd,J=10.0,15.0 Hz), 5.70(1H,dd,J=8.5,15.0 Hz), 5.74(1H,dd,J=10.0,15.0 Hz), 6.13(1H,d,J=10.5 Hz), 6.36(1H,dd,J=10.5,15.0 Hz); ESI-MS m/z 551(M+H)$^+$, 573(M+Na)$^+$.

Compound B8-2

$^1$H-NMR Spectrum(CD$_3$OD,500 MHz) δ (ppm): 0.92 (6H,d,J=7.0 Hz), 0.93(3H,t,J=7.0 Hz), 1.13(3H,d,J=6.5 Hz), 1.24(3H,s), 1.32–1.72(9H,m), 1.78(3H,s), 2.10(3H,s), 2.44–2.79(6H,m), 3.17–3.24(1H,m), 3.41(3H,s), 3.42(3H,s), 3.42–3.50(1H,m), 4.99(1H,d,J=11.0 Hz), 5.07(1H,d,10.0 Hz), 5.58(1H,dd,J=10.0,15.0 Hz), 5.70(1H,dd,J=8.5,15.0 Hz), 5.75(1H,dd,J=9.5,15.0 Hz), 6.13(1H,d,J=11.0 Hz), 6.36 (1H,dd,J=11.0,15.0 Hz); ESI-MS m/z 565(M+H)$^+$, 587(M+Na)$^+$.

Compound B8-3

ESI-MS m/z 601(M+Na)$^+$.

Compound B8-4

$^1$H-NMR Spectrum(CD$_3$OD,500 MHz) δ (ppm): 0.95 (3H,d,J=7.0 Hz), 0.97(3H,d,J=7.0 Hz), 1.01(3H,t,J=7.5 HZ), 1.15(3H,d,J=7.0 Hz), 1.24–1.34(1H, m), 1.26(3H,s), 1.34–1.46(2H,m), 1.47–1.64(3H,m), 1.66–1.74(2H,m), 1.74–1.84(1H,m), 1.81(3H,s), 2.13(3H,s), 2.49(1H,dd, J=3.0,14.5 Hz), 2.48–2.68(2H,m), 2.73(1H,dd,J=2.0,8.5 Hz), 2.75–2.82(2H,m), 3.43(3H,s), 3.45–3.52(1H,m), 3.55–3.62(1H,m), 5.02(1H,d,J=10.5 Hz), 5.09(1H,d,J=9.5 Hz), 5.61(1H,dd,J=10.0,15.0 Hz), 5.73(1H,dd,J=8.5,15.0 Hz), 5.77(1H,dd,J=10.0,15.0 Hz), 6.16(1H,d,J=11.0 Hz), 6.39(1H,dd,J=11.0,15.0 Hz; ESI-MS m/z 573(M+Na)$^+$, 549 (M−H)$^-$, 585(M+Cl)$^-$.

Compound B8-5

$^1$H-NMR Spectrum (CD$_3$OD,500 MHz) δ (ppm): 0.94 (3H,d,J=6.5 Hz), 0.97(3H,d,J=7.0 Hz), 1.01(3H,t,J=7.5 Hz), 1.15(3H,d,J=6.5 Hz), 1.22–1.33(1H,m), 1.27(3H,s), 1.46–1.74(8H,m), 1.82(3H,s), 2.11(3H,s), 2.48–2.68(4H,m), 2.73(1H,d,J=8.0 Hz), 2.79(1H,t,J=6.0 Hz), 3.39(3H,s), 3.55–3.62(1H,m), 3.85– 3.92(1H,m), 5.11(1H,d,J=11.0 Hz), 5.19(1H,d,J=9.5 Hz), 5.63(1H,dd,J=10.0,15.0 Hz), 5.73(1H,dd,J=8.5,15.0 Hz), 5.78(1H,dd,J=10.0,15.0 Hz), 6.16(1H,d,J=11.0 Hz), 6.40(1H,dd,J=11.0,15.0 Hz); ESI-MS m/z 573 (M+Na)$^+$, 549(M−H)$^-$, 585(M+Cl)$^-$.

Compound B8-6

$^1$H-NMR Spectrum (CD$_3$OD,500 MHz) δ (ppm): 0.85–0.92(9H,m) 1.09(3H,d,J=7.0 Hz), 1.20(3H,s), 1.21–1.40(3H,m), 1.42–1.54(2H,m), 1.56–1.68(3H,m), 1.68–1.76(1H,m), 1.74(3H,s), 2.06(3H,s), 2.43(1H,dd, J=8.0,14.5 Hz), 2.40–2.62(2H,m), 2.64(1H,dd,J=2.5,7.5 Hz), 2.68–2.75(2H,m), 3.12–3.20(1H,m), 3.37(3H,s), 3.38 (3H,s), 3.38–3.46(1H,m), 4.95(1H,d,J=11.0 HZ), 5.03(1H, d,J=9.5 Hz), 5.54(1H,dd,J=9.5,15.0 Hz), 5.66(1H,dd,J=8.0, 15.0 Hz), 5.71(1H,dd,J=10.0,15.0 Hz), 6.09(1H,d,J=11.0 Hz), 6.32(1H,dd,J=11.0,15.0 Hz); ESI-MS m/z 565(M+H)$^+$, 587(M+Na)$^+$.

Example B9

(8E,12E,14E)-7-Acetoxy-3,6,17-trihydroxy-21-methoxy-6,10,12,16,20-pentamethyl-18,19-epoxytricosa-8,12,14-trien-11-olide (Compound B9)

Compound B9

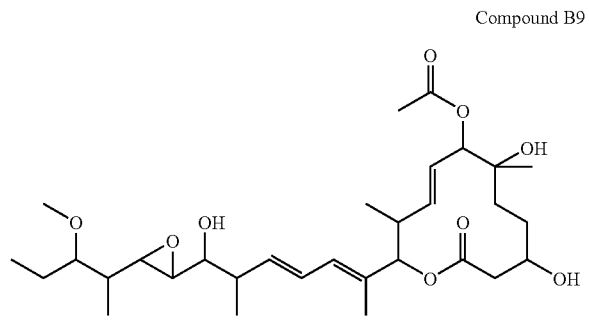

By using (8E,12E,14E)-7-acetoxy-3,6,17,21 -tetrahydroxy-6,10,12,16,20-pentamethyl-18,19-epoxytricosa-8,12, 14-trien-11-olide (2.3 mg, 4.2 μmol) obtained in Example A22, methylation of the hydroxy group was carried out in the same manner as Example B8, to give the title compound (30 μg).

$^1$H-NMR Spectrum (CDCl$_3$,500 MHz) δ (ppm): 0.86–0.94(9H,m), 1.16(3H,d,J=6.5 Hz), 1.22(3H,s), 1.22–1.74(7H,m), 1.75(3H,s), 2.10(3H,s), 2.46–2.58(3H,m), 2.63(1H,dd,J=3.5,14.5 Hz), 2.82(1H,dd,J=2.0,5.0 Hz), 2.91 (1H,d,J=2.0,8.0 Hz), 3.18(1H,dt,J=4.0,10.5 Hz), 3.29–3.35 (1H,m), 3.41(3H,s), 3.72–3.80(1H,m), 5.09(1H,d,J=9.5 Hz), 5.16(1H,d,J=11.0 HZ), 5.58–5.74(3H,m), 6.09(1H,d,J=10.5 Hz), 6.32(1H,dd,J=11.0,15.0 Hz); ESI-MS m/z 589(M+Na)$^+$, 601(M+Cl)$^-$.

Example B10

(8E,12E,14E)-7-Acetoxy-3,21-bis(t-butyldimethylsiloxy)-6-hydroxy-6,10,12,16,20-pentamethyl-18,19-epoxytricosa-8,12,14-trien-11-olide (Compound B10-1), (8E,12E,14E)-7-acetoxy-3-t-butyldimethylsiloxy-6,21-dihydroxy-6,10,12,16,20-pentamethyl-18,19-epoxytricosa-8,12,14-trien-11-olide (Compound B10-2) and (8E,12E,14E)-7-acetoxy-21-(t-butyldimethylsiloxy)-3,6-dihydroxy-6,10,12,16,20-pentamethyl-18,19-epoxytricosa-8,12,14-trien-11-olide (Compound B10-3)

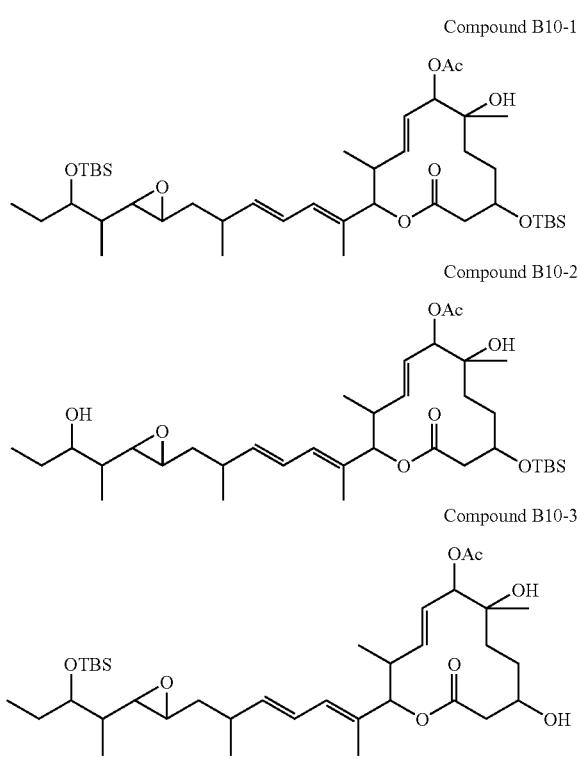

(wherein TBS is the abbreviation of t-butyldimethylsilyl, and so forth.)

To a solution of (8E,12E,14E)-7-acetoxy-3,6,21-trihydroxy-6,10,12,16,20-pentamethyl-18,19-epoxytricosa-8,12, 14-trien-11-olide (10 mg, 56 μmol) and imidazole (4.2 mg, 61 μmol) in 0.4 mL of N,N-dimethylformamide was added a solution of t-butylchlorodimethylsilane in 0.1 mL of N,N-dimethylformamide, followed by stirring at room temperature for 12 hours under nitrogen atmosphere. The reaction solution was diluted with ethyl acetate, washed with distilled water and brine, dried over anhydrous magnesium sulfate and evaporated. The resulting residue was purified by silica gel column chromatography (Kanto silica gel 60N spherical, neutral, 40 to 100 μm, eluate; hexane:ethyl acetate=3:1 to 1:1) to obtain the title Compound B10-1 (5.3 mg, 38%), Compound B10-2 (2.4 mg, 40%) and Compound B10-3 (1.5 mg, 12%) as colorless oils, respectively.

Compound B10-1

$^1$H-NMR Spectrum (CD$_3$OD,600 MHz) δ (ppm): 0.12 (6H,s), 0.13(3H,s), 0.14(3H,s), 0.38(3H,t,J=7.2 Hz), 0.90 (3H,d,J=6.8 Hz), 0.93(3H,d,J=6.8 Hz), 0.95(9H,s), 0.96(9H, s), 1.22(3H,d,J=6.6 Hz), 1.26–1.33(1H,m), 1.36–1.63(6H, m), 1.67–1.75(2H,m), 1.77(3H,s), 2.11(3H,s), 2.42(1H,dd, J=4.8,15.0 Hz), 2.48–2.64(3H,m), 2.66(1H,dd,J=3.0,8.4 Hz), 2.77(1H,dt,J=2.4,6.0 Hz), 3.75–3.80(1H,m), 3.93–3.99 (1H,m), 4.94(1H,d,J=10.8 Hz), 5.07(1H,d,J=9.6 Hz), 5.61 (1H,dd,J=9.6,15.0 Hz), 5.68(1H,dd,J=8.4,15.0 Hz), 5.75 (1H,dd,J=9.6,15.0 Hz), 6.14(1H,d,J=10.8 Hz), 6.36(1H,dd, J=10.8,15.0 Hz); ESI-MS m/z 765(M+H)$^+$.

Compound B10-2

$^1$H-NMR Spectrum (CD$_3$OD,600 MHz) δ (ppm): 0.13 (3H,s), 0.14(3H,s), 0.93(3H,d,J=6.8 Hz), 0.94(3H,d,J=6.8 Hz), 0.96(9H,s), 0.98(3H,t,J=7.2 Hz), 1.13(3H,d,J=7.2 Hz), 1.13(3H,d,J=6.6 Hz), 1.20–1.28(1H,m), 1.34–1.76(8H,m), 1.77(3H,s), 2.10(3H,s), 2.42(1H,dd,J=4.8,13.8 Hz), 2.47–2.65(3H,m), 2.70(1H,dd,J=2.4,8.4 Hz), 2.77(1H,dt, J=2.4,6.0 Hz), 3.53–3.58(1H,m), 3.93–4.00(1H,m), 4.94 (1H,d,J=10.8 Hz), 5.07(1H,d,J=9.6 Hz), 5.61(1H,dd,J=9.6, 15.0 Hz), 5.71(1H,dd,J=8.4,15.0 Hz), 5.74(1H,dd,J=9.6, 15.0 Hz), 6.15(1H,d,J=10.8 Hz), 6.36(1H,dd,J=10.8,15.0 Hz); ESI-MS m/z 651(M+H)$^+$, 673(M+Na)$^+$.

Compound B10-3

$^1$H-NMR Spectrum (CD$_3$OD,600 MHz) δ (ppm): 0.12 (6H,s), 0.86(3H,d,J=7.2 Hz), 0.90(3H,d,J=7.2 Hz), 0.92(9H, s), 0.95(3H,t,J=6.6 Hz), 1.12(3H,d,J=6.6 Hz), 1.23(3H,s), 1.26–1.74(9H,m), 1.78(3H,s), 2.10(3H,s), 2.44–2.68(4H,m), 2.66(1H,dd,J=2.4,8.4 Hz), 2.77(1H,dt,J=2.4,6.0 Hz), 3.75–3.85(2H,m), 5.08(1H,d,J=10.8 Hz), 5.09(1H,d,J=9.6 Hz), 5.61(1H,dd,J=9.6,15.0 Hz), 5.68(1H,dd,J=8.4,15.0 Hz), 5.74(1H,dd,J=9.6,15.0 Hz), 6.13(1H,d,J=10.8 Hz), 6.36(1H,dd,J=10.8,15.0 Hz); ESI-MS m/z 651(M+H)$^+$, 673 (M+Na)$^+$.

Example B11

(8E,12E,14E)-7-Acetoxy-6,21-bis(1-ethoxyethoxy)-3-(t-butyldimethylsiloxy)-6,10,12,16,20-pentamethyl-18,19-epoxytricosa-8,12,14-trien-11-olide (Compound B11)

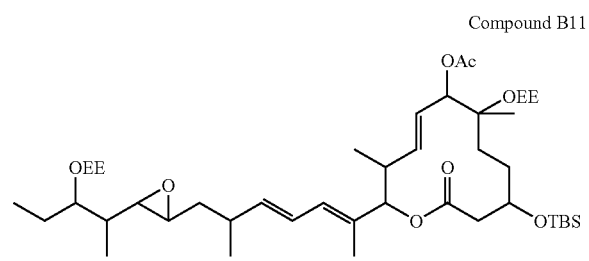

Compound B11

(wherein EE is the abbreviation of 1-ethoxyethyl, and so forth.)

Pyridinium p-toluenesulfonate (1.8 mg, 7 μmol) was added to a solution of (8E,12E,14E)-7-acetoxy-3-(t-butyldimethylsiloxy)-6,21-dihydroxy-6,10,12,16,20-pentamethyl-18,19-epoxytricosa-8,12,14-trien-11-olide (44 mg, 67 μmol) obtained in Example B10 and ethyl vinyl ether (98 mg, 1.35 mmol) in methylene chloride (3 mL), and the mixture was stirred at room temperature for 18 hours. The reaction solution was diluted with ethyl acetate, washed with distilled water and brine, dried over anhydrous magnesium sulfate and evaporated. The resulting residue was purified by silica gel column chromatography (Kanto silica gel 60N, 40 to 50 μm, ethyl acetate:hexane=1:4 to 1:2) to obtain the title compound (35 mg, 66%) as a colorless oil.

ESI-MS m/z 817(M+Na)$^+$.

Example B12

(8E,12E,14E)-3,21-bis(t-Butyldimethylsiloxy)-6,7-dihydroxy-6,10,12,16,20-pentamethyl-18,19-epoxytricosa-8,12,14-trien-11-olide (Compound B12)

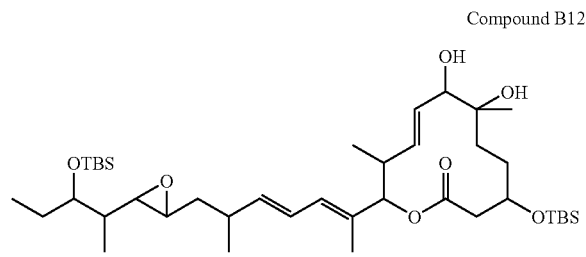

Compound B12

Potassium carbonate (48 mg, 0.35 mmol) was added to a solution of (8E,12E,14E)-7-acetoxy-3,21-bis(t-butyldimethylsiloxy)-6-hydroxy-6,10,12,16,20-pentamethyl-18,19-epoxytricosa-8,12,14-trien-11-olide (220 mg, 0.29 mmol) obtained in Example B11 methanol (15 mL), followed by stirring at room temperature for 15 hours. After acetic acid (40 μL, 0.69 mmol) was added, the reaction solution was evaporated. The residue was dissolved in ethyl acetate, and the solution was washed with a saturated sodium bicarbonate aqueous solution and brine, dried over anhydrous magnesium sulfate and then concentrated to dryness under reduced pressure to obtain the title compound (0.2 g, 95%) as a colorless amorphous.

ESI-MS m/z 762(M+K)$^+$.

Example B13

(8E,12E,14E)-3,21-bis(t-Butyldimethylsiloxy)-6,7-carbonyldioxy-6,10,12,16,20-pentamethyl-18,19-epoxytricosa-8,12,14-trien-11-olide (Compound B13)

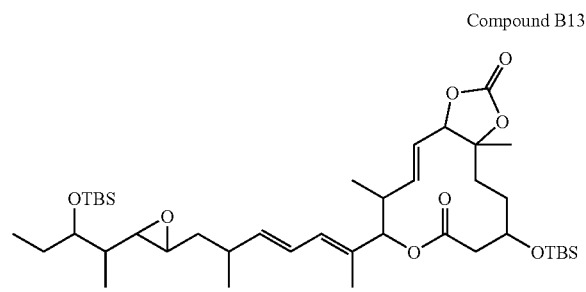

Compound B13

(8E,12E,14E)-3,21-bis(t-Butyldimethylsiloxy)-6,7-dihydroxy-6,10,12,16,20-pentamethyl-18,19-epoxytricosa-8,12, 14-trien-11-olide (15 mg, 20 mmol) obtained in Example B12 and N,N'-carbonyldiimidazole (20 mg, 120 μmol) were dissolved in 0.5 mL of tetrahydrofuran, followed by stirring at 60° C. for one hour. The reaction solution was diluted with ethyl acetate, washed with brine, dried over anhydrous magnesium sulfate and then evaporated. The resulting residue was purified by silica gel column chromatography (Kanto silica gel 60N, 40 to 100 μm, eluate; hexane:ethyl acetate=6:1) to obtain the title compound (15.4 mg, 86%) as a colorless oil.

Example B14

(8E,12E,14E)-21-(t-Butyldimethylsiloxy)-6,7-carbonyldioxy-3-hydroxy-6,10,12,16,20-pentamethyl-18,19-epoxytricosa-8,12,14-trien-11-olide (Compound B14-1) and (8E,12E,14E)-6,7-carbonyldioxy-3,21-dihydroxy-6,10,12,16,20-pentamethyl-18,19-epoxytricosa-8,12,14-trien-11-olide (Compound B14-2)

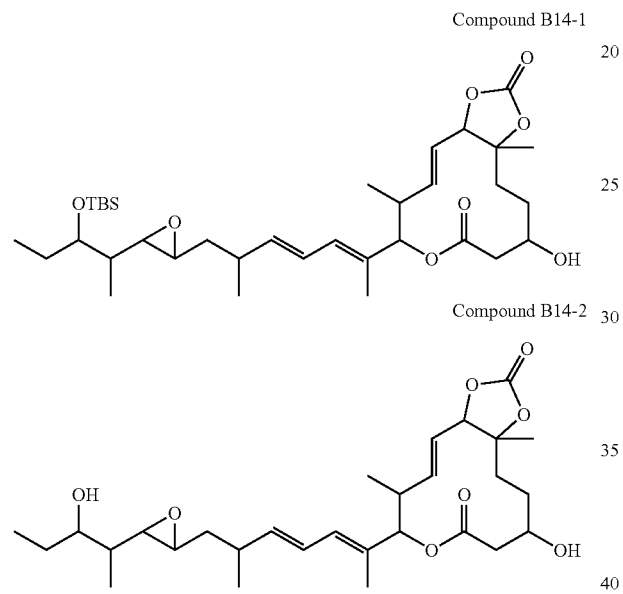

Compound B14-1

Compound B14-2

A solution of 1.0 M of tetrabutylammoniumfluoride in tetrahydrofuran (240 μL, 240 μmol) was added to a solution of (8E,12E,14E)-3,21-bis(t-butyldimethylsiloxy)-6,7-carbonyldioxy-6,10,12,16,20-pentamethyl-18,19-epoxytricosa-8,12,14-trien-11-olide (9 mg, 12 μmol) obtained in Example B13 in tetrahydrofuran (2.5 mL), followed by stirring at room temperature for 20 hours. Acetic acid (14 μL, 240 μmol) was added to the reaction solution, and it was diluted with ethyl acetate. Then, the reaction solution was washed with distilled water and brine, dried over anhydrous magnesium sulfate and evaporated. The resulting residue was purified by thin layer chromatography (MERCK Silicagel 60 F254, 0.2 mm, developing solution; hexane:ethyl acetate=2: 3) to obtain the title Compound B14-1 (4.3 mg, 56%) as a colorless oil and Compound B14-2 (0.92 mg, 15%) as a white powder, respectively.

Compound B14-1

$^1$H-NMR spectrum (CD$_3$OD, 500 MHz) δ (ppm): 0.08 (6H,m), 0.08(6H,s), 0.83(3H,t,J=7.3 Hz), 0.86(3H,d,J=7.3 Hz), 0.91(3H,d,J=7.3 Hz), 0.92(9H,s), 1.08(3H,d,J=7.0 Hz), 1.22–1.58(10H,m), 1.66(1H,dt,J=5.5,14.0 Hz), 1.75(3H,s), 1.84(1H,t,J=12.0 Hz), 2.07(1H,dt,J=7.5,8.0 Hz), 2.30(1H, dd,J=9.5,10.5 Hz), 2.42–2.54(1H,m), 2.60–2.76(4H,m), 3.71–3.76(1H,m), 3.88–3.96(1H,m), 4.80(1H, covered with CD$_3$OH), 4.95(1H,d,J=11.0 Hz), 5.65(1H,dd,J=8.5,15.0 Hz), 5.69(1H,dd,J=10.0,15.0 Hz), 5.77(1H,dd,J=10.0,15.0 Hz), 6.09(1H,d,J=10.5 Hz), 6.32(1H,dd,J=11.0,15.0 Hz); ESI-MS m/z 657(M+Na)$^+$.

Compound B14-2

$^1$H-NMR spectrum (CD$_3$OD, 500 MHz) δ (ppm): 0.90 (3H,d,J=7.0 Hz), 0.91(3H,d,J=6.5 Hz), 0.94(3H,t,J=7.5 Hz), 1.09(3H,d,J=6.5 Hz), 1.06–1.21(1H,m), 1.21–1.51(8H,m), 1.64(1H,dt,J=13.5,5.5 Hz), 1.75(3H,s), 1.85(1H,t,J=11.0 Hz), 2.07(1H,dt,J=7.5,13.0 Hz), 2.30(1H,dd,J=10.0,15.0 Hz), 2.42–2.54(1H,m), 2.64–2.76(4H,m), 3.49–3.55(1H,m), 3.88–3.95(1H,m), 4.80(1H,d,J=8.5 Hz), 4.95(1H,d,J=11.0 Hz), 5.67(1H,dd,J=8.5,15.0 Hz), 5.68(1H,dd,J=9.0,15.0 Hz), 5.76(1H,dd,J=9.0,15.0 Hz), 6.10(1H,d,J=11.0 Hz), 6.32 (1H,dd,J=11.0,15.0 Hz); ESI-MS m/z 543(M+Na)$^+$.

Example B15

(8E,12E,14E)-21-(t-butyldimethyl)siloxy-3-hydroxy-6,7-dimethoxy-6,10,12,16,20-pentamethyl-18,19-epoxytricosa-8,12,14-trien-11-olide (Compound B15-1) and (8E,12E,14E)-3,21-dihydroxy-6,7-dimethoxy-6,10,12,16,20-pentamethyl-18,19-epoxytricosa-8,12,14-trien-11-olide (Compound B15-2)

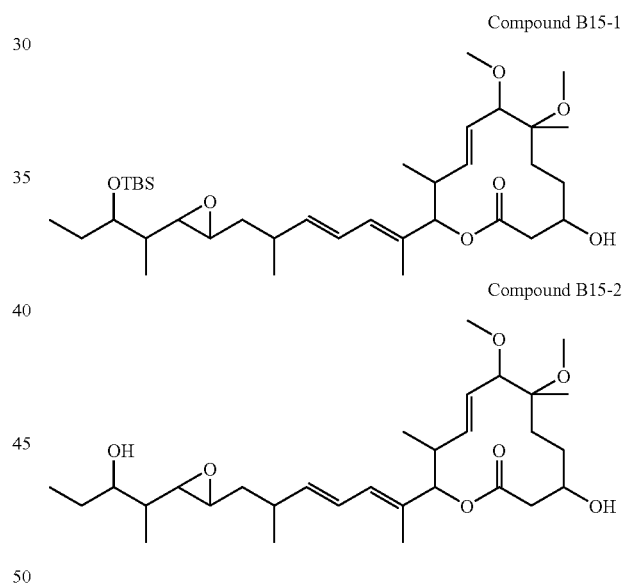

Compound B15-1

Compound B15-2

By using (8E,12E,14E)-3,21-bis(t-butyldimethylsiloxy)-6,7-dihydroxy-6,10,12,16,20-pentamethyl-18,19-epoxytricosa-8,12,14-trien-11-olide (20 mg, 28 μmol) obtained in Example B12, the methylation of the hydroxy group was carried out in the same manner as Example B8, and then the deprotection was carried out in the same manner as in Example B14, to obtain the title Compound B15-1 (8.4 mg, 40%) and Compound B15-2 (8.6 mg, 42%) as colorless oils, respectively.

Compound B15-1

$^1$H-NMR spectrum (CD$_3$OD, 500 MHz) δ (ppm): 0.08 (6H,s), 0.83(3H,t,J=7.5 Hz), 0.87(3H,d,J=7.0 Hz), 0.92(9H, s), 0.94(3H,d,J=7.0 Hz), 1.24–1.62(12H,m), 1.29(3H,s), 1.76(3H,s), 2.44–2.68(5H,m), 2.73(1H,dt,J=2.0,6.0 Hz), 3.23(3H,s), 3.27(3H,s), 3.71–3.76(1H,m), 4.78–4.82(1H covered with CD$_3$OH), 5.07(1H,d,J=10.5 Hz), 5.45(1H,dd, J=10.0,15.0 Hz), 5.58(1H,dd,J=9.5,15.0 Hz), 5.64(1H,dd, J=8.5,15.0 Hz), 6.09(1H,d,J=11.0 Hz), 6.33(1H,dd,J=11.0, 15.0 Hz).

Compound B15-2

$^1$H-NMR spectrum (CD$_3$OD, 500 MHz) δ (ppm): 0.91 (3H,d,J=7.0 Hz), 0.94(3H,t,J=7.5 Hz), 0.95(3H,d,6.5 Hz), 1.09(3H,d,J=7.0 Hz), 1.11–1.26(1H,m), 1.26–1.68(8H,m), 1.29(3H,s), 1.76(3H,s), 2.44–2.56(3H,m), 2.58–2.68(2H,m), 2.73(1H,dt,J=2.0,6.0 Hz), 3.23(3H,s), 3.27(3H,s), 3.48–3.55 (1H,m), 3.76–3.84(1H covered with CD$_3$OH), 5.07(1H,d, J=11.0 Hz), 5.45(1H,dd,J=10.0,15.0 Hz), 5.59(1H,dd, J=10.0,15.0 Hz), 5.67(1H,dd,J=8.5,15.0 Hz), 6.09(1H,d, J=11.0), 6.33(1H,dd,J=11.0,15.0 Hz); ESI-MS m/z 545(M+ Na)$^+$.

Example B16

(8E,12E,14E)-7-Acetoxy-3,6-dihydroxy-21-methanesulfonyloxy-6,10,12,16,20-pentamethyl-18,19-epoxytricosa-8,12,14-trien-11-olide (Compound B16-1) and (8E,12E,14E)-7-acetoxy-6-hydroxy-3,21-dimethanesulfonyloxy-6,10,12,16,20-pentamethyl-18,19-epoxytricosa-8,12,14-trien-11-olide (Compound B16-2)

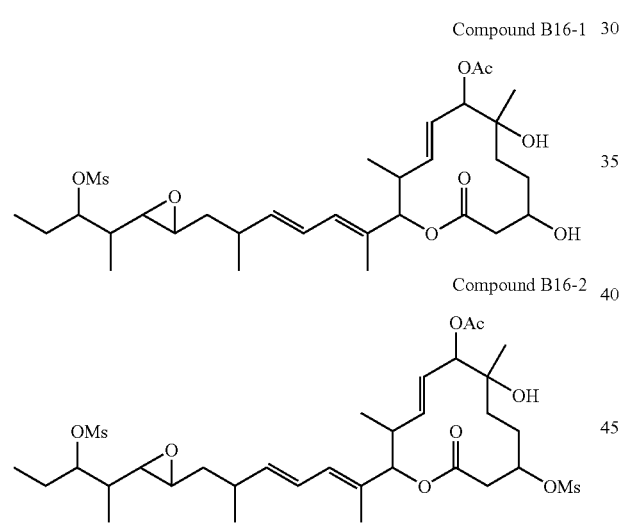

Compound B16-1

Compound B16-2

A solution of (8E,12E,14E)-7-acetoxy-3,6,21-trihydroxy-6,10,12,16,20-pentamethyl-18,19-epoxytricosa-8,12,14-trien-11-olide (56.3 mg, 104.9 μmol) in dichloromethane (1.0 mL) was ice-cooled, and dimethylaminopyridine (39.6 mg, 324.1 μmol) was added thereto. After stirring for about 30 min., mesyl chloride (12.5 μL, 161.5 μmol) was added and the temperature was raised to room temperature. After stirring for about 3 hours, it was diluted with ethyl acetate (10 mL), and washed with distilled water (2 mL) for two times and with brine (2 mL). The organic layer obtained was dried over anhydrous sodium sulfate, filtered and then concentrated. The resulting crude product was purified by thin layer chromatography (MERCK Silicagel 60 F254, 0.5 mm, developing solution; ethyl acetate) to obtain the title Compound B16-2 (22.1 mg, 31.9 μmol, 30.4%) and Compound B16-1 (22.5 mg, 36.6 μmol, 34.9%) as colorless oils, respectively.

Compound B16-1

$^1$H-NMR spectrum (CD$_3$OD, 400 MHz) δ (ppm): 0.87 (1H,d,J=7 Hz), 0.94(3H,t,J=7 Hz), 0.96(3H,d,J=7 Hz), 1.07 (3H,d,J=7 Hz), 1.18(3H,s), 1.33–1.40(2H,m), 1.51–1.71(5H,m), 1.52–1.89(2H,m), 1.74(3H,d,J=1.1 Hz), 2.05(3H,s), 2.43–2.60(2H,m), 2.51(1H,d,J=4 Hz), 2.67(1H, dd,J=2,8 Hz), 2.78(1H,dt,J=2,6 Hz), 3.08(3H,s), 3.74–3.81 (1H,m), 4.68(1H,dt,J=4,7 Hz), 5.02(1H,d,J=11 Hz), 5.04 (1H,d,J=10 Hz), 5.56(1H,dd,J=10,15 Hz), 5.65(1H,dd,J=9, 16 Hz), 5.69(1H,dd,J=10,15 Hz), 6.09(1H,d,J=11 Hz), 6.32 (1H,dd,J=11,15 Hz); FAB-MS m/z 637(M+Na)$^+$.

Compound B16-2

$^1$H-NMR spectrum (CD$_3$OD, 400 MHz)δ(ppm): 0.88(1H, d,J=7 Hz), 0.94(3H,t,J=8 Hz), 0.96(3H,d,J=7 Hz), 1.08(3H, d,J=7 Hz), 1.19(3H,s), 1.40–1.70(2H,m), 1.70–1.89(5H,m), 1.75(3H,d,J=1.1 Hz), 2.06(3H,s), 2.42–2.52(1H,m), 2.53–2.62(1H,m), 2.64–2.73(2H,m), 2.78(1H,dd,J=2,6 Hz), 2.83(1H,dd,J=4,15 Hz), 3.08(3H,s), 3.12(3H,s), 4.67(1H,dt, J=4,7 Hz), 4.68–4.75(1H,m), 5.02(1H,d,J=11 Hz), 5.03(1H, d,J=10 Hz), 5.58(1H,dd,J=10,15 Hz), 5.67(1H,dd,J=8,16 Hz), 5.71(1H,dd,J=10,15 Hz), 6.10(1H,d,J=10 Hz), 6.33 (1H,dd,J=10,15 Hz); FAB-MS m/z 715(M+Na)$^+$.

Example B17

(8E,12E,14E)-7-Acetoxy-3,6-dihydroxy-21-(toluene-4-sulfonyloxy)-6,10,12,16,20-pentamethyl-18, 19-epoxytricosa-8,12,14-trien-11-olide (Compound B17)

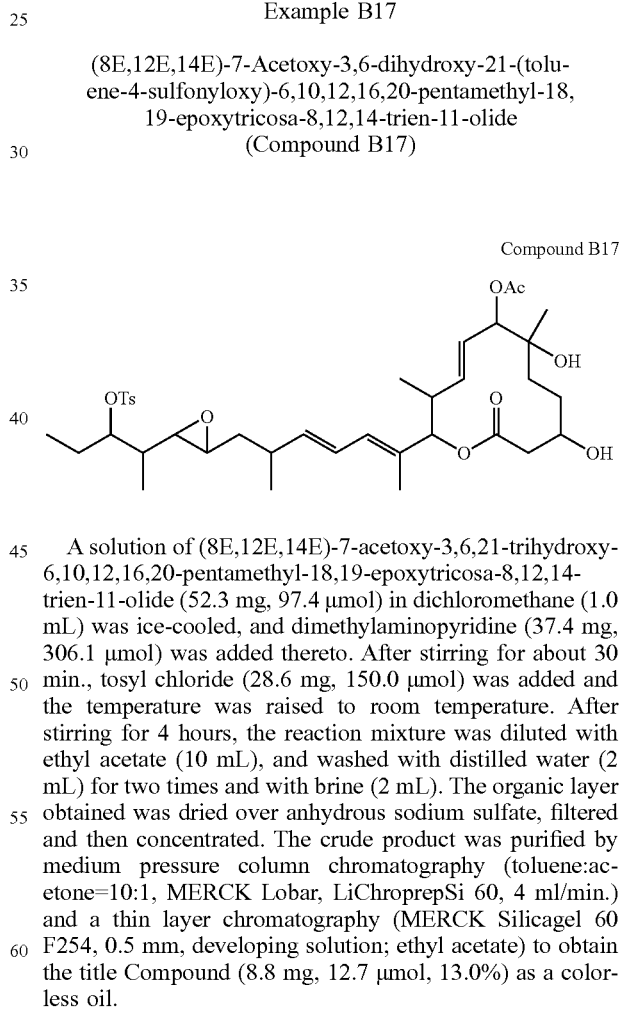

Compound B17

A solution of (8E,12E,14E)-7-acetoxy-3,6,21-trihydroxy-6,10,12,16,20-pentamethyl-18,19-epoxytricosa-8,12,14-trien-11-olide (52.3 mg, 97.4 μmol) in dichloromethane (1.0 mL) was ice-cooled, and dimethylaminopyridine (37.4 mg, 306.1 μmol) was added thereto. After stirring for about 30 min., tosyl chloride (28.6 mg, 150.0 μmol) was added and the temperature was raised to room temperature. After stirring for 4 hours, the reaction mixture was diluted with ethyl acetate (10 mL), and washed with distilled water (2 mL) for two times and with brine (2 mL). The organic layer obtained was dried over anhydrous sodium sulfate, filtered and then concentrated. The crude product was purified by medium pressure column chromatography (toluene:acetone=10:1, MERCK Lobar, LiChroprepSi 60, 4 ml/min.) and a thin layer chromatography (MERCK Silicagel 60 F254, 0.5 mm, developing solution; ethyl acetate) to obtain the title Compound (8.8 mg, 12.7 μmol, 13.0%) as a colorless oil.

$^1$H-NMR spectrum (CD$_3$OD, 400 MHz)δ(ppm): 0.80(3H, t,J=7 Hz), 0.83(3H,d,J=7 Hz), 0.85(3H,d,J=7 Hz), 1.04(3H, d,J=7 Hz), 1.18(3H,s), 1.20–1.40(4H,m), 1.50–1.72(5H,m), 1.72(3H,d,J=1.1 Hz), 2.06(3H,s), 2.25(1H,dd,J=2,8 Hz), 2.35–2.45(1H,m), 2.44(3H,s), 2.52(2H,d,J=3 Hz), 2.52–2.60

(1H,m), 2.66(1H,dt,J=2,6 Hz), 3.75–3.81(1H,m), 4.64(1H, dt,J=4,6 Hz), 5.02(1H,d,J=8 Hz), 5.04(1H,d,J=7 Hz), 5.555 (1H,dd,J=8,15 Hz), 5.558(1H,dd,J=10,15 Hz), 5.69(1H,dd, J=10,15 Hz), 6.05(1H,d,J=11 Hz), 6.28(1H,dd,J=11,15 Hz), 7.42(1H,d,J=8 Hz), 7.79(1H,d,J=8 Hz); FAB-MS m/z 713 (M+Na)+.

Example B18

(8E,12E,14E)-7-Acetoxy-21-fluoro-3,6-dihydroxy-6, 10,12,16,20-pentamethyl-18,19-epoxytricosa-8,12, 14-trien-11-olide (Compound B18–1), (8E,12E, 14E)-7-acetoxy-21-fluoro-3-hydroxy-6-methylene-10,12,16,20-tetramethyl-18,19-epoxytricosa-8,12,14-trien-11-olide (Compound B18-2), (8E,12E,14E)-7-acetoxy-6-fluoro-31,21 -dihydroxy-6,10,12,16,20-pentamethyl-18,19-epoxytricosa-8,12,14-trien-11-olide and (8E,12E,14E)-7-acetoxy-20-fluoro-3,6-dihydroxy-6,10,12,16,20-pentamethyl-18,19-epoxytricosa-8,12,14-trien-11-olide (Compound B18-3), (8E,12E,14E)-7-acetoxy-6,21-difluoro-3-hydroxy-6,10,12,16,20-pentamethyl-18,19-epoxytricosa-8,12,14-trien-11-olide (Compound B18-4), and (8E,12E,14E)-7-acetoxy-6,20-difluoro-3-hydroxy-6, 10,12,16,20-pentamethyl-18,19-epoxytricosa-8,12, 14-trien-11-olide (Compound B18-5)

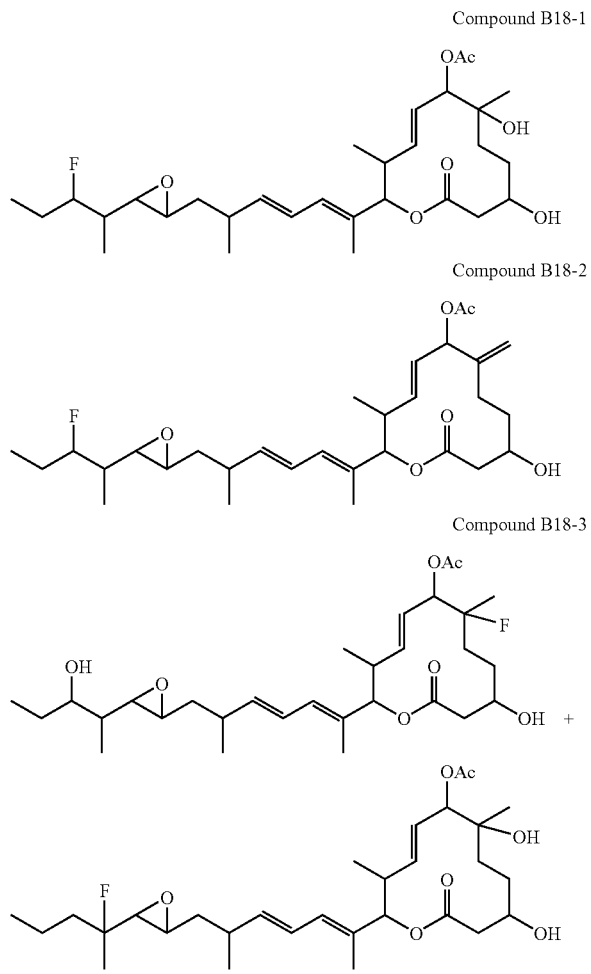

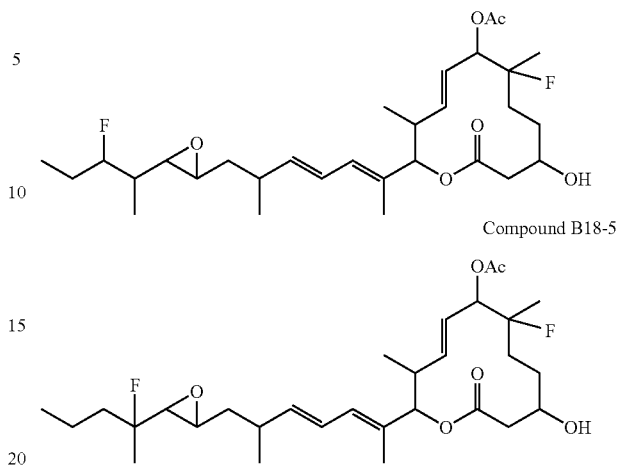

A solution of (8E,12E,14E)-7-acetoxy-3-t-butyldimethylsiloxy-6,21-dihydroxy-6,10,12,16,20-pentamethyl-18,19-epoxytricosa-8,12,14-trien-11-olide (48.3 mg, 74.2 μmol) in dichloromethane (0.5 mL) was cooled to −35° C., and DAST (15.0 μL, 113.5 μmol) was added thereto. After 30 min., DAST (10.0 μL, 75.7 μmol) was further added, followed by stirring for 15 min. The reaction mixture was diluted with dichloromethane (4 mL), a saturated sodium bicarbonate aqueous solution (1 mL) was added thereto and the temperature was raised to room temperature. The organic layer was washed with a saturated sodium bicarbonate aqueous solution (1 mL) and brine (1 mL). The organic layer obtained was dried over anhydrous sodium sulfate, filtered and then concentrated. The resulting crude product was purified by thin layer chromatography (MERCK Silicagel 60 F254, 0.5 mm, developing solution; hexane:ethyl acetate=4: 1) to obtain 9.4 mg and 7.2 mg as a mixture. These products were provided for the following procedures, respectively. 9.4 mg of the resulting product was dissolved in tetrahydrofuran (0.1 mL), and purified water (0.2 mL) and acetic acid (0.3 mL) were added thereto. After stirring overnight, the mixture was diluted with ethyl acetate (20 mL), and washed with a saturated sodium bicarbonate aqueous solution (2 mL), purified water (2 mL) and brine (2 mL). The organic layer obtained was dried over anhydrous sodium sulfate, filtered and then concentrated. The resulting crude product was purified by preparative HPLC (SHISEIDO Capcell pak C18, 10 mm I.D.×250 mm, acetonitrile:water=60:40, 4.0 mL/min.) to obtain Compound B18-2 (0.91 mg, 1.8 μmol, 2.4% (two steps)), Compound B18-4 (2.34 mg, 4.3 μmol, 5.8% (two steps)) and Compound B18-5 (1.33 mg, 2.5 μmol, 3.4% (two steps)), as colorless oils, respectively. Further, 7.2 mg of the resulting product was dissolved in tetrahydrofuran (0.1 mL), and purified water (0.1 mL) and acetic acid (0.3 mL) were added thereto. After stirring overnight, the mixture was diluted with ethyl acetate (20 mL), and washed with purified water (2 mL) for two times and with brine (2 mL). The organic layer obtained was dried over anhydrous sodium sulfate, filtered and then concentrated. The resulting crude product was purified by preparative HPLC (SHISEIDO Capcell pak C18, 10 mm I.D.×250 mm, acetonitrile:water=50:50, 4.0 mL/min.) to obtain Compound B18-1 (1.20 mg, 2.2 μmol, 3.0% (two steps)) and Compound B18-3 (mixture) (1.37 mg, 2.5 μmol, 3.4% (two steps)) as colorless oils, respectively.

Compound B18-1

$^1$H-NMR spectrum (CD$_3$OD, 400 MHz)δ(ppm): 0.87(1H, d,J=7 Hz), 0.94(3H,d,J=7 Hz), 0.97(3H,t,J=7 Hz), 1.07(3H, d,J=7 Hz), 1.18(3H,s), 1.31–1.79(9H,m), 1.73(3H,d,J=0.7 Hz), 2.05(3H,s), 2.41–2.61(2H,m), 2.51(1H,d,J=4 Hz), 2.66–2.72(2H,m), 3.74–3.81(1H,m),4.31(1H,ddd,J=4,8,48 Hz), 5.03(1H,d,J=11 Hz), 5.04(1H,d,J=10 Hz), 5.56(1H,dd, J=10,15 Hz), 5.64(1H,dd,J=8,15 Hz), 5.69(1H,dd,J=10,15 Hz), 6.08(1H,d,J=11 Hz), 6.32(1H,dd,J=11,15 Hz); FAB-MS m/z 561(M+Na)$^+$.

Compound B18-2

$^1$H-NMR spectrum (CD$_3$OD, 400 MHz) δ (ppm): 0.73–0.96(8.0H,m), 1.05–1.10(3.3H,m), 1.15–1.70(13H,m), 1.72–1.75(3.3H,m), 2.03–2.07(3.1H,m), 2.43–2.91(5.1H,m), 3.48–3.53(0.2H,m), 3.73–3.80(1.0H,m), 5.00–5.08(1.7H,m), 5.36–5.76(3.3H,m), 6.08–6.12(1.0H,m), 6.28–6.38(1.0H,m); FAB-MS m/z 539(M+H)$^+$.

Compound B18-3

$^1$H-NMR spectrum (CD$_3$OD, 400 MHz) δ (ppm): 0.86 (1H,d,J=7 Hz), 0.94(3H,d,J=7 Hz), 0.97(3H,t,J=8 Hz), 1.07 (3H,d,J=7 Hz), 1.30–1.77(7H,m), 1.72(3H,d,J=1.1 Hz), 2.01 (3H,s), 2.14(1H,dd,J=11,13 Hz), 2.31–2.38(1H,m), 2.42–2.59(3H,m), 2.66–2.72(3H,m), 3.80–3.87(1H,m), 4.31 (1H,ddd,J=4,9,48 Hz), 4.93(1H,d,J=11 Hz), 5.03(1H,s), 5.17 (1H,s), 5.28(1H,d,J=9 Hz), 5.41–5.52(2H,m), 5.64(1H,dd, J=8,15 Hz), 6.07(1H,d,J=11 Hz), 6.31(1H,dd,J=10,15 Hz); FAB-MS m/z 543(M+Na)$^+$.

Compound B18-4

$^1$H-NMR spectrum (CD$_3$OD, 400 MHz) δ (ppm): 0.88 (1H,d,J=7 Hz), 0.94(3H,d,J=7 Hz), 0.97(3H,t,J=8 Hz), 1.07 (3H,d,J=7 Hz), 1.44(3H,d,J=22 Hz), 1.21–1.85(9H,m), 1.73 (3H,d,J=1.1 Hz), 2.03(3H,s), 2.41–2.63(2H,m), 2.49(2H,d, J=4 Hz), 2.67–2.72(2H,m), 3.73–3.80(1H,m), 4.31(1H,ddd, J=4,9,48 Hz), 5.03(1H,d,J=11 Hz), 5.36–5.50(2H,m), 5.65 (1H,dd,J=8,15 Hz), 5.72(1H,dd,J=10,14 Hz), 6.09(1H,d, J=12 Hz), 6.31(1H,dd,J=11,15 Hz); FAB-MS m/z 563(M+Na)$^+$.

Compound B18-5

$^1$H-NMR spectrum (CD$_3$OD, 400 MHz) δ (ppm): 0.87 (1H,d,J=7 Hz), 0.94(3H,t,J=7 Hz), 1.08(3H,d,J=7 Hz), 1.20 (3H,d,J=22 Hz), 1.37–1.70(9H,m), 1.44(3H,d,J=22 Hz), 1.73(3H,d,J=0.7 Hz), 1.74–1.85(1H,m), 2.03(3H,s), 2.41–2.51(1H,m), 2.49(2H,d,J=4 Hz), 2.52–2.62(1H,m), 2.83(1H,dd,J=2,16 Hz), 2.89(1H,dt,J=2,6 HZ), 3.72–3.80 (1H,m), 5.03(1H,d,J=11 Hz), 5.36–5.50(2H,m), 5.66(1H,dd, J=8,15 Hz), 5.71(1H,dd,J=10,14 Hz), 6.10(1H,d,J=11 Hz), 6.32(1H,dd,J=11,15 Hz); FAB-MS m/z 563(M+Na)$^+$.

Example B19

(8E,12E,14E)-7-Acetoxy-21-fluoro-6,10,12,16,20-pentamethyl-3,6,18,19-diepoxytricosa-8,12,14-trien-11-olide (Compound B19-1), (8E,12E,14E)-7-acetoxy-20-fluoro-6,10,12,16,20-pentamethyl-3,6,18,19-diepoxytricosa-8,12,14-trien-11-olide (Compound B19-2), and (8E,12E,14E,21E)-7-acetoxy-6,10,12,16,20-pentamethyl-3,6,18,19-diepoxytricosa-8,12,14,21-tetraen-11-olide (Compound B19-3)

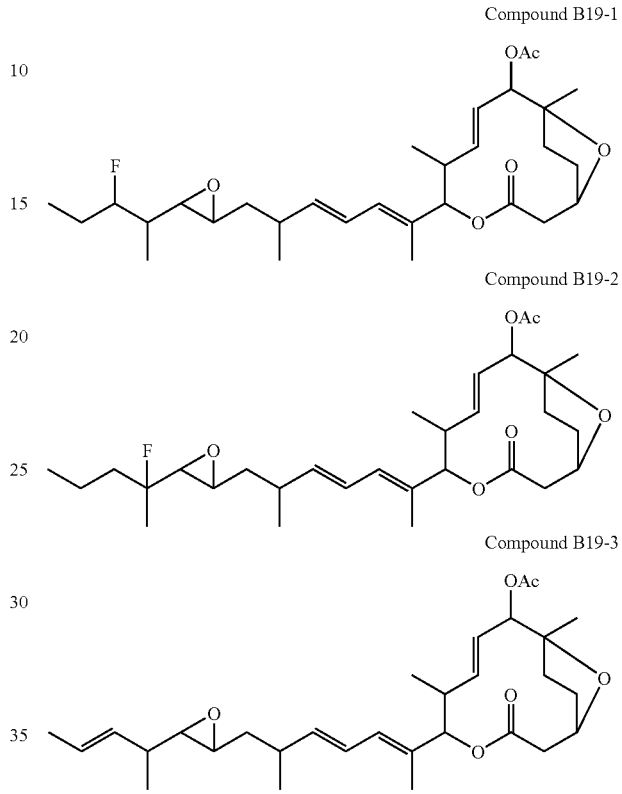

(8E,12E,14E)-7-Acetoxy-3,6,21-trihydroxy-6,10,12,16, 20-pentamethyl-18,19-epoxytricosa-8,12,14-trien-11-olide (10.2 mg, 19.0 μmol) was dissolved in dichloromethane (0.3 mL) and cooled to −30° C. Then, DAST (15.0 μL, 113.5 μmol) was added dropwise. After stirring for 30 min., the mixture was diluted with dichloromethane (4 mL), and washed with a 5% aqueous sodium bicarbonate, water and brine. The organic layer obtained was dried over anhydrous sodium sulfate and concentrated. The resulting crude product was purified by preparative HPLC (SHISEIDO Capcell pak C18, 10 mm I.D.×250 mm, acetonitrile:water=60:40, 4.0 mL/min.) to obtain the title Compound B19-1 (2.0 mg, 3.6 μmol, 19.1%), Compound B19-2 (1.1 mg, 1.9 μmol, 10.3%) and Compound B19-3 (0.9 mg, 1.7 μmol, 9.1%), as colorless oils, respectively.

Compound B19-1

$^1$H-NMR spectrum (CD$_3$OD, 400 MHz) δ (ppm): 0.91 (3H,d,J=7 Hz), 0.95(3H,d,J=7 Hz), 0.97(3H,t,J=7 Hz), 1.07 (3H,d,J=7 Hz), 1.13(3H,s), 1.38–1.79(7H,m), 1.75(3H,s), 2.06(3H,s), 2.11–2.23(1H,m), 2.23(1H,dd,J=3,13 Hz), 2.31–2.52(3H,m), 2.56(1H,dd,J=3,13 Hz), 2.66–2.73(2H, m), 4.31(1H,ddt,J=4,8,48 Hz), 4.43–4.48(1H,m), 4.91(1H, d,J=11 Hz), 5.16(1H,d,J=8 Hz), 5.50(1H,dd,J=8,16 Hz), 5.22(1H,dd,J=9,16 Hz), 5.64(1H,dd,J=8,15 Hz), 6.05(1H,d, J=11 Hz), 6.32(1H,dd,J=11,15 Hz); FAB-MS m/z 520(M)$^-$.

Compound B19-2

$^1$H-NMR spectrum (CD$_3$OD, 400 MHz)δ(ppm): 0.90(3H, d,J=7 Hz), 0.94(3H,t,J=8 Hz), 1.08(3H,d,J=7 Hz), 1.13(3H, s), 1.15(3H,d,J=20 Hz), 1.36–1.77(8H,m), 1.75(3H,d,J=1 Hz), 2.06(3H,s), 2.11–2.23(1H,m), 2.23(1H,dd,J=4,13 Hz), 2.31–2.51(3H,m), 2.56(1H,dd,J=3,13 Hz), 2.83(1H,dd,J=2,16 Hz), 2.89(1H,dt,J=2,6 Hz), 4.42–4.49(1H,m), 4.91(1H,d,J=10 Hz), 5.16(1H,d,J=8 Hz), 5.22(1H,dd,J=8,16 Hz), 5.50(1H,dd,J=8,16 Hz), 5.65(1H,dd,J=8,15 Hz), 6.06(1H,d,J=11 Hz), 6.33(1H,dd,J=11,15 Hz); FAB-MS m/z 520(M)⁻.

Compound B19-3

¹H-NMR spectrum (CD₃OD, 400 MHz) δ (ppm): 0.91 (3H,d,J=7 Hz), 0.97(3H,d,J=7 Hz), 1.07(3H,d,J=7 Hz), 1.13(3H,s), 1.42(1H,ddd,J=6,9,14 Hz), 1.54–1.67(2H,m), 1.65(3H,d,J=6 Hz), 1.68–1.78(1H,m), 1.75(3H,d,J=0.7 Hz), 1.93–2.00(1H,m), 2.06(3H,s), 2.11–2.23(1H,m), 2.23(1H,dd,J=4,13 Hz), 2.32–2.49(3H,m), 2.55(1H,dd,J=2,7 Hz), 2.56(1H,dd,J=3,13 Hz), 2.73(1H,dd,J=2,6 Hz), 4.46(1H,ddt,J=3,3,9 Hz), 4.91(1H,d,J=11 Hz), 5.16(1H,d,J=8 Hz), 5.22(1H,dd,J=9,16 Hz), 5.35(1H,ddq,J=2,7,15 Hz), 5.49(1H,ddq,J=0.7,6,15 Hz), 5.50(1H,dd,J=8,15 Hz), 5.63(1H,dd,J=8,15 Hz), 6.06(1H,d,J=11 Hz), 6.31(1H,dd,J=11,15 Hz); FAB-MS m/z 500(M)⁻.

Example B20

(8E,12E,14E)-3,7,21-Triacetoxy-6-hydroxy- 6,10, 12,16,20-pentamethyl-18,19-epoxytricosa-8,12,14-trien-11-olide (Compound B20-1), (8E,12E,14E)-7, 21-diacetoxy-3,6-dihydroxy-6,10,12,16,20-pentamethyl-18,19-epoxytricosa-8,12,14-trien-11-olide (Compound B20-2), and (8E,12E,14E)-3,6,7, 21-tetraacetoxy-6-hydroxy-6,10,12,16,20-pentamethyl-18,19-epoxytricosa-8,12,14-trien-11-olide (Compound B20-3)

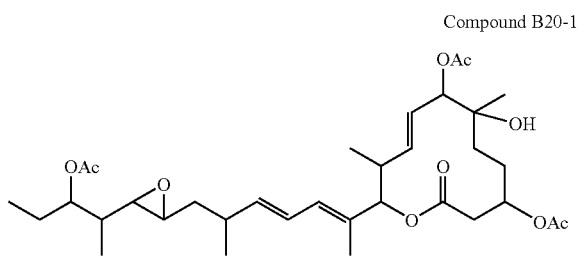

Compound B20-1

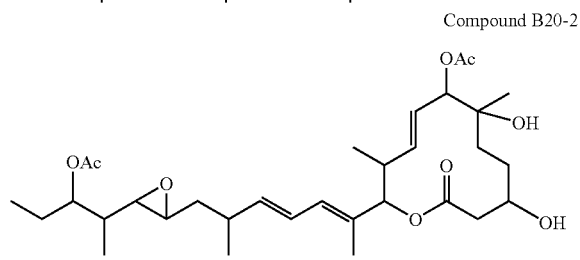

Compound B20-2

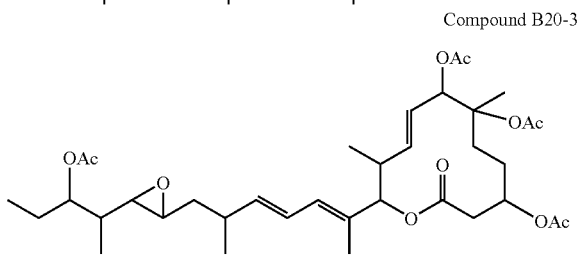

Compound B20-3

(8E,12E,14E)-7-Acetoxy-3,6,21-trihydroxy-6,10,12,16, 20-pentamethyl-18,19-epoxytricosa-8,12,14-trien-11-olide (11.0 mg, 20.5 µmol) was dissolved in dichloromethane (0.5 mL), and cooled to −20° C. Then, triethylamine (15.0 µL, 107.6 µmol) and dimethylaminopyridine (1.1 mg, 9.0 µmol) were added. After stirring for 30 min., acetic anhydride (1.0 µL, 10.6 µmol) was added thereto. After stirring for 30 min., acetic anhydride (0.5 µL, 5.3 µmol) was additionally added, and further, acetic anhydride (0.5 µL, 5.3 µmol) was additionally added after one hour. Successively, acetic anhydride (0.5 µL, 5.3 µmol) was additionally added after 30 minutes and methanol (1 mL) was added after one and half hours, followed by concentrating. The resulting crude product was purified by thin layer chromatography (MERCK Silicagel 60 F254, 0.5 mm, developing solution; hexane:ethyl acetate=1: 4) to obtain the title Compound B20-1 (4.5 mg, 7.3 µmol, 35.4%), Compound B20-2 (7.2 mg, 12.4 µmol, 60.7%) and Compound B20-3 (0.4 mg, 0.6 µmol, 2.9%) as colorless oils, respectively.

Compound B20-1

¹H-NMR spectrum (CD₃OD, 400 MHz) δ (ppm): 0.86 (3H,t,J=7 Hz), 0.88(3H,d,J=6 Hz), 0.90(3H,d,J=7 Hz), 1.07(3H,d,J=7 Hz), 1.17(3H,s), 1.35–1.73(9H,m), 1.74(3H,d,J=1.1 Hz), 2.039(3H,s), 2.044(3H,s), 2.06(3H,s), 2.40–2.50(1H,m), 2.50–2.68(2H,m), 2.54(1H,dd,J=2,8 Hz), 2.65(1H,dd,J=4,15 Hz), 2.71(1H,dt,J=2,6 Hz), 4.80–4.93(2H,m), 4.97(1H,d,J=11 Hz), 5.02(1H,d,J=10 Hz), 5.57(1H,dd,J=10,15 Hz), 5.65(1H,dd,J=8,15 Hz), 5.71(1H,dd,J=10,15 Hz), 6.09(1H,d,J=10 Hz), 6.31(1H,dd,J=11,14 Hz); FAB-MS m/z 621(M+H)⁺.

Compound B20-2

¹H-NMR spectrum (CD₃OD, 400 MHz)δ(ppm): 0.86(3H, t,J=7 Hz), 0.87(3H,d,J=7 Hz), 0.90(3H,d,J=7 Hz), 1.07(3H, d,J=7 Hz), 1.18(3H,s), 1.30–1.48(4H,m), 1.50–1.66(5H,m), 1.74(3H,d,J=1.1 Hz), 2.04(3H,s), 2.05(3H,s), 2.41–2.62(2H, m), 2.51(2H,d,J=4 Hz), 2.54(1H,dd.J=2,8 Hz), 2.71(1H,dt, J=2,6 Hz), 3.72–3.81(1H,m), 4.80–4.92(1H,m), 5.03(1H,d, J=11 Hz), 5.04(1H,d,J=10 Hz), 5.56(1H,dd,J=10,15 Hz), 5.64(1H,dd,J=8,15 Hz), 5.69(1H,dd,J=10,15 Hz), 6.08(1H, d,J=10 Hz), 6.31(1H,dd,J=11,15 Hz); FAB-MS m/z 579(M+H)⁺.

Compound B20-3

¹H-NMR spectrum (CD₃OD, 400 MHz)δ(ppm): 0.86(3H, t,J=7 Hz), 0.89(3H,d,J=7 Hz), 0.90(3H,d,J=7 Hz), 1.07(3H, d,J=7 Hz), 1.39–1.48(2H,m), 1.53(3H,s), 1.54–1.71(3H,m), 1.74(3H,d,J=1.1 Hz), 1.74–1.88(1H,m), 2.03(6H,s), 2.04(3H,s), 2.05(3H,s), 2.34(1H,dt,J=4,13 Hz), 2.39–2.52(1H, m), 2.54(1H,dd,J=2,8 Hz), 2.56–2.67(1H,m), 2.59(2H,d,J=4 Hz), 2.71(1H,dt,J=2,6 Hz), 4.83–4.93(2H,m), 4.98(1H,d, J=11 Hz), 5.11(1H,d,J=10 Hz), 5.63(1H,dd,J=10,15 Hz), 5.65(1H,dd,J=8,15 Hz), 5.76(1H,dd,J=10,15 Hz), 6.10(1H, d,J=11 Hz), 6.32(1H,dd,J=10,15 Hz); FAB-MS m/z 663(M+H)⁺.

Example B21

(8E,12E,14E)-7,19-Diacetoxy-18-chloro-3,6,21-trihydroxy-6,10,12,16,20-pentamethyltricosa-8,12, 14-trien-11-olide (Compound B21-1), (8E,12E, 14E)-7,21-diacetoxy-18-chloro-3,6,19-trihydroxy-6, 10,12,16,20-pentamethyltricosa-8,12,14-trien-11-olide (Compound B21-2), (8E,12E,14E)-3,7,19-triacetoxy-18-chloro-6,21-dihydroxy-6,10,12,16,20-pentamethyltricosa-8,12,14-trien-11-olide (Compound B21-3), (8E,12E,14E)-7,19,21-triacetoxy-18-chloro-3,6-dihydroxy-6,10,12,16,20-pentamethyltricosa-8,12,14-trien-11-olide (Compound B21-4), (8E,12E,14E)-3,7,19,21-tetraacetoxy-18-chloro-6-hydroxy-6,10,12,16,20-pentamethyltricosa-8,12,14-trien-11-olide (Compound B21-5), and (8E, 12E, 14E)-3,7,21-triacetoxy-18-chloro-6,19-dihydroxy-6,10,12,16,20-pentamethyltricosa-8,12, 14-trien-11-olide (Compound B21-6)

Compound B21-1
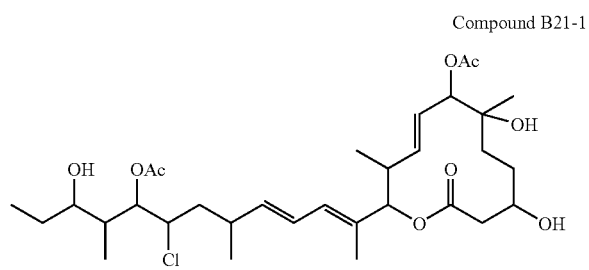

Compound B21-2
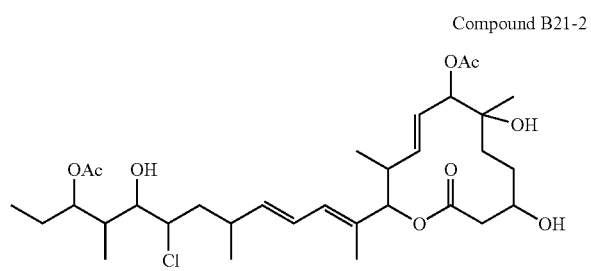

Compound B21-3
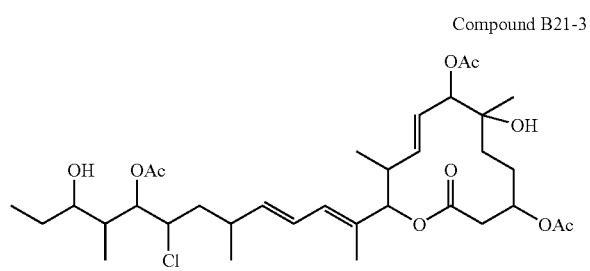

Compound B21-4
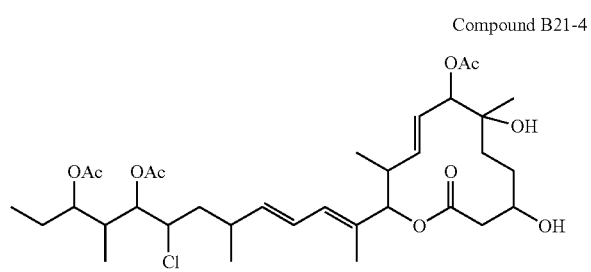

Compound B21-5
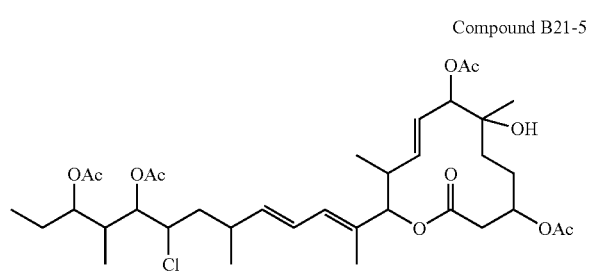

Compound B21-6
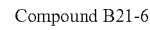
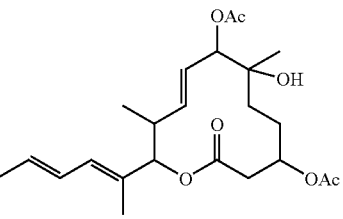

A solution of (8E,12E,14E)-7-acetoxy-18-chloro-3,6,19,21-tetrahydroxy-6,10,12,16,20-pentamethyltricosa-8,12,14-trien-11-olide (24.3 mg, 42.5 μmol) in dichloromethane (0.5 mL) was cooled to −20° C., followed by adding dimethylaminopyridine (2.4 mg, 19.6 μmol) and triethylamine (48 μL, 344 μmol). After stirring for about 5 min., acetic anhydride (6 μL, 63.6 μmol) was added dropwise and the mixture was stirred at the same temperature for about one hour. Methanol (1 mL) was added to the reaction mixture, and after the temperature was raised to room temperature, the mixture was concentrated. The resulting crude product was purified by preparative HPLC (SHISEIDO Capcell pak C18, 10 mm I.D.×250 mm, acetonitrile:water=50:50, 4.0 mL/min.) to obtain the title Compound B21-1 (5.8 mg, 9.4 μmol, 22.1%), Compound B21-2 (2.6 mg, 4.6 μmol, 9.8%), Compound B21-3 (2.3 mg, 3.5 μmol, 8.3%), Compound B21-4 (3.7 mg, 5.7 μmol, 13.3%), Compound B21-6 (1.0 mg, 1.5 μmol, 3.5%) and Compound B21-5 (1.6 mg, 2.2 μmol, 5.2%), as colorless oils, respectively.

Compound B21-1
$^1$H-NMR spectrum (CD$_3$OD, 400 MHz)δ(ppm): 0.88(3H, d,J=7 Hz), 0.89(3H,d,J=7 Hz), 0.92(3H,t,J=8 Hz), 1.05(3H, d,J=7 Hz), 1.18(3H,s), 1.32–1.41(3H,m), 1.48–1.70(5H,m), 1.74(3H,d,J=0.7 Hz), 1.79–1.87(2H,m), 2.05(3H,s), 2.10 (3H,s), 2.52(2H,d,J=3 Hz), 2.52–2.60(2H,m), 3.45(1H,ddd, J=2,5,8 Hz), 3.74–3.81(1H,m), 4.30(1H,dt,J=3,11 Hz), 5.037(1H,d,J=10 Hz), 5.039(1H,d,J=11 Hz), 5.24(1H,dd, J=3,9 Hz), 5,56(1H,dd,J=10,15 Hz), 5.69(1H,dd,J=10,15 Hz), 5.72(1H,dd,J=8,15 Hz), 6.08(1H,d,J=11 Hz), 6.29(1H, dd,J=10,15 Hz); FAB-MS m/z 637(M+Na)$^+$.

Compound B21-2
$^1$H-NMR spectrum (CD$_3$OD, 400 MHz)δ(ppm): 0.87(3H, d,J=7 Hz), 0.88(3H,t,J=7 Hz), 0.93(3H,d,J=7 Hz), 1.04(3H, d,J=7 Hz), 1.18(3H,s), 1.29–1.40(2H,m), 1.47–1.74(5H,m), 1.74(3H,d,J=1.1 Hz), 1.79–1.89(2H,m), 2.02(3H,s), 2.05 (3H,s), 2.51(2H,d,J=4 Hz), 2.51–2.61(2H,m), 3.53(1H,dd, J=4,8 HZ), 3.74–3.80(1H,m), 4.20(1H,ddd,J=3,4,11 Hz), 5.04(1H,d,J=10 Hz), 5.23(1H,ddd,J=2,6,8 Hz), 5.56(1H,dd, J=10,15 Hz), 5,69(1H,dd,J=10,15 Hz), 5.74(1H,dd,J=8,15 Hz), 6.07(1H,d,J=11 Hz), 6.29(1H,dd,J=11,15 Hz); FAB-MS m/z 637(M+Na)$^+$.

Compound B21-3
$^1$H-NMR spectrum (CD$_3$OD, 400 MHz)δ(ppm): 0.886 (3H,d,J=7 Hz), 0.889(3H,d,J=7 Hz), 0.92(3H,t,J=7 Hz), 1.05(3H,d,J=7 Hz), 1.17(3H,s), 1.32–1.73(7H,m), 1.74(3H, d,J=1.1 Hz), 1.79–1.87(2H,m), 2.04(3H,s), 2.05(3H,s), 2.10

(3H,s), 2.52–2.68(4H,m), 3.45(1H,ddd,J=2,5,10 Hz), 4.30 (1H,dt,J=3,11 Hz), 4.98(1H,d,J=11 Hz), 5.02(1H,d,J=10 Hz), 5.24(1H,dd,J=3,9 Hz), 5,57(1H,dd,J=10,15 Hz), 5.71 (1H,dd,J=10,15 Hz), 5.72(1H,dd,J=.8,15 Hz), 6.09(1H,d, J=11 Hz), 6.29(1H,dd,J=10,14 Hz); FAB-MS m/z 657(M+H)⁺.

Compound B21-4

¹H-NMR spectrum (CD₃OD, 400 MHz)δ(ppm): 0.87(3H, t,J=8 Hz) 0.88(3H,d,J=7 Hz), 0.99(3H,d,J=7 Hz), 1.04(3H, d,J=7 Hz), 1.18(3H,s), 1.27–1.40(2H,m), 1.46–1.70(5H,m), 1.74(3H,d,J=0.7 Hz), 1.74–1.82(1H,m), 2.00(3H,s), 2.045 (3H,s), 2.052(3H,s), 2.09–2.18(1H,m), 2.52(2H,d,J=4 Hz), 2.52–2.60(2H,m), 3.73–3.80(1H,m), 4.32(1H,dt,J=4,11 Hz), 4.85–4.92(1H,m), 5.04(2H,d,J=10 Hz), 5.09(1H,dd,J=4,9 Hz), 5,56(1H,dd,J=10,15 Hz), 5.69(1H,dd,J=10,15 Hz), 5.71(1H,dd,J=8,15 Hz), 6.08(1H,d,J=11 Hz), 6.29(1H,dd,J=11,15 Hz); FAB-MS m/z 679(M+Na)⁺.

Compound B21-6

¹H-NMR spectrum (CD₃OD, 400 MHz)δ(ppm): 0.876 (3H,t,J=8 Hz), 0.881(3H,d,J=7 Hz), 0.93(3H,d,J=7 Hz), 1.04(3H,d,J=7 Hz), 1.17(3H,s), 1.32–1.73(7H,m), 1.73(3H, d,J=0.7 Hz), 1.79–1.88(2H,m), 2.02(3H,s), 2.04(3H,s), 2.05 (3H,s), 2.52–2.68(4H,m), 3.53(1H,dd,J=4 Hz), 4.19(1H,dt, J=3,11 Hz), 4.98(1H,d,J=11 Hz), 5.02(1H,d,J=10 HZ), 5.23 (1H,ddd,J=2,6,14 Hz), 5,56(1H,dd,J=10,15 Hz), 5.71(1H, dd,J=10,15 Hz), 5.74(1H,dd,J=7,15 Hz), 6.08(1H,d,J=10 Hz), 6.29(1H,dd,J=11,15 Hz); FAB-MS m/z 679(M+Na)⁺.

Compound B21-5

¹H-NMR spectrum (CD₃OD, 400 MHz)δ(ppm): 0.86(3H, t,J=7 Hz), 0.89(3H,d,J=7 Hz), 0.99(3H,d,J=7 Hz), 1.04(3H, d,J=7 Hz), 1.17(3H,s), 1.32–1.70(7H,m), 1.74(3H,s), 1.75–1.82(1H,m), 2.00(3H,s), 2.037(3H,s), 2.045(3H,s), 2.054(3H,s), 2.102–2.16(1H,m), 2.50–2.68(4H,m), 4.32 (1H,dt,J=3,11 Hz), 4.98(1H,d,J=11 Hz), 5.02(1H,d,J=10 Hz), 5.09(1H,dd,J=4,9 Hz), 5,56(1H,dd,J=10,15 Hz), 5.711 (1H,dd,J=10,15 Hz), 5.713(1H,dd,J=8,15 Hz), 6.09(1H,d, J=11 Hz), 6.29(1H,dd,J=11,15 Hz); FAB-MS m/z 699(M+H)⁺.

Example B22

(8E,12E,14E)-7,18,21-Triacetoxy-19-chloro-3,6 -dihydroxy-6,10,12,16,20-pentamethyltricosa-8,12,14-trien-11-olide (Compound B22-1) and (8E,12E, 14E)-3,7,18,21-tetraacetoxy-19-chloro-6-hydroxy-6, 10,12,16,20-pentamethyltricosa-8,12,14-trien-11-olide (Compound B22-2)

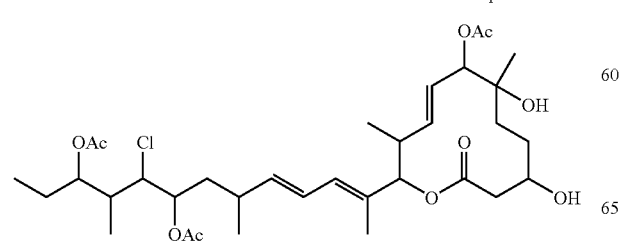

Compound B22-1

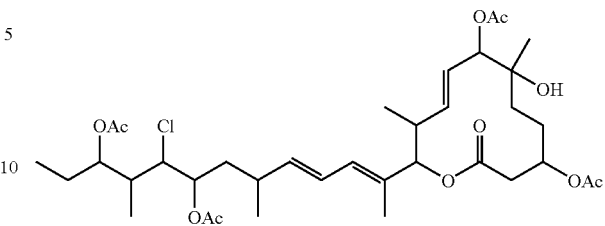

Compound B22-2

A solution of (8E,12E,14E)-7-acetoxy-19-chloro-3,6,18, 21-tetrahydroxy-6,10,12,16,20-pentamethyltricosa-8,12,14-trien-11-olide (20.2 mg, 35.3 μmol) in dichloromethane (0.5 mL) was cooled to −20° C., and dimethylaminopyridine (1.5 mg, 12.3 μmol) and triethylamine (40 μL, 289 μmol) were added thereto. After stirring for about 5 min., acetic anhydride (5 μL, 52.9 μmol) was added dropwise and the mixture was stirred at the same temperature for about one hour. Further, acetic anhydride (5 μL, 52.9 μmol) was added dropwise and the mixture was stirred at the same temperature for about one hour. Methanol (1 mL) was added to the reaction solution, and after the temperature was raised to room temperature, the mixture was concentrated. The resulting crude product was purified by preparative HPLC (SHISEIDO Capcell pak C18, 10 mm I.D.×250 mm, acetonitrile:water=50:50, 4.0 mL/min.) to obtain the title Compound B22-1 (5.62 mg, 8.55 μmol, 24.2%) and Compound B22-2 (3.17 mg, 4.82 μmol, 13.7%) as colorless oils, respectively.

Compound B22-1

¹H-NMR spectrum (CD₃OD, 400 MHz)δ(ppm): 0.86(3H, t,J=7 Hz), 0.89(3H,d,J=7 Hz), 1.03(3H,d,J=7 Hz), 1.06(3H, d,J=7 Hz), 1.18(3H,s), 1.28–1.42(2H,m), 1.51–1.70(5H,m), 1.73(3H,d,J=1.1 Hz), 1.76–1.86(1H,m), 2.02(3H,s), 2.04 (3H,s), 2.05(3H,s), 2.25–2.36(1H,m), 2.48–2.61(3H,m), 3.73–3.82(1H,m), 4.06(1H,t,J=6 Hz), 4.79–4.86(1H,m), 4.96–5.02(1H,m), 5.04(1H,d,J=10 Hz), 5.05(1H,d,J=11 Hz), 5.56(1H,dd,J=10,15 Hz), 5.57(1H,dd,J=9,15 Hz), 5.69(1H, dd,J=10,15 Hz), 6.09(1H,d,J=11 Hz), 6.23(1H,dd,J=11,15 Hz); FAB-MS m/z 679(M+Na)⁺.

Compound B22-2

¹H-NMR spectrum (CD₃OD, 400 MHz)δ(ppm): 0.86(3H, t,J=7 Hz), 0.90(3H,d,J=7 Hz), 1.03(3H,d,J=7 Hz), 1.06(3H, d,J=7 Hz), 1.17(3H,s), 1.34–1.71(7H,m), 1.72(3H,d,J=1.1 Hz), 1.79–1.87(1H,m), 1.99–2.08(1H,m), 2.02(3H,s), 2.037 (3H,s), 2.040(3H,s), 2.05(3H,s), 2.26–2.35(1H,m), 2.53–2.68(3H,m), 4.06(1H,t,J=6 Hz), 4.95–5.02(2H,m), 4.96–5.03(1H,m), 4.98(1H,d,J=11 Hz), 5.02(1H,d,J=10 Hz), 5.566(1H,dd,J=10,15 Hz), 5.572(1H,dd,J=8,15 Hz), 5.71 (1H,dd,J=10,15 Hz), 6.09(1H,d,J=11 Hz), 6.22(1H,dd,J=11, 15 Hz); FAB-MS m/z 699(M+H)⁺.

Example B23

(8E,12E,14E)-7,18,21-Triacetoxy-19-bromo-3,6-dihydroxy-6,10,12,16,20-pentamethyltricosa-8,12, 14-trien-11-olide (Compound B23-1) and (8E,12E, 14E)-3,7,18,21-tetraacetoxy-19-bromo-6-hydroxy-6,10,12,16,20-pentamethyltricosa-8,12,14-trien-11-olide (Compound B23-2)

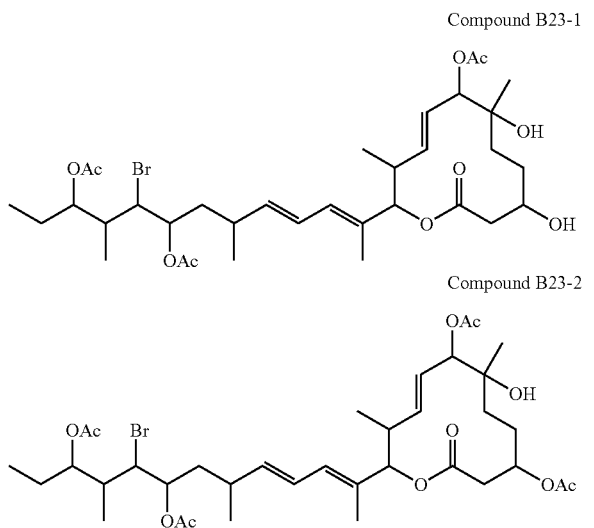

A solution of (8E,12E,14E)-7-acetoxy-19-bromo-3,6,18,21-tetrahydroxy-6,10,12,16,20-pentamethyltricosa-8,12,14-trien-11-olide (17.0 mg, 27.5 µmol) in dichloromethane (0.4 mL) was cooled to −20° C., and dimethylaminopyridine (1.8 mg, 14.7 µmol) and triethylamine (30 µL, 216 µmol) were added thereto. After stirring for about 5 min., acetic anhydride (5 µL, 52.9 µmol) was added dropwise and the mixture was stirred at the same temperature for about one hour. Further, acetic anhydride (3 µL, 31.7 µmol) was added dropwise and the mixture was stirred at the same temperature for about one hour. Methanol (1 mL) was added to the reaction solution, and after the temperature was raised to room temperature, the mixture was concentrated. The resulting crude product was purified by preparative HPLC (SHISEIDO Capcell pak C18, 10 mm I.D.×250 mm, acetonitrile:water=50:50–60:40, 4.0 mL/min.) to obtain the title Compound B23-1 (5.90 mg, 8.41 µmol, 30.6%) and Compound B23-2 (3.91 mg, 5.26 µmol, 19.1%) as colorless oils, respectively.

Compound B23-1

$^1$H-NMR spectrum (CD$_3$OD, 400 MHz)δ(ppm): 0.86(3H, t,J=8 Hz), 0.89(3H,d,J=7 Hz), 1.05(3H,d,J=7 Hz), 1.06(3H, d,J=7 Hz), 1.18(3H,s), 1.30–1.41(2H,m), 1.53–1.78(4H,m), 1.73(3H,d,J=0.7 Hz), 1.89–1.90(1H,m), 1.93–2.02(1H,m), 2.03(3H,s), 2.04(3H,s), 2.05(3H,s), 2.25–2.37(1H,m), 2.50–2.62(3H,m), 3.74–3.82(1H,m), 4.16(1H,t,J=6 Hz), 4.80–4.85(1H,m), 4.94(1H,ddd,J=2,6,10 HZ), 5.04(1H,d, J=10 Hz), 5.05(1H,d,J=11 Hz), 5.56(1H,dd,J=10,15 Hz), 5.58(1H,dd,J=8,15 Hz), 5.69(1H,dd,J=10,15 Hz), 6.09(1H, d,J=11 Hz), 6.23(1H,dd,J=11,15 Hz); FAB-MS m/z 723(M+Na)$^+$.

Compound B23-2

$^1$H-NMR spectrum (CD$_3$OD, 400 MHz)δ(ppm): 0.86(3H, t,J=7 Hz), 0.91(3H,d,J=7 Hz), 1.05(3H,d,J=7 Hz), 1.06(3H, d,J=7 Hz), 1.17(3H,s), 1.35–1.77(7H,m), 1.73(3H,d,J=1.1 Hz), 1.82–1.91(1H,m), 1.95–2.04(1H,m), 2.03(3H,s), 2.038 (3H,s), 2.043(3H,s), 2.05(3H,s), 2.25–2.36(1H,m), 2.54–2.68(3H,m), 4.16(1H,t,J=6 Hz), 4.79–4.85(2H,m), 4.94(1H,ddd,J=2,6,10 Hz), 4.99(1H,d,J=11 Hz), 5.02(1H,d, J=10 Hz), 5.58(1H,dd,J=8,15 Hz), 5.57(1H,dd,J=10,15 Hz), 5.71(1H,dd,J=10,15 Hz), 6.10(1H,d,J=11 Hz), 6.23(1H,dd, J=11,15 Hz); FAB-MS m/z 743(M+H)$^+$.

Example B24

(8E,12E,14E)-7-Acetoxy-3-ethoxyacetoxy-6,21-dihydroxy-6,10,12,16,20-pentamethyl-18,19-epoxytricosa-8,12,14-trien-11-olide (Compound B24)

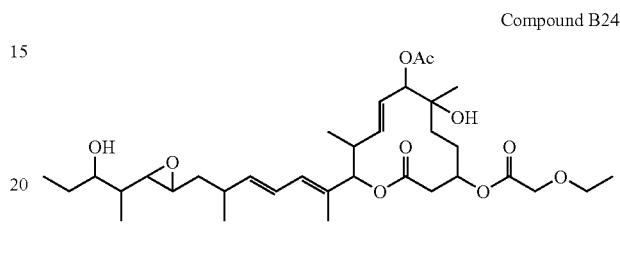

(8E,12E,14E)-7-Acetoxy-3-t-butyldimethylsiloxy-6,21-bis(1-ethoxyethoxy)-6,10,12,16,20-pentamethyl-18,19-epoxytricosa-8,12,14-trien-11-olide

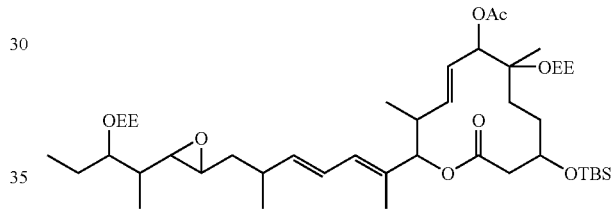

Ethyl vinyl ether (485 mg, 6.7 mmol) and pyridinium p-toluenesulfonate (28 mg, 0.11 mmol) were added to a solution of (8E,12E,14E)-7-acetoxy-3-t-butyldimethylsiloxy-6,21-dihydroxy-6,10,12,16,20-pentamethyl-18,19-epoxytricosa-8,12,14-trien-11-olide (146 mg, 0.22 mmol) in dichloromethane (5 mL) at room temperature. The mixture was stirred at room temperature for 18 hours. The reaction mixture was diluted with ethyl acetates, washed with brine, dried over anhydrous magnesium sulfate and evaporated. The resulting crude product was purified by silica gel column chromatography (Kanto silica gel 60N, spherical, neutral, 40 to 100 µm, eluate; hexane:ethyl acetate=70:30) to obtain the title compound (112 mg, 63%) as a colorless oil.

ESI-MS m/z 817(M+Na)$^+$.

(8E,12E,14E)-7-Acetoxy-6,21-bis(1-ethoxyethoxy)-3-hydroxy-6,10,12,16,20-pentamethyl-18,19-epoxytricosa-8,12,14-trien-11-olide

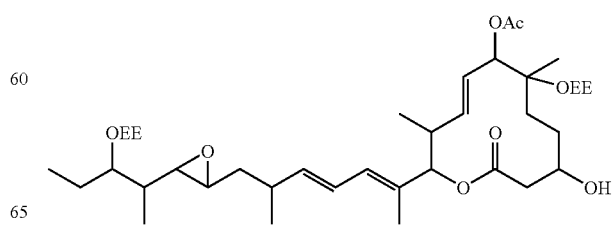

A 1.0 M solution of tetrabutylammonium fluoride (0.026 mmol) in tetrahydrofuran (0.026 mL, 0.026 mmol) was added to a solution of (8E,12E,14E)-7-acetoxy-3-t-butyldimethylsiloxy-6,21-bis(1-ethoxyethoxy)-6,10,12,16,20-pentamethyl-18,19-epoxytricosa-8,12,14-trien-11-olide (19 mg, 0.024 mmol) in tetrahydrofuran (0.5 mL) at room temperature. The mixture was stirred at room temperature for 2 hours. Further, 0.026 mL of a 1.0 M solution of tetrabutylammonium fluoride in tetrahydrofuran (0.026 mL, 0.026 mmol) was added thereto at room temperature. After the reaction mixture was diluted with ethyl acetate, it was washed with brine, dried over anhydrous magnesium sulfate and evaporated. The resulting crude product was purified by silica gel column chromatography (Kanto silica gel 60N, spherical, neutral, 40 to 100 μm, eluate; hexane:ethyl acetate=70:30) to obtain the title compound (112 mg, 63%) as a colorless oil.

ESI-MS m/z 703(M+Na)$^+$.

(8E,12E,14E)-7-Acetoxy-3-ethoxyacetoxy-6,21-bis(1-ethoxyethoxy)-6,10,12,16,20-pentamethyl-18,19-epoxytricosa-8,12,14-trien-11-olide

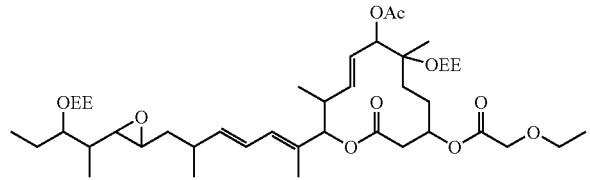

A solution of ethoxyacetic acid (8.2 mg, 0.079 mmol) in dichloromethane (1.6 mL) was added to (8E,12E,14E)-7-acetoxy-6,21-di(1-ethoxyethoxy)-3-hydroxy-6,10,12,16,20-pentamethyl-18,19-epoxytricosa-8,12,14-trien-11-olide (13 mg, 0.016 mmol) at room temperature, and dicyclohexylcarbodiimide (20 mg, 0.094 mmol) and dimethylaminopyridine (1.9 mg, 0.016 mmol) were further added at room temperature. The mixture was stirred at room temperature for 6 hours. The reaction solution was diluted with ethyl acetate, and filtered through Celite. The filtrate was washed with brine, dried over anhydrous magnesium sulfate and evaporated. The resulting crude product was purified by silica gel column chromatography (Kanto silica gel 60N, spherical, neutral, 40 to 100 μm, eluate; hexane:ethyl acetate=70:30) to obtain the title compound (11 mg, 91%) as a colorless oil.

ESI-MS m/z 789(M+Na)$^+$.

(8E,12E,14E)-7-Acetoxy-3-ethoxyacetoxy-6,21-dihydroxy-6,10,12,16,20-pentamethyl-18,19-epoxytricosa-8,12,14-trien-11-olide (Compound B24)

Compound B24

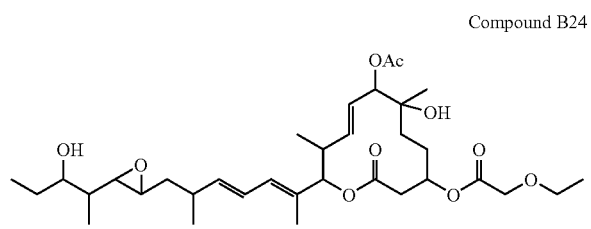

Pyridinium p-toluenesulfonate (9.8 mg, 0.039 mmol) was added to a solution of (8E,12E,14E)-7-acetoxy-3-ethoxyacetoxy-6,21-bis(1-ethoxyethoxy)-6,10,12,16,20-pentamethyl-18,19-epoxytricosa-8,12,14-trien-11-olide (6.0 mg, 0.0078 mmol) in methanol (1.0 mL) at room temperature, followed by stirring at the same temperature for 15 hours. The reaction mixture was diluted with 15 mL of ethyl acetate, washed with brine, dried over anhydrous magnesium sulfate and evaporated. The resulting crude product was purified by thin layer chromatography (MERCK Silicagel 60 F254, 0.2 mm, developing solution; ethyl acetate) to obtain the title compound (1.7 mg, 35%) as a colorless oil.

$^1$H-NMR spectrum (CD$_3$OD, 400 MHz)δ(ppm): 0.88(3H, d,J=6.4 Hz) 0.89(3H,d,J=6.8 Hz), 0.93(3H,t,J=7.2 Hz), 1.08 (3H,d,J=6.8 Hz), 1.18(3H,s), 1.21(3H,t,J=7.2 Hz), 1.28–1.72(9H,m), 1.74(3H,s), 2.06(3H,s), 2.39–2.74(6H,m), 3.46–3.52(1H,m), 3.54–3.63(2H,m), 4.11(2H,s), 4.88–4.98 (1H,d,J=10.8 Hz), 4.98(1H,d,J=10.8 Hz), 5.02(1H,d,J=9.6 Hz), 5.56(1H,dd,J=9.6,15.2 Hz), 5.66(1H,dd,J=8.4,14.4 Hz), 5.72(1H,dd,J=9.6,15.2 Hz), 6.09(1H,d,J=10.4 Hz), 6.32(1H,dd,J=10.4,14.8 Hz); ESI-MS m/z 645(M+Na)$^+$.

Example 25

(8E,12E,14E)-7-Acetoxy-21-ethoxyacetoxy-3,6-dihydroxy-6,10,12,16,20-pentamethyl-18,19-epoxytricosa-8,12,14-trien-11-olide (Compound B25)

Compound B25

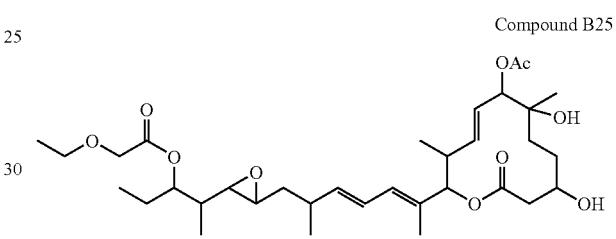

(8E,12E,14E)-7-Acetoxy-3-t-butyldimethylsiloxy-21-ethoxyacetoxy-6-hydroxy-6,10,12,16,20-pentamethyl-18,19-epoxytricosa-8,12,14-trien-11-olide

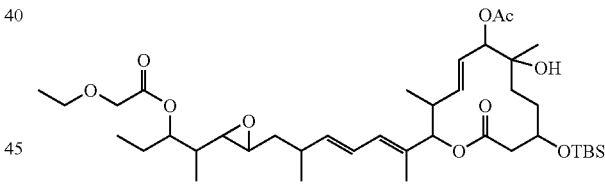

Ethoxyacetic acid (23 mg, 0.22 mmol), dicyclohexylcarbodiimide (55 mg, 0.27 mmol) and dimethylaminopyridine (5.4 mg, 0.27 mmol) were added to a solution of (8E,12E,14E)-7-acetoxy-3-t-butyldimethylsiloxy-6,21-dihydroxy-6,10,12,16,20-pentamethyl-18,19-epoxytricosa-8,12,14-trien-11-olide (29 mg, 0.044 mmol) in dichloromethane (3 mL) at room temperature. The mixture was stirred at room temperature for 4 hours. The reaction mixture was diluted with ethyl acetate, and filtered through Celite. The filtrate was washed with brine, dried over anhydrous magnesium sulfate and evaporated. The resulting crude product was purified by silica gel column chromatography (Kanto silica gel 60N, spherical, neutral, 40 to 100 μm, eluate; hexane:ethyl acetate=70:30) to obtain the title compound (28 mg, 85%) as a colorless oil.

ESI-MS m/z 759(M+Na)$^+$.

(8E,12E,14E)-7-Acetoxy-3-t-butyldimethylsiloxy-21-ethoxyacetoxy-6-(1-ethoxyethoxy)-6,10,12,16,20-pentamethyl-18,19-epoxytricosa-8,12,14-trien-11-olide

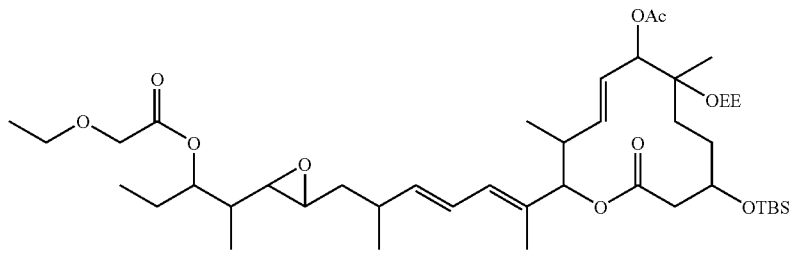

Ethyl vinyl ether (82 mg, 1.1 mmol) and pyridinium p-toluenesulfonate (9.2 mg, 0.036 mmol) were added to a solution of 7-acetoxy-3-t-butyldimethylsiloxy-21-ethoxyacetoxy-6-hydroxy-6,10,12,16,20-pentamethyl-18,19-epoxytricosa-8,12,14-trien-11-olide (27 mg, 0.036 mmol) in dichloromethane (1.5 mL) at room temperature. The mixture was stirred at room temperature for 17 hours. The reaction solution was diluted with ethyl acetate, washed with brine, dried over anhydrous magnesium sulfate and evaporated. The resulting crude product was purified by silica gel column chromatography (Kanto silica gel 60N, spherical, neutral, 40 to 100 μm, eluate; hexane:ethyl acetate=80:20) to obtain the title compound (16 mg, 54%) as a colorless oil.

ESI-MS m/z 831(M+Na)$^+$.

(8E,12E,14E)-7-Acetoxy-21-ethoxyacetoxy-6-(1-ethoxyethoxy)- 3-hydroxy-6,10,12,16,20-pentamethyl-18,19-epoxytricosa-8,12,14-trien-11-olide solution of (8E,12E,14E)-7-acetoxy-3-t-butyldimethylsiloxy-21-ethoxyacetoxy-6-(1-ethoxyethoxy)-6,10,12,16,20-pentamethyl-18,19-epoxytricosa-8,12,14-trien-11-olide (15 mg, 0.018 mmol) in tetrahydrofuran (1 mL) at room temperature. The mixture was stirred at room temperature for 2 hours. The reaction mixture was diluted with ethyl acetate, washed with brine, dried over anhydrous magnesium sulfate and evaporated. The resulting crude product was purified by silica gel column chromatography (Kanto silica gel 60N, spherical, neutral, 40 to 100 μm, eluate; hexane:ethyl acetate=50:50) to obtain the title compound (8.8 mg, 68%) as a colorless oil.

ESI-MS m/z 717(M+Na)$^+$.

(8E,12E,14E)-7-Acetoxy-21-ethoxyacetoxy-3,6-dihydroxy-6,10,12,16,20-pentamethyl-18,19-epoxytricosa-8,12,14-trien-11-olide (Compound B25)

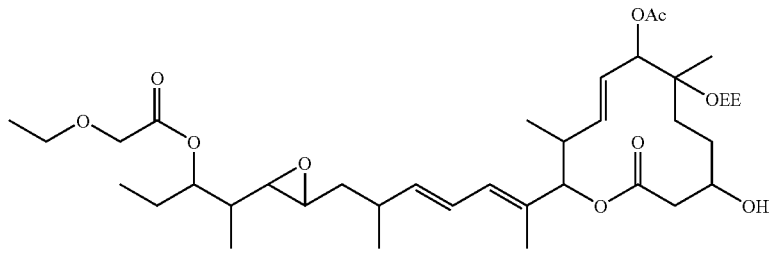

A 1.0 M solution of tetrabutylammonium fluoride in tetrahydrofuran (0.037 mL, 0.037 mmol) was added to a

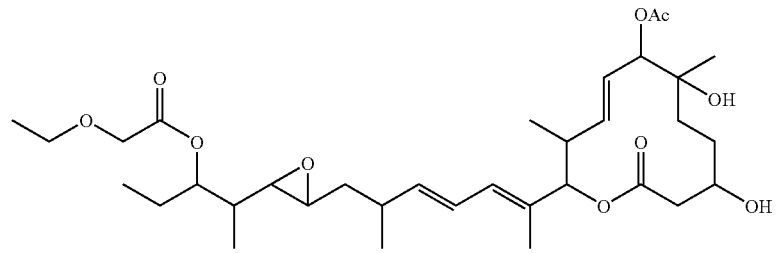

Compound B25

Pyridinium p-toluenesulfonate (29 mg, 0.12 mmol) was added to a solution of (8E,12E,14E)-7-acetoxy-21-ethoxyacetoxy-6-(1-ethoxyethoxy)-3-hydroxy-6,10,12,16,20-pentamethyl-18,19-epoxytricosa-8,12,14-trien-11-olide (8.0 mg, 0.012 mmol) in methanol (1.0 mL) at room temperature, followed by stirring at the same temperature for one hour. After the reaction mixture was diluted with ethyl acetate, it was washed with brine, dried over anhydrous magnesium sulfate and evaporated. The resulting crude product was purified by thin layer chromatography (MERCK Silicagel 60 F254, 0.25 mm, developing solution; hexane:ethyl acetate=1:2) to obtain the title compound (4.0 mg, 56%) as a colorless oil.

$^1$H-NMR spectrum (CD$_3$OD, 400 MHz)δ(ppm): 0.87(3H, d,J=6.8 Hz), 0.89(3H,d,J=7.2 Hz), 0.90(3H,t,J=7.2 Hz), 1.07 (3H,d,J=6.8 Hz), 1.18(3H,s), 1.21(3H,t,J=7.2 Hz), 1.24–1.70(9H,m), 1.74(3H,s), 2.05(3H,s), 2.41–2.50(1H,m), 2.51(2H,d,J=3.6 Hz), 2.55(1H,dd,J=2.4,8.0 Hz), 2.54–2.60 (1H,m), 2.72(1H,dt,J=2.4,5.6 Hz), 3.58(2H,q,J=7.2 Hz), 3.74–3.81(1H,m), 4.11(2H,s), 4.94–5.00(2H,m), 5.03(1H,d, J=10.8 Hz), 5.56(1H,dd,J=9.6,15.2 Hz), 5.64(1H,dd,J=8.0, 14.8 Hz), 5.69(1H,dd,J=9.6,14.8 Hz), 6.08(1H,d,J=10.8 Hz), 6.32(1H,dd,J=10.8,14.8 Hz); ESI-MS M/z 645(M+ Na)$^+$.

Example B26

(8E,12E,14E)-7-Acetoxy-3-ethoxyacetylacetoxy-6,21-dihydroxy-6,10,12,16,20-pentamethyl-18,19-epoxytricosa-8,12,14-trien-11-olide
(Compound B26)

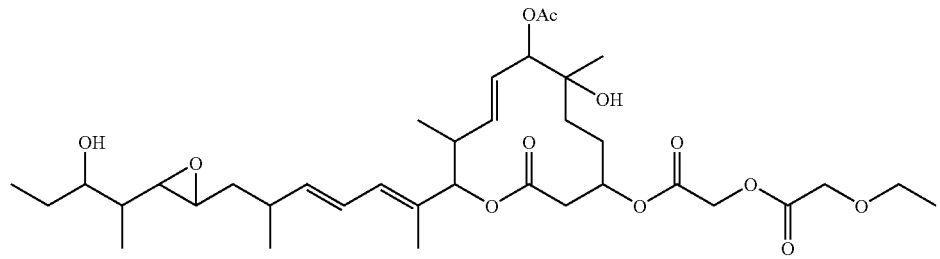

Compound B26

Ethoxyacetylacetic acid was esterified with (8E,12E,14E)-7-acetoxy-6,21-bis(1-ethoxyethoxy)-3-hydroxy-6,10,12,16,20-pentamethyl-18,19-epoxytricosa-8,12,14-trien-11-olide through the similar synthetic route as Example B24, to give the title compound as a colorless oil.

$^1$H-NMR spectrum (CD$_3$OD, 400 MHz)δ(ppm): 0.88(3H, d,J=6.4 Hz), 0.90(3H,d,J=7.2 Hz), 0.93(3H,t,7.2 Hz), 1.08 (3H,d,J=6.8 Hz), 1.18(3H,s), 1.21(3H,t,J=7.2 Hz), 1.26–1.72(9H,m), 1.74(3H,s), 2.06(3H,s), 2.42–2.52(1H,m), 2.54–2.62(1H,m), 2.63(2H,d,J=4.4 Hz), 2.65(1H,dd,J=2.0, 8.4 Hz), 2.72(1H,dt,J=2.4,5.6 Hz), 3.46–3.52(1H,m), 3.62 (2H,q,J=7.2 Hz), 4.24(2H,s), 4.72(2H,s), 4.93–4.97(1H,m), 4.99(1H,d,J=6.0 Hz), 5.02(1H,d,J=4.8 Hz), 5.56(1H,dd, J=9.6,15.2 Hz), 5.66(1H,dd,J=8.4,14.8 Hz), 5.71(1H,dd, J=9.6,15.2 Hz), 6.09(1H,d,J=10.0 Hz), 6.32(1H,dd,J=10.8, 15.2 Hz); ESI-MS m/z 703(M+Na)$^+$.

Example B27

(8E,12E,14E)-7-Acetoxy-3,6-dihydroxy-21-dihydroxyacetoxy-6,10,12,16,20-pentamethyl-18,19-epoxytricosa-8,12,14-trien-11-olide
(Compound B27)

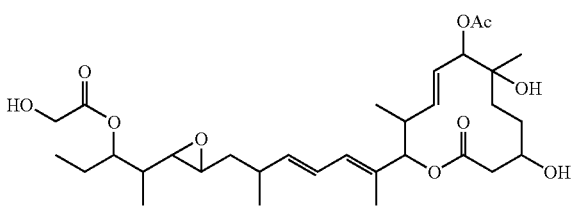

Compound B27

Ethoxyacetylacetic acid was esterified with (8E,12E,14E)-7-acetoxy-6,21-dihydroxy-3-t-butyldimethylsiloxy-6,10,12,16,20-pentamethyl-18,19-epoxytricosa-8,12,14-trien-11-olide through the similar synthetic route as Example B25, to give the title compound was obtained as a colorless oil.

$^1$H-NMR spectrum (CD$_3$OD, 400 MHz)δ(ppm): 0.87(3H, d,J=6.4 Hz), 0.89(3H,d,J=7.2 Hz), 0.90(3H,t,J=7.2 Hz), 1.07 (3H,d,J=6.8 Hz), 1.18(3H,s), 1.28–1.70(9H,m), 1.74(3H,d, J=1.2 Hz), 2.06(3H,s), 2.41–2.50(1H,m), 2.50–2.60(1H,m), 2.52(2H,d,J=4 Hz), 2.56(1H,dd,J=2.0,8.0 Hz), 2.72(1H,dt, J=2.4,6.0 Hz), 3.74–3.82(1H,m), 4.13(2H,s), 4.96–5.20(2H, m), 5.04(1H,d,J=9.6 Hz), 5.60(1H,dd,J=10.0,15.2 Hz), 5.65 (1H,dd,J=8.4,15.2 Hz), 5.69(1H,dd,J=9.6,15.2 Hz), 6.08 (1H,d,J=10.8 Hz), 6.32(1H,dd,J=10.8,14.4 Hz); ESI-MS m/z 617(M+Na)$^+$.

Example B28

(8E,12E,14E)-7-Acetoxy-3,6-dihydroxy-6,10,12,16,20-pentamethyl-21-dimethylaminoacetoxy-18,19-epoxytricosa-8,12,14-trien-11-olide
(Compound B28)

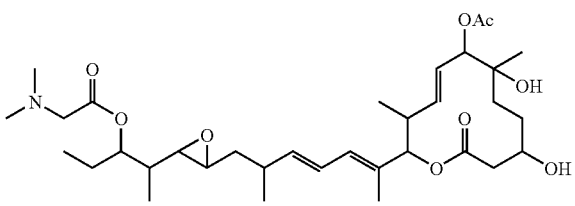

Compound B28

(8E,12E,14E)-7-acetoxy-3-t-butyldimethylsiloxy-21-dimethylaminoacetoxy)-6-hydroxy-6,10,12,16,20-pentamethyl-18,19-epoxytricosa-8,12,14-trien-11-olide was synthesized by the similar synthetic method as Example B25. To the compound (4.0 mg, 0.0054 mmol) was added a mixed solution of trifluoroacetic acid:tetrahydrofuran:H₂O=1:10:5, followed by stirring for 2 hours. The reaction mixture was poured into an aqueous saturated sodium bicarbonate solution, and the mixture was extracted with ethyl acetate. The organic layer was washed with brine, dried over MgSO₄ and evaporated. The resulting crude product was purified by thin layer chromatography (MERCK Silicagel 60 F254, 0.25 mm, developing solution; hexane:ethyl acetate=1:2) to obtain the title compound (1.0 mg, 29%) as a colorless oil.

¹H-NMR spectrum (CD₃OD, 400 MHz)δ(ppm): 0.86–0.91(6H,m), 0.90(3H,t,J=7.2 Hz), 1.07(3H,d,J=6.8 Hz), 1.18(3H,s), 1.26–1.71(9H,m), 1.74(3H,d,J=0.8 Hz), 2.06(3H,s), 2.34(6H,s), 2.41–2.50(1H,m), 2.52(2H,d,J=4.0 Hz), 2.55(1H,dd,J=2.0,8.4 Hz), 2.50–2.58(1H,m), 2.71(1H,dt,J=2.0,5.6 Hz), 3.24(2H,s), 3.74–3.82(1H,m), 4.94–5.00 (1H,m), 5.04(2H,d,J=9.6 Hz), 5.56(1H,dd,J=9.6,15.2 Hz), 5.64(1H,dd,J=8.0,15.2 Hz), 5.69(1H,dd,J=9.6,15.2 Hz), 6.08(1H,d,J=11.2 Hz), 6.32(1H,dd,J=10.8,14.8 Hz); ESI-MS m/Z 622(M+H)⁺.

Example B29

(8E,12E,14E)-7-Acetoxy-3-6-dihydroxy-6,10,12,16,20-pentamethyl-21-nicotinoxy-18,19-epoxytricosa-8,12,14-trien-11-olide (Compound B29)

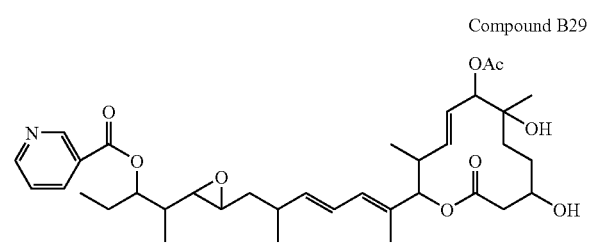

Compound B29

The title compound was obtained as a colorless oil by the similar synthetic method as Example B25, using nicotinic acid as the 21-position substituent.

¹H-NMR spectrum (CD₃OD, 400 MHz)δ(ppm): 0.86(3H, d,J=6.8 Hz), 0.94(3H,t,J=7.2 Hz), 1.01(3H,d,J=6.8 Hz), 1.04 (3H,d,J=6.8 Hz), 1.18(3H,s), 1.24–1.84(9H,m), 1.72(3H,d, J=1.2 Hz), 2.06(3H,s), 2.40–2.48(1H,m), 2.51(2H,d,J=4.0 Hz), 2.50–2.59(1H,m), 2.62(1H,dd,J=2.4,8.4 Hz), 2.75(1H, dt,J=2.0,5.6 Hz), 3.72–3.83(1H,m), 5.03(1H,d,J=10.8 Hz), 5.04(1H,d,J=10.0 Hz), 5.17–5.24(1H,m), 5.55(1H,dd,J=9.6, 15.2 Hz), 5.60(1H,dd,J=8.8,14.8 Hz), 5.69(1H,dd,J=9.6, 15.2 Hz), 6.06(1H,dd,J=9.6 Hz), 6.29(1H,dd,J=11.2,14.4 Hz), 7.59(1H,ddd,J=1.2,4.8,8.0 Hz), 8.41(1H,ddd,J=1.6,1.6,8.0 Hz), 8.76(1H,dd,J=1.6,4.8 Hz), 9.13(1H,dd,J=0.8,2.0 Hz); ESI-MS m/z 664(M+Na)⁺.

Example B30

(8E,12E,14E)-7-Acetoxy-3-21-dibenzoloxy-6-hydroxy-6,10,12,16,20-pentamethyl-18,19-epoxytricosa-8,12,14-trien-11-olide (Compound B30-1), (8E,12E,14E)-7-acetoxy-3-benzoloxy-6,21-dihydroxy-6,10,12,16,20-pentamethyl-18,19-epoxytricosa-8,12,14-trien-11-olide (Compound B30-2), and (8E,12E,14E)-7-acetoxy-21-benzoloxy-3,6-dihydroxy-6,10,12,16,20-pentamethyl-18,19-epoxytricosa-8,12,14-trien-11-olide (Compound B30-3)

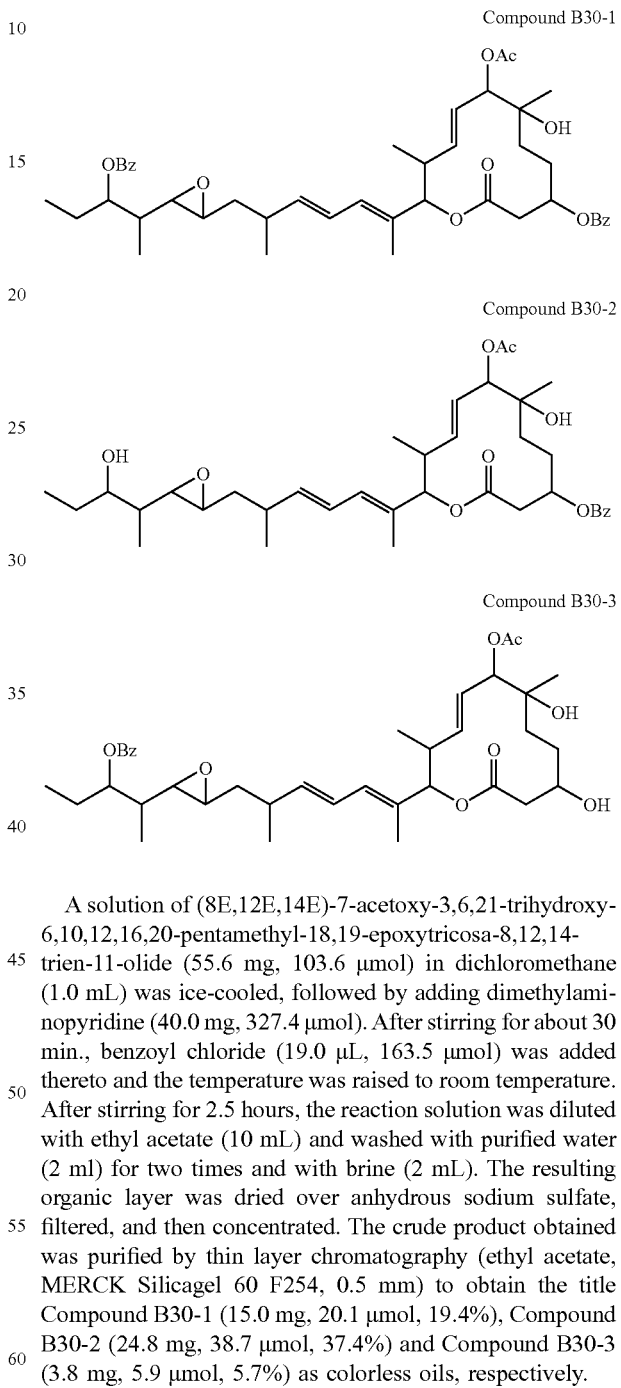

A solution of (8E,12E,14E)-7-acetoxy-3,6,21-trihydroxy-6,10,12,16,20-pentamethyl-18,19-epoxytricosa-8,12,14-trien-11-olide (55.6 mg, 103.6 μmol) in dichloromethane (1.0 mL) was ice-cooled, followed by adding dimethylaminopyridine (40.0 mg, 327.4 μmol). After stirring for about 30 min., benzoyl chloride (19.0 μL, 163.5 μmol) was added thereto and the temperature was raised to room temperature. After stirring for 2.5 hours, the reaction solution was diluted with ethyl acetate (10 mL) and washed with purified water (2 ml) for two times and with brine (2 mL). The resulting organic layer was dried over anhydrous sodium sulfate, filtered, and then concentrated. The crude product obtained was purified by thin layer chromatography (ethyl acetate, MERCK Silicagel 60 F254, 0.5 mm) to obtain the title Compound B30-1 (15.0 mg, 20.1 μmol, 19.4%), Compound B30-2 (24.8 mg, 38.7 μmol, 37.4%) and Compound B30-3 (3.8 mg, 5.9 μmol, 5.7%) as colorless oils, respectively.

Compound B30-1

¹H-NMR spectrum (CD₃OD, 400 MHz)δ(ppm): 0.89(3H, d,J=7 Hz), 0.92(3H,t,J=7 Hz), 0.98(3H,d,J=7 Hz), 1.01(3H, d,J=7 Hz), 1.20(3H,s), 1.32–1.41(1H,m), 1.42–1.51(1H,m), 1.53–1.68(3H,m), 1.70–1.82(4H,m), 1.73(3H,d,J=0.7 Hz), 2.06(3H,s), 2.35–2.47(1H,m), 2.55–2.78(5H,m), 5.02(1H,d, J=11 Hz), 5.06(1H,d,J=10 Hz), 5.08–5.15(1H,m), 5.17(1H, dt,J=5,7 Hz), 5.57(1H,dd,J=9,15 Hz), 5.62(1H,dd,J=10,15 Hz), 5.74(1H,dd,J=10,15 Hz), 6.08(1H,d,J=11 Hz), 6.28 (1H,dd,J=10,15 Hz), 7.43–7.50(4H,m), 7.58–7.62(2H,m), 7.99–8.02(2H,m), 8.03–8.08(2H,m); FAB-MS m/z 745(M+H)⁺.

Compound B30-2

¹H-NMR spectrum (CD₃OD, 400 MHz)δ(ppm): 0.89(3H, d,J=7 Hz), 0.90(3H,d,J=7 Hz), 0.93(3H,t,J=8 Hz), 1.06(3H, d,J=7 Hz), 1.14–1.21(1H,m), 1.20(3H,s), 1.41–1.54(4H,m), 1.59–1.68(2H,m), 1.68–1.80(2H,m), 1.75(3H,s), 2.06(3H,s), 2.40–2.50(1H,m), 2.56–2.72(2H,m), 2.64(1H,dd,J=2,8 Hz), 2.69(1H,dd,J=3,15 Hz), 2.76(1H,dd,J=4,15 Hz), 3.50(1H,dt, J=4,8 Hz), 5.03(1H,d,J=11 Hz), 5.06(1H,d,J=10 Hz), 5.03–5.14(1H,m), 5.62(1H,dd,J=10,15 Hz), 5.66(1H,dd, J=8,15 Hz), 5.74(1H,dd,J=10,15 Hz), 6.11(1H,d,J=11 Hz), 6.32(1H,dd,J=10,15 Hz), 7.43–7.50(2H,m), 7.58–7.62(1H, m), 8.03–8.08(2H,m); FAB-MS m/z 639(M-H)⁻.

Compound B30-3

¹H-NMR spectrum (CD₃OD, 400 MHz)δ(ppm): 0.86(3H, d,J=7 Hz), 0.92(3H,t,J=8 Hz), 0.99(3H,d,J=7 Hz), 1.02(3H, d,J=7 Hz), 1.18(3H,s), 1.33–1.44(3H,m), 1.54–1.70(4H,m), 1.72(3H,d,J=1.1 Hz), 1.72–1.84(2H,m), 2.06(3H,s), 2.48–2.50(1H,m), 2.51(2H,d,J=3 Hz), 2.50–2.62(1H,m), 2.60(1H,dd,J=2,7 Hz), 2.74(1H,dt,J=2,6 Hz), 3.72–3.80(1H, m), 5.03(1H,d,J=11 Hz), 5.04(1H,d,J=10 Hz), 5.18(1H,dt, J=5,7 Hz), 5.55(1H,dd,J=10,15 Hz), 5.57(1H,dd,J=8,15 Hz), 5.69(1H,dd,J=10,15 Hz), 6.05(1H,d,J=11 Hz), 6.28(1H,dd, J=11,15 Hz), 7.46–7.53(2H,m), 7.59–7.65(1H,m), 7.99–8.05(2H,m); FAB-MS m/z 641(M+H)⁺.

Example B31

(8E,12E)-7-Acetoxy-3,6,21-trihydroxy-6,10,12,16,20-pentamethyl-14,15,18,19-diepoxytricosa-8,12-dien-11-olide and (8E,14E)-7-acetoxy-3,6,21-trihydroxy-6,10,12,16,20-pentamethyl-12,13,18,19-diepoxytricosa-8,14-dien-11-olide (Compound B31)

Compound B31

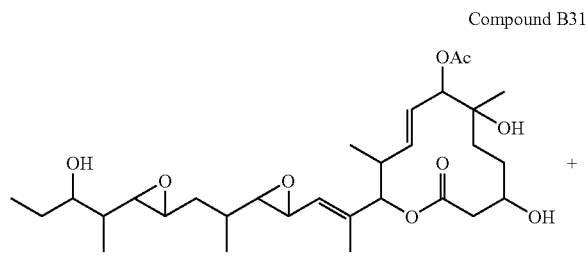

+

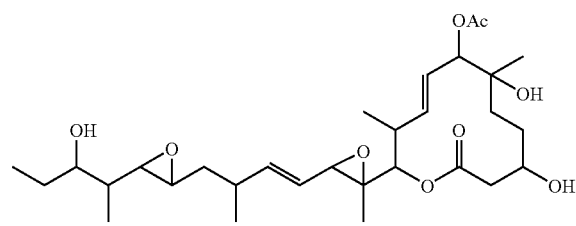

A solution of (8E,12E,14E)-7-acetoxy-3,6,21-trihydroxy-6,10,12,16,20-pentamethyl-18,19-epoxytricosa-8,12,14-trien-11-olide (21.7 mg, 40.4 μmol) in methylene chloride (0.5 mL) was cooled to −30° C. MCPBA (26.4 mg, 76.5 μmol) was added thereto, followed by stirring for 17.5 hours. After the temperature was raised to room temperature, a saturated sodium bicarbonate aqueous solution (1.0 mL) was added, and the mixture was extracted with chloroform (12 mL). The organic layer obtained was dried over anhydrous sodium sulfate, filtered and then concentrated. The resulting crude product was purified by thin layer chromatography (MERCK Silicagel 60 F25, 0.5 mm, developing solution; toluene:acetone=1:1) to obtain the title compound (9.3 mg, 16.8 μmol, 41.6%) as a colorless oil.

¹H-NMR Spectrum(CD₃OD,400 MHz) δ (ppm): 0.83–0.97(23.6H,m), 0.98–1.12(13.2H), 1.15–1.19(8.7H,m), 1.21–1.40(13.4H,m), 1.43–1.65(17.8H, m), 1.70–1.84(6.9H,m), 2.03–2.06(8.9H,m), 2.43–2.77(15.5H,m), 2.84–2.88(1.6H,m), 3.40–3.47(2.5H, m), 3.47–3.56(2.7H,m), 3.70–3.80(3.0H,m), 4.48–4.52(1.0H,m), 5.00–5.08(4.3H,m), 5.19–5.23(1.4H,m), 5.39–5.46(1.2H,m), 5.50–5.72(5.91H, m), 5.92–6.00(1.0H,m); FAB-MS m/z 553(M+H)⁺.

Example B32

(8E,12E,14E)-7-Acetoxy-6-hydroxy-6,10,12,16,20-pentamethyl-3,21-di(4-nitro-phenoxycarboxy)-18,19-epoxytricosa-8,12,14-trien-11-olide (Compound B32)

Compound B32

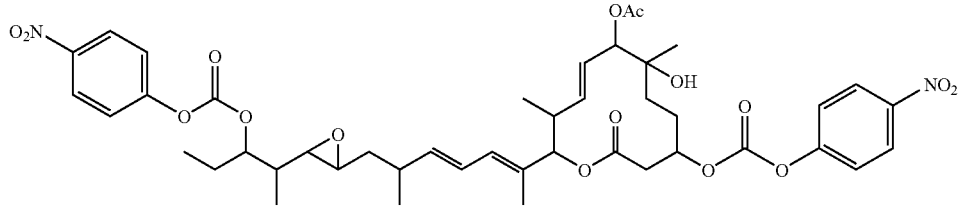

A solution of (8E,12E,14E)-7-acetoxy-3,6,21-trihydroxy-6,10,12,16,20-pentamethyl-18,19-epoxytricosa-8,12,14-trien-11-olide (32.1 mg, 60.0 μmol) in dichloromethane (2.0 mL) was ice-cooled, followed by adding dimethylaminopyridine (4.2 mg, 34.4 μmol) and triethylamine (85.0 μL, 0.6 mmol). After stirring for about 20 min., 4-nitrophenyl chloroformate (61.8 mg, 306.4 μmol) was added. The temperature was raised to room temperature and the mixture was stirred for 2.5 hours. Further, dimethylaminopyridine (4.2 mg, 34.4 μmol) and 4-nitrophenyl chloroformate (23.4 mg, 116.4 μmol) were added thereto under ice-cooling, and the temperature was raised to room temperature. After stirring for 1.5 hours, the mixture was diluted with ethyl acetate (20 mL), and washed with a saturated sodium bicarbonate aqueous solution (4 mL) and brine (2 mL). The organic layer obtained was dried over anhydrous sodium sulfate, filtered and then concentrated. The resulting crude product was purified by silica gel column chromatography (MERCK Silicagel 60, 63 to 200 μm, eluate; hexane:ethyl acetate=2:1) to obtain the title compound (23.3 mg, 26.9 μmol, 44.8%) as a colorless oil.

$^1$H-NMR Spectrum(CD$_3$OD,400 MHz)δ(ppm): 0.88(1H, d,J=7 Hz), 0.96(3H,t,J=8 Hz), 0.98(3H,d,J=7 Hz), 1.08(3H, d,J=7 Hz), 1.20(3H,s), 1.39–1.48(2H,m), 1.55–1.82(7H,m), 1.74(3H,d,J=0.7 Hz), 2.06(3H,s), 2.43–2.52(1H,m), 2.55–2.63(1H,m), 2.64(1H,dd,J=2,8 Hz), 2.68(1H,dd,J=3,15 Hz), 2.78(1H,dt,J=2,6 Hz), 2.87(1H,dd,J=4,15 Hz), 5.01(1H,d,J=11 Hz), 5.04(1H,dd,J=8,15 Hz), 5.73(1H,dd,J=10,15 Hz), 6.11(1H,d,J=10 Hz), 6.32(1H,dd,J=11,15 Hz), 7.43–7.50(4H,m), 8.27–8.32(4H,m); FAB-MS m/z 867(M+H)$^+$.

Example B33

(8E,12E,14E)-7-Acetoxy-3,21-dicarbamoyloxy-6-hydroxy-6,10,12,16,20-pentamethyl-18,19-epoxytricosa-8,12,14-trien-11-olide (Compound B33-1) and (8E,12E,14E)-7-acetoxy-21-carbamoyloxy-3-ethylcarboxy-6-hydroxy-6,10,12,16,20-pentamethyl-18,19-epoxytricosa-8,12,14-trien-11-olide (Compound B33-2)

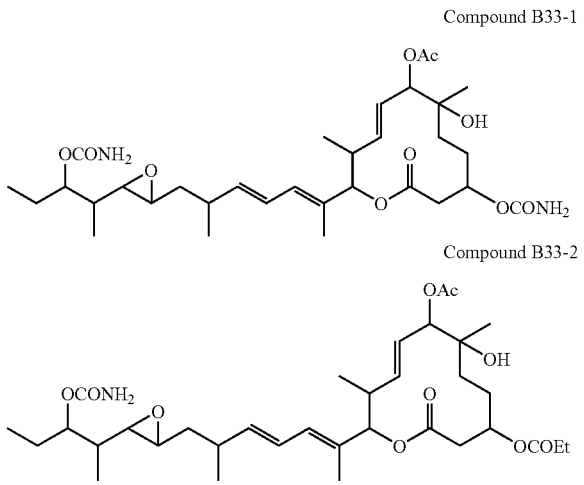

Compound B33-1

Compound B33-2

(8E,12E,14E)-7-acetoxy-6-hydroxy-6,10,12,16,20-pentamethyl-3,21-di(4-nitro-phenylcarboxy)-18,19-epoxytricosa-8,12,14-trien-11-olide (42.2 mg, 48.7 μmol) was dissolved in ethanol (1.0 mL), followed by adding a 28% aqueous ammonia (40 μL) under ice-cooling. The temperature was raised to room temperature and the mixture was stirred overnight. The reaction solution was concentrated, and the resulting crude product was purified by thin layer chromatography (MERCK Silicagel 60 F254, 0.5 mm, developing solution; ethyl acetate:hexane=5:1) to obtain the title Compound B33-2 (6.0 mg, 9.2 μmol, 18.9%) and Compound B33-1 (9.2 mg, 14.8 μmol, 30.4%) as colorless oils, respectively.

Compound B33-1
$^1$H-NMR Spectrum(CD$_3$OD,400 MHz) δ (ppm): 0.88 (3H,d,J=8 Hz), 0.89(3H,t,J=7 Hz), 0.90(3H,d,J=7 Hz), 1.07 (3H,d,J=7 Hz), 1.17(3H,s), 1.35–1.52(4H,m), 1.55–1.73(5H,m), 1.74(3H,d,J=0.7 Hz), 2.05(3H,s), 2.41–2.50(1H,m), 2.54–2.67(3H,m), 2.58(1H,dd,J=2,8 Hz), 2.72(1H,dt,J=2,6 Hz), 4.67–4.74(2H,m), 4.99(1H,d,J=11 Hz), 5.01(1H,d,J=10 Hz), 5.55(1H,dd,J=10,15 Hz), 5.66 (1H,dd,J=8,15 Hz), 5.71(1H,dd,J=10,15 Hz), 6.08(1H,d, J=11 Hz), 6.32(1H,dd,J=11,15 Hz); FAB-MS m/z 623(M+H)$^+$.

Compound B33-2
$^1$H-NMR Spectrum(CD$_3$OD,400 MHz) δ (ppm): 0.88 (3H,d,J=8 Hz), 0.89(3H,t,J=7 Hz), 0.90(3H,d,J=7 Hz), 1.07 (3H,d,J=7 Hz), 1.18(3H,s), 1.27(3H,t,J=7 Hz), 1.37–1.70 (9H,m), 1.74(3H,s), 2.05(3H,s), 2.41–2.50(1H,m), 2.54–2.64(3H,m), 2.69–2.76(2H,m), 4.16(2H,q,J=7 Hz), 4.68-4.73(2H,m), 4.98(1H,d,J=11 Hz), 5.02(1H,d,J=10 Hz), 5.57(1H,dd,J=10,15 Hz), 5.66(1H,dd,J=8,15 Hz), 5.71(1H, dd,J=10,15 Hz), 6.09(1H,d,J=11 Hz), 6.31(1H,dd,J=11,15 Hz); FAB-MS m/z 652(M+H)$^+$.

Example B34

(12E,14E)-7-Acetoxy-3,6,18-trihydroxy- 6,10,12,16,20-pentamethyl-19,21-carbonyldioxytricosa-8,12,14-trien-11-olide (Compound B34-1) and (8E,12E,14E)-7-acetoxy-6-carbamoyloxy-3,18-dihydroxy-6,10,12,16,20-pentamethyl-19,21-carbonyldioxytricosa-8,12,14-trien-11-olide (Compound B34-2)

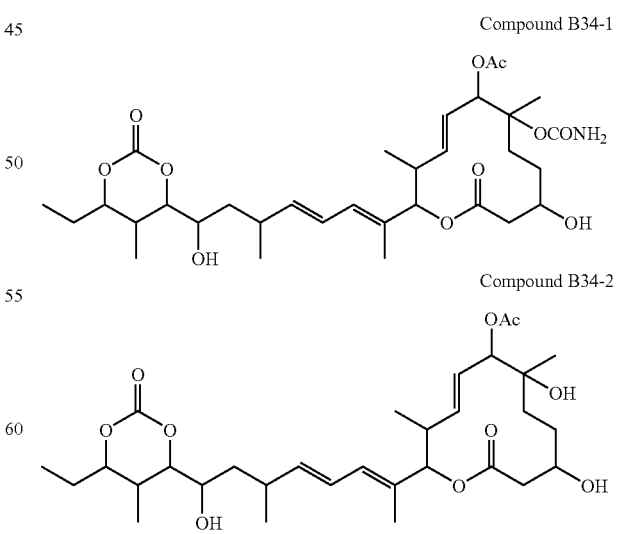

Compound B34-1

Compound B34-2

A solution of (8E,12E,14E)-7-acetoxy-3-t-butyldimethylsilyloxy-6,21-dihydroxy-6,10,12,16,20-pentamethyl-18,19- epoxytricosa-8,12,14-trien-11-olide (28.5 mg, 43.8 μmol) in dichloromethane (1.0 mL) was ice-cooled, and dimethylaminopyridine (7.4 mg, 60.6 μmol) and triethylamine (38.0 μL, 274.2 μmol) were added thereto. After stirring for about 20 min., 4-nitrophenyl chloroformate (27.2 mg, 135.0 μmol) was added, the temperature was raised to room temperature and the mixture was stirred for 16 hours. Further, dimethylaminopyridine (9.2 mg, 75.3 μmol), triethylamine (38.0 μL, 274.2 μmol) and 4-nitrophenyl chloroformate (35.9 mg, 177.9 μmol) were added thereto under ice-cooling, and the temperature was raised to room temperature. After stirring for 19 hours, the reaction soluiton was diluted with ethyl acetate (20 mL), and washed with a saturated sodium bicarbonate aqueous solution (1 mL), purified water (2 mL) and brine (2 mL). The resulting organic layer was dried over anhydrous sodium sulfate, filtered and then concentrated. The product was dissolved in tetrahydrofuran (0.5 mL) and 28% aqueous ammonia (60 μL) was added thereto, followed by stirring for 1.5 hours. The reaction solution was diluted with ethyl acetate (20 mL), and washed with purified water (2 mL) twice and brine (2 mL). The resulting organic layer was dried over anhydrous sodium sulfate, filtered, and then concentrated. The resulting crude product was purified by thin layer chromatography (MERCK Silicagel 60 F254, 0.5 mm, developing solution; ethyl acetate:hexane=1:1) to obtain (8E,12E,14E)-7-acetoxy-3-t-butyldimethylsilyloxy-21-carbamoyloxy-6-hydroxy-6,10,12,16,20-pentamethyl-18,19-epoxytricosa-8,12,14-trien-11-olide (18.5 mg, 26.7 μmol, 56.9% (2 steps)) and (8E,12E,14E)-7-acetoxy-3-t-butyldimethylsilyloxy-6,21-dicarbamoyloxy-6,10,12,16,20-pentamethyl-18,19-epoxytricosa-8,12,14-trien-11-olide (10.5 mg, 14.2 μmol, 30.3% (2 steps)). The resulting (8E,12E,14E)-7-acetoxy-3-t-butyldimethylsilyloxy-21-carbamoyloxy-6-hydroxy-6,10,12,16,20-pentamethyl-18,19-epoxytricosa-8,12,14-trien-11-olide was dissolved in tetrahydrofuran (0.1 mL), and purified water (0.2 mL) and acetic acid (0.3 mL) were added thereto. After stirring overnight, the reaction solution was diluted with ethyl acetate (20 mL), and washed with a saturated sodium bicarbonate aqueous solution (2 mL), purified water (2 mL) and brine (2 mL). The resulting organic layer was dried over anhydrous sodium sulfate, filtered and then concentrated. The resulting crude product was purified by preparative HPLC (SHISEIDO Capcell pak C18, 10 mm I.D.×250 mm, acetonitrile:water=40:60, 4.0 mL/min.) to obtain the title Compound B34-1 (5.98 mg, 10.3 μmol, 38.6%) as a colorless oil. Further, (8E,12E,14E)-7-acetoxy-3-t-butyldimethylsilyloxy-6,21-dicarbamoyloxy-6,10,12,16,20-pentamethyl-18,19-epoxytricosa-8,12,14-trien-11-olide was dissolved in tetrahydrofuran (0.1 mL), and purified water (0.2 mL) and acetic acid (0.3 mL) were added thereto. After stirring over night, it was diluted with ethyl acetate (20 mL), and washed with a saturated sodium bicarbonate aqueous solution (2 mL), purified water (2 mL) and brine (2 mL). The resulting organic layer was dried over anhydrous sodium sulfate, filtered and then concentrated. The resulting crude product was purified by preparative HPLC (SHISEIDO Capcell pak C18, 10 mm I.D.×250 mm, acetonitrile:water=40:60, 4.0 mL/min.) to obtain the title Compound B34-2 (3.66 mg, 5.9 μmol, 41.5%) as a colorless oil.

Compound B34-1

$^1$H-NMR Spectrum(CD$_3$OD,400 MHz)δ(ppm): 0.87(3H,d,J=7 Hz), 0.90(3H,d,J=7 Hz), 1.01(3H,t,J=8 Hz), 1.08(3H,d,J=7 Hz), 1.18(3H,s), 1.33–1.42(3H,m), 1.55–1.67(3H,m), 1.74(3H,d,J=1.1 Hz), 1.69–1.83(2H,m), 2.05(3H,s), 2.32–2.40(1H,m), 2.52(2H,d,J=4 Hz), 2.53–2.62(2H,m), 3.55(1H,ddd,J=2,10,10 Hz), 3.74–3.81(1H,m), 4.22(1H,dd,J=3,9 HZ), 4.50(1H,ddd,J=2,6,8 Hz), 5.04(1H,d,J=10 Hz), 5.05(1H,d,J=11 Hz), 5.56(1H,dd,J=10,15 Hz), 5.61(1H,dd,J=8,15 Hz), 5.69(1H,dd,J=10,15 Hz), 6.10(1H,d,J=11 Hz), 6.34(1H,dd,J=11,15 Hz); FAB-MS m/z 579 (M-H)$^-$.

Compound B34-2

$^1$H-NMR Spectrum(CD$_3$OD,400 MHz)δ(ppm): 0.89(3H,d,J=7 Hz), 0.90(3H,d,J=7 Hz), 1.01(3H,t,J=7 Hz), 1.08(3H,d,J=7 Hz), 1.35–1.52(2H,m), 1.54–1.67(3H,m), 1.57(3H,s), 1.71–1.85(2H,m), 1.75(3H,d,J=1.1 Hz), 2.01(3H,s), 2.31–2.40(2H,m), 2.49(2H,d,J=4 Hz), 2.53–2.63(2H,m), 3.55(1H,ddd,J=2,10,10 Hz), 3.75–3.81(1H,m), 4.22(1H,dd,J=3,9 Hz), 4.50(1H,ddd,J=2,6,8 Hz), 4.96(1H,d,J=10 Hz), 5.06(1H,d,J=11 Hz), 5.60(1H,dd,J=10,15 Hz), 5.61(1H,dd,J=8,15 Hz), 5.74(1H,dd,J=10,15 Hz), 6.11(1H,d,J=12 Hz), 6.34(1H,dd,J=10,15 Hz); FAB-MS m/z 646(M+Na)$^+$, 622 (M-H)$^-$.

Example B35

(8E,12E,14E)-7-Acetoxy-3-carbamoyloxy-6,21-dihydroxy-6,10,12,16,20-pentamethyl-18,19-epoxytricosa-8,12,14-trien-11-olide (Compound B35-1) and (8E,12E,14E)-7-acetoxy-21-carbamoyloxy-3,6-dihydroxy-6,10,12,16,20-pentamethyl-18,19-epoxytricosa-8,12,14-trien-11-olide (Compound B35-2)

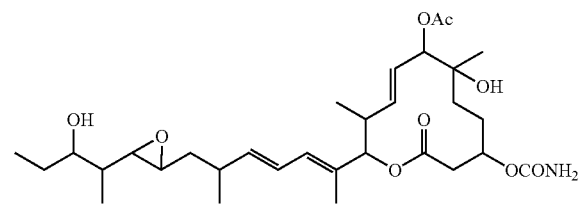

Compound B35-1

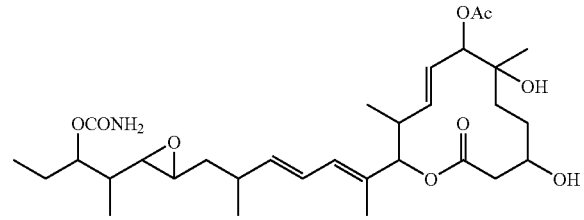

Compound B35-2

A solution of (8E,12E,14E)-7-acetoxy-3,6,21-trihydroxy-6,10,12,16,20-pentamethyl-18,19-epoxytricosa-8,12,14-trien-11-olide (105 mg, 195.6 μmol) in dichloromethane (4.0 mL) was ice-cooled, followed by adding dimethylaminopyridine (34.1 mg, 279.1 μmol) and triethylamine (165 μL, 1.18 mmol). After stirring for about 20 min., 4-nitrophenyl chloroformate (123.0 mg, 610.2 μmol) was added thereto, and the temperature was raised to room temperature and the solution was stirred for 16 hours. The reaction mixture diluted with ethyl acetate (40 mL), and washed with a saturated sodium bicarbonate aqueous solution (4 mL) for three times, purified water (4 mL) and brine (4 mL). The organic layer obtained was dried over anhydrous sodium sulfate, filtered and then concentrated. The resulting crude product was purified by silica gel column chromatography (MERCK Silicagel 60, 63 to 200 μm, eluate; hexane:ethyl acetate=3:2 to 1:1) and thin layer chromatography (MERCK Silicagel 60 F254, 0.5 mm, developing solution; ethyl acetate:hexane=4:1) to obtain (8E,12E,14E)-7-acetoxy-6,21-dihydroxy-6,10,12,16,20-pentamethyl-3-(4-nitrophenylcarboxy)-18,19-epoxytricosa-8,12,14-trien-11-olide (8.2 mg, 11.7 μmol, 6.0%) and (8E,12E,14E)-7-acetoxy- 3,6-dihydroxy-6,10,12,16,20-pentamethyl-21-(4-nitrophenylcarboxy)-18,19-epoxytricosa-8,12,14-trien-11-olide (10.9 mg, 15.5 μmol, 7.9%). The resulting (8E,12E,14E)-7-acetoxy-6,21-dihydroxy-6,10,12,16,20-pentamethyl-3-(4-nitrophenylcarboxy)-18,19-epoxytricosa-8,12,14-trien-11-olide was dissolved in tetrahydrofuran (0.5 mL) and 28% aqueous ammonia (20 μL) was added thereto, followed by stirring for 21.5 hours. The reaction solution was diluted with ethyl acetate (20 mL), and washed with purified water (4 mL) twice and brine (4 mL). The resulting organic layer was dried over anhydrous sodium sulfate, filtered and concentrated. The resulting crude product was purified by thin layer chromatography (MERCK silicagel 60 F254, 0.5 mm, developing solution; ethyl acetate) to obtain the title Compound B35-1 (6.8 mg, 11.7 μmol, 100.0%) as a colorless oil. Further, (8E,12E,14E)-7-acetoxy-3,6-dihydroxy-6,10,12,16,20-pentamethyl-21-(4-nitrophenylcarboxy)-18,19-epoxytricosa-8,12,14-trien-11-olide was dissolved in tetrahydrofuran (0.5 mL), 28% aqueous ammonia (20 μL) was added, and the mixture was stirred for 21.5 hours. The reaction solution was diluted with ethyl acetate (20 mL) and washed with purified water (4 mL) twice and brine (4 mL). The resulting organic layer was dried over anhydrous sodium sulfate, filtered and then concentrated. The resulting crude product was purified by thin layer chromatography (MERCK Silicagel 60 F254, 0.5 mm, developing solution; ethyl acetate) to obtain the title Compound B35-2 (8.0 mg, 13.8 μmol, 89.0%) as a colorless oil.

Compound B35-1

$^1$H-NMR Spectrum(CD$_3$OD,400 MHz)δ(ppm): 0.88(3H,d,J=7 Hz), 0.89(3H,d,J=7 Hz), 0.93(3H,t,J=7 Hz), 1.08(3H,d,J=7 Hz), 1.17(3H,s), 1.17–1.24(1H,m), 1.37–1.55(5H,m), 1.56–1.72(3H,m), 1.74(3H,d,J=1.1 Hz), 2.05(3H,s), 2.42–2.51(1H,m), 2.51–2.63(3H,m), 2.65(1H,dd,J=2,8 Hz), 2.72(1H,dt,J=2,6 Hz), 3.50(1H,dt,J=4,8 Hz), 4.66–4.73(1H,m), 5.00(1H,d,J=11 Hz), 5.01(1H,d,J=10 Hz), 5.55(1H,dd,J=10,15 Hz), 5.66(1H,dd,J=8,15 Hz), 5.71(1H,dd,J=10,15 HZ), 6.08(1H,d,J=11 Hz), 6.32(1H,dd,J=10,15 Hz); FAB-MS m/z 580(M+H)$^+$.

Compound B35-2

$^1$H-NMR Spectrum(CD$_3$OD,400 MHz)δ(ppm): 0.87(3H,d,J=7 Hz), 0.89(3H,t,J=7 Hz), 0.90(3H,d,J=7 Hz), 1.07(3H,d,J=7 Hz), 1.18(3H,s), 1.33–1.52(4H,m), 1.55–1.67(5H,m), 1.74(3H,d,J=1.1 Hz), 2.05(3H,s), 2.42–2.52(1H,m), 2.52 (2H,d,J=4 Hz), 2.52–2.60(1H,m), 2.58(1H,dd,J=2,5 Hz), 2.72(1H,dt,J=2,6 Hz), 3.74–3.80(1H,m), 4.70(1H,dt,J=6,7 Hz), 5.03(1H,d,J=12 Hz), 5.04(1H,d,J=10 Hz), 5.56(1H,dd,J=10,15 Hz), 5.65(1H,dd,J=8,15 Hz), 5.69(1H,dd,J=10,15 Hz), 6.08(1H,d,J=11 Hz), 6.31(1H,dd,J=10,15 Hz); FAB-MS m/z 580(M+H)$^+$.

Example B36

(8E,12E,14E)-7-Acetoxy-3-((4-methylpiperazin-1-yl)carbonyl)oxy-6,21-dihydroxy-6,10,12,16,20-pentamethyl-18,19-epoxytricosa-8,12,14-trien-11-olide (Compound B36-1) and (8E,12E,14E)-7-acetoxy-21-((4-methylpiperazin-1-yl)carbonyl)oxy-3,6-dihydroxy-6,10,12,16,20-pentamethyl-18,19-epoxytricosa-8,12,14-trien-11-olide (Compound B36-2)

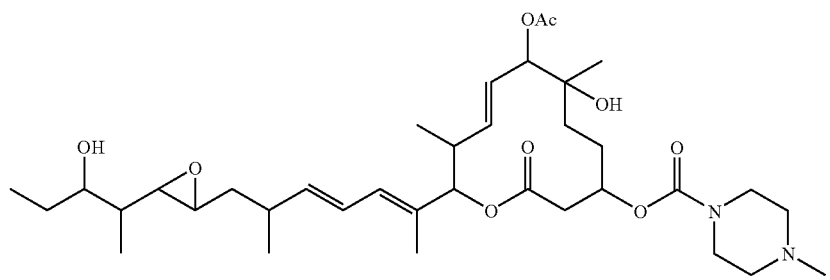

Compound B36-1

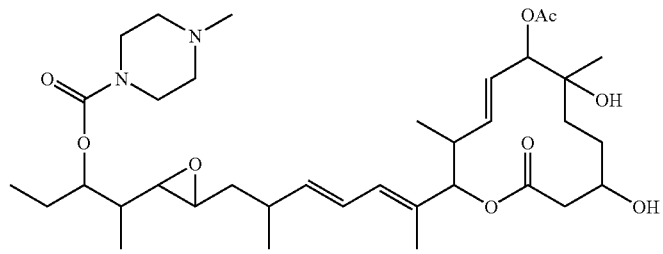

Compound B36-2

The title Compound B36-1 (a colorless oil) and Compound B36-2 (a colorless oil) were synthesized by the similar method as Example B35.

Compound B36-1

$^1$H-NMR Spectrum(CD$_3$OD,400 MHz)δ(ppm): 0.88(3H,d,J=5.1 Hz), 0.89(3H,d,J=5.5 Hz), 0.94(3H,t,J=7.3 Hz), 1.07 (3H,d,J=7.0 Hz), 1.18(3H,s), 1.15–1.22(1H,m), 1.34–1.55 (5H,m), 1.57–1.72(3H,m), 1.73(3H,d,J=1.1 Hz), 2.05(3H,s), 2.30(3H,s), 2.35–2.51(5H,m), 2.52–2.63(3H,m), 2.65(1H,dd,J=2.2,8.1 Hz), 2.72(1H,dt,J=2.2,5.9 Hz), 3.45–3.55(4H,m), 3.55–3.69(1H,m), 4.71–4.80(1H,m), 4.97(1H,d,J=10.6 Hz), 5.02(1H,d,J=9.5 Hz), 5.56(1H,dd,J=9.9,15.0 Hz), 5.66

(1H,dd,J=8.4,15.0 Hz), 5.71(1H,dd,J=9.9,15.0 Hz), 6.09 (1H,d,J=10.6 Hz), 6.32(1H,dd,J=10.6,15.0 Hz); ESI-MS m/z 663(M+H)+, 685(M+Na)+.

Compound B36-2

$^1$H-NMR Spectrum(CD$_3$OD,400 MHz)δ(ppm): 0.87(3H, d,J=6.6 Hz), 0.89(3H,t,J=7.3 Hz), 0.90(3H,d,J=7.0 Hz), 1.07 (3H,d,J=7.0 Hz), 1.18(3H,s), 1.33–1.69(9H,m), 1.74(3H,d, J=1.1 Hz), 2.05(3H,s), 2.30(3H,s), 2.38–2.60(6H,m), 2.51 (2H,d,J=3.7 Hz), 2.55(1H,dd,J=2.2,7.7 Hz), 2.71(1H,dt, J=2.2,5.9 Hz), 3.44–3.53(4H,m), 3.74–3.80(1H,m), 4.75–4.83(1H,m), 5.03(1H,d,J=10.6 Hz), 5.04(1H,d,J=9.5 Hz), 5.55(1H,dd,J=9.5,15.0 Hz), 5.65(1H,dd,J=8.1,15.0 Hz), 5.69(1H,dd,J=9.5,15.0 Hz), 6.08(1H,d,J=11.0 Hz), 6.31 (1H,dd,J=11.0,15.0 Hz); ESI-MS m/z 663(M+H)+, 685(M+Na)+.

Example B37

(8E,12E,14E)-7-Acetoxy-3-((4-piperidin-1-yl)-piperidin-1-yl)carbonyl)oxy-6,21-dihydroxy-6,10,12,16,20-pentamethyl-18,19-epoxytricosa-8,12,14-trien-11-olide (Compound B37-1) and (8E,12E,14E)-7-acetoxy-21-((4-piperidin-1-yl)-piperidin-1-yl) carbonyl)-3,6-dihydroxy-6,10,12,16,20-pentamethyl-18,19-epoxytricosa-8,12,14-trien-11-olide (Compound B37-2)

The title Compound B37-1 (a colorless oil) and Compound B37-2 (a colorless oil) were synthesized by the similar method as Example B35.

Compound B37-1

$^1$H-NMR Spectrum(CD$_3$OD,400 MHZ)δ(ppm): 0.88(3H, d,J=5.1 Hz), 0.89(3H,d,J=5.5 Hz), 0.94(3H,t,J=7.3 Hz), 1.07 (3H,d,J=6.6 Hz), 1.14–1.20(1H,m), 1.18(3H,s), 1.34–1.56 (9H,m), 1.56–1.76(7H,m), 1.73(3H,d,J=1.1 Hz), 1.83–1.92 (2H,m), 2.05(3H,s), 2.42–2.65(9H,m), 2.65(1H,dd,J=2.2,8.4 Hz), 2.71(1H, dt,J=2.2,5.9 Hz), 2.71–2.86(2H,m), 3.50(1H, dt,J=4.8,8.8 Hz), 4.12–4.33(2H,m), 4.69–4.76(1H,m), 4.97 (1H,d,J=10.6 Hz), 5.02(1H,d,J=9.5 Hz), 5.56(1H,dd,J=9.9, 15.0 Hz), 5.65(1H,dd,J=8.4,15.0 Hz), 5.71(1H,dd,J=9.5, 15.0 Hz), 6.09(1H,d,J=11.0 Hz), 6.32(1H,dd,J=11.0,15.0 Hz); ESI-MS m/z 731(M+H)+, 753(M+Na)+.

Compound B37-2

$^1$H-NMR Spectrum(CD$_3$ OD,400 MHz)δ(ppm): 0.87(3H, d,J=7.0 Hz), 0.88(3H,t,J=7.0 Hz), 0.90(3H,d,J=7.0 Hz), 1.07 (3H,d,J=6.6 Hz), 1.18(3H,s), 1.30–1.53(9H,m), 1.53–1.69 (8H,m), 1.74(3H,d,J=1.1 Hz), 1.86–1.93(2H,m), 2.05(3H,s), 2.41–2.65(7H,m), 2.51(2H,d,J=3.3 Hz), 2.54(1H,dd,J=2.2, 7.7 Hz), 2.71(1H,dt,J=2.2,5.9 Hz), 2.72–2.90(2H,m), 3.75–3.80(1H,m), 4.14–4.22(2H,m), 4.73–4.80(1H,m), 5.03 (1H,d,J=11.4 Hz), 5.04(1H,d,J=9.5 Hz), 5.55(1H,dd,J=9.5, 15.0 Hz), 5.64(1H,dd,J=8.4,15.0 Hz), 5.69(1H,dd,J=9.5, 15.0 Hz), 6.08(1H,d,J=11.0 Hz), 6.31(1H,dd,J=11.0,15.0 Hz); ESI-MS m/z 731(M+H)+, 753(M+Na)+.

Example B38

(8E,12E,14E)-7-Acetoxy-3,21-bis(diethylcarbamoyloxy)-6-hydroxy-6,10,12,16,20-pentamethyl-18,19-epoxytricosa-8,12,14-trien-11-olide (Compound B38)

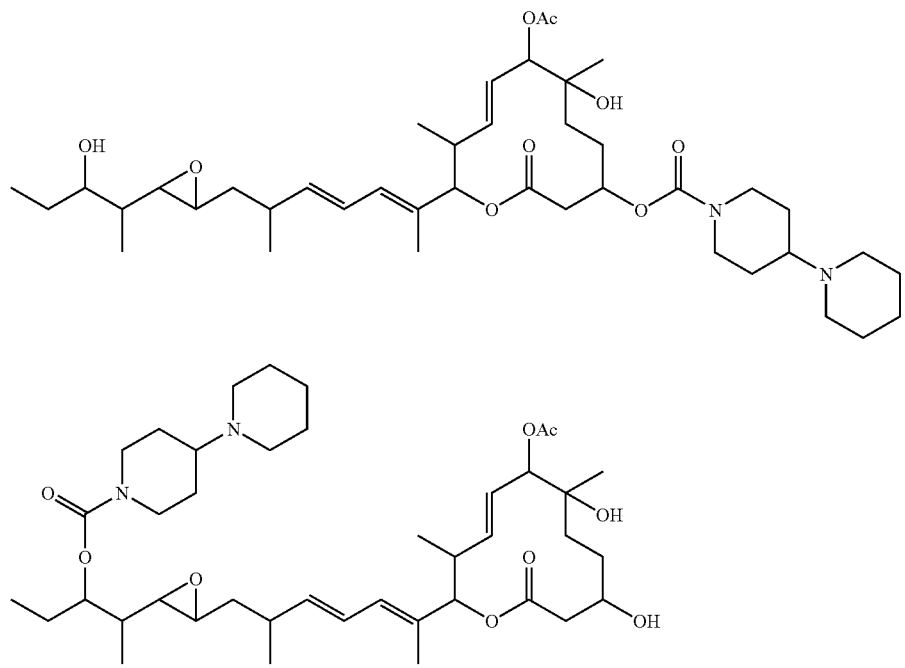

Compound B37-1

Compound B37-2

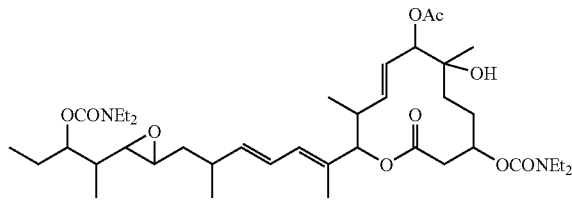

Compound B38

(8E,12E,14E)-7-Acetoxy-6-hydroxy-6,10,12,16,20-pentamethyl-3,21-di(4-nitro-phenylcarboxy)-18,19-epoxytricosa-8,12,14-trien-11-olide (12.6 mg) was dissolved in tetrahydrofuran (0.5 mL), and diethylamine (20 μL) was added thereto, followed by stirring for 21.0 hours. The reaction solution was diluted with ethyl acetate (20 mL), and washed with purified water (4 mL) twice and brine (4 mL). The resulting organic layer was dried over anhydrous sodium sulfate, filtered and then concentrated. The resulting crude product was purified by thin layer chromatography (MERCK Silicagel 60 F254, 0.5 mm, developing solution; ethyl acetate) to obtain the title compound (10.7 mg, 14.5 μmol, 100.0%) as a colorless oil.

$^1$H-NMR Spectrum(CD$_3$OD,400 MHZ)δ(ppm): 0.88(3H, d,J=7 Hz), 0.89(3H,t,J=7 Hz), 0.91(3H,d,J=7 Hz), 1.07(3H, d,J=7 Hz), 1.06–1.18(12H,m), 1.18(3H,s), 1.35–1.55(4H, m), 1.56–1.73(5H,m), 1.73(3H,d,J=0.7 Hz), 2.06(3H,s), 2.40–2.51(1H,m), 2.55(1H,dd,J=2,8 Hz), 2.53–2.60(2H,m), 2.63(1H,dd,J=4,15 Hz), 2.71(1H,dt,J=2,6 Hz), 3.25–3.32 (8H,m), 4.70–4.83(2H,m), 4.97(1H,d,J=11 Hz), 5.03(1H,d, J=10 Hz), 5.56(1H,dd,J=10,15 Hz), 5.65(1H,dd,J=9,15 Hz), 5.72(1H,dd,J=10,15 Hz), 6.09(1H,d,J=11 Hz), 6.31(1H,dd, J=11,15 Hz); FAB-MS m/z 735 (M+H)$^+$.

Example B39

(8E,12E,14E)-7-Chloroacetoxy-3,6,21-trihydroxy-6,10,12,16,20-pentamethyl-18,19-epoxytricosa-8,12,14-trien-11-olide (Compound B39)

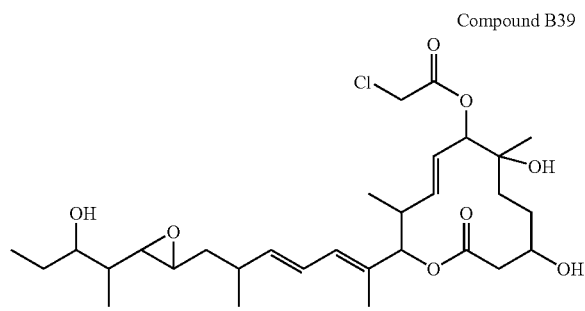

Compound B39

(8E,12E,14E)-7-Acetoxy-3,6,21-tri(1-ethoxyethoxy)-6,10,12,16,20-pentamethyl-18,19-epoxytricosa-8,12,14-trien-11-olide

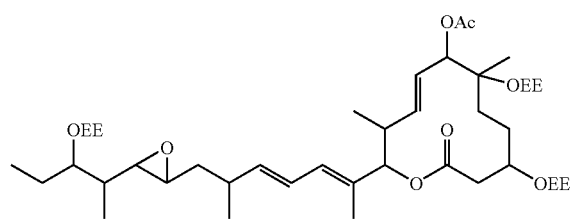

Pyridinium p-toluenesulfonate (9 mg, 35.4 μmol) was added to a solution of (8E,12E,14E)-7-acetoxy-3,6,21-trihydroxy-6,10,12,16,20-pentamethyl-18,19-epoxytricosa-8,12,14-trien-11-olide (200 mg, 0.354 mmol) in dichloromethane (10 mL) and ethyl vinyl ether (521 mg, 7.08 mmol) at room temperature, followed by stirring at the same temperature overnight. Ethyl Acetate and water were added to the reaction solution, and the mixture was extracted with ethyl acetate, dried over anhydrous magnesium sulfate, filtered and then evaporated. The resulting residue was purified by silica gel column chromatography (Kanto silica gel 60N, 40 to 50 μm; ethyl acetate-hexane=1:4, 1:3 and 1:1, successively) to obtain the title compound (250 mg, 94%) as a colorless oil.

ESI-MS m/z 775(M+Na)$^+$.

(8E,12E,14E)-3,6,21-Tri(1-ethoxyethoxy)-7-hydroxy-6,10,12,16,20-pentamethyl-18,19-epoxytricosa-8,12,14-trien-11-olide

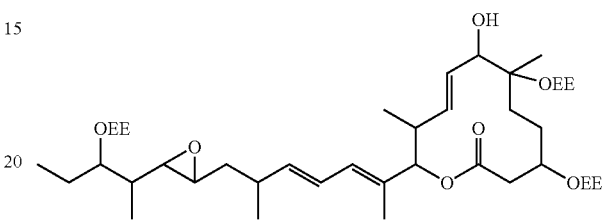

Potassium carbonate (138 mg, 0,996 mmol) was added to a solution of (8E,12E,14E)-7-acetoxy-3,6,21-tri(1-ethoxyethoxy)-6,10,12,16,20-pentamethyl-18,19-epoxytricosa-8,12,14-trien-11-olide (250 mg, 0.332 mmol) in methanol (5 mL) at room temperature, followed by stirring at the same temperature for 2 hours. Acetic acid (60 mg, 1 mmol), ethyl acetate and water were added to the reaction solution, and the mixture was extracted with ethyl acetate. The organic layer was washed with water, dried over anhydrous magnesium sulfate, filtered and then evaporated. The resulting residue was purified by silica gel column chromatography (Kanto silica gel 60N, spherical, neutral, 40 to 50 μm, ethyl acetate-hexane=1:2 and 1:1, successively) to obtain the title compound (242 mg, 100%) as a colorless oil.

ESI-MS m/z 734(M+Na)$^+$.

(8E,12E,14E)-7-Chloroacetoxy-3,6,21-tri(1-ethoxyethoxy)-6,10,12,16,20-pentamethyl-18,19-epoxytricosa-8,12,14-trien-11-olide

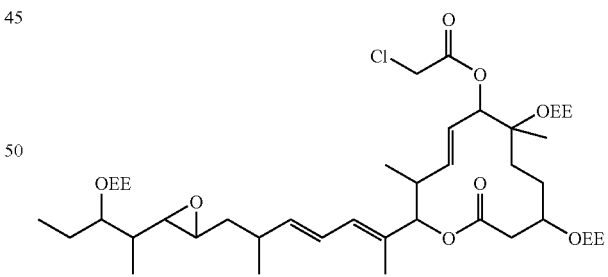

A solution of chloroacetic anhydride (21.5 mmol, 0.122 mmol) and dimethylaminopyridine (1.2 mg, 10 μmol) in dichloromethane (0.5 mL) were added to a solution of (8E,12E,14E)-3,6,21-tri(1-ethoxyethoxy)-7-hydroxy-6,10,12,16,20-pentamethyl-18,19-epoxytricosa-8,12,14-trien-11-olide (17.4 mg, 24.4 μmol) and triethylamine (25 mg, 0.244 mmol) in dichloromethane (2 mL) at room temperature, followed by stirring at the same temperature for one hour. Ethyl Acetate and water were added to the reaction solution, and the mixture was extracted with ethyl acetate, dried over anhydrous magnesium sulfate, filtered and then evaporated.

(8E,12E,14E)-7-Chloroacetoxy-3,6,21-trihydroxy-6,10,12,16,20-pentamethyl-18,19-epoxytricosa-8,12,14-trien-11-olide

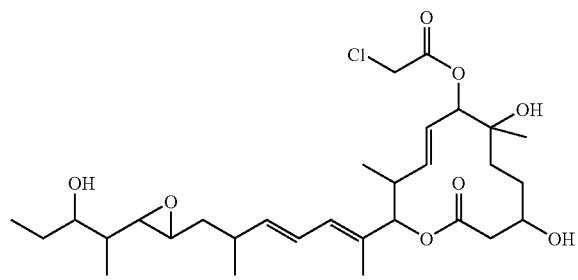

Pyridinium p-toluenesulfonate (1 mg, 4.1 µmol) was added to a solution of (8E,12E,14E)-7-chloroacetoxy-3,6,21-tri(1-ethoxyethoxy)-6,10,12,16,20-pentamethyl-18,19-epoxytricosa-8,12,14-trien-11-olide (3.2 mg, 4.06 µmol) in methanol (1 mL), followed by stirring at room temperature for one hour. The reaction solution was evaporated, and the resulting residue was purified by thin layer chromatography (MERCK Silica gel 60 F254, 0.2 mm, developing solution; ethyl acetate-hexane=2:1) to obtain the title compound (1.6 mg, 70%) as a colorless oil.

$^1$H-NMR Spectrum(CD$_3$OD, 400 MHz)δ(ppm): 0.79(3H, d,J=6.8 Hz), 0.80(3H,d,J=6.8 Hz), 0.84(3H,t,J=7.6 Hz), 0.98 (3H,d,J=6.8 Hz), 1.05–1.13(4H,m), 1.25–1.31(2H,m), 1.32–1.58(6H,m), 1.65(3H,d,J=0.8 Hz), 2.32–2.52(4H,m), 2.56(1H,dd,J=2.4,8.4 Hz), 2.62(1H,dt,J=2.4,6.0 Hz), 3.41 (1H,dt,J=4.4,8.4 Hz), 3.66–3.72(1H,m), 4.09(1H,d,J=14.8 Hz), 4.15(1H,d,J=14.8 Hz), 4.95(1H,d,J=10.8 Hz), 5.00(1H, d,J=9.6 Hz), 5.53(1H,dd,J=9.6,15.2 Hz), 5.56(1H,dd,J=8.0, 14.4 Hz), 5.62(1H,dd,J=9.2,15.2 Hz), 6.00(1H,d,J=10.8 Hz), 6.23(1H,dd,J=10.8,15.2 Hz); ESI-MS m/z 593(M+ Na)$^+$.

Example B40

(8E,12E,14E)-3,6,21-Trihydroxy-6,10,12,16,20 -pentamethyl-7-(morpholin-4-yl)acetoxy-18,19-epoxytricosa-8,12,14-trien-11-olide (Compound B40)

Compound B40

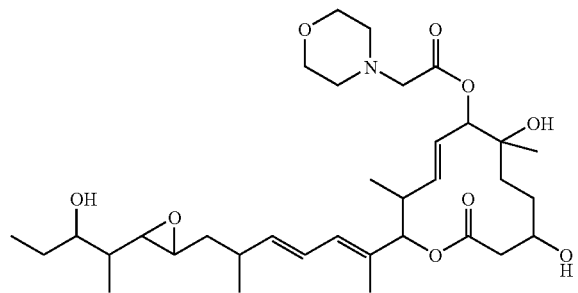

(8E,12E,14E)-3,6,21-Tri(1-ethoxyethoxy)-7-(morpholin-4-yl)acetoxy-6,10,12,16,20-pentamethyl-18,19-epoxytricosa-8,12,14-trien-11-olide

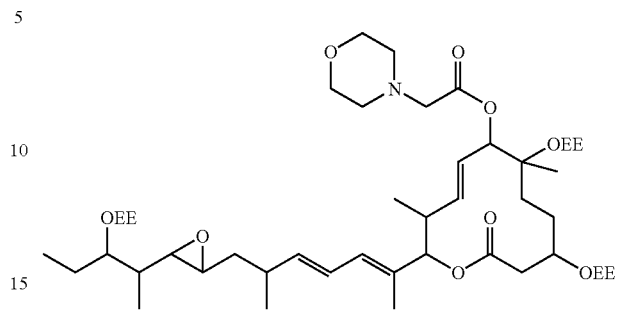

Morpholine (9 mg, 0.103 mmol) was added to a solution of (8E,12E,14E)-7-chloroacetoxy-3,6,21-tri(1-ethoxyethoxy)-6,10,12,16,20-pentamethyl-18,19-epoxytricosa-8,12,14-trien-11-olide (8.1 mg, 10.3 µmol) in N,N-dimethylformamide (1 mL) at room temperature, followed by stirring at 60° C. for one hour. Ethyl Acetate and water were added to the reaction solution, and the mixture was extracted with ethyl acetate, and the organic layer was washed with water. The resulting organic layer was dried over anhydrous magnesium sulfate, filtered and then evaporated. The resulting residue was purified by silica gel column chromatography (Kanto silica gel 60N, 40 to 50 µm; ethyl acetate-hexane= 1:2 and 1:1, successively) to obtain the title compound (7.3 mg, 85%) as a colorless oil.

(8E,12E,14E)-3,6,21-Trihydroxy-6,10,12,16,20-pentamethyl-7-(morpholin-4-yl)acetoxy-18,19-epoxytricosa-8,12, 14-trien-11-olide

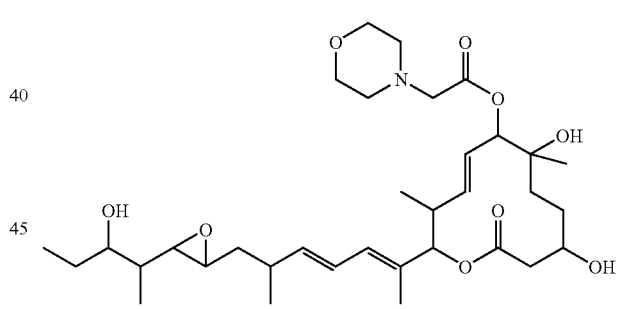

Pyridinium p-toluenesulfonate (2.2 mg, 8.71 µmol) was added to a solution of (8E,12E,14E)-3,6,21-tri(1-ethoxyethoxy)-6,10,12,16,20-pentamethyl-7-(morpholin-4-yl)acetoxy-18,19-epoxytricosa-8,12,14-trien-11-olide (7.3 mg, 8.71 µmol) in methanol (1 mL), followed by stirring at room temperature overnight. The reaction solution was evaporated, and to the resulting residue were added ethyl acetate, water and a saturated sodium bicarbonate aqueous solution. The mixture was extracted with ethyl acetate, and the resulting organic layer was dried over anhydrous magnesium sulfate, filtered and then evaporated. The resulting residue was purified by thin layer chromatography (MERCK Silica gel 60 F254, 0.2 mm, developing solution; methanol-dichloromethane=1:19) to obtain the title compound (4.4 mg, 82%) as a colorless oil.

$^1$H-NMR Spectrum(CD$_3$OD,400 MHZ)δ(ppm): 0.87(3H, d,J=6.8 Hz), 0.90(3H,d,J=7.2 Hz), 0.93(3H,t,J=7.6 Hz), 1.08 (3H,d,J=6.8 Hz), 1.14–1.22(4H,m), 1.34–1.67(8H,m), 1.74

(3H,d,J=0.8 Hz), 2.42–2.61(8H,m), 2.65(1H,dd,J=2.4,8.0 Hz), 2.72(1H,dt,J=2.4,6.0 Hz), 3.28(2H,s), 3.51(1H,dt, J=4.4,8.8 Hz), 3.71(4H,t,J=4.8 Hz), 3.75–3.81(1H,m), 5.04 (1H,d,J=10.4 Hz), 5.11(1H,d,J=9.6 Hz), 5.60(1H,dd,J=9.6, 15.2 Hz), 5.65(1H,dd,J=8.4,14.8 Hz), 5.70(1H,dd,J=9.6, 15.2 Hz), 6.09(1H,d,J=10.8 Hz), 6.32(1H,dd,J=10.8,15.2 Hz); ESI-MS m/z 622(M+H)$^+$.

Example B41

(8E,12E,14E)-7-Benzoyloxy-3,6,21-trihydroxy-6,10, 12,16,20-pentamethyl-18,19-epoxytricosa-8,12,14-trien-11-olide (Compound B41)

Compound B41

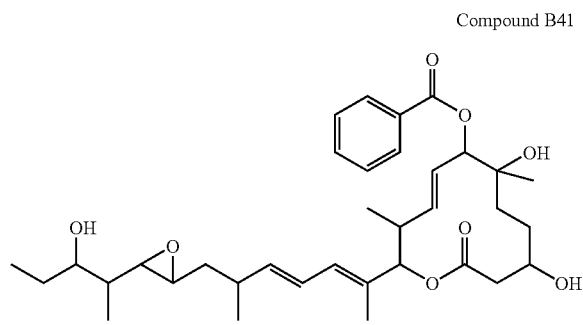

(8E,12E,14E)-7-Benzoyloxy-3,6,21-tri(1-ethoxyethoxy)-6, 10,12,16,20-pentamethyl-18,19-epoxytricosa-8,12,14-trien-11-olide

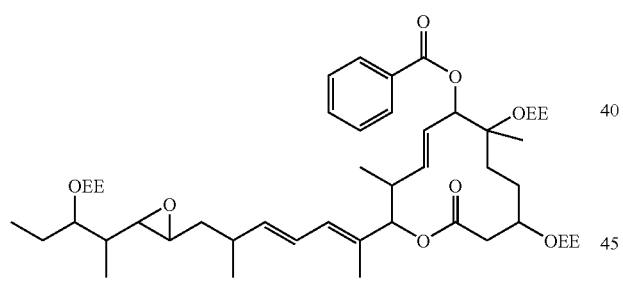

LiHMDS (1.0 M tetrahydrofuran solution, 81 µL, 81 µmol) was added dropwise to a solution of (8E,12E,14E)-3,6,21-tri(1-ethoxyethoxy)-7-hydroxy-6,10,12,16,20-pentamethyl-18,19-epoxytricosa-8,12,14-trien-11-olide (10 mg, 14 µmol) in tetrahydrofuran (1 mL) at −40° C. under nitrogen atmosphere. After stirring at the same temperature for 15 min., a solution of benzoyl chloride (17.8 mg, 125 µmol) in tetrahydrofuran (0.4 mL) was added dropwise thereto and the mixture was stirred at 0° C. for 7 hours. Ethyl Acetate and water were added to the reaction solution, and the mixture was extracted with ethyl acetate. The resulting organic layer was dried over anhydrous magnesium sulfate, filtered and then evaporated. The resulting residue was purified by silica gel column chromatography (Kanto silica gel 60N, 40 to 50 µm; ethyl acetate-hexane=1:4) to obtain the title compound (6.1 mg, 54%) as a colorless oil.

(8E,12E,14E)-7-Benzoyloxy-3,6,21-trihydroxy-6,10,12,16, 20-pentamethyl-18,19-epoxytricosa-8,12,14-trien-11-olide

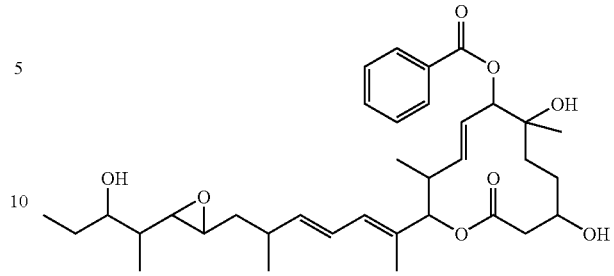

Pyridinium p-toluenesulfonate (2 mg, 7.5 µmol) was added to a solution of (8E,12E,14E)-7-benzoyloxy-3,6,21-tri(1-ethoxyethoxy)-6,10,12,16,20-pentamethyl-18,19-epoxytricosa-8,12,14-trien-11-olide (6.1 mg, 7.48 µmol) in methanol (1 mL), followed by stirring at room temperature for one hour. The reaction solution was evaporated, ethyl acetate, water and a saturated sodium bicarbonate aqueous solution were added to the resulting residue, and the mixture was extracted with ethyl acetate. The resulting organic layer was dried over anhydrous magnesium sulfate, filtered and then evaporated. The resulting residue was purified by thin layer chromatography (MERCK Silica gel 60 F254, 0.2 mm, developing solution; ethyl acetatehexane=2:1) to obtain the title compound (3.3 mg, 74%) as a colorless oil.

$^1$H-NMR Spectrum(CD$_3$OD,400 MHz)δ(ppm): 0.88(3H, d,J=6.8 Hz), 0.89(3H,d,J=6.8 Hz), 0.93(3H,t,J=7.6 Hz), 1.08 (3H,d,J=6.8 Hz), 1.13–1.23(1H,m), 1.25(3H,s), 1.40–1.55 (5H,m), 1.58–1.74(3H,m), 1.75(3H,s), 2.43–2.64(4H,m), 2.65(1H,dd,J=2.4,7.6 Hz), 2.71(1H,dd,J=2.4,6.0 Hz), 3.50 (1H,dt,J=4.4,8.8 Hz), 3.78–3.84(1H,m), 5.08(1H,d,J=10.4 Hz), 5.29(1H,d,J=9.6 Hz), 5.66(1H,dd,J=8.8,15.2 Hz), 5.69 (1H,dd,J=10.0,15.2 Hz), 5.82(1H,dd,J=9.6,15.2 Hz), 6.10 (1H,d,J=10.4 Hz), 6.32(1H,dd,J=10.8,15.2 Hz), 7.47(2H,t, J=7.6 Hz), 7.60(1H,t,J=7.6 Hz), 8.12(2H,d,J=7.6 Hz); ESI-MS m/z 621(M+Na)$^+$.

Example B42

(8E,12E,14E)-7-Butyloxy-3,6,21-trihydroxy-6,10, 12,16,20-pentamethyl-18,19-epoxytricosa-8,12,14-trien-11-olide (Compound B42)

Compound 42

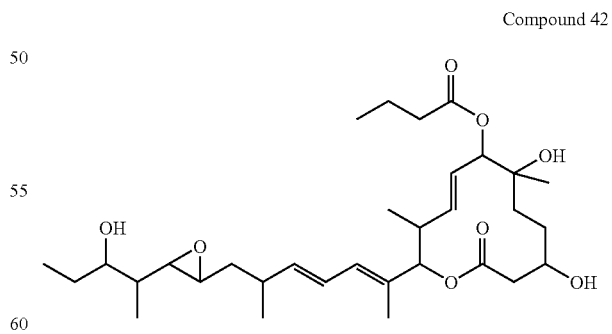

By using (8E,12E,14E)-3,6,21-tri(1-ethoxyethoxy)-7-hydroxy-6,10,12,16,20-pentamethyl-18,19-epoxytricosa-8,12, 14-trien-11-olide as a starting material, the title compound was synthesized by the similar method as Example B39.

$^1$H-NMR Spectrum(CD$_3$OD,400 MHz)δ(ppm): 0.87(3H, d,J=6.8 Hz), 0.90(3H,d,J=7.2 Hz), 0.93(6H,t,J=7.2 Hz), 1.08

(3H,d,J=6.8 Hz), 1.18(3H,s), 1.19–1.70(11H,m), 1.74(3H,d, J=0.8 Hz), 2.32(2H,dt,J=2.4,9.6 Hz), 2.42–2.60(2H,m), 2.52 (2H,d,J=3.2 Hz), 2.65(1H,dd,J=2.0,8.0 Hz), 2.72(1H,dt, J=2.0,5.6 Hz), 3.50(1H,dt,J=4.4,4.4 Hz), 3.74–3.84(1H,m), 5.05(1H,d,J=10.4 Hz), 5.06(1H,d,J=9.6 Hz), 5.57(1H,dd, J=9.6,15.2 Hz), 5.65(1H,dd,J=8.4,14.8 Hz), 5.69(1H,dd, J=10.0,15.2 Hz), 6.09(1H,d,J=11.2 Hz), 6.32(1H,dd,J=11.6, 14.8 Hz); ESI-MS m/z 587(M+Na)$^+$.

Example B43

(2Z,8E,12E,14E)-7,21-Diacetoxy-6-hydroxy-6,10, 12,16,20-pentamethyl-18,19-epoxytricosa-8,12,14-trien-11-olide (Compound B43-1) and (2Z,8E,12E, 14E)-7-acetoxy-6,21-dihydroxy-6,10,12,16,20-pentamethyl-18,19-epoxytricosa-2,8,12,14-tetraen-11-olide (Compound B43-2)

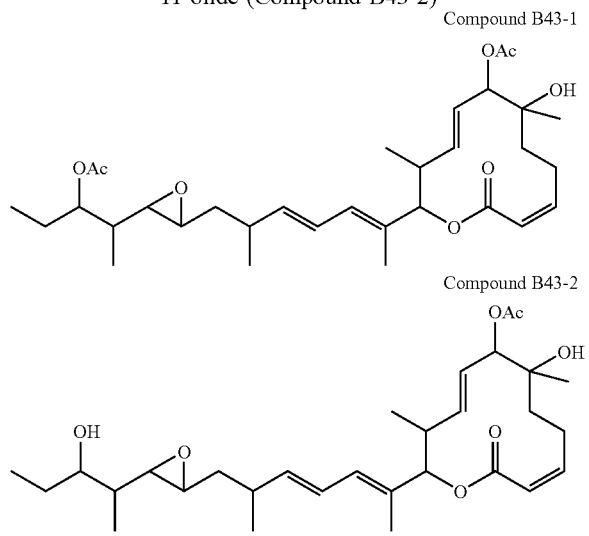

(2Z,8E,12E,14E)-6,21-di(1-Ethoxyethoxy)-7-hydroxy-6,10, 12,16,20-pentamethyl-18,19-epoxytricosa-2,8,12,14-tetraen-11-olide Lithium bis(trimethylsilyl)amide (1.0 M tetrahydrofuran solution, 50 μL, 50 μmol) was added dropwise to a solution of (8E,12E,14E)-3,6,21-tri(1-ethoxyethoxy)-7-hydroxy-6, 10,12,16,20-pentamethyl-18,19-epoxytricosa-8,12,14-trien-11-olide (10.8 mg, 15.2 μmol) in tetrahydrofuran (2 mL) at −40° C. under nitrogen atmosphere, followed by stirring at the same temperature for 20 min. Then, a solution of nicotinoyl chloride hydrochloride (5.7 mg, 30.4 μmol) in tetrahydrofuran-triethylamine (tetrahydrofuran: 0.5 mL and triethyamine: 1 drop) was added dropwise thereinto, followed by stirring at 0° C. for 30 min. Ethyl Acetate and water were added to the reaction solution, and the mixture was extracted with ethyl acetate. The resulting organic layer was dried over anhydrous magnesium sulfate, filtered and then evaporated. The resulting residue was purified by silica gel column chromatography (Kanto silica gel 60N, 40 to 50 μm; ethyl acetate-hexane=1:4) to obtain the title compound (6.3 mg, 67%) as a colorless oil.

(2Z,8E,12E,14E)-6,7,21-Trihydroxy-6,10,12,16,20-pentamethyl-18,19-epoxytricosa-2,8,12,14-tetraen-11-olide

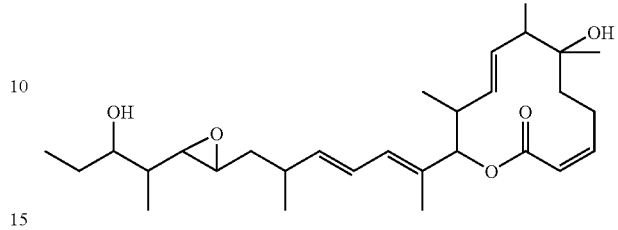

Pyridinium p-toluenesulfonate (2 mg, 7.7 μmol) was added to a solution of (2Z,8E,12E,14E)-6,21-di(1-ethoxyethoxy)-7-hydroxy-6,10,12,16,20-pentamethyl-18,19-epoxytricosa-2,8,12,14-tetraen-11-olide (6.3 mg, 10.1 μmol) in methanol (1.5 mL), followed by stirring at room temperature for one hour. The reaction solution was evaporated, and to the resulting residue were added ethyl acetate, water and a saturated sodium bicarbonate aqueous solution. The mixture was extracted with ethyl acetate, and the resulting organic layer was dried over anhydrous magnesium sulfate, filtered and then evaporated. The resulting residue was purified by thin layer chromatography (MERCK Silica gel 60 F254, 0.2 mm, developing solution; ethyl acetate-hexane=4:3) to obtain the title compound (3.3 mg, 68%) as a colorless oil.

ESI-MS m/z 499(M+Na)$^+$.

(2Z,8E,12E,14E)-7,21-Diacetoxy-6-hydroxy-6,10,12,16, 20-pentamethyl-18,19-epoxytricosa-8,12,14-trien-11-olide (Compound B43-1) and (2Z,8E,12E,14E)-7-acetoxy-6,21-dihydroxy-6,10,12,16,20-pentamethyl-18,19-epoxytricosa-2,8,12,14-tetraen-11-olide (Compound B43-2)

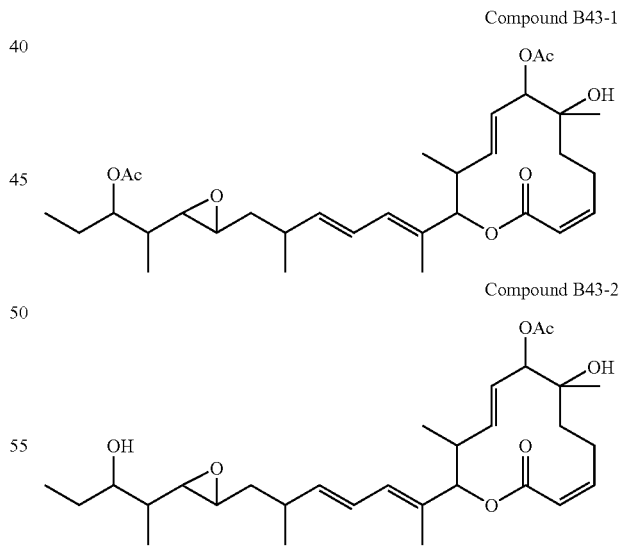

A solution of acetic anhydride (0.74 mg, 7 μmol) in dichloromethane (0.1 mL) was added dropwise to a solution of (8E,12E,14E)-6,7,21-trihydroxy-6,10,12,16,20-pentamethyl-18,19-epoxytricosa-2,8,12,14-tetraen-11-olide (3.3 mg, 6.9 μmol), triethylamine (3.6 mg, 35 μmol) and dimethylaminopyridine (0.4 mg, 3.5 μmol) in dichloromethane (1 mL), followed by stirring at room temperature for 30 min.

under nitrogen atmosphere. A solution of acetic anhydride (0.2 mg, 1.9 μmol) in dichloromethane (20 μL) was added dropwise thereto and the mixture was stirred at the same temperature for 30 min. Further, a dichloromethane solution (20 μL) of acetic anhydride (0.2 mg, 1.9 μmol) was added dropwise thereinto and the mixture was stirred at the same temperature for 30 min. Ethyl Acetate and water were added to the reaction solution, and the mixture was extracted with ethyl acetate. The resulting organic layer was dried over anhydrous magnesium sulfate, filtered and then evaporated. The resulting residue was purified by thin layer chromatography (MERCK Silica gel 60 F254, 0.2 mm, developing solution; ethyl acetate-hexane, 4:5) to obtain the title Compound B43-1 (0.8 mg, 21%) and Compound B43-2 (2.6 mg, 73%) as colorless oils, respectively.

Compound B43-1

$^1$H-NMR Spectrum(CD$_3$OD,400 MHz)δ(ppm): 0.87(3H, t,J=7.2 Hz), 0.90(3H,d,J=7.2 Hz), 0.92(3H,d,J=6.8 Hz), 1.08 (3H,d,J=6.8 Hz), 1.19(3H,s), 1.27–1.32(1H,m), 1.39–1.49 (3H,m), 1.58–1.68(4H,m), 1.73(3H,d,J=0.8 Hz), 2.05(3H,s), 2.06(3H,s), 2.18–2.29(1H,m), 2.41–2.51(2H,m), 2.54(1H, dd,J=2.4,8.0 Hz), 2.57–2.67(1H,m), 2.72(1H,dt,J=2.0,6.0 Hz), 4.82–4.88(1H,m), 5.02(1H,d,J=9.2 Hz), 5.60–5.77(4H, m), 6.04–6.14(2H,m), 6.32(1H,dd,J=10.8,15.2 Hz); ESI-MS m/z 583(M+Na)$^+$.

Compound B43-2

$^1$H-NMR Spectrum(CD$_3$OD,400 MHz)δ(ppm): 0.90(3H, d,J=6.8 Hz), 0.92(3H,d,J=6.8 Hz), 0.93(3H,t,J=7.6 Hz), 1.08 (3H,d,J=6.8 Hz), 1.14–1.24(4H,m), 1.40–1.56(4H,m), 1.59–1.68(2H,m), 1.72(3H,d,J=1.2 Hz), 2.06(3H,s), 2.17–2.29(1H,m), 2.41–2.52(2H,m), 2.56–2.67(2H,m), 2.72 (1H,dt,J=2.4,6.0 Hz), 3.51(1H,dt,J=4.4,8.8 Hz), 4.84–4.87 (1H,m), 5.02(1H,d,J=9.2 Hz), 5.62–5.77(4H,m), 6.04–6.13 (2H,m), 6.33(1H,dd,J=10.8,15.2 Hz); ESI-MS m/z 541(M+ Na)$^+$.

Example B44

(8E,12E,14E)-7-Carbamoyloxy-3,6,21-trihydroxy-6, 10,12,16,20-pentamethyl-18,19-epoxytricosa-8,12, 14-trien-11-olide (Compound B44)

Compound B44

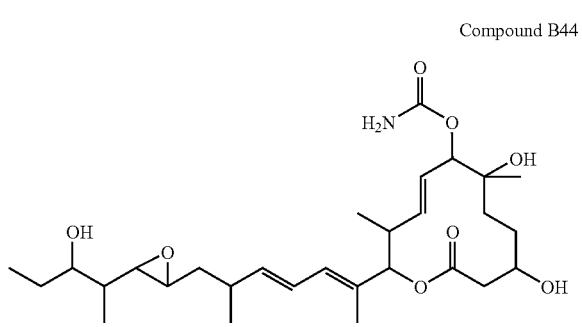

(8E,12E,14E)-3,6,21-Tri(1-ethoxyethoxy)-6,10,12,16,20-pentamethyl-7-(4-nitrophenoxy)carboxy-18,19-epoxytricosa-8,12,14-trien-11-olide

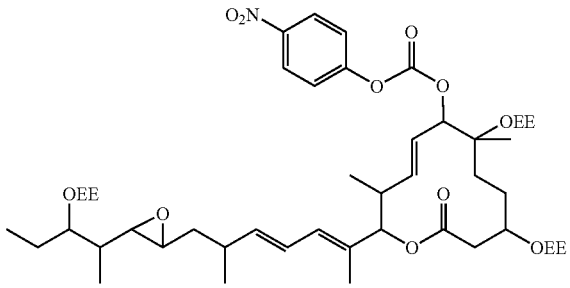

A solution of 4-nitrophenyl chloroformate (62 mg, 300 μmol) in dichloromethane (2.5 mL) was added dropwise into a solution of (8E,12E,14E)-3,6,21-tri(1-ethoxyethoxy)-7-hydroxy-6,10,12,16,20-pentamethyl-18,19-epoxytricosa-8, 12,14-trien-11-olide (35 mg, 49.2 μmol), triethylamine (61 mg, 600 μmol) and dimethylaminopyridine (4 mg, 30 μmol) in dichloromethane (2.5 mL), followed by stirring at room temperature for 2.5 hours under nitrogen atmosphere. Ethyl acetate, water and saturated sodium bicarbonate aqueous solution were added to the reaction mixture, and the mixture was extracted with ethyl acetate, then the organic layer was washed with water. The resulting organic layer was dried over anhydrous magnesium sulfate, filtered and then evaporated to give the title crude compound (92.2 mg) as a yellow oil. This was used for the following reaction without purification.

(8E,12E,14E)-7-Carbamoyloxy-3,6,21-tri(1-ethoxyethoxy)-6,10,12,16,20-pentamethyl-18,19-epoxytricosa-8,12,14-trien-11-olide

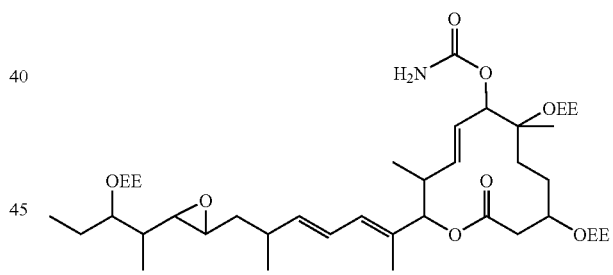

28% Aqueous ammonia solution (20 μL, 300 μmol) was added dropwise to a solution of the crude (8E,12E,14E)-3,6,21-tri(1-ethoxyethoxy)-6,10,12,16,20-pentamethyl-7-(4-nitrophenoxy)carboxy-18,19-epoxytricosa-8,12,14-trien-11-olide 10 mg, about 5.3 μmol) in tetrahydrofuran (1.5 mL), followed by stirring at room temperature for 3 hours. Ethyl Acetate and water were added to the reaction mixture, and the mixture was extracted with ethyl acetate. The resulting organic layer was dried over anhydrous magnesium sulfate, filtered and then evaporated. The resulting residue was purified by thin layer chromatography (MERCK Silica gel 60 F254, 0.2 mm, developing solution; ethyl acetate-hexane, 1:1) to give the title compound (3.6 mg, 90%, 2 steps) as a colorless oil.

(8E,12E,14E)-7-Carbamoyloxy-3,6,21-trihydroxy-6,10,12, 16,20-pentamethyl-18,19-epoxytricosa-8,12,14-trien-11-olide (Compound B44)

Compound B44

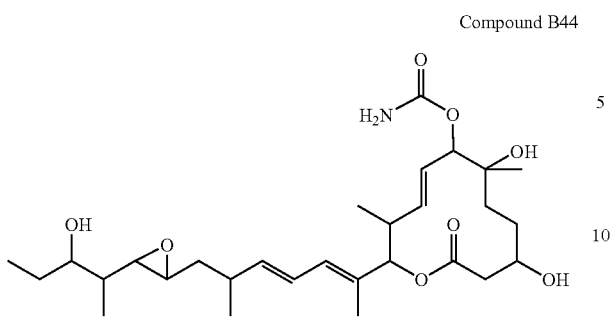

Pyridinium p-toluenesulfonate (1.2 mg, 4.8 μmol) was added to a solution of (8E,12E,14E)-7-carbamoyloxy-3,6, 21-tri(1-ethoxyethoxy)-6,10,12,16,20-pentamethyl-18,19-epoxytricosa-8,12,14-trien-11-olide (3.6 mg, 4.77 μmol) in methanol (1 mL), followed by stirring at room temperature for 3 hours. The reaction mixture was evaporated, ethyl acetate, water and a saturated sodium bicarbonate aqueous solution were added to the resulting residue, and the mixture was extracted with ethyl acetate. The resulting organic layer was dried over anhydrous magnesium sulfate, filtered and then evaporated. The resulting residue was purified by thin layer chromatography (MERCK Silica gel 60 F254, 0.2 mm, developing solution; methanol-dichloromethane, 1:29) to give the title compound (1.9 mg, 74%) as a colorless oil.

$^1$H-NMR Spectrum(CD$_3$OD,400 MHZ)δ(ppm): 0.89(3H, d,J=6.8 Hz), 0.90(3H,d,J=6.8 Hz), 0.93(3H,t,J=7.6 Hz), 1.08 (3H,d,J=6.8 Hz), 1.14–1.23(4H,m), 1.32–1.67(8H,m), 1.74 (3H,d,J=0.8 Hz), 2.41–2.62(4H,m), 2.65(1H,dd,J=2.4,8.4 Hz), 2.72(1H,dt,J=2.4,6.0 Hz), 3.51(1H,dt,J=4.8,8.8 Hz), 3.74–3.80(1H,m), 4.85–4.89(1H,m), 5.04(1H,d,J=10.8 HZ), 5.54(1H,dd,J=10.0,15.2 Hz), 5.65(1H,dd,J=8.4,15.2 Hz), 5.69(1H,dd,J=10.0,15.2 Hz), 6.09(1H,d,J=9.6 Hz), 6.32(1H,dd,J=10.8,14.8 Hz); ESI-MS m/z 560(M+Na)$^+$.

Example B45

(8E,12E,14E)-3,6,21-Trihydroxy-6,10,12,16,20-pentamethyl-7-N-methylcarbamoyloxy-18,19-epoxytricosa-8,12,14-trien-11-olide (Compound B45)

Compound B45

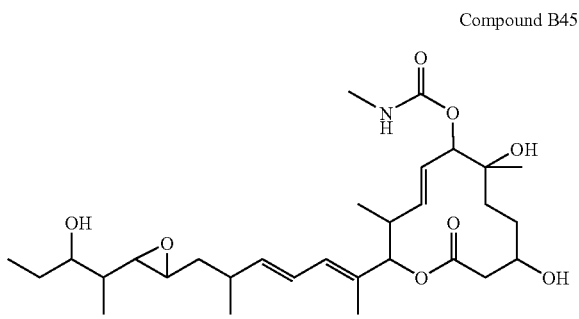

The title compound (a colorless oil) was synthesized by the similar method as Example B44.

$^1$H-NMR Spectrum(CD$_3$OD,400 MHz)δ(ppm): 0.88(3H, d,J=6.8 Hz) 0.90(3H,d,J=6.8 Hz), 0.93(3H,t,J=7.6 Hz), 1.08 (3H,d,J=6.8 Hz), 1.14–1.23(4H,m), 1.31–1.67(8H,m), 1.74 (3H,d,J=0.8 Hz), 2.42–2.61(4H,m), 2.65(1H,dd,J=2.4,6.8 Hz), 2.68–2.75(4H,m), 3.51(1H,dt,J=4.8,8.8 Hz), 3.74–3.80 (1H,m), 4.87–4.91(1H,m), 5.04(1H,d,J=10.8 Hz), 5.55(1H, dd,J=9.6,15.2 Hz), 5.65(1H,dd,J=8.8,15.2 Hz), 5.68(1H,dd, J=9.6,15.2 Hz), 6.09(1H,d,J=10.8 Hz), 6.32(1H,dd,J=10.8, 15.2 Hz); ESI-MS m/z 574(M+Na)$^+$.

Example B46

(8E,12E,14E)-3,6,21-Trihydroxy-6,10,12,16,20-pentamethyl-7-N,N-dimethylcarbamoyloxy-18,19-epoxytricosa-8,12,14-trien-11-olide
(Compound B46)

Compound B46

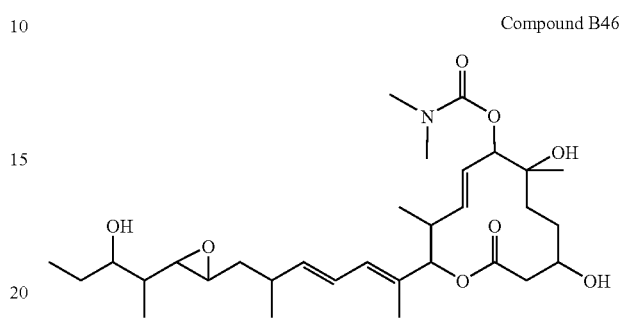

The title compound (a colorless oil) was synthesized by the similar method as Example B44.

$^1$H-NMR Spectrum(CD$_3$OD,400 MHz)δ(ppm): 0.88(3H, d,J=6.4 Hz), 0.90(3H,d,J=6.8 Hz), 0.93(3H,t,J=7.6 Hz), 1.08 (3H,d,J=6.8 Hz), 1.14–1.23(4H,m), 1.33–1.68(8H,m), 1.74 (3H,d,J=1.2 Hz), 2.42–2.61(4H,m), 2.65(1H,dd,J=2.0,8.4 Hz), 2.72(1H,dt,J=2.4,6.0 Hz), 2.89(3H,s), 2.98(3H,s), 3.51 (1H,dt,J=4.4,8.4 Hz), 3.75–3.81(1H,m), 4.91(1H,d,J=9.6 Hz), 5.04(1H,d,J=10.8 Hz), 5.55(1H,dd,J=10.0,15.2 Hz), 5.65(1H,dd,J=8.4,15.2 Hz), 5.72(1H,dd,J=10.0,15.2 Hz), 6.09(1H,d,J=11.2 Hz), 6.32(1H,dd,J=10.8,14.8 Hz); ESI-MS m/z 588(M+Na)$^+$.

Example B47

(8E,12E,14E)-3,6,21-Trihydroxy-6,10,12,16,20-pentamethyl-7-N-(2-(2-pyridyl)ethyl)carbamoyloxy-18,19-epoxytricosa-8,12,14-trien-11-olide
(Compound B47)

Compound B47

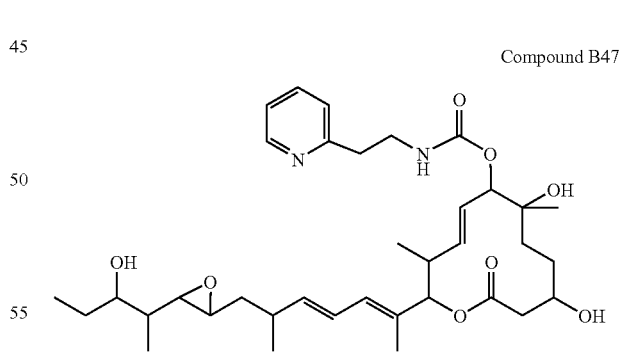

The title compound (a colorless oil) was synthesized by the similar method as Example B44.

$^1$H-NMR Spectrum(CD$_3$OD,400 MHz)δ(ppm): 0.88(3H, d,J=6.8 Hz), 0.90(3H,d,J=6.8 Hz), 0.93(3H,t,J=7.6 Hz), 1.08 (3H,d,J=6.4 Hz), 1.14–1.24(4H,m), 1.28–1.67(8H,m), 1.74 (3H,s), 2.42–2.61(4H,m), 2.65(1H,dd,J=2.0,8.4 Hz), 2.72 (1H,dt,J=2.4,6.0 Hz), 2.96(2H,t,J=7.2 Hz), 3.42–3.54(3H, m), 3.74–3.80(1H,m), 4.84–4.90(1H,m), 5.04(1H,d,J=10.8 Hz), 5.53(1H,dd,J=9.6,15.2 Hz), 5.65(1H,dd,J=8.4,14.8

Hz), 5.67(1H,dd,J=9.6,15.2 Hz), 6.09(1H,d,J=10.8 Hz), 6.32(1H,dd,J=10.8,15.2 Hz), 7.26(1H,dd,J=5.2,7.2 Hz), 7.31(1H,d,J=7.6 Hz), 7.75(1H,dt,J=1.6,7.6 Hz), 8.45(1H,d, J=4.8 Hz); ESI-MS m/z 665(M+Na)+.

Example B48

(8E,12E,14E)-3,6,21-Trihydroxy-7-((4-hydroxypiperidin-1-yl)carbonyl)oxy-6,10,12,16,20-pentamethyl-18,19-epoxytricosa-8,12,14-trien-11-olide (Compound B48)

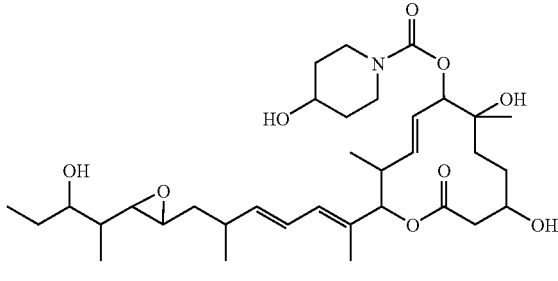

Compound B48

The title compound (a colorless oil) was synthesized by the similar method as Example B44.

$^1$H-NMR Spectrum(CD$_3$OD,400 MHz)δ(ppm): 0.89(3H, d,J=6.4 Hz) 0.90(3H,d,J=6.8 Hz), 0.93(3H,t,J=7.6 Hz), 1.08 (3H,d,J=6.8 Hz), 1.14–1.23(4H,m), 1.30–1.67(10H,m), 1.74 (3H,s), 1.79–1.86(2H,m), 2.42–2.62(4H,m), 2.65(1H,dd, J=2.0,8.4 Hz), 2.72(1H,dt,J=2.0,6.0 Hz), 2.99–3.23(2H,m), 3.51(1H,dt,J=4.4,8.8 Hz), 3.74–4.13(4H,m), 4.92(1H,d, J=9.6 Hz), 5.05(1H,d,J=10.8 Hz), 5.57(1H,dd,J=10.0,15.2 Hz), 5.65(1H,dd,J=8.4,14.8 Hz), 5.71(1H,dd,J=9.6,14.8 Hz), 6.09(1H,d,J=10.4 Hz), 6.32(1H,dd,J=10.8,14.8 Hz); ESI-MS m/z 644(M+Na)+.

Example B49

(8E,12E,14E)-3,6,21-Trihydroxy-6,10,12,16,20-pentamethyl-7-((morpholin-4-yl)carbonyl)oxy-18,19-epoxytricosa-8,12,14-trien-11-olide (Compound B49)

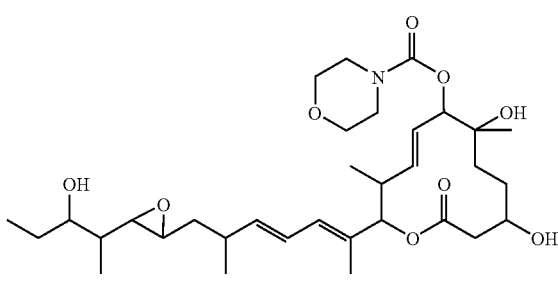

Compound B49

The title compound (a colorless oil) was synthesized by the similar method as Example B44.

$^1$H-NMR Spectrum(CD$_3$OD,400 MHZ)δ(ppm): 0.89(3H, d,J=6.8 Hz), 0.90(3H,d,J=7.2 Hz), 0.93(3H,t,J=7.6 Hz), 1.08 (3H,d,J=6.8 Hz), 1.14–1.23(4H,m), 1.30–1.67(8H,m), 1.74 (3H,s), 2.42–2.61(4H,m), 2.65(1H,dd,J=2.4,8.4 Hz), 2.72 (1H,dt,J=2.4,6.0 Hz), 3.35–3.68(9H,m), 3.75–3.81(1H,m), 4.95(1H,d,J=9.6 Hz), 5.04(1H,d,J=10.8 Hz), 5.57(1H,dd, J=9.6,15.2 Hz), 5.65(1H,dd,J=8.4,14.8 Hz), 5.71(1H,dd, J=9.6,15.2 Hz), 6.09(1H,d,J=10.8 Hz), 6.32(1H,dd,J=10.8, 14.8 Hz); ESI-MS m/z 630(M+Na)+.

Example B50

(8E,12E,14E)-3,6,21-Trihydroxy-6,10,12,16,20-pentamethyl-7-((4-methylpiperazin-1-yl)carbonyl)oxy-18,19-epoxytricosa-8,12,14-trien-11-olide (Compound B50)

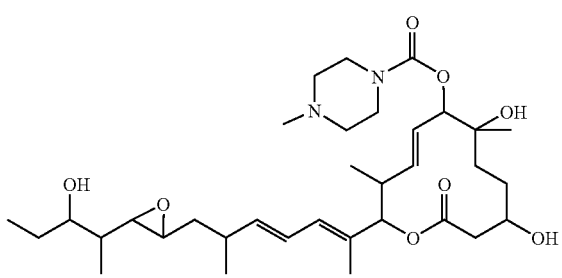

Compound B50

The title compound (a colorless oil) was synthesized by the similar method as Example B44.

$^1$H-NMR Spectrum(CD$_3$OD,400 MHZ) δ (ppm): 0.89 (3H,d,J=6.4 Hz), 0.90(3H,d,J=6.8 Hz), 0.93(3H,t,J=7.6 Hz), 1.08(3H,d,J=6.8 Hz), 1.14–1.23(4H,m), 1.31–1.67(8H,m), 1.74(3H,s), 2.30(3H,s), 2.37–2.62(8H,m), 2.65(1H,dd, J=2.0,8.4 Hz), 2.72(1H,dt,J=2.0,6.0 Hz), 3.39–3.71(5H,m), 3.75–3.81(1H,m), 4.93(1H,d,J=9.6 Hz), 5.04(1H,d,J=10.4 Hz), 5.57(1H,dd,J=10.0,15.2 Hz), 5.65(1H,dd,J=8.4,15.2 Hz), 5.71(1H,dd,J=9.6,14.8 Hz), 6.09(1H,d,J=10.0 Hz), 6.32(1H,dd,J=10.8,14.8 Hz); ESI-MS m/z 621(M+H)+.

Example B51

(8E,12E,14E)-7-((4-Acetylpiperazin-1-yl)carbonyl)oxy-3,6,21-trihydroxy-6,10,12,16,20-pentamethyl-18,19-epoxytricosa-8,12,14-trien-11-olide (Compound B51)

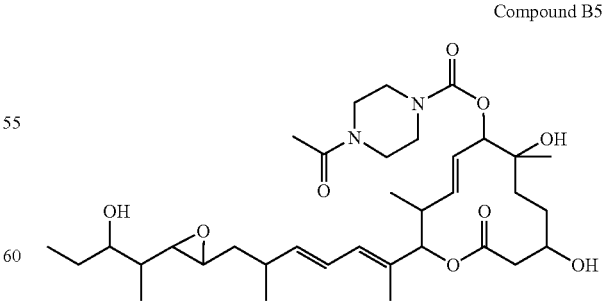

Compound B51

The title compound (a colorless oil) was synthesized by the similar method as Example B44.

$^1$H-NMR Spectrum(CD$_3$OD,400 MHz)δ(ppm): 0.88(3H, d,J=6.8 Hz), 0.90(3H,d,J=7.2 Hz), 0.93(3H,t,J=7.6 Hz), 1.08

(3H,d,J=6.8 Hz), 1.14–1.23(4H,m), 1.32–1.68(8H,m), 1.74 (3H,d,J=1.2 Hz), 2.12(3H,s), 2.41–2.62(4H,m), 2.65(1H,dd, J=2.4,8.4 Hz), 2.71(1H,dt,J=2.0,6.0 Hz), 3.35–3.72(9H,m), 3.74–3.82(1H,m), 4.96(1H,d,J=9.6 Hz), 5.04(1H,d,J=10.4 Hz), 5.58(1H,dd,J=9.6,15.2 Hz), 5.65(1H,dd,J=8.4,14.8 Hz), 5.72(1H,dd,J=9.6,15.2 Hz), 6.09(1H,d,J=10.8 Hz), 6.32(1H,dd,J=10.8,14.8 Hz); ESI-MS m/z 671(M+Na)$^+$.

Example B52

(8E,12E,14E)-3,6,21-Trihydroxy-6,10,12,16,20-pentamethyl-7-((piperazin-1-yl)carbonyl)oxy-18,19-epoxytricosa-8,12,14-trien-11-olide
(Compound B52)

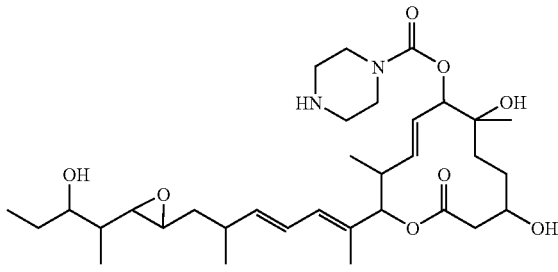

Compound B52

The title compound (a colorless oil) was synthesized by the similar method as Example B44.

$^1$H-NMR Spectrum(CD$_3$OD,400 MHz)δ(ppm): 0.89(3H, d,J=6.8 Hz), 0.90(3H,d,J=6.8 Hz), 0.93(3H,t,J=7.6 Hz), 1.08 (3H,d,J=6.8 Hz), 1.11–1.23(4H,m), 1.26–1.67(8H,m), 1.74 (3H,s), 2.42–2.62(4H,m), 2.65(1H,dd,J=2.0,8.4 Hz), 2.69–2.81(5H,m), 3.36–3.69(5H,m), 3.75–3.82(1H,m), 4.94 (1H,d,J=9.6 Hz), 5.04(1H,d,J=10.8 Hz), 5.57(1H,dd,J=10.0, 15.2 Hz), 5.66(1H,dd,J=8.8,15.6 Hz), 5.71(1H,dd,J=9.6, 15.2 Hz), 6.09(1H,d,J=10.8 Hz), 6.32(1H,dd,J=10.8,14.8 Hz); ESI-MS m/z 607(M+H)$^+$.

Example B53

(8E,12E,14E)-3,6,21-Trihydroxy-7-(N-(2-methoxyethyl))carbamoyloxy-6,10,12,16,20-pentamethyl-18,19-epoxytricosa-8,12,14-trien-11-olide
(Compound B53)

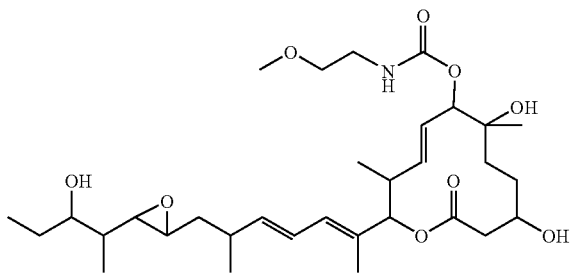

Compound B53

The title compound was obtained as a colorless oil by the similar method as Example B44.

Compound B53

$^1$H-NMR Spectrum (CD$_3$OD,500 MHz)δ(ppm): 0.90(3H, d,J=6.5 Hz), 0.91(3H,d,J=7.0 Hz), 0.94(3H,t,J=8.0 Hz), 1.09 (3H,d,J=7.0 Hz), 1.16–1.26(1H,m), 1.21(3H,s), 1.28–1.68 (8H,m), 1.75(3H,s), 2.42–2.62(4H,m), 2.66(1H,dd,J=2.5,8.5 Hz), 2.73(1H,dt,J=2.0,6.0 Hz), 3.25–3.32(2H,m), 3.34(3H, m), 3.44(2H,t,J=5.5 Hz), 3.48–3.51(1H,m), 3.74–3.82(1H, m), 4.90(1H,d,J=9.5 Hz), 5.05(1H,d,J=10.5 Hz), 5.56(1H, dd,J=10.0,15.0 Hz), 5.62–5.76(2H,m), 6.09(1H,d,J=10.0 HZ), 6.32(1H,dd,J=11.0,15.0 Hz); ESI-MS m/z 618(M+Na)$^+$.

Example B54

(8E,12E,14E)-7-(N-(2-Dimethylamino)ethyl)carbamoyloxy-3,6,21-trihydroxy-6,10,12,16,20-pentamethyl-18,19-epoxytricosa-8,12,14-trien-11-olide
(Compound B54)

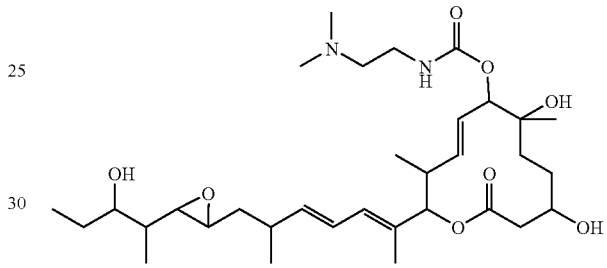

Compound B54

The title compound was obtained as a colorless oil by the similar method as Example B44.

$^1$H-NMR Spectrum (CD$_3$OD,500 MHz)δ(ppm): 0.89(3H, d,J=7.5 Hz), 0.90(3H,d,J=7.5 Hz), 0.94(3H,t,J=7.5 Hz), 1.09 (3H,d,J=7.0 Hz), 1.16–1.26(1H,m), 1.21(3H,s), 1.28–1.68 (8H,m), 1.75(3H,s), 2.26(6H,s), 2.44(2H,t,J=6.5 Hz), 2.44–2.62(4H,m), 2.67(1H,dd,J=2.0,8.5 Hz), 2.73(1H,dt, J=2.0,6.0 Hz), 3.25(2H,t,J=6.0 Hz), 3.48–3.54(1H,m), 3.75–3.82(1H,m), 4.90(1H,d,J=10.0 Hz), 5.05(1H,d,J=11.0 Hz), 5.63–5.74(2H,m), 6.09(1H,d,J=10.5 Hz), 6.32(1H,dd, J=11.0,15.0 Hz); ESI-MS m/z 609(M+H)$^+$.

Example B55

(8E,12E,14E)-7-(N-(3-Dimethylamino)propyl)carbamoyloxy-3,6,21-trihydroxy- 6,10,12,16,20-pentamethyl-18,19-epoxytricosa-8,12,14-trien-11-olide
(Compound B55)

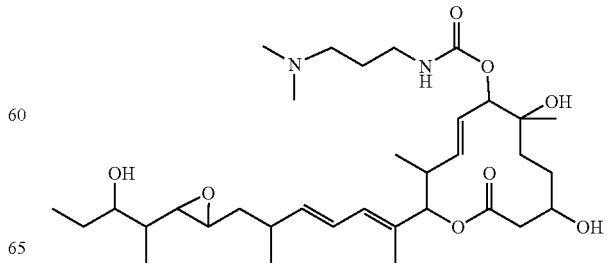

Compound B55

The title compound was obtained as a colorless oil by the similar method as Example B44.

¹H-NMR Spectrum (CD₃OD,500 MHz)δ(ppm): 0.89(3H, d,J=7.0 Hz), 0.91(3H,d,J=7.0 Hz), 0.94(3H,t,J=7.0 Hz), 1.09 (3H,d,J=7.0 Hz), 1.16–1.72(1H,m), 1.21(3H,s), 1.75(3H,s), 2.24(6H,s), 2.36(2H,t,J=8.0 Hz), 2.42–2.62(4H,m), 2.66 (1H,dd,J=2.0,8.0 Hz), 2.73(1H,dt,J=2.0,9.0 Hz), 3.14(2H,t, J=7.0 Hz), 3.48–3.55(1H,m), 3.75–3.82(1H,m), 4.90(1H,d, J=10.5 Hz), 5.05(1H,d,J=10.5 Hz), 5.64–5.74(2H,m), 6.09 (1H,d,J=10.5 Hz), 6.32(1H,dd,J=11.0,15.0 Hz); ESI-MS m/z 623(M+H)⁺.

Example B56

(8E,12E,14E)-3,6,21-Trihydroxy-6,10,12,16,20-pentamethyl-7-N-(2-pyridylmethyl)carbamoyloxy-18,19-epoxytricosa-8,12,14-trien-11-olide
(Compound B56)

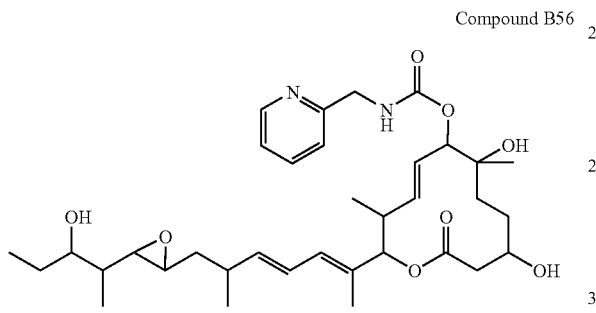

Compound B56

The title compound was obtained as a colorless oil by the similar method as Example B44.

¹H-NMR Spectrum(CD₃OD,400 MHz)δ(ppm): 0.88(3H, d,J=7.2 Hz), 0.89(3H,d,J=7.2 Hz), 0.94(3H,t,J=7.6 Hz), 1.08 (3H,d,J=6.8 Hz), 1.16–1.64(9H,m), 1.23(3H,s), 1.74(3H,s), 2.40–2.60(2H,m), 2.52(2H,d,J=4.0 Hz), 2.64(1H,dd,J=2.4, 8.4 Hz), 2.72(1H,dt,J=2.4,5.6 Hz), 3.43–3.52(1H,m), 3.70–3.81(1H,m), 4.40(2H,s), 4.95(1H,d,J=9.2 Hz), 5.04 (1H,d,J=10.8 Hz), 5.56(1H,dd,J=9.2,15.6 Hz), 5.65(1H,dd, J=8.8,15.2 Hz), 5.73(1H,dd,J=10.4,15.2 Hz), 6.08(1H,d, J=10.8 Hz), 6.32(1H,dd,J=11.2,15.2 Hz), 7.29(1H,t,J=5.6 Hz), 7.37(1H,d,J=8.0 Hz), 7.80(1H,t,J=8.0 Hz), 8.47(1H,d, J=5.6 Hz); ESI-MS m/z 629(M+H)⁺, 651(M+Na)⁺.

Example B57

(8E,12E,14E)-3,6,21-Trihydroxy-6,10,12,16,20-pentamethyl-7-N-(3-pyridylmethyl)carbamoyloxy-18,19-epoxytricosa-8,12,14-trien-11-olide
(Compound B57)

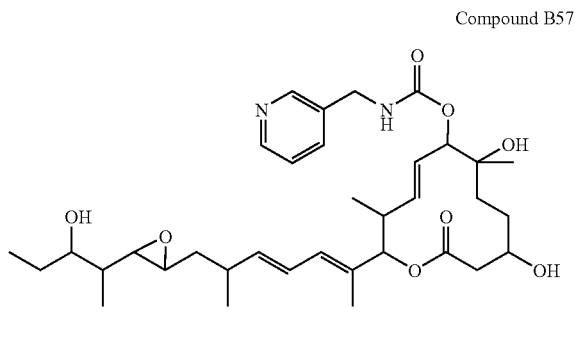

Compound B57

The title compound was obtained as a colorless oil by the similar method as Example B44.

¹H-NMR Spectrum(CD₃OD,400 MHz)δ(ppm): 0.87(3H, d,J=6.8 Hz), 0.90(3H,d,J=6.8 Hz), 0.93(3H,t,J=7.2 Hz), 1.08 (3H,d,J=6.8 Hz), 1.17–1.66(9H,m), 1.21(3H,s), 1.74(3H,s), 2.40–2.60(2H,m), 2.52(2H,d,J=3.6 Hz), 2.65(1H,dd,J=2.4, 8.4 Hz), 2.72(1H,dt,J=2.4,6.0 Hz), 3.43–3.54(1H,m), 3.72–3.82(1H,m), 4.33(2H,s), 4.92(1H,d,J=9.2 Hz), 5.04 (1H,d,J=10.8 Hz), 5.55(1H,dd,J=10.0,15.2 Hz), 5.65(1H,dd, J=8.4,14.8 Hz), 5.70(1H,dd,J=9.6,15.6 Hz), 6.08(1H,d, J=10.8 Hz), 6.32(1H,dd,J=10.8,14.8 Hz), 7.39(1H,dd,J=5.2, 8.0 Hz), 7.77(1H,d,J=7.6 Hz), 8.42(1H,d,J=4.8 Hz), 8.47 (1H,brs); ESI-MS m/z 651(M+Na)⁺.

Example B58

(8E,12E,14E)-3,6,21-Trihydroxy-6,10,12,16,20-pentamethyl-7-N-(4-pyridylmethyl)carbamoyloxy-18,19-epoxytricosa-8,12,14-trien-11-olide
(Compound B58)

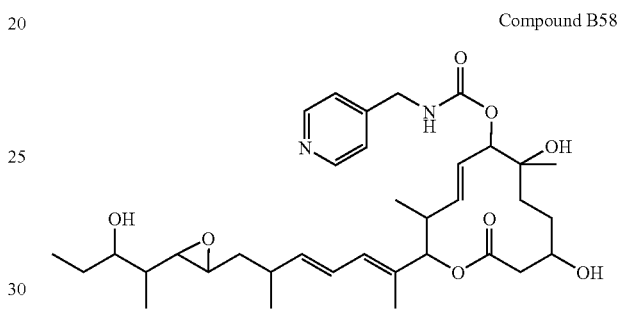

Compound B58

The title compound was obtained as a colorless oil by the similar method as Example B44.

¹H-NMR Spectrum(CD₃OD,400 MHz)δ(ppm): 0.88(3H, d,J=7.2 Hz), 0.89(3H,d,J=6.8 Hz), 0.94(3H,t,J=7.6 Hz), 1.08 (3H,d,J=6.4 Hz), 1.15–1.66(9H,m), 1.23(3H,s), 1.74(3H,s), 2.46–2.62(4H,m), 2.65(1H,dd,J=2.0,8.4 Hz), 2.72(1H,dt, J=2.4,6.0 Hz), 3.46–3.55(1H,m), 3.72–3.82(1H, m), 4.35 (2H,s), 4.93(1H,d,J=9.6 Hz), 5.04(1H,d,J=10.8 Hz), 5.56 (1H,dd,J=9.6,15.2 Hz), 5.65(1H,dd,J=8.4,14.8 Hz), 5.72 (1H,dd,J=9.6,15.2 Hz), 6.09(1H,d,J=11.2 Hz), 6.32(1H,dd, J=10.8,14.8 Hz), 7.34(2H,d,J=5.2 Hz), 8.45(2H,dd,J=1.6, 4.8 Hz); ESI-MS m/z 629(M+H)⁺, 651(M+Na)⁺.

Example B59

(8E,12E,14E)-3,6,21-Trihydroxy-6,10,12,16,20-pentamethyl-7-N-(2-(morpholin-4-yl)ethyl)carbamoyloxy-18,19-epoxytricosa-8,12,14-trien-11-olide
(Compound B59)

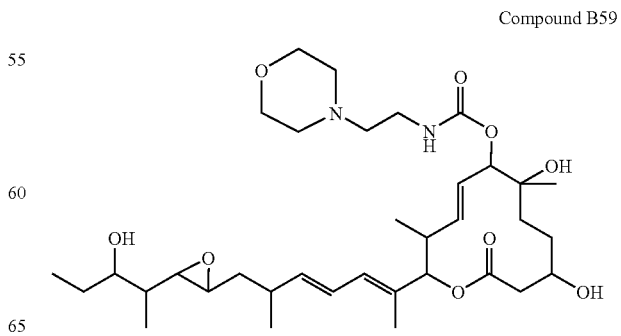

Compound B59

The title compound was obtained as a colorless oil by the similar method as Example B44.

¹H-NMR Spectrum(CD₃OD,400 MHz)δ(ppm): 0.88(3H, d,J=5.2 Hz), 0.89(3H,d,J=7.2 Hz), 0.93(3H,t,J=7.2 Hz), 1.07 (3H,d,J=6.8 Hz), 1.17–1.66(9H,m), 1.20(3H,s), 1.74(3H,s), 2.44–2.62(8H,m), 2.65(1H,dd,J=2.4,8.4 Hz), 2.72(1H,dt, J=2.4,6.0 Hz), 3.26(2H,t,J=6.8 Hz), 3.28–3.36(2H,m), 3.46–3.54(1H,m), 3.62–3.72(4H,m), 3.74–3.83(1H,m), 4.84–4.88(1H,m), 5.04(1H,d,J=10.8 Hz), 5.54(1H,dd, J=10.4,15.2 Hz), 5.65(1H,dd,J=8.8,15.2 Hz), 5.69(1H,dd, J=10.0,15.6 Hz), 6.09(1H,d,J=10.8 Hz), 6.32(1H,dd,J=10.8, 14.8 Hz); ESI-MS m/z 651(M+H)⁺.

Example B60

(8E,12E,14E)-3,6,21-Trihydroxy-6,10,12,16,20-pentamethyl-7-N-(3-(morpholin-4-yl)propyl)carbamoyloxy-18,19-epoxytricosa-8,12,14-trien-11-olide (Compound B60)

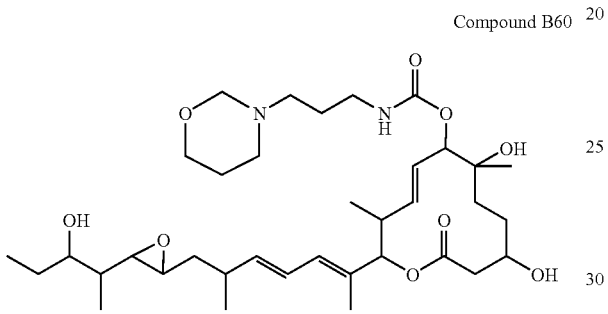

Compound B60

The title compound was obtained as a colorless oil by the similar method as Example B44.

¹H-NMR Spectrum(CD₃OD,400 MHz)δ(ppm): 0.88(3H, d,J=5.2 Hz), 0.90(3H,d,J=7.2 Hz), 0.93(3H,t,J=7.2 Hz), 1.08 (3H,d,J=8.0 Hz), 1.16–1.73(11H,m), 1.20(3H,s), 1.74(3H,s), 2.36–2.62(8H,m), 2.65(1H,dd,J=2.0,8.4 Hz), 2.72(1H,dt, J=2.4,6.0 Hz), 3.10–3.16(4H,m), 3.46–3.54(1H,m), 3.62–3.72(4H,m), 3.74–3.82(1H,m), 4.84–4.88(1H,m), 5.04 (1H,d,J=10.8 Hz), 5.54(1H,dd,J=10.0,14.8 Hz), 5.62–5.74 (2H,m), 6.09(1H,d,J=10.8 Hz), 6.32(1H,dd,J=10.8,15.2 Hz); ESI-MS m/z 665(M+H)⁺.

Example B61

(8E,12E,14E)-3,6,21-Trihydroxy-6,10,12,16,20-pentamethyl-7-((homopiperazin-1-yl)carbonyl)oxy-18,19-epoxytricosa-8,12,14-trien-11-olide (Compound B61)

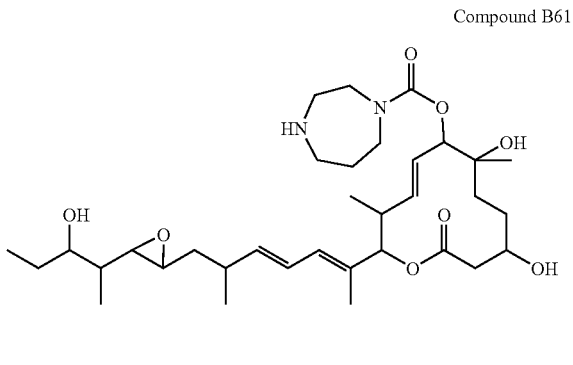

Compound B61

The title compound (a colorless oil) was synthesized by the similar method as Example B44.

¹H-NMR Spectrum (CD₃OD,400 MHz)δ(ppm): 0.89(3H, d,J=6.8 Hz), 0.90(3H,d,J=6.8 Hz), 0.93(3H,t,J=7.6 Hz), 1.08 (3H,d,J=6.8 Hz), 1.14–1.25(4H,m), 1.34–1.68(8H,m), 1.74 (3H,d,J=0.8 Hz), 1.77–1.86(2H,m), 2.41–2.63(4H,m), 2.65 (1H,dd,J=2.4,8.4 HZ), 2.72(1H,dt,J=2.4,6.0 Hz), 2.73–2.94 (4H,m), 3.41–3.68(5H,m), 3.75–3.82(1H,m), 4.94(1H,d, J=9.6 Hz), 5.05(1H,d,J=10.4 Hz), 5.57(1H,dd,J=10.0,15.2 Hz), 5.65(1H,dd,J=8.4,15.2 Hz), 5.72(1H,dd,J=10.0,15.2 Hz), 6.09(1H,d,J=10.8 Hz), 6.32(1H,dd,J=10.8,14.8 Hz); ESI-MS m/z 621(M+H)⁺.

Example B62

(8E,12E,14E)-3,6,21-Trihydroxy-6,10,12,16,20-pentamethyl-7-((4-methylhomopiperazin-1-yl)carbonyl)oxy-18,19-epoxytricosa-8,12,14-trien-11-olide (Compound B62)

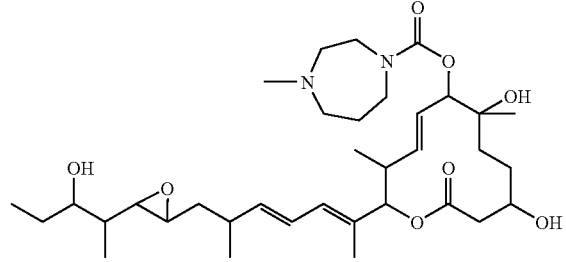

Compound B62

The title compound (a colorless oil) was synthesized by the similar method as Example B44.

¹H-NMR Spectrum (CD₃OD,400 MHz)δ(ppm): 0.79(3H, d,J=6.4 Hz), 0.80(3H,d,J=7.2 Hz), 0.84(3H,t,J=7.6 Hz), 0.98 (3H,d,J=6.8 Hz), 1.05–1.16(4H,m), 1.24–1.58(8H,m), 1.65 (3H,d,J=0.8 Hz), 1.76–1.84(2H,m), 2.25(3H,s), 2.33–2.58 (9H,m), 2.62(1H,dt,J=2.4,6.0 Hz), 3.37–3.46(3H,m), 3.48–3.58(2H,m), 3.66–3.72(1H,m), 4.85(1H,d,J=9.6 Hz), 4.95(1H,d,J=10.8 Hz), 5.48(1H,dd,J=9.6,15.2 Hz), 5.56(1H, dd,J=8.4,15.2 Hz), 5.63(1H,dd,J=9.6,15.2 Hz), 6.00(1H,d, J=10.8 Hz), 6.23(1H,dd,J=10.8,14.8 Hz); ESI-MS m/z 635 (M+H)⁺.

Example B63

(8E,12E,14E)-3,6,21-Trihydroxy-6,10,12,16,20-pentamethyl-7-N-(2-(piperidin-1-yl)ethyl)carbamoyloxy-18,19-epoxytricosa-8,12,14-trien-11-olide (Compound B63)

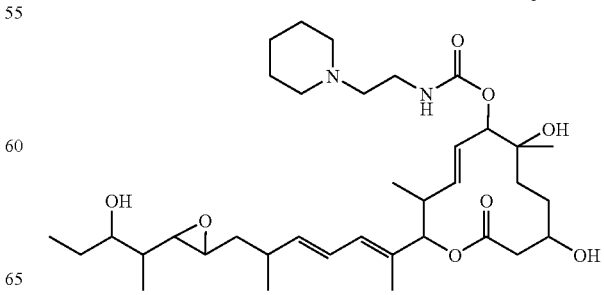

Compound B63

The title compound (a colorless oil) was synthesized by the similar method as Example B44.

¹H-NMR Spectrum (CD₃OD,400 MHz)δ(ppm): 0.88(3H, d,J=6.0 Hz), 0.90(3H,d,J=6.8 Hz), 0.93(3H,t,J=7.6 Hz), 1.08 (3H,d,J=6.8 Hz), 1.14–1.25(4H,m), 1.32–1.67(14H,m), 1.74 (3H,d,J=0.8 Hz), 2.40–2.62(10H,m), 2.65(1H,dd,J=2.4,8.4 Hz), 2.72(1H,dt,J=2.4,6.0 Hz), 3.26(2H,t,J=6.8 Hz), 3.51 (1H,dt,J=4.4,8.4 Hz), 3.74–3.81(1H,m), 4.86–4.92(1H,m), 5.04(1H,d,J=10.8 Hz), 5.54(1H,dd,J=9.6,15.2 Hz), 5.65(1H, dd,J=8.4,14.8 Hz), 5.69(1H,dd,J=10.0,14.8 Hz), 6.09(1H,d, J=10.8 Hz), 6.32(1H,dd,J=10.8,14.4 Hz); ESI-MS m/z 649 (M+H)⁺.

Example B64

(8E,12E,14E)-3,6,21-Trihydroxy-6,10,12,16,20-pentamethyl-7-N-(2-(pyrrolidin-1-yl)ethyl)carbamoyloxy-18,19-epoxytricosa-8,12,14-trien-11-olide (Compound B64)

Compound B64

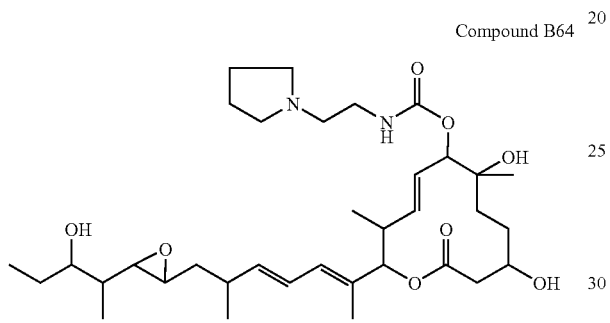

The title compound (a colorless oil) was synthesized by the similar method as Example B44.

¹H-NMR Spectrum (CD₃OD,400 MHz)δ(ppm): 0.88(3H, d,J=6.4 Hz), 0.90(3H,d,J=6.8 Hz), 0.93(3H,t,J=7.6 Hz), 1.08 (3H,d,J=6.8 Hz), 1.14–1.25(4H,m), 1.32–1.67(8H,m), 1.74 (3H,s), 1.78–1.83(4H,m), 2.42–2.62(10H,m), 2.65(1H,dd, J=2.4,8.4 Hz), 2.72(1H,dt,J=2.4,6.0 Hz), 3.27(2H,t,J=6.8 Hz), 3.51(1H,dt,J=4.4,8.4 Hz), 3.74–3.81(1H,m), 4.86–4.92 (1H,m), 5.04(1H,d,J=10.8 Hz), 5.54(1H,dd,J=9.6,15.2 Hz), 5.65(1H,dd,J=8.4,14.8 Hz), 5.69(1H,dd,J=9.6,15.2 Hz), 6.09(1H,d,J=10.8 Hz), 6.32(1H,dd,J=10.8,15.2 Hz); ESI-MS m/z 635(M+H)⁺.

Example B65

(8E,12E,14E)-3,6,21-Trihydroxy-6,10,12,16,20-pentamethyl-7-((4-ethylpiperazin-1-yl)carbonyl)oxy-18,19-epoxytricosa-8,12,14-trien-11-olide (Compound B65)

Compound B65

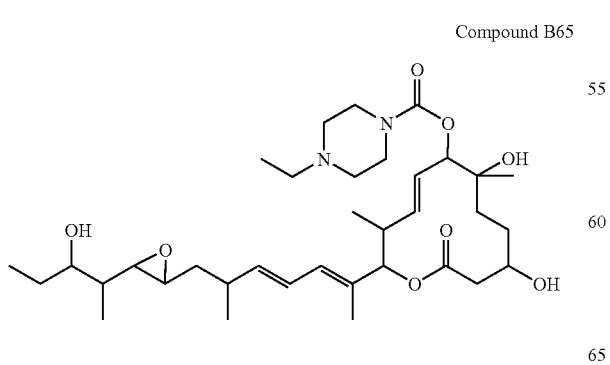

The title compound (a colorless oil) was synthesized by the similar method as Example B44.

¹H-NMR Spectrum (CD₃OD,400 MHz)δ(ppm): 0.89(3H, d,J=6.4 Hz), 0.90(3H,d,J=6.8 Hz), 0.93(3H,t,J=7.6 Hz), 1.08 (3H,d,J=6.8 Hz), 1.11(3H,t,J=7.2 Hz), 1.14–1.23(4H,m), 1.33–1.67(8H,m), 1.74(3H,d,J=1.2 Hz), 2.40–2.63(10H,m), 2.65(1H,dd,J=2.4,8.4 Hz), 2.72(1H,dt,J=2.4,6.0 Hz), 3.40–3.72(5H,m), 3.75–3.81(1H,m), 4.93(1H,d,J=10.0 Hz), 5.04(1H,d,J=10.4 Hz), 5.57(1H,dd,J=9.6,15.2 Hz), 5.65(1H, dd,J=8.4,15.2 Hz), 5.71(1H,dd,J=9.6,15.2 Hz), 6.09(1H,d, J=10.8 Hz), 6.32(1H,dd,J=10.8,14.8 Hz); ESI-MS m/z 635 (M+H)⁺.

Example B66

(8E,12E,14E)-3,6,21-Trihydroxy-6,10,12,16,20-pentamethyl-7-((4-(2-hydroxyethyl)piperazin-1-yl) carbonyl)oxy-18,19-epoxytricosa-8,12,14-trien-11-olide (Compound B66)

Compound B66

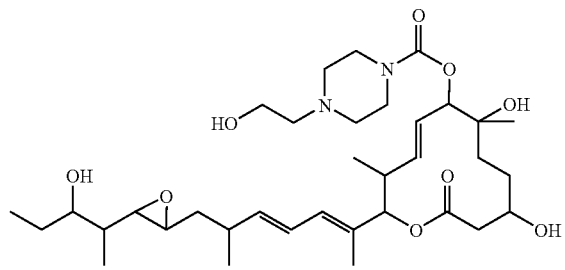

The title compound (a colorless oil) was synthesized by the similar method as Example B44.

¹H-NMR Spectrum (CD₃OD,400 MHz)δ(ppm): 0.89(3H, d,J=6.8 Hz) 0.90(3H,d,J=6.8 Hz), 0.93(3H,t,J=7.6 Hz), 1.08 (3H,d,J=6.8 Hz), 1.14–1.23(4H,m), 1.33–1.67(8H,m), 1.74 (3H,d,J=1.2 Hz), 2.43–2.61(10H,m), 2.65(1H,dd,J=2.4,8.4 Hz), 2.72(1H,dt,J=2.4,6.0 Hz), 3.38–3.72(7H,m), 3.74–3.81 (1H,m), 4.93(1H,d,J=9.6 Hz), 5.04(1H,d,J=10.8 Hz), 5.57 (1H,dd,J=9.6,15.2 Hz), 5.65(1H,dd,J=8.4,14.8 Hz), 5.71 (1H,dd,J=9.6,15.2 Hz), 6.09(1H,d,J=10.8 Hz), 6.32(1H,dd, J=10.8,14.8 Hz); ESI-MS m/z 651(M+H)⁺.

Example B67

(8E,12E,14E)-3,6,21-Trihydroxy-6,10,12,16,20-pentamethyl-7-((2,5-dimethylpiperazin-1-yl)carbonyl)oxy-18,19-epoxytricosa-8,12,14-trien-11-olide (Compound B67)

Compound B67

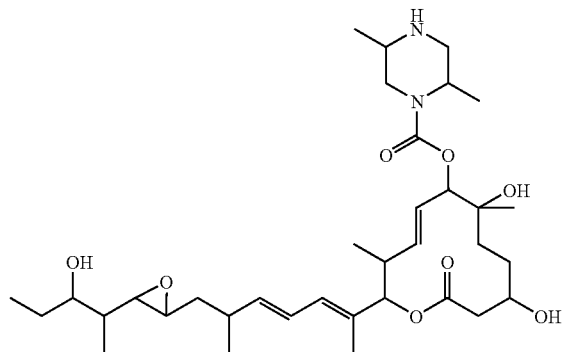

The title compound (a colorless oil) was synthesized by the similar method as Example B44.

$^1$H-NMR Spectrum (CD$_3$OD,400 MHz)δ(ppm): 0.88(3H, d,J=6.4 Hz), 0.90(3H,d,J=6.8 Hz), 0.93(3H,t,J=7.6 Hz), 1.08 (3H,d,J=6.8 Hz), 1.11–1.26(10H,m), 1.34–1.68(8H,m), 1.74 (3H,d,J=0.8 Hz), 2.42–2.62(5H,m), 2.65(1H,dd,J=2.4,8.4 Hz), 2.72(1H,dt,J=2.4,6.0 Hz), 3.04–3.36(2H,m), 3.24–3.30 (1H,m), 3.51(1H,dt,J=4.4,8.8 Hz), 3.65–3.73(1H,m), 3.75–3.82(1H,m), 4.18–4.28(1H,m), 4.88–5.00(1H,m), 5.05 (1H,d,J=10.8 Hz), 5.57(1H,dt,J=10.0,15.2 Hz), 5.65(1H,dd, J=8.4,14.8 Hz), 5.71(1H,dt,J=9.6,15.2 Hz), 6.09(1H,d, J=10.8 Hz), 6.32(1H,dd,J=10.8,14.8 Hz); ESI-MS m/z 635 (M+H)$^+$.

Example B68

(8E,12E,14E)-7-N-Ethylcarbamoyloxy-3,6,21-trihydroxy-6,10,12,16,20-pentamethyl-18,19-epoxytricosa-8,12,14-trien-11-olide (Compound B68)

Compound B68

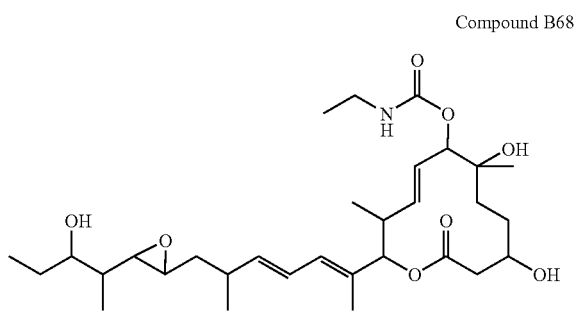

(8E,12E,14E)-3,6,21-Tris(1-ethoxyethoxy)-7-N-ethylcarbamoyloxy-6,10,12,16,20-pentamethyl-18,19-epoxytricosa-8,12,14-trien-11-olide

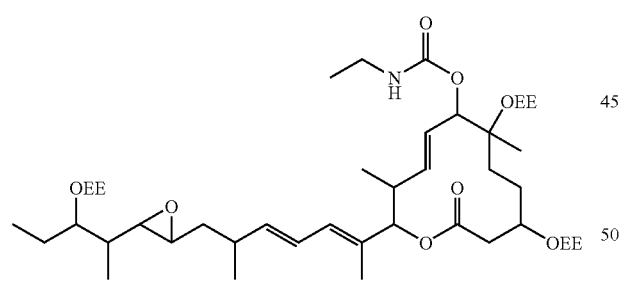

Cuprous chloride (I) (13 mg, 0.13 mmol) and ethyl isocyanate (16 mg, 0.23 mmol) were added to a solution of (8E,12E,14E)-3,6,21-tris(1-ethoxyethoxy)-7-hydroxy-6,10,12,16,20-pentamethyl-18,19-epoxytricosa-8,12,14-trien-11-olide (16 mg, 0.023 mmol) in dichloromethane (2.5 mL) at room temperature. The mixture was stirred at room temperature for 16 hours. The reaction mixture was diluted with ethyl acetate, washed with brine, dried over anhydrous magnesium sulfate and evaporated. The resulting crude product was purified by silica gel column chromatography (Kanto silica gel 60N, spherical, neutral, 40 to 100 μm, eluate; ethyl acetate:hexane=50:50) to give the title compound (11 mg, 61%) as a colorless oil.

ESI-MS m/z 781(M+Na)$^+$.

(8E,12E,14E)-7-N-Ethylcarbamoyloxy-3,6,21-trihydroxy-6,10,12,16,20-pentamethyl-18,19-epoxytricosa-8,12,14-trien-11-olide (Compound B68)

Compound B68

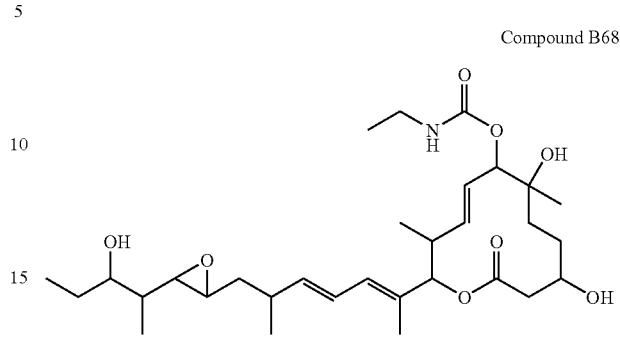

Pyridinium p-toluenesulfonate (17 mg, 0.069 mmol) was added to a solution of (8E,12E,14E)-3,6,21-tris(1-ethoxyethoxy)-7-N-ethylcarbamoyloxy-6,10,12,16,20-pentamethyl-18,19-epoxytricosa-8,12,14-trien-11-olide (11 mg, 0.014 mmol) in methanol (1.5 mL) at room temperature, followed by stirring at the same temperature for one hour. The reaction mixture was diluted with 1.5 mL of ethyl acetate, washed with brine, dried over anhydrous magnesium sulfate and evaporated. The resulting crude product was purified by silica gel column chromatography (Kanto silica gel 60N, spherical, neutral, 40 to 100 μm, eluate: ethyl acetate) to give the title compound (6.0 mg, 61%) as a colorless oil.

$^1$H-NMR Spectrum(CD$_3$OD,400 MHZ)δ(ppm): 0.89(3H, d,J=7.2 Hz), 0.90(3H,d,J=6.8 Hz), 0.93(3H,t,J=7.2 Hz), 1.08 (3H,d,J=6.8 Hz), 1.10(3H,t,J=7.2 Hz), 1.18–1.66(9H,m), 1.20(3H,s), 1.74(3H,s), 2.40–2.61(2H,m), 2.52(2H,d,J=4 Hz), 2.65(1H,dd,J=2.4,8.4 Hz), 2.72(1H,dt,J=2.4,5.6 Hz), 3.12(2H,q,J=7.2 Hz), 3.51(1H,dt,J=4.4,4.4 Hz), 3.74–3.82 (1H,m), 4.88(1H,m), 5.04(1H,d,J=10.8 Hz), 5.55(1H,dd, J=10,15.2 Hz), 5.62–5.72(2H,m), 6.09(1H,d,J=10.8 Hz), 6.32(1H,dd,J=10.8,15.2 Hz); ESI-MS m/z 588(M+Na)$^+$.

Example B69

(8E,12E,14E)-7-(N-Chloroacetyl)carbamoyloxy-3,6,21-trihydroxy-6,10,12,16,20-pentamethyl-18,19-epoxytricosa-8,12,14-trien-11-olide (Compound B69)

Compound B69

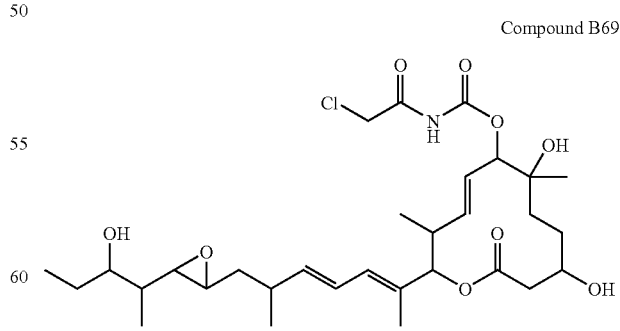

Using chloroacetyl isocyanate, the title compound was obtained as a colorless oil by the similar method as Example B68.

$^1$H-NMR Spectrum (CD$_3$OD,500 MHz)δ(ppm): 0.90(3H, d,J=6.5 Hz), 0.90(3H,d,J=7.0 Hz), 0.94(3H,t,J=7.5 Hz), 1.09 (3H,d,J=7.0 Hz), 1.16–1.21(4H,m), 1.32–1.68(8H,m), 1.75 (3H,s), 2.42–2.64(4H,m), 2.66(1H,dd,J=2.0,6.0 Hz), 3.48–3.56(1H,m), 3.74–3.84(1H,m), 4.44(2H,s), 5.01(1H,d, J=9.5 Hz), 5.06(1H,d,J=10.0 Hz), 5.60–5.70(2H,m), 5.73 (1H,dd,J=10.0,15.0 Hz), 6.10(1H,d,J=11.0 Hz), 6.33(1H,dd, J=11.0,15.0 Hz); ESI-MS m/z 636(M+Na)$^+$.

Example B70

(8E,12E,14E)-3-(t-Butyldimethylsiloxy)-7-(N-ethyl) carbamoyloxy- 3,6,21-trihydroxy-6,10,12,16,20-pentamethyl-18,19-epoxytricosa-8,12,14-trien-11-olide (Compound B70)

Compound B70

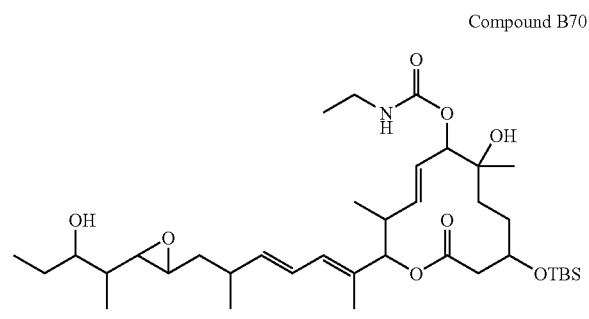

The 7-acetoxy of the compound obtained in Example B11 was solvolyzed by the similar method as the compound B12. Then, using ethylamine, it was converted into 7-(N-ethyl) carbamethoxy moiety by the similar method as Example B44, and then the ethoxyethyl group was deprotected by the similar method as Example B44 to give the title compound as a colorless oil.

$^1$H-NMR Spectrum (CD$_3$OD,500 MHZ)δ(ppm): 0.09(3H, s), 0.10(3H,s), 0.88–0.97(18H,m), 1.09(3H,d,J=7.5 Hz), 1.12(3H,d,J=7.5 Hz), 1.20(3H,s), 1.20–1.26(1H,m), 1.27–1.72(8H,m), 1.73(3H,s), 2.38(1H,dd,J=4.0,13.0 Hz), 2.42–2.64(3H,m), 2.66(1H,d,J=8.0 Hz), 2.73(1H,t,J=6.0 Hz), 3.08–3.20(2H,m), 3.48–3.56(1H,m), 3.88–3.96(1H,m), 4.88(1H,d,J=11.0 Hz), 4.90(1H,d,J=11.0 Hz), 5.56(1H,dd, J=10.0,15.0 Hz), 5.64–5.84(2H,m), 6.11(1H,d,J=11.0 Hz), 6.32(1H,dd,J=11.0,15.0 Hz); ESI-MS m/z 702(M+Na)$^+$.

Example B71

(8E,12E,14E)-7-Acetoxy-3,6-dihydroxy- 6,10,12,16, 20-pentamethyl-21-oxo-18,19-epoxytricosa-8,12,14-trien-11-olide (11107C)

A solution of Compound B10-2 (37 mg, 57 μmol) obtained in Example B10 in chloroform (5 mL) was added to a suspension of Dess-Martin reagent (72 mg, 170 μmol) in chloroform (2.5 mL), followed by stirring at room temperature for one hour. A 10% aqueous sodium thiosulfate solution was added to the reaction mixture and the mixture was vigorously stirred. Then, the organic layer was washed with brine, dried over anhydrous magnesium sulfate and evaporated. The resulting residue was purified by silica gel column chromatography (Kanto silica gel 60N, spherical, neutral, 40 to 100 μm, eluate; hexane:ethyl acetate=2:1 to 1:1) to give a 3-t-butyldimethylsiloxy-21-keto compound (30 mg, 81%). A solution of the resulting 3-t-butyldimethylsiloxy-21-keto compound (25 mg, 39 μmol) in tetrahydrofuran (100 μL) was added to a mixture of trifluoroacetic acid:tetrahydrofuran:water=1:10:5 (2 mL), followed by stirring at room temperature for 5 hours. After ethyl acetate was added to the reaction mixture, the organic layer was washed with a saturated sodium bicarbonate aqueous solution and brine, dried over anhydrous magnesium sulfate and then evaporated. The resulting residue was purified by silica gel column chromatography (Kanto silica gel 60N, spherical, neutral, 40 to 100 μm, eluate; hexane:ethyl acetate=1:3) to give a colorless oil (11.1 mg, 54%). It was confirmed by TLC and HPLC that this product was identical to 11107C obtained from the cultured broth of microbial.

Example B72

(8E,12E,14E)-3,6,21-Trihydroxy-7-oxo-6,10,12,16, 20-pentamethyl-18,19-epoxytricosa-8,12,14-trien-11-olide (Compound B72)

Compound B72

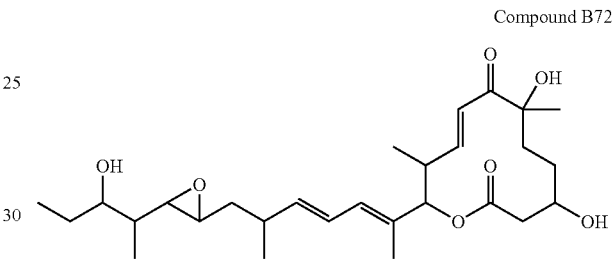

A solution of (8E,12E,14E)-3,6,21-tri(1-ethoxyethoxy)-7-hydroxy-6,10,12,16,20-pentamethyl-18,19-epoxytricosa-8, 12,14-trien-11-olide (10 mg, 14 μmol) obtained in Example B39 in chloroform (0.5 mL) was added to a suspension of Dess-Martin reagent (60 mg, 140 μmol) in chloroform (2 mL), followed by stirring at room temperature for 3 hours. The reaction mixture was poured into a sodium thiosulfate aqueous solution, and the mixture was vigorously stirred. Then, ethyl acetate was added thereto, and the organic layer was washed with brine, dried over anhydrous sodium sulfate and evaporated. The resulting residue was dissolved in 2 mL of methanol and pyridinium p-toluenesulfonate (3 mg, 11 μmol) was added thereto, followed by stirring at room temperature for 20 hours. The solvent was removed, and the resulting residue was dissolved in ethyl acetate. The mixture was washed with a saturated sodium bicarbonate aqueous solution and brine, dried over anhydrous magnesium sulfate and evaporated. The resulting residue was purified by thin layer chromatography (MERCK Silica gel 60 F254, 0.2 mm, developing solution; hexane:ethyl acetate=1:5) and preparative HPLC (Shiseido CAPCELL PAK C18, 10 mm I.D.×250 mm, eluate; acetonitrile:water=20:80–80:20) to give the title compound (0.11 mg, 2%) as a colorless oil.

$^1$H-NMR Spectrum (CD$_3$OD,500 MHz)δ(ppm): 0.91(3H, d,J=7.5 Hz), 0.94(3H,t,J=7.5 Hz), 0.96(3H,d,J=7.0 Hz), 1.10 (3H,d,J=7.0 Hz), 1.10–1.26(2H,m), 1.29(3H,m), 1.30–1.56 (4H,m), 1.58–1.72(2H,m), 1.78(3H,s), 1.77–1.86(1H,m), 2.31(1H,dd,J=8.0,14.0 Hz), 2.44–2.54(1H,m), 2.64–2.76(4H,m), 3.48–3.56(1H,m), 4.13–4.20(1H,m), 5.05 (1H,d,J=10.5 Hz), 5.69(1H,dd,J=9.0,15.0 Hz), 6.11(1H,d, J=11.0 Hz), 6.28(1H,dd,J=10.5,15.5 Hz), 6.34(1H,dd, J=11.0,15.0 Hz), 7.03(1H,d,J=15.5 Hz); ESI-MS m/z 515 (M+Na)$^+$.

Example B73

(2E,8E,12E,14E)-7-Acetoxy-6,21-dihydroxy-6,10,12,16,20-pentamethyl-18,19-epoxy-3-oxotricosa-4,8,12,14-tetraen-11-olide (Compound B73)

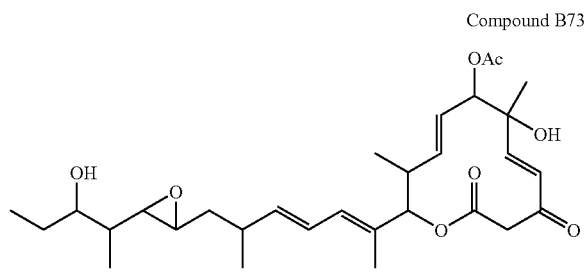

Compound B73

(2E,8E,12E,14E)-7-Acetoxy-3,6,21-trihydroxy- 6,10,12,16,20-pentamethyl-18,19-epoxytricosa-4,8,12,14-tetraen-11-olide (11.2 mg, 20.9 μmol) was dissolved in dichloromethane (0.5 mL), followed by cooling to 0° C. MnO$_2$ (54.5 mg) was added to the solution, followed by stirring at 0° C. for 2 hours and at room temperature for one hour. The reaction mixture was filtered through Celite, and then evaporated. The resulting crude product was purified by thin layer chromatography (MERCK Silica gel 60 F254, 0.5 mm, developing solution; ethyl acetate:hexane=3:1) to give the title Compound B73 (9.8 mg, 18.3 μmol, 87.6%).

$^1$H-NMR Spectrum(CD$_3$OD,400 MHz)δ(ppm): 0.84(1H, d,J=7 Hz), 0.89(3H,d,J=7 Hz), 0.93(3H,t,J=8 Hz), 1.07(3H, d,J=7 Hz), 1.14–1.23(1H,m),1.34(3H,s), 1.41–1.55(3H,m), 1.59–1.67(1H,m), 1.69(3H,d,J=0.7 Hz), 2.09(3H,s), 2.41–2.51(1H,m), 2.51–2.60(1H,m), 2.64(1H,dd,J=2,8 Hz), 2.71(1H,dt,J=2,6 Hz), 3.50(1H,dt,J=5,9 Hz), 3.56(1H,d, J=15 Hz), 3.68(1H,d,J=15 Hz), 5.02(1H,d,J=11 Hz), 5.04 (1H,d,J=10 Hz), 5.40(1H,dd,J=10,15 Hz), 5.59(1H,dd,J=10, 15 Hz), 5.65(1H,dd,J=9,15 Hz), 6.05(1H,d,J=11 Hz), 6.21 (1H,d,J=16 Hz), 6.30(1H,dd,J=11,15 Hz), 6.66(1H,d,J=17 Hz); FAB-MS m/z 533(M+H)$^+$.

Example B74

(8E,12E,14E)-7-Acetoxy-3,6-dihydroxy-21-methoxyimino-6,10,12,16,20-pentamethyl-18,19-epoxytricosa-8,12,14-trien-11-olide (Compound B74)

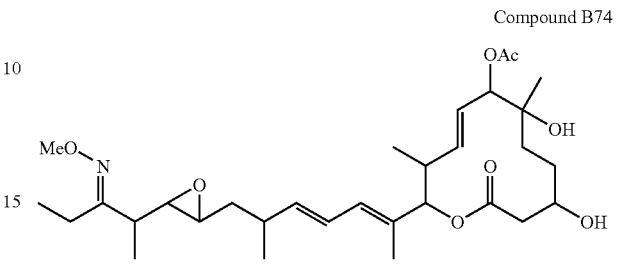

Compound B74

A solution of methoxyhydroxylamine (1.2 mg, 0.014 mmol) in pyridine (0.5 mL) was added to a solution of (8E,12E,14E)-7-acetoxy-3,6,21-trihydroxy-6,10,12,16,20-pentamethyl-21-oxo-18,19-epoxytricosa-8,12,14-trien-11-olide (5.0 mg, 0.0093 mmol) in pyridine (0.5 mL) at room temperature. The mixture was stirred at 60° C. for 16 hours. The reaction mixture was diluted with ethyl acetate, washed with brine, dried over anhydrous magnesium sulfate and evaporated. The resulting crude product was purified by thin layer chromatography (MERCK Silica gel 60 F254, 0.2 mm, developing solution; ethyl acetate) to give the title compound (2.2 mg, 42%) as a colorless oil.

$^1$H-NMR Spectrum(CD$_3$OD,400 MHz)δ(ppm): 0.87(3H, d,J=6.4 Hz), 1.03(3H,d,J=7.4 Hz), 1.05–1.10(6H,m), 1.18 (3H,s), 1.26–1.70(6H,m), 1.74(3H,s), 2.06(3H,s), 2.20–2.32 (2H,m), 2.42–2.60(3H,m), 2.52(2H,d,J=4.0 Hz), 2.70–2.88 (2H,m), 3.73–3.80(1H,m), 3.78(3H,s), 5.04(2H,d,J=10.0 Hz), 5.56(1H,dd,J=10.0,15.2 Hz), 5.66(1H,dd,J=8.4,16.4 Hz), 5.69(1H,dd,J=9.2,15.6 Hz), 6.09(1H,d,J=10.8 Hz), 6.32(1H,dd,J=12.8,14.8 Hz); ESI-MS m/z 586(M+Na)$^+$.

Example B75

(8E,12E,14E)-7-Acetoxy-21-benzyloxyimino-3,6-dihydroxy-6,10,12,16,20-pentamethyl-18,19-epoxytricosa- 8,12,14-trien-11-olide (Compound B75)

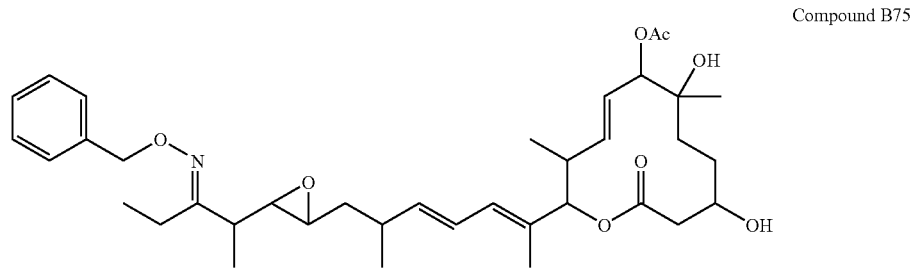

Compound B75

The title compound (a colorless oil) was synthesized by the similar method as Example B74.

¹H-NMR Spectrum(CD₃OD,400 MHz)δ(ppm): 0.85(3H, t,J=6.8 Hz), 1.03–1.15(10H,m), 1.18(3H,s), 1.32–1.47(3H, m), 1.52–1.68(3H,m), 1.71–1.74(3H,m), 2.06(3H,s), 2.10–2.37(2H,m), 2.38–2.61(4H,m), 2.66–2.91(2H,m), 3.74–3.81(1H,m), 4.99–5.06(4H,m), 5.51–5.73(3H,m), 6.02–6.11(1H,m), 6.24–6.35(1H,m), 7.23–7.34(5H,m); ESI-MS m/z 662(M+Na)⁺.

Example B76

(8E,12E)-7-Acetoxy-3,6-dihydroxy-6,10,12-trimethyltricosa-8,12,14-trien-11-olide (Compound B76)

Compound B76

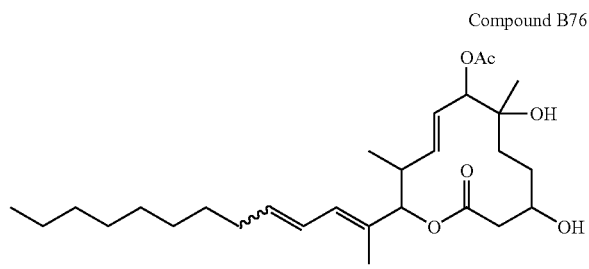

(8E,12E)-7-Acetoxy-3,6-bis(1-ethoxyethoxy)-6,10,12-trimethyl-14-oxotetradeca-8,12-dien-11-olide

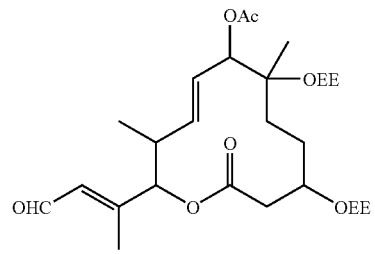

A solution of osmium tetraoxide (4.9 mg, 0.13 mmol) in pyridine (1.2 mL) was added to (8E,12E,14E)-7-acetoxy-3, 6,21-tris(1-ethoxyethoxy)-6,10,12,16,20-pentamethyl-18, 19-epoxytricosa-8,12,14-trien-11-olide (18 mg, 0.024 mmol) at –10° C. The mixture was stirred at the same temperature for one hour. An aqueous solution of NaHSO₃ was added to the reaction mixture, followed by stirring at the room temperature for 10 min. The mixture was diluted with ethyl acetate, washed with 1N hydrochloric acid and brine, dried over anhydrous magnesium sulfate and evaporated, to give a crude diol compound (14 mg, 71%) as a colorless oil. The resulting crude product was used for the next reaction without purification. Lead tetraacetate (41 mg, 0.092 mmol) and potassium carbonate (18 mg, 0.13 mmol) were added to a solution of the crude diol compound (15 mg, 0.018 mmol) in toluene (1.0 mL) at room temperature, followed by stirring at the same temperature for 3 hours. The reaction mixture was diluted with 15 mL of ethyl acetate, washed with brine, dried over anhydrous magnesium sulfate and evaporated. The resulting crude product was purified by silica gel column chromatography (Kanto silica gel 60N, spherical, neutral, 40 to 100 μm, eluate; hexane:ethyl acetate=50:50) to give the title compound (5.4 mg, 57%) as a colorless oil.

¹H-NMR Spectrum(CD₃OD,400 MHz)δ(ppm): 0.95(3H, d,J=6.8 Hz), 1.12–1.36(15H,m), 1.38–1.78(4H,m), 2.04(3H, s), 2.19(3H,s), 2.46–2.68(3H,m), 3.46–3.90(5H,m), 4.74–5.23(4H,m), 5.58(1H,dd,J=10.0,15.6 Hz), 5.74–5.86 (1H,m), 6.02(1H,d,J=7.6 Hz), 10.03(1H,d,J=7.6 Hz); ESI-MS m/z 535(M+Na)⁺.

(8E,12E)-7-Acetoxy-3,6-bis(1-ethoxyethoxy)-6,10,12-trimethyltricosa-8,12,14-trien-11-olide

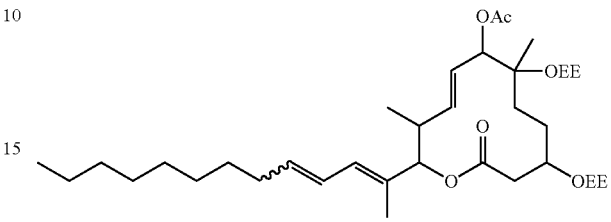

A solution of 1.57 M n-BuLi in hexane (0.17 mL) was added dropwise to a solution of diisopropylamine (31 mg, 0.36 mmol) in tetrahydrofuran (1.8 mL) at –78° C., followed by stirring at the same temperature for 20 min. To the resulting solution, a solution of 1,3-benzothiazol-2-ylnonylsulfone (44 mg, 0.14 mmol) in tetrahydrofuran (1 mL) at –78° C., followed by stirring at the same temperature for 30 min. 0.6 mL of the resulting solution (which corresponds to 8.8 mg, 0.027 mmol of the anion of 1,3-benzothiazol-2-ylnonylsulfone) was added to asolution of (8E,12E)-7-acetoxy-3,6-bis(1-ethoxyethoxy)-6,10,12-trimethyl-14-oxotetradeca-8,12-dien-11-olide (6.9 mg, 0.013 mmol) in tetrahydrofuran (0.5 mL) at –78° C. The temperature of the resulting solution was gradually (during one hour 50 min.) raised to room temperature with stirring. A saturated aqueous ammonium chloride solution was added to the reaction mixture and the mixture was further diluted with ethyl acetate. Then, the mixture was washed with brine, dried over anhydrous magnesium sulfate and evaporated. The resulting crude product was purified by silica gel column chromatography (Kanto silica gel 60N, spherical, neutral, 40 to 100 μm, eluate; hexane:ethyl acetate=80:20) to give the title compound (3.2 mg, 38%) as a pale yellow oil.

ESI-MS m/z 645(M+Na)⁺.

(8E,12E)-7-Acetoxy-3,6-dihydroxy-6,10,12-trimethyl-tricosa-8,12,14-trien-11-olide (Compound 76)

Compound 76

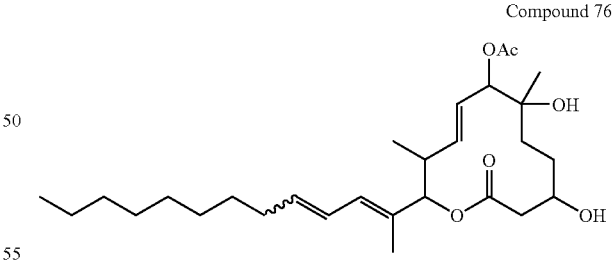

Pyridinium p-toluenesulfonate (13 mg, 0.051 mmol) was added to a solution of (8E,12E)-7-acetoxy-3,6-bis(1-ethoxyethoxy)-6,10,12-trimethyltricosa-8,12,14-trien-11-olide (3.2 mg, 0.0051 mmol) in methanol (1 mL) at room temperature, followed by stirring at the same temperature for 2.5 hours. The reaction mixture was diluted with 1 mL of ethyl acetate, washed with brine, dried over anhydrous magnesium sulfate and evaporated. The resulting crude product was purified by thin layer chromatography (MERCK Silica gel 60 F254, 0.25 mm, developing solution; hexane:ethyl acetate=1:2) to give the title compound (1.2 mg, 49%) as a pale yellow oil.

¹H-NMR Spectrum(CD₃OD,400 MHz)δ(ppm): 0.85–0.92(6H,m), 1.18(3H,s), 1.20–1.65(16H,m), 1.73(3H,d,J=4 Hz), 2.06(3H,s), 2.07–2.23(2H,m), 2.50–2.62(3H,m), 3.75–3.82(1H,m), 5.02–5.12(2H,m), 5.50–5.62(1H,m), 5.62–5.80(2H,m), 6.04–6.43(2H,m); ESI-MS m/z 501(M+Na)⁺.

Example B77

(8E,12E,14E)-3,6,21-Trihydroxy-6,10,12,16,20-pentamethyl-((4-piperidin-1-yl)-piperidin-1-yl)carbonyl)oxy-18,19-epoxytricosa-8,12,14-trien-11-olide (Compound B77)

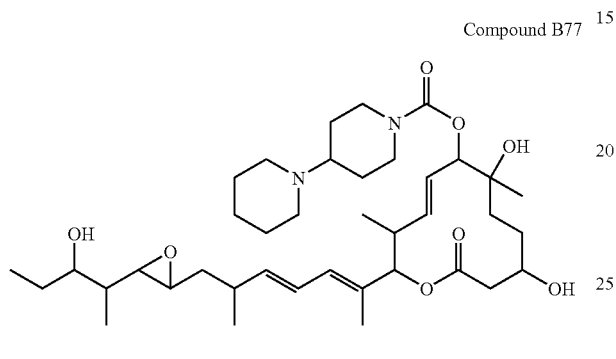

Compound B77

The title compound was obtained as a colorless oil by the similar method as Example B44.

¹H-NMR Spectrum(CD₃OD,400 MHz)δ(ppm): 0.88(3H,d,J=5.2 Hz), 0.89(3H,d,J=7.2 Hz), 0.93(3H,t,J=7.2 Hz), 1.08 (3H,d,J=6.8 Hz), 1.20(3H,s), 1.14–1.67(17H,m), 1.74(3H,s), 1.86–1.92(2H,m), 2.42–2.62(10H,m), 2.65(1H,dd,J=2.4,8.4 Hz), 2.72(1H,dt,J=2.4,5.6 Hz), 2.73–2.83(2H,m), 3.46–3.54(1H,m), 3.74–3.82(1H,m), 4.13–4.22(1H,m), 4.91(1H,d,J=9.6 Hz), 5.04(1H,d,J=10.8 Hz), 5.56(1H,dd,10.0,15.2 Hz), 5.65(1H,dd,J=8.4,15.2 Hz), 5.71(1H,dd,J=9.6,15.2 Hz), 6.09(1H,d,J=10.4 Hz), 6.32(1H,dd,J=10.8,15.2 Hz); ESI-MS M/z 689(M+H)⁺.

Example B78

(8E,12E,14E)-3,6,21-Trihydroxy-6,10,12,16,20-pentamethyl-7-N-(3-(4-methylpiperazin-1-yl)propyl)carbamoyloxy-18,19-epoxytricosa-8,12,14-trien-11-olide (Compound B78)

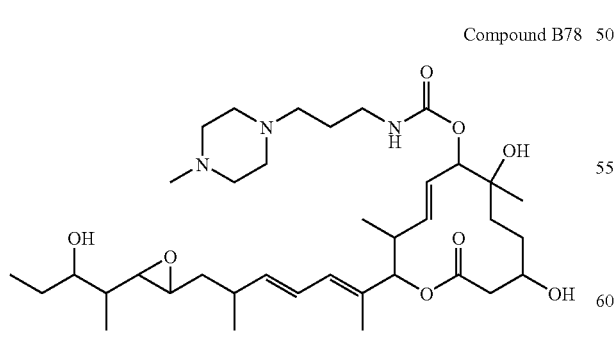

Compound B78

The title compound was obtained as a colorless oil by the similar method as Example B44.

¹H-NMR Spectrum(CD₃OD,400 MHZ)δ(ppm): 0.88(3H,d,J=5.2 Hz), 0.90(3H,d,J=7.2 Hz), 0.93(3H,t,J=7.6 Hz), 1.07 (3H,d,J=6.8 Hz), 1.20(3H,s), 1.16–1.72(11H,m), 1.74(3H,s), 2.28(3H,s), 2.36–2.62(14H,m), 2.65(1H,dd,J=2.4,8.4 Hz), 2.72(1H,dt,J=2.4,6.0 Hz), 3.13(2H,t,J=6.8 Hz), 3.46–3.54 (1H,m), 3.74–3.82(1H,m), 5.04(1H,d,J=10.4 Hz), 5.54(1H,dd,J=10.0,15.2 Hz), 5.65(1H,dd,J=8.4,14.8 Hz), 5.69(1H,dd,J=9.6,15.2 Hz), 6.09(1H,d,J=11.2 Hz), 6.32(1H,dd,J=10.8,14.8 Hz); ESI-MS m/z 678(M+H)⁺.

Example B79

(8E,12E,14E)-3,6,21-Trihydroxy-6,10,12,16,20-pentamethyl-7-N-(1-methylpiperidin-4-yl)carbamoyloxy-18,19-epoxytricosa-8,12,14-trien-11-olide (Compound B79)

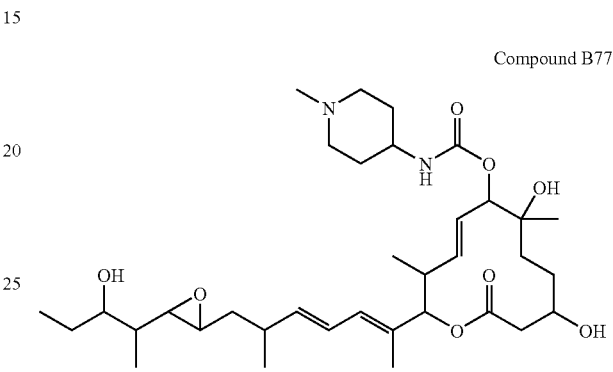

Compound B77

The title compound was obtained as a colorless oil by the similar method as Example B44.

¹H-NMR Spectrum (CD₃OD,500 MHz)δ(ppm): 0.89(3H,d,J=7.0 Hz), 0.89(3H,d,J=8.0 Hz), 0.94(3H,t,J=7.0 Hz), 1.07 (3H,d,J=7.0 Hz), 1.14–1.24(1H,m), 1.20(3H,s), 1.26–1.68 (10H,m), 1.74(3H,s), 1.84–1.94(2H,m), 2.10–2.20(2H,m), 2.28(3H,s), 2.40–2.64(4H,m), 2.66(1H,dd,J=2.0,8.0 Hz), 2.73(1H,dt,J=2.5,6.0 Hz), 2.78–2.88(2H,m), 3.30–3.46(1H,br), 3.48–3.55(1H,m), 3.74–3.82(1H,m), 4.89(1H,d,J=10.0 Hz), 5.05(1H,d,J=11.0 Hz), 5.55(1H,dd,J=9.5,15.0 Hz), 5.62–5.74(2H,m), 6.09(1H,d,J=11.0 Hz), 6.31(1H,dd,J=11.0,15.0 Hz); ESI-MS m/z 635(M+H)⁺.

Example B80

(8E,12E,14E)-3,6,21-Trihydroxy-6,10,12,16,20-pentamethyl-7-N-methyl-N-(1-methylpiperidin-4-yl)carbamoyloxy-18,19-epoxytricosa-8,12,14-trien-11-olide (Compound B80)

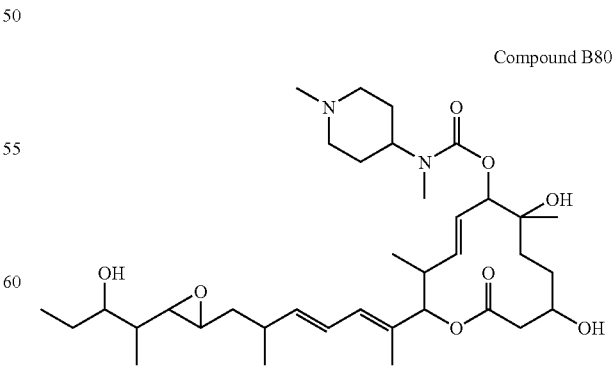

Compound B80

The title compound was obtained as a colorless oil by the similar method as Example B44.

$^1$H-NMR Spectrum (CD$_3$OD,400 MHz)δ(ppm): 0.88(3H, d,J=6.4 Hz), 0.90(3H,d,J=6.8 Hz), 0.93(3H,t,J=7.6 Hz), 1.08 (3H,d,J=6.8 Hz), 1.14–1.22(4H,m), 1.33–1.68(10H,m), 1.74 (3H,s), 1.74–1.87(2H,m), 2.06–2.21(2H,m), 2.28(3H,s), 2.42–2.62(4H,m), 2.65(1H,dd,J=2.4,8.4 Hz), 2.72(1H,dt, J=2.4,6.0 Hz), 2.84(3H,br-s), 2.87–2.97(2H,m), 3.51(1H,dt, J=4.4,8.4 Hz), 3.75–3.81(1H,m), 3.87–4.14(1H,m), 4.95 (1H,d,J=9.6 Hz), 5.05(1H,d,J=10.8 Hz), 5.56(1H,dd,J=10.0, 15.2 Hz), 5.65(1H,dd,J=8.4,14.8 Hz), 5.72(1H,dd,J=9.6, 14.8 Hz), 6.09(1H,d,J=10.0 Hz), 6.32(1H,dd,J=10.8,14.8 Hz); ESI-MS m/z 649(M+H)$^+$.

Example B81

(8E,12E,14E)-3,6,21-Trihydroxy-6,10,12,16,20-pentamethyl-7-((3,5-dimethylpiperazin-1-yl)carbonyl)oxy-18,19-epoxytricosa-8,12,14-trien-11-olide (Compound B81)

Compound B81

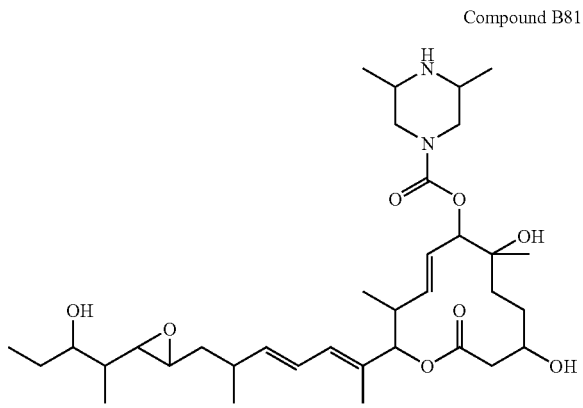

The title compound was obtained as a colorless oil by the similar method as Example B44.

$^1$H-NMR Spectrum (CD$_3$OD,400 MHz)δ(ppm): 0.88(3H, d,J=6.4 Hz), 0.90(3H,d,J=6.8 Hz), 0.93(3H,t,J=7.6 Hz), 1.05–1.10(9H,m), 1.14–1.22(4H,m), 1.33–1.68(8H,m), 1.74 (3H,d,J=0.8 Hz), 2.30–2.62(6H,m), 2.65(1H,dd,J=2.4,8.4 Hz), 2.66–2.77(3H,m), 3.51(1H,dt,J=4.4,8.4 Hz), 3.75–3.81 (1H,m), 3.90–4.02(1H,m), 4.15–4.28(1H,m), 4.88–4.99(1H, m), 5.04(1H,d,J=10.4 Hz), 5.57(1H,dd,J=10.0,15.2 Hz), 5.65(1H,dd,J=8.4,15.2 Hz), 5.71(1H,dd,J=9.6,15.2 Hz), 6.09(1H,d,J=10.0 Hz), 6.32(1H,dd,J=10.8,15.2 Hz); ESI-MS m/z 635(M+H)$^+$.

Example B82

(8E,12E,14E)-3,6,21-Trihydroxy-6,10,12,16,20-pentamethyl-7-N-(1,2,2,6,6-pentamethylpiperidin-4-yl)carbamoyloxy-18,19-epoxytricosa-8,12,14-trien-11-olide (Compound B82)

Compound B82

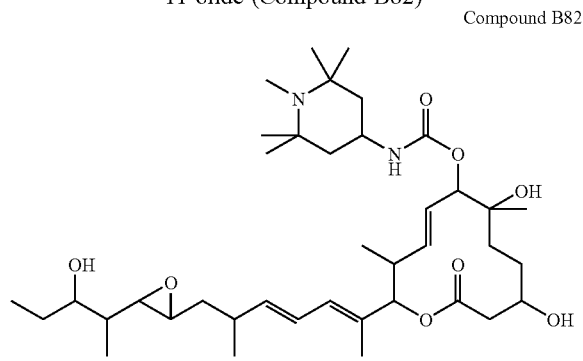

The title compound was obtained as a colorless oil by the similar method as Example B44.

$^1$H-NMR Spectrum (CD$_3$OD,400 MHz)δ(ppm): 0.89(3H, d,J=6.8 Hz), 0.90(3H,d,J=6.8 Hz), 0.93(3H,t,J=7.6 Hz), 1.06–1.80(34H,m), 2.27(3H,s), 2.42–2.61(4H,m), 2.65(1H, dd,J=2.4,8.4 Hz), 2.72(1H,dt,J=2.4,6.0 Hz), 3.51(1H,dt, J=4.4,8.4 HZ), 3.74–3.83(2H,m), 4.87–4.92(1H,m), 5.05 (1H,d,J=10.8 Hz), 5.55(1H,dd,J=10.0,15.2 Hz), 5.65(1H,dd, J=8.4,14.8 HZ), 5.69(1H,dd,J=9.6,14.8 Hz), 6.09(1H,d, J=10.8 Hz), 6.32(1H,dd,J=11.2,14.8 Hz); ESI-MS m/z 691 (M+H)$^+$.

Example C1

VEGF Production Suppressing Action of 11107A–G in U251 Human Glioma Cell

U251 human glioma cell cultured in DULBECCO-modified eagle medium (DMEM; manufactured by SIGMA Co., Ltd.) containing 10% fetal calf serum, penicillin (100 unit/ml) and streptomycin (100 μg/ml) was dispensed in 96-well plates by 4×10$^4$ cells/well. After culturing at 37° C. overnight in a CO$_2$ incubator (5% CO$_2$), the media were removed, and 180 μl of the above-mentioned incubation solution was charged. After adding 20 μL of the above-mentioned incubation solution containing the test compound diluted with 3-fold succession, they were incubated in a low oxygen (2% O2) incubator for 18 hours. The supernatants thereof were measured by an ELISA kit (Immunobiology Research Institute).

Concentration at which the amount of VEGF expressed by low oxygen stimulation was suppressed to 50% (IC50 value) was determined and results are shown in Table 9. As shown in Table, 11107B suppressed most strongly VEGF production, and 11107C and 11107D were strong successive to 11107B. The activities of 11107F and 11107G were very weak.

| Compound | VEGF production suppressing action:IC$_{50}$(ng/ml) |
|---|---|
| 11107 B | 0.8 |
| 11107 C | 3.0 |
| 11107 D | 3.2 |
| 11107 E | 36.3 |
| 11107 A | 111 |

Example C2

VEGF Production Suppressing Action of 11107B in Various Carcinoma Cells

WiDr human colon cancer cell, PC3 human prostate cancer cell, DU145 human colon cancer cell and HT1080 human colon cancer cell, which were cultured in DULBECCO-modified eagle medium (manufactured by DMEM SIGMA Co., Ltd.) containing 10% fetal calf serum, penicillin (100 unit/ml) and streptomycin (100 μg/ml) were dispensed in 96 well plates by 3×10$^4$ cells/well. After culturing at 37° C. overnight in a CO$_2$ incubator (5% CO$_2$), the media were removed, and 180 μl of the above-mentioned incubation solution was charged. After adding 20 μL of the above-mentioned incubation solution containing the test compound diluted with 3-fold succession, they were incubated in a low oxygen (2% CO$_2$) incubator for 18 hours. The supernatants thereof were measured by an ELISA kit (Immunobiology Research Institute).

Concentration at which the amount of VEGF expressed by low oxygen stimulation was suppressed to 50% (IC50 value) was determined and results are shown in Table 10. 11107B suppressed most strongly VEGF production, and 11107C and 11107D were strong successive to 11107B. 11107B showed the VEGF production suppressing effect to all cells used for the experiment.

| Various cancer cells | VEGF production suppressing action:$IC_{50}$(ng/ml) |
|---|---|
| WiDr | 0.65 |
| PC 3 | 0.71 |
| DU-145 | 1.05 |
| HT 1080 | 1.89 |

Example C3

Solid Cancer Proliferation Suppressing Action of 11107B

In order to study solid cancer proliferation suppressing action of 11107B in vivo, human breast cancer BSY-1 cell was transplanted to the subcutaneous body sides of mice. The animals were grouped so that the average of the volumes of the respective groups became uniform, when it reached about 100 mm$^3$. Control group was made as 10 mice and 11107B-administering groups were made as 5 mice. 11107B was administrated for the 11107B-administering groups once by intravenous injection so as to be 10 mg/kg, and a vehicle was administered to the control group. The tumor volumes on the fifth day, eighth day, 12th day and 15th day were measured, and relative tumor volumes were determined setting the tumor volume at the initiation of administration as 1. The results are shown in Table 11.

As shown in Table, 11107B showed the effect of suppressing solid tumor by a single administration.

| Days after the administration | 1 | 5 | 8 | 12 | 15 |
|---|---|---|---|---|---|
| Control group | 1 | 1.79 | 2.05 | 2.54 | 2.59 |
| 11107 B group | 1 | 1.08 | 1.28 | 1.40 | 1.70 |

Example C4

Construction of Reporter System of Screening Compound which Suppresses the Transcription of VEGF (1) Construction of reporter vector reflecting transcription from VEGF promoter In order to prepare reporter system reflecting transcription from VEGF promoter, VEGF promoter sequence was cloned, and inserted in secretory alkali phosphatase (PLAP) vector to construct reporter vector.

In order to obtain the promoter region of human VEGF, VEGF genome was cloned from phage library. PCR primers having the sequences described in Sequence Numbers 1 and 2 were designed based on VEGF cDNA (GenBank accession number: X62568) and a fragment having about 340 bp was obtained by carrying out PCR. Human genome phage library (Human genomic library, Clontech Co.) was screened using this as a probe to obtain pUC18-VEGFA containing about 5.4 kb of VEGF 5' flanking region. The pUC18-VEGFA was cleaved by KpnI/NheI, VEGF promoter region of about 2.3 kb obtained was inserted in the multi cloning site KpnI/NheI of secretory alkali phosphatase (PLAP) vector (Goto et al, Mol. Pharmacol., 49, 860–873, 1996), and thus, VEGF-PLAP vector was constructed.

The above-mentioned VEGF-PLAP vector was introduced in the U251 cell cultured in the DULBECCO-modified eagle medium (DMEM; manufactured by SIGMA Co., Ltd.) containing 10% fetal calf serum, and cultured in the presence of 1 mg/ml G418 (Merck Co.) to establish G418 resistant stable clone (U251/1-8 cell).

It was confirmed that U251/1-8 cell secreted PLAP under low oxygen (2% 02 incubator) in the same manner as in the report (Cell. Mol. Biol. Res. 40, 35–39, 1994) and was a reporter system reflecting the transcription from VEGF promoter. The screening of the compound suppressing VEGF production which was induced by low oxygen stimulation was carried out below using the clone.

Example C5

VEGF Transcription-suppressing Activity of Various 11107 Analogues and Derivatives In order to remove the influence of alkaline phosphates in serum, U251/1-8 cell was rinsed twice with the adequate amount of PBS (Phosphate buffered saline), diluted in the DMEM medium containing 10% of serum in which alkaline phosphates was inactivated by the treatment of 60° C. for 20 min., and dispensed in 96-well plates by $4 \times 10^4$ cells/180 µL.

After culturing at 37° C. overnight in a $CO_2$ incubator (5% $CO_2$), 20 µL of the above-mentioned incubation solution containing the test compound diluted with 3-fold succession was added, and then they were incubated in a low oxygen (2% $CO_2$) incubator for 18 hours. With respect to the PLAP activity in the culture supernatants, 10 µl of the supernatants was added to 50 µl of 0.28 M $Na_2CO_3$—$NaHCO_3$ buffer solution (pH 10.0, 8.0 mM $MgSO_4$), and finally 50 µl of alkaline phosphatase substrate (LUMISTEIN, Genomescience Co.) was added. After reacting for one hour, the alkaline phosphatase activity of the PLAP was measured by detecting the chemical luminescence by a micro plate reader (Perkin-Elmer Co.).

The PLAP activity under usual oxygen was set as 0%, the PLAP activity of cell which was treated under low oxygen was set as 100%, and the concentration suppressing the PLAP activity by 50% was set as the IC50 value of PLAP.

The IC50 values of VEGF transcription-suppressing activity of 11107 Analogues obtained in Examples A1 to A82 were measured, and as a result, the IC50 values of 11107B, 11107C, 11107D, 11107E, 11107H, 11107I, 11107J, 11107K, 11107L, 11107M, 11107N, 11107P, 11107Q, 11107R, 11107T, 11107U, 11107W, 11107X, 11107Y, 11107Z, 11107AB, 11107AD, 11107AE, 11107AJ, 11107AL, 11107AM, 11107AN, 11107AP, 11107AQ, 11107AW, 11107AX, 11107AY, 11107AZ, 11107BF, 11107BG, 11107BH and 11107BI were within a range of 1 to 100 nM, and they showed VEGF transcription-suppressing activity.

Further, the IC50 values of VEGF transcription suppressing activity of the 11107 derivatives obtained in Examples B1 to B58 were measured, and as a result, the IC50 values of Compounds B1-1, B1-2, B2-1, B2-2, B3-1, B3-2, B8-1, B8-2, B8-4, B8-5, B9, B16-1, B17, B18-1, B18-3, B20-2, B21-2, B21-3, B21-4, B23-1, B24, B25, B26, B27, B28, B29, B30-2, B30-3, B33-1, B33-2, B35-1, B35-2, B36-2, B37-1, B39, B40, B41, B42, B43-1, B43-2, B44, B45, B46, B47, B48, B49, B50, B51, B52, B53, B54, B55, B56, B57, B58, B59, B60, B61, B62, B63, B64, B65, B66, B67, B69, B74, B75, B77, B78, B79, B80, B81, B82 were within a range of 0.5 to 100 nM, and they showed VEGF transcription-suppressing activity.

Specifically, IC50 values were shown in Table below.

| Analogues and derivatives | VEGF transcription suppressing activity (IC50: nM) |
| --- | --- |
| 11107B | 1.8 |
| 11107C | 8.2 |
| 11107D | 6.6 |
| 11107H | 3.1 |
| 11107J | 5.9 |
| 11107K | 2.7 |
| 11107AM | 2.6 |
| 11107BH | 2.6 |
| Compound B20-2 | 1.6 |

Example C6

Growth Suppressing Activity of 11107B to Various Cancer Cells (1) Growth Suppressing Activity of 11107B to Leukemia Cell Dami human blood megakaryocytic cell, MOLT 4 human acute lymphoblastic cell, K562 human chronic myelogenous cell, U937 human histcytic lymphoma and p388 mouse lymphoma cultured in RPMI 1640 (manufactured by SIGMA Co., Ltd.) containing 10% fetal calf serum were dispensed in 96-well plates by $2 \times 10^3$ cells/180 µl, and they were cultured at 37° C. overnight in a $CO_2$ incubator (5% $CO_2$). Then, 20 µL of the above-mentioned incubation solution containing 11107B diluted with 2-fold succession was added, and they were further cultured in a $CO_2$ incubator for 3 days.

20 µL of Alamar Blue reagent (Biosource Co.) was added to the cultured cell, and fluorescence activity (ex 530 nm/em 590 nm) was measured by a micro plate reader (ARBO, Perkin-Elmer Co.) after 3 to 5 hours. The cell growth of the control to which the compound is not added is set as 100%, the concentration at which it was suppressed by 50% was determined. As shown in Table, 11107B showed the growth suppressing activity to a wide range of leukemia cells.

| Cell strain | Multiplication suppressing activity IC50 (nM) |
| --- | --- |
| Dami | 1.2 |
| MOLT4 | 1.5 |
| U937 | 1.1 |
| K562 | 2.1 |
| p388 | 2 |

(2) Growth Suppressing Activity of 11107B to Various Cancer Cells

H460 human lung cancer cell, U251 human glioma cell, BSY-1 and MDA-MB435 human breast cancer cell, PC-3 And DU145 human prostate cancer cell, OVCAR-3 human ovarian cancer cell, WiDr human colon cancer cell and B16 melanoma mouse melanoma cell cultured in DMEM (manufactured by SIGMA Co., Ltd.) containing 10% fetal calf serum were dispensed in 96-well plates by $2 \times 10^3$ cells/180 µl, and they were cultured at 37° C. overnight in a $CO_2$ incubator (5% $CO_2$). Then, 20 µL of the above-mentioned incubation solution containing test compounds diluted with 2-fold succession was added, and they were further cultured in a $CO_2$ incubator for 3 days.

20 µL of Alamar Blue reagent (Biosource Co.) was added to the cultured cells, and after 3 to 5 hours, fluorescence activity (ex 530 nm/em 590 nm) was measured by a micro plate reader (ARBO, Perkin-Elmer Co.). The cell growth of the control to which the compound is not added is set as 100%, the concentration at which it was suppressed by 50% was determined. The IC50 values for the studied cell lines were 0.9 to 2.9 nM, and 11107B showed the growth suppressing activity to a wide range of cancer species.

Example C7

Solid Cancer Growth Suppressing Action of Various 11107 Analogues and Derivatives In order to study solid cancer growth suppressing action of various 11107 Analogues and derivatives in vivo, WiDr human colon cancer cells were transplanted to the subcutaneous body sides of mice. The animals were grouped so that the average of the volumes of the respective groups becomes uniform, when it reached about 100 mm³. Control group was made as 10 mice and various 11107 Analogues and derivatives-administering groups were made as 5 mice. Various 11107 Analogues and derivatives were administered for the administering groups for 5 days by intravenous injection so as to be any of 0.625 mg, 2.5 mg and 10 mg/kg/day, and a vehicle was administered to the control group. The tumor volumes on the fifteenth day or sixteenth day were measured, and relative tumor volume ratios (T/C %) were determined setting the tumor volume of the control group as 1. Among the studied 11107 Analogues and derivatives, 11107B, 11107D, 11107BH and Compounds B20-2, B50, B52, B54 and B55 showed the effect of suppressing the increase in the tumor volume, and the relative tumor volume ratios (T/C %) to the control group were within a range of 1 to 50%.

What is claimed is:

1. A compound represented by the formula (5), a pharmacologically acceptable salt thereof or a hydrate of them

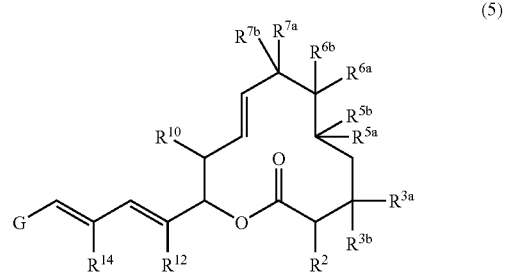

(5)

In the formula (5),
R², R¹⁰, R¹² and R¹⁴ are the same as or different from each other and each represents hydrogen or methyl;
R³ᵃ, R³ᵇ, R⁵ᵃ, R⁵ᵇ, R⁶ᵃ and R⁶ᵇ are the same as or different from each other and each represents
(1) hydrogen,
(2) hydroxy, (3) <1> $C_{1-22}$ alkyl,
<2> $C_{1-22}$ alkoxy,
<3> $ArCH_2O$— (wherein Ar represents $C_{6-14}$ aryl or 5-membered to 14-membered heteroaryl which may have substituents),
<4> $C_{2-22}$ acyloxy,
<5> unsaturated $C_{3-22}$ acyloxy,
<6> —$OCOR^{CO}$ (wherein $R^{CO}$ represents (i) $C_{6-14}$ aryl, (ii) 5-membered to 14-membered heteroaryl, (iii) $C_{1-22}$ alkoxy, (iv) unsaturated $C_{2-22}$ alkoxy, (v) $C_{6-14}$ aryloxy or (vi) 5-membered to 14-membered heteroaryloxy, each of which may have substituents),
<7> $C_{1-22}$ alkylsulfonyloxy,
<8> benzenesulfonyloxy or
<9> —$OSiR^{s1}R^{s2}R^{s3}$ (wherein $R^{s1}$, $R^{s2}$ and $R^{s3}$ are the same as or different from each other and each represents methyl, ethyl, i-propyl, t-butyl or phenyl,
(4) halogen or
(5) —$R^M$—$NR^{N1}R^{N2}$ (wherein $R^M$ represents a single bond or —CO—O—; and $R^{N1}$ and $R^{N2}$ are 1) the same as or different from each other and each represents <1> hydrogen or <2> (i) $C_{1-22}$ alkyl, (ii) unsaturated $C_{3-22}$ alkyl, (iii) $C_{2-22}$ acyl, (iv) unsaturated $C_{3-22}$ acyl, (v) $C_{6-14}$ aryl, (vi) 5-membered to 14-membered heteroaryl, (vii) benzyl, (viii) $C_{1-22}$ alkylsulfonyl or (ix) benzenesulfonyl, each of which may have substituents, or 2) $NR^{N1}R^{N2}$ may be bound together to represent 3-membered to 14-membered nitrogen-containing non-aromatic heterocyclic ring which may have substituents);
$R^{7a}$ and $R^{7b}$ are
(1) different from each other and each represents
1) hydrogen,
2) —$OR^H$ (wherein $R^H$ is hydrogen, methyl or acetyl),
3) —$OR^D$ (wherein $R^D$ represents
(i) $C_{1-22}$ alkyl (provided that in case of methyl, it always has substituents),
(ii) —$CH_2Ar$,
(iii) $C_{3-22}$ acyl,
(iv) unsaturated $C_{3-22}$ acyl,
(v) —$COR^{CO}$,
(vi) $C_{1-22}$ alkylsulfonyl,
(vii) benzenesulfonyl or
(viii) —$SiR^{s1}R^{s2}R^{s3}$) or
4) —$R^M$—$NR^{N1}R^{N2}$, or
(2) $R^{7a}$ and $R^{7b}$ may be bound together to represent <1> a ketone structure (=O) or represent an oxime structure (=$NOR^{OX}$;
wherein $R^{OX}$ represents <1> $C_{1-22}$ alkyl, <2> unsaturated $C_{3-22}$ alkyl, <3> $C_{6-14}$ aryl, <4> 5-membered to 14-membered heteroaryl or <5> benzyl, each of which may have substituents);
further, $R^{3a}$ and $R^{3b}$ may be bound together to represent a ketone structure (=O) or an oxime structure (=$NOR^{OX}$);
further, $R^{6a}$ or $R^{6b}$ may be bound together to represent a spirooxyrane ring or exomethylene;
further, either of $R^{6a}$ or $R^{6b}$ and either of $R^{7a}$ or $R^{7b}$ may be bound together to form a 1,3-dioxolane ring;

G is represented by
[1]

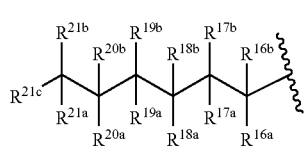
(G-I)

{wherein $R^{16a}$ and $R^{16b}$ are the same as or different from each other and each represents hydrogen, methyl or hydroxy;
$R^{17a}$, $R^{17b}$, $R^{18a}$, $R^{18b}$, $R^{19a}$, $R^{19b}$, $R^{20a}$, $R^{20b}$, $R^{21a}$ and $R^{21b}$ are the same as or different from each other and each represents
(1) hydrogen,
(2) methyl which may optionally have substituents,
(3) —$OR^H$
(4) —$OR^D$
(5) halogen or
(6) —$R^M$—$NR^{N1}R^{N2}$; and
$R^{21c}$ means (1) hydrogen or (2)

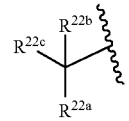

(wherein $R^{22a}$, $R^{22b}$ and $R^{22c}$ are the same as or different from each other and each represents <1> hydrogen, <2> methyl, <3> hydroxy, <4> —$OR^H$, <5> —$OR^D$, <6> —$R^M$—$NR^{N1}R^{N2}$ or <7> halogen);
further, either of $R^{18a}$ or $R^{18b}$ and either of $R^{19a}$ or $R^{19b}$ may form a single bond together to represent the partial structure

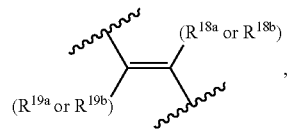
, or may be bonded with an oxygen to represent the partial structure

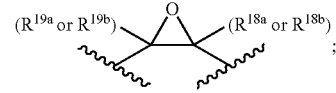
;

further, either of $R^{19a}$ or $R^{19b}$ and either of $R^{20a}$ or $R^{20b}$ may form a single bond together to represent

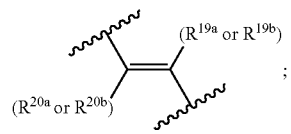
;

further, $R^{21a}$ and $R^{21b}$ may be bound together to represent <1> a ketone structure (=O) or represent <2> an oxime structure (=NOR$^{OX}$);

further, either of $R^{21a}$ or $R^{21b}$ and either of $R^{22a}$ or $R^{22b}$ may be bound together to represent the partial structure

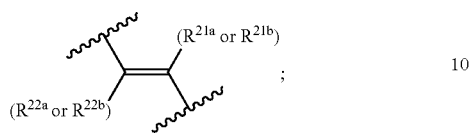

further, either of $R^{19a}$ or $R^{19b}$ and either of $R^{21a}$ or $R^{21b}$ may be bound together to represent the partial structure

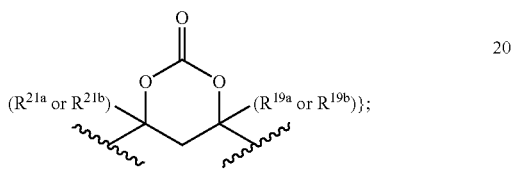

[2]

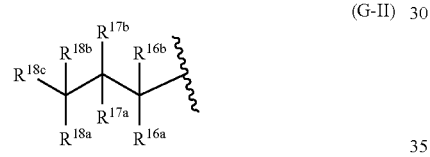
(G-II)

{wherein $R^{16a}$, $R^{16b}$, $R^{17a}$, $R^{17b}$, $R^{18a}$ and $R^{18b}$ have the same meanings as the definitions in the formula (G-I); and $R^{18c}$ represents (1) hydrogen or (2) the formula

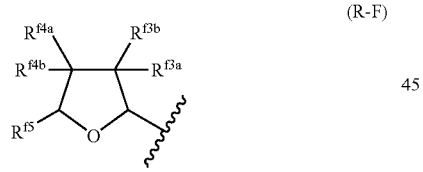
(R-F)

(wherein $R^{f3a}$, $R^{f3b}$ $R^{f4a}$ and $R^{f4b}$ are the same as or different from each other and each represents hydrogen, methyl, hydroxy, methoxy or acetoxy; and $R^{f5}$ represents methyl or ethyl)}; or

[3]

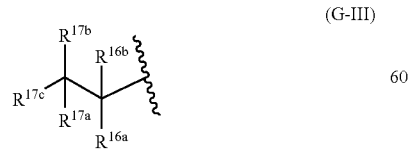
(G-III)

{wherein $R^{16a}$, $R^{16b}$, $R^{17a}$ and $R^{17b}$ have the same meanings as the definitions in the formula (G-I); and $R^{17c}$ represents (1) hydrogen or (2) the formula

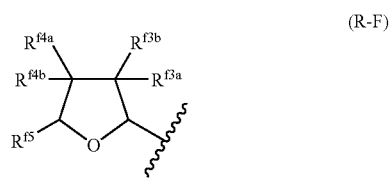
(R-F)

(wherein $R^{f3a}$, $R^{f3b}$, $R^{f4a}$ and $R^{f4b}$ are the same as or different from each other and each represents hydrogen, methyl, hydroxy, methoxy or acetoxy; and $R^{f5}$ represents methyl or ethyl)}, provided that (Restricted clause 1) when the above-mentioned compound is represented by the following formula (2):

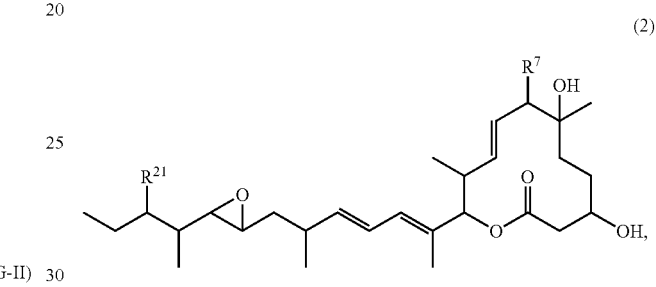
(2)

at least one of $R^7$ and $R^{21}$ is hydroxy, acetoxy or methoxy;

(Restricted clause 2) when the above-mentioned compound is represented by the following formula (3):

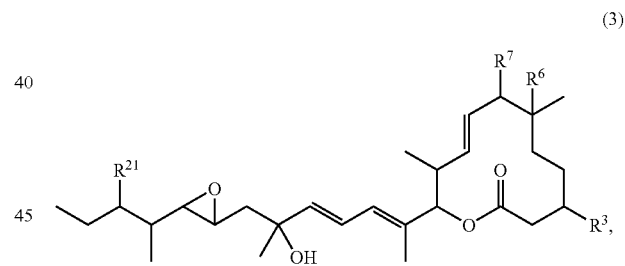
(3)

$R^7$ is hydroxy or acetoxy; and $R^3$, $R^6$ and $R^{21}$ are OH; and (Restricted clause 3) a compound represented by the formula (4) is excluded

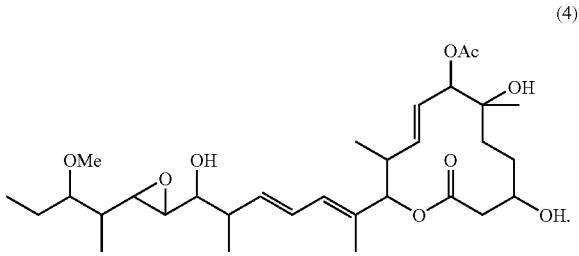
(4)

2. A compound represented by the formula (6), a pharmacologically acceptable salt thereof or a hydrate of them (6)

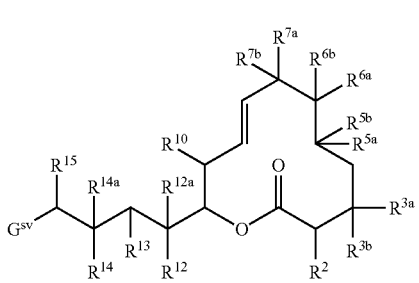

In the formula (6), $R^2$, $R^{3a}$, $R^{3b}$, $R^{5a}$, $R^{5b}$, $R^{6a}$, $R^{6b}$, $R^{7a}$, $R^{7b}$, $R^{10}$, $R^{12}$ and $R^{14}$ have the same meanings as the definitions of the formula 5 (in the claim 1);

$R^{12a}$ and $R^{13}$ (1) each represents hydrogen, or (2) are bound together to <1> form a single bond and represent

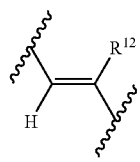

or <2> form epoxy and represent

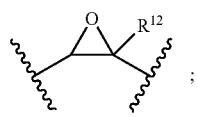

$R^{14a}$ and $R^{15}$ (1) each represents hydrogen, or (2) are bound together to <1> form a single bond and represent

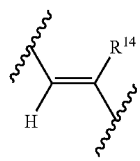

or <2> form epoxy and represent

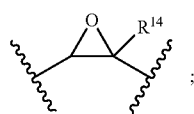

provided that (1) when $R^{12a}$ and $R^{13}$ are bound together to form a single bond in the formula (6), $R^{14a}$ and $R^{15}$ <1> are each hydrogen or <2> are bound together to be an epoxy; and (2) when $R^{14a}$ and $R^{15}$ are bound together to form a single bond, $R^{12a}$ and $R^{13}$ <1> are each hydrogen or <2> are bound together to be an epoxy; and $G^{sv}$ (1) has the same meaning as the definition of G in the formula 5, or (2) represents

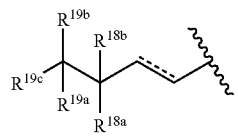

(wherein ===represents a single bond or a double bond; $R^{18a}$, $R^{18b}$, $R^{19a}$ and $R^{19b}$ have the same meanings as the definitions in the formula (5); $R^{19c}$ is hydrogen or $C_{1-4}$ alkyl).

3. A compound represented by the formula (7), a pharmacologically acceptable salt thereof or a hydrate of them (7)

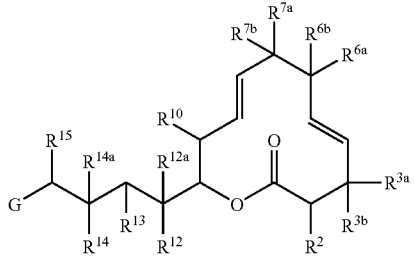

In the formula (7), $R^2$, $R^{3a}$, $R^{3b}$, $R^{6a}$, $R^{6b}$, $R^{7a}$, $R^{7b}$, $R^{10}$, $R^{12}$, $R^{14}$ And G have the same meanings as the definitions in the formula 5 of the claim 1; $R^{12a}$ and $R^{13}$ (1) each represents hydrogen or (2) are bound together to <1> form a single bond and represent

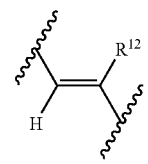

or <2> form epoxy and represent

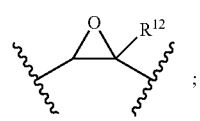

and $R^{14a}$ and $R^{15}$ (1) each represents hydrogen or (2) are bound together to <1> form a single bond and represent

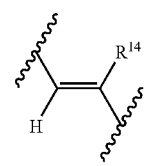

or <2> form epoxy and represent

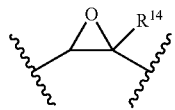

4. A compound represented by the formula (8), a pharmacologically acceptable salt thereof or a hydrate of them

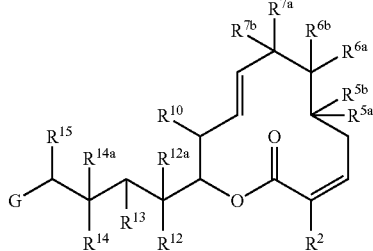
(8)

In the formula (8), $R^2$, $R^{5a}$, $R^{5b}$, $R^{6a}$, $R^{6b}$, $R^{7a}$, $R^{7b}$, $R^{10}$, $R^{12}$, $R^{14}$ And G have the same meanings as the definitions in the formula 5 of the claim 1; and $R^{12a}$, $R^{13}$, $R^{14a}$ and $R^{15}$ have the same meanings as the definitions in the formula 7 of the claim 3.

5. A compound represented by the formula (9), a pharmacologically acceptable salt thereof or a hydrate of them

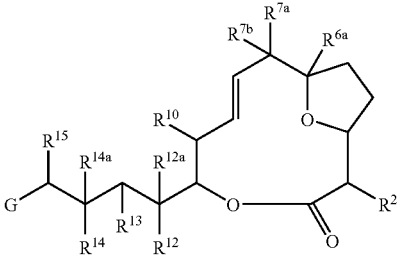

In the formula (9), $R^2$, $R^{6a}$, $R^{6b}$, $R^{7a}$, $R^{7b}$, $R^{10}$, $R^{12}$, $R^{14}$ and G have the same meanings as the definitions in the formula 5 of the claim 1; and $R^{12a}$, $R^{13}$, $R^{14a}$ and $R^{15}$ have the same meanings as the definitions in the formula 7 of the claim 3.

6. A compound represented by the formula (10), a pharmacologically acceptable salt thereof or a hydrate of them

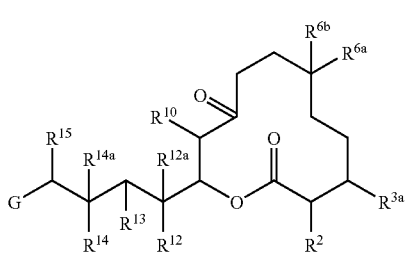
(10)

In the formula (10), $R^2$, $R^{3a}$, $R^{6a}$, $R^{6b}$, $R^{10}$, $R^{12}$, $R^{14}$ and G have the same meanings as the definitions in the formula 5 of the claim 1; and $R^{12a}$, $R^{13}$, $R^{14a}$ and $R^{15}$ have the same meanings as the definitions in the formula 7 of the claim 3.

7. A compound represented by the formula (11), a pharmacologically acceptable salt thereof or a hydrate of them

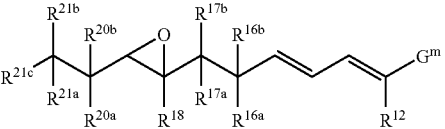
(11)

In the formula (11), $R^{12}$, $R^{16a}$, $R^{16b}$, $R^{17a}$, $R^{17b}$, $R^{20a}$, $R^{20b}$, $R^{21a}$, $R^{21b}$ and $R^{21c}$ have the same meanings as the definitions in the formula 5 of the claim 1; $R^{18}$ represents hydrogen or methyl; and $G^M$ is represented by (1)

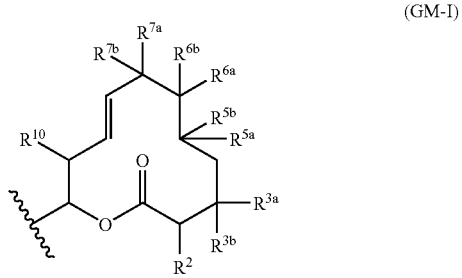
(GM-I)

(wherein $R^2$, $R^{3a}$, $R^{3b}$, $R^{5a}$, $R^{5b}$, $R^{6a}$, $R^{6b}$, $R^{7a}$, $R^{7b}$ and $R^{10}$ have the same meanings as the definitions in the formula 5 of the claim 1, (2)

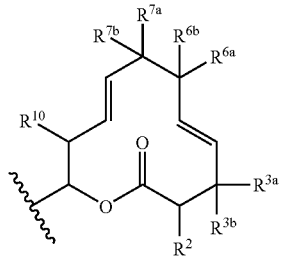
(GM-II)

(wherein $R^2$, $R^{3a}$, $R^{3b}$, $R^{6a}$, $R^{6b}$, $R^{7a}$, $R^{7b}$ and $R^{10}$ have the same meanings as the definitions in the formula 7 of the claim 3), (3)

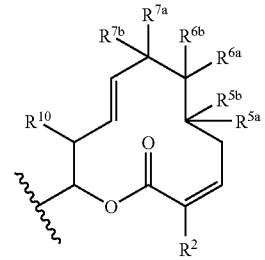
(GM-III)

(wherein $R^2$, $R^{5a}$, $R^{5b}$, $R^{6a}$, $R^{6b}$, $R^{7a}$, $R^{7b}$ and $R^{10}$ have the same the definitions in the formula 8 of the claim 4), (4)

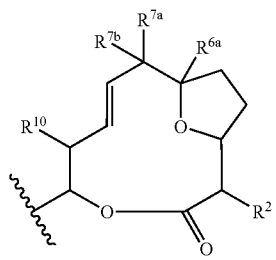

(wherein $R^2$, $R^{6a}$, $R^{7a}$, $R^{7b}$ and $R^{10}$ have the same meanings as the definitions in the formula 9 of the claim 5) or (5)

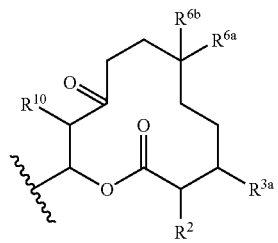

(GM-V)

(wherein $R^2$, $R^{3a}$, $R^{6a}$, $R^{6b}$ and $R^{10}$ have the same meanings as the definitions in the formula 10 of the claim 6), provided that the restricted clauses 1, 2 and 3 according to claim 1 are included.

8. A compound represented by the formula (12), a pharmacologically acceptable salt thereof or a hydrate of them

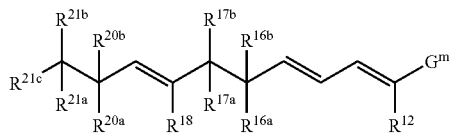

(12)

In the formula (12), $R^{12}$, $R^{16a}$, $R^{16b}$, $R^{17}$, $R^{17a}$, $R^{17b}$, $R^{20a}$, $R^{20b}$, $R^{21a}$, $R^{21b}$ and $R^{21c}$ have the same meanings as the definitions in the formula 5 of claim 1; and $R^{18}$ and $G^M$ have the same meanings as the definitions in the formula 11 of claim 7.

9. A compound represented by the formula (13), a pharmacologically acceptable salt thereof or a hydrate of them

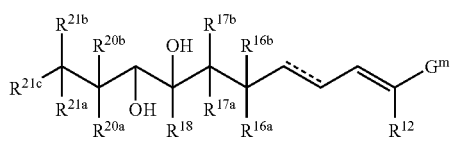

(13)

In the formula (13), ====represents a single bond or a double bond; $R^{12}$, $R^{16a}$, $R^{16b}$, $R^{17a}$, $R^{17b}$, $R^{20a}$, $R^{20b}$, $R^{21a}$, $R^{21b}$ and $R^{21c}$ have the same meanings as the definitions in the formula 5 of claim 1; and $R^{18}$ and $G^M$ have the same meanings as the definitions in the formula 11 of claim 7.

10. A compound represented by the formula (14), a pharmacologically acceptable salt thereof or a hydrate of them

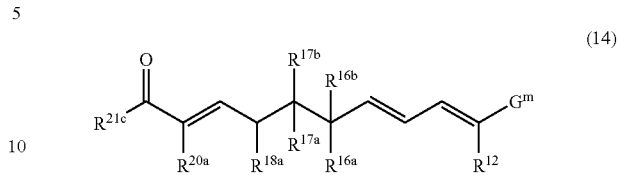

(14)

In the formula (14), $R^{12}$, $R^{16a}$, $R^{16b}$, $R^{17a}$, $R^{17b}$, $R^{18a}$, $R^{20a}$, $R^{20b}$ And $R^{21c}$ have the same meanings as the definitions in the formula 5 of claim 1; and $G^M$ has the same meaning as the definition in the formula 11 of claim 7.

11. A compound represented by the formula (H-I), a pharmacologically acceptable salt thereof or a hydrate of them

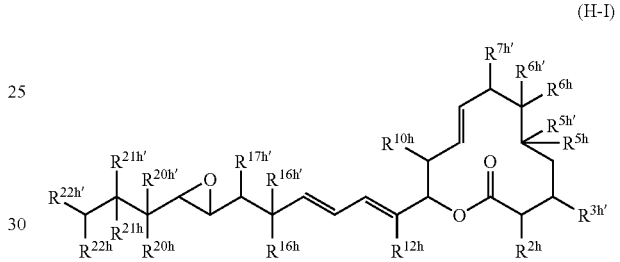

(H-I)

In the formula (H-I), $R^{2h}$, $R^{5h}$, $R^{6h}$, $R^{10h}$, $R^{12h}$, $R^{16h}$, $R^{20h}$, $R^{21h}$ And $R^{22h}$ are the same as or different from each other and each represent
  (1) hydrogen,
  (2) methyl,
  (3) hydroxymethyl or
  (4) $C_{2-8}$ acyloxymethyl;
$R^{3h'}$, $R^{5h'}$, $R^{6h'}$, $R^{7h'}$, $R^{16h'}$, $R^{17h'}$, $R^{20h'}$, $R^{21h'}$ and $R^{22h'}$ are the same as or different from each other and each represents
  (1) hydrogen,
  (2) hydroxy,
  (3) methoxy or
  (4) $C_{2-8}$ acyloxy;
$R^{5h}$ and $R^{5h'}$ may be bound together to form a ketone structure (═O); $R^{21h}$ and $R^{21h'}$ may be bound together to form a ketone structure (═O); and $R^{6h}$ and $R^{6h'}$ may be bound together to form a spirooxyrane structure, provided that the restricted clauses 1, 2 and 3 According to claim 1 are included.

12. A compound represented by the formula (H-1) according to claim 11, a pharmacologically acceptable salt thereof or a hydrate of them, which is selected from the group consisting of a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen and $R^{22h}$ is methyl;
  a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, both of $R^{21h}$ and $R^{21h'}$ are bound together to form a ketone structure, $R^{22h'}$ is hydrogen and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydroxy, $R^{17h'}$ is hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydroxy, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is hydroxy, all of $R^{10h}$, $R^{12h}$ and $R^{16h}$ are methyl, $R^{16'}$ is hydroxy, $R^{17h'}$ is hydrogen $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydroxy, $R^{21h'}$ s hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is propanoyloxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, R is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, and all of $R^{21h}$, $R^{22h'}$ and $R^{22h}$ are hydrogen;

a compound in which $R^{2h}$ is hydrogen, $R^{3h'}$ is hydroxy, $R^{5h}$ is hydrogen, $R^{5h'}$ is hydroxy, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h}$ is hydrogen, $R^{20h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, $R^{5h}$ is hydrogen, $R^{5h'}$ is acetoxy, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is acetoxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is acetoxymethyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydrogen, $R^{17h'}$ are hydroxy, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, both of $R^{20h}$ and $R^{20h'}$ are hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, both of $R^{10h}$ and $R^{12h}$ are methyl, all of $R^{16h}$, $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, both of $R^{10h}$ and $R^{16h}$ are methyl, all of $R^{12h}$, $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, both of $R^{12h}$ and $R^{16h}$ are methyl, all of $R^{10h}$, $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is acetoxymethyl, $R^{6h'}$ is hydroxy, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h}$ and $R^{21h'}$ are bound together to form a ketone structure, $R^{22h'}$ is hydrogen, and $R^{22h}$ is methyl;

a compound in which $R^{2h}$ is hydrogen, $R^{3h'}$ is hydroxy, all of $R^{5h}$, $R^{5h'}$, $R^{6h}$ are hydrogen, $R^{6h'}$ is acetoxy, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is methyl, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, $R^{5h}$ is hydrogen, $R^{5h'}$ is hydroxy, $R^{6h}$ is methyl, $R^{6h'}$ is hydrogen, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, all of $R^{5h}$, $R^{5h'}$, $R^{6h}$ and $R^{6h'}$ are hydrogen, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ And $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ and $R^{6h'}$ are bound together to form a spirooxyrane structure, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ and $R^{6h'}$ are bound together to form a spirooxyrane structure, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is acetoxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydroxy, $R^{17h'}$ is hydrogen, $R^{20h}$ is methyl, $R^{20h'}$ is hydrogen, $R^{21h}$ and $R^{21h'}$ are bound together to form a ketone structure, $R^{22h'}$ is hydrogen, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydroxy, and $R^{22}$ is methyl;

a compound in which $R^{2h}$ is hydrogen, $R^{3h'}$ is hydroxy, $R^{5h}$ is hydrogen, $R^{5h'}$ is hydroxy, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h}$ is hydrogen, both of $R^{21h'}$ and $R^{22h'}$ are hydroxy, and $R^{22h}$ is methyl;

a compound in which $R^{2h}$ is hydrogen, $R^{3h'}$ is hydroxy, $R^{5h}$ is hydrogen, $R^{5h'}$ is hydroxy, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h}$ is hydrogen, both of $R^{21h'}$ and $R^{22h'}$ are hydroxy, and $R^{22h}$ is methyl;

a compound in which $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is hydroxy, both of $R^{10h}$ and $R^{16h}$ are methyl, all of $R^{12h}$, $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl; and a compound in which $R^{2h}$ is hydrogen, $R^{3h'}$ is hydroxy, both of $R^{5h}$ and $R^{5h'}$ are bound together to form a ketone structure, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl.

13. A compound represented by the formula (H-II), a pharmacologically acceptable salt thereof or a hydrate of them

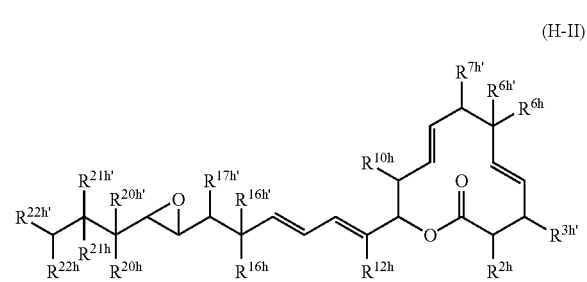

(H-II)

In the formula (H-II), $R^{2h}$, $R^{6h}$, $R^{10h}$, $R^{12h}$, $R^{16h}$, $R^{20h}$, $R^{21h}$ and $R^{22h}$ are the same as or different from each other and each represents
 (1) hydrogen,
 (2) methyl,
 (3) hydroxymethyl or
 (4) $C_{2-8}$ acyloxymethyl;
$R^{3h'}$, $R^{6h'}$, $R^{7h'}$, $R^{16h'}$, $R^{17h'}$, $R^{20h'}$, $R^{21h'}$ and $R^{22h'}$ are the same as or different from each other and each represents
 (1) hydrogen,
 (2) hydroxy,
 (3) methoxy or
 (4) $C_{2-8}$ acyloxy;
further, $R^{21h}$ and $R^{21h'}$ may be bound together to form a ketone structure (=O); and further, $R^{6h}$ and $R^{6h'}$ may be bound together to form a spirooxyrane structure.

14. A compound represented by the formula (H-II) according to claim 13, a pharmacologically acceptable salt thereof or a hydrate of them, which is selected from the group consisting of a compound in which $R^{2h}$ is hydrogen, $R^{3h'}$ is hydroxy, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ And $R^{22h'}$ are hydrogen and $R^{22h}$ is methyl;

a compound in which $R^{2h}$ is hydrogen, $R^{3h'}$ is hydroxy, $R^{6h}$ is methyl, $R^{6h'}$ is hydroxy, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, both of $R^{21h}$ and $R^{21h'}$ are bound together to form a ketone structure, $R^{22h'}$ is hydrogen, and $R^{22h}$ is methyl;

a compound in which $R^{2h}$ is hydrogen, $R^{3h'}$ is hydroxy, $R^{6h}$ And $R^{6h'}$ are bound together to form a spirooxyrane structure, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl;

a compound in which $R^{2h}$ is hydrogen, $R^{3h'}$ is hydroxy, $R^{6h}$ is methyl, $R^{6h'}$ is acetoxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h}$ are hydrogen, and $R^{22h}$ is methyl; and a compound in which $R^{2h}$ is hydrogen, $R^{3h'}$ is hydroxy, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydrogen, $R^{17h'}$ is hydroxy, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl.

15. A compound represented by the formula (H-III), a pharmacologically acceptable salt thereof or a hydrate of them

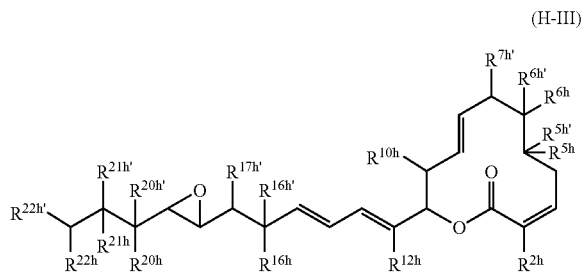

(H-III)

In the formula, $R^{2h}$, $R^{5h}$, $R^{6h}$, $R^{10h}$, $R^{12h}$, $R^{16h}$, $R^{20h}$, $R^{21h}$ and $R^{22h}$ are the same as or different from each other and each represents
(1) hydrogen,
(2) methyl,
(3) hydroxymethyl or
(4) $C_{2-8}$ acyloxymethyl;

$R^{5h'}$, $R^{6h'}$, $R^{7h'}$, $R^{16h'}$, $R^{17h'}$, $R^{20h'}$, $R^{21h'}$ and $R^{22h'}$ are the same as or different from each other and each represents
(1) hydrogen,
(2) hydroxy,
(3) methoxy or
(4) $C_{2-8}$ acyloxy;
further, $R^{5h}$ and $R^{5h'}$ may be bound together to form a ketone structure (=O); further, $R^{21h}$ and $R^{21h'}$ may be bound together to form a ketone structure (=O); further, $R^{6h}$ and $R^{6h'}$ may be bound together to form a spirooxyrane structure.

16. A compound represented by the formula (H-III) according to claim 15, a pharmacologically acceptable salt thereof or a hydrate of them, which is selected from the group consisting of a compound in which $R^{2h}$ is hydrogen, both of $R^{5h'}$ and $R^{5h'}$ are hydrogen, $R^{6h}$ is methyl, $R^{6h'}$ is hydroxy, $R^{7h'}$ is hydroxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen and $R^{22h}$ is methyl;

a compound in which $R^{2h}$ is hydrogen, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is acetoxy, both of $R^{21h}$ And $R^{22h'}$ are hydrogen and $R^{22h}$ is methyl; and a compound in which $R^{2h}$ is hydrogen, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ And $R^{22h'}$ are hydrogen and $R^{22h}$ is methyl.

17. A compound represented by the formula (H-IV), a pharmacologically acceptable salt thereof or a hydrate of them

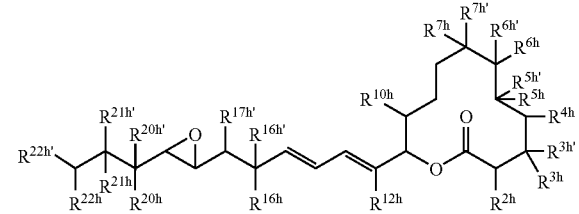

(H-V)

In the formula, $R^{2h}$, $R^{3h}$, $R^{4h}$, $R^{5h}$, $R^{6h}$, $R^{7h}$, $R^{10h}$, $R^{12h}$, $R^{16h}$, $R^{20h}$, $R^{21h}$ and $R^{22h}$ are the same as or different from each other and each represents
(1) hydrogen,
(2) methyl,
(3) hydroxymethyl or
(4) $C_{2-8}$ acyloxymethyl;

$R^{3h'}$, $R^{5h'}$, $R^{6h'}$, $R^{7h'}$, $R^{16h'}$, $R^{17h'}$, $R^{20h'}$, $R^{21h'}$ and $R^{22h'}$ are the same as or different from each other and each represents
(5) hydrogen,
(6) hydroxy,
(7) methoxy or
(8) $C_{2-8}$ acyloxy;
further, $R^{3h}$ and $R^{3h'}$ may be bound together to form a ketone structure (=O); further, $R^{5h}$ and $R^{5h'}$ may be bound together to form a ketone structure (=O); further, further, $R^{7h}$ and $R^{7h'}$ may be bound together to form a ketone structure (=O); $R^{21h}$ and $R^{21h'}$ may be bound together to form a ketone structure (=O); further, $R^{4h}$ and $R^{5h}$ may form a single bond to represent

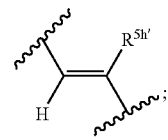

and
further, $R^{6h}$ and $R^{6h'}$ may be bound together to form a spirooxyrane structure, provided that the restricted clauses 1, 2 and 3 According to claim 1 are included.

18. The compound represented by the formula (H-IV) according to claim 17, a pharmacologically acceptable salt thereof or a hydrate of them, which is selected from the group consisting of a compound in which $R^{2h}$ is hydrogen, $R^{3h}$ and $R^{3h'}$ are bound together to form a ketone structure, $R^{4h}$ and $R^{5h}$ form a single bond to represent

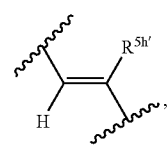

$R^{5h'}$ is hydrogen, $R^{6h}$ is methyl, $R^{6h'}$ is hydroxy, $R^{7h}$ is hydrogen, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ And $R^{22h'}$ are hydrogen, and $R^{22h}$ is methyl; and a compound in which $R^{2h}$ is hydrogen, $R^{3h}$ is hydrogen, $R^{3h'}$ is hydroxy, all of $R^{4h}$, $R^{5h}$ and $R^{5h'}$ are hydrogen, $R^{6h}$ is methyl, $R^{6h'}$ is hydroxy, $R^{7h}$ and $R^{7h'}$ are bound together to form a ketone structure, all of $R^{10h}$, $R^{12h}$ and $R^{16h}$ are methyl, both of $R^{16h'}$ and $R^{17h'}$ are hydrogen, $R^{20h}$ is methyl, $R^{20h'}$ is hydrogen, $R^{21h'}$ is hydroxy, both of $R^{21h}$ and $R^{22h'}$ are hydrogen, and $R^{22h}$ is methyl.

19. A compound represented by the formula (H-V), a pharmacologically acceptable salt thereof or a hydrate of them

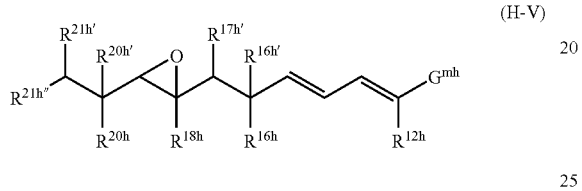
(H-V)

In the formula (H-V), $R^{12h}$, $R^{16h}$, $R^{16h'}$, $R^{17h'}$, $R^{20h}$, $R^{20h'}$ and $R^{21h'}$ have the same meanings as the definitions in the formula (H-I) of claim 11; $R^{18h}$ represents hydrogen or methyl; $R^{21h''}$ represents hydrogen, methyl or ethyl; and $G^{mh}$ is represented by the formula (1):

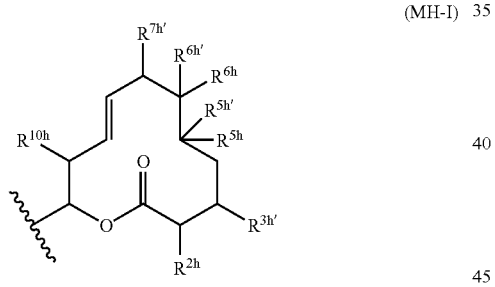
(MH-I)

(wherein $R^{2h}$, $R^{3h'}$, $R^{5h}$, $R^{5h'}$, $R^{6h}$, $R^{6h'}$, $R^{7h'}$ and $R^{10h}$ have the same meanings as the definitions in the formula (H-I) of claim 11), the formula (2):

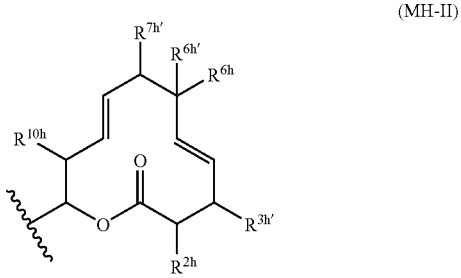
(MH-II)

(wherein $R^{2h}$, $R^{3h'}$, $R^{6h}$, $R^{6h'}$, $R^{7h'}$ and $R^{10h}$ have the same meanings as the definitions in the formula (H-II) of claim 13), the formula (3):

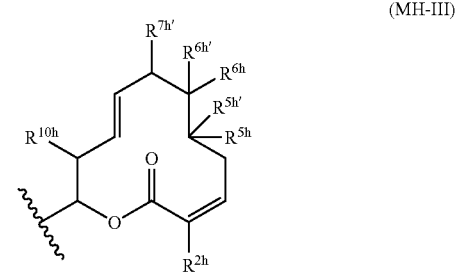
(MH-III)

(wherein $R^{2h}$, $R^{5h}$, $R^{5h'}$, $R^{6h}$, $R^{6h'}$, $R^{7h'}$ and $R^{10h}$ have the same meanings as the definitions in the formula (H-III) of claim 15), the formula (4):

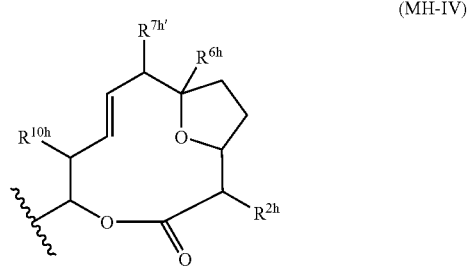
(MH-IV)

(wherein $R^{2h}$, $R^{6h}$, $R^{7h'}$ and $R^{10h}$ have the same meanings as the definitions in the formula (H-I) of claim 11), or the formula (5):

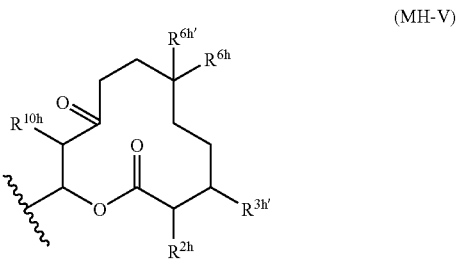
(MH-V)

(wherein $R^{2h}$, $R^{3h'}$, $R^{6h}$, $R^{6h'}$ and $R^{10h}$ have the same meanings as the definitions in the formula (H-I) of claim 11), provided that the restricted clauses 1, 2 and 3 According to claim 1 are included.

20. A compound represented by the formula (H-V) according to claim 19, a pharmacologically acceptable salt thereof or a hydrate of them, which is selected from the group consisting of a compound in which $G^{mh}$ is represented by the formula (MH-I), $R^{2h}$ is hydrogen, $R^{3h'}$ is hydroxy, both of $R^{5h}$ And $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, all of $R^{16h'}$, $R^{17h'}$ and $R^{18h}$ are hydrogen, all of $R^{20h}$, $R^{21h'}$ and $R^{21h''}$ are hydrogen and $R^{20h'}$ is hydroxy;

a compound in which $G^{mh}$ is represented by the formula (MH-I), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydrogen, $R^{17h'}$ is hydroxy, and all of $R^{18h}$, $R^{20h}$, $R^{20h'}$, $R^{21h'}$ and $R^{21h''}$ are hydrogen;

a compound in which $G^{mh}$ is represented by the formula (MH-I), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydroxy, and all of $R^{17h'}R^{18h}$, $R^{20h}$, $R^{20h'}$, $R^{21h'}$ and $R^{21h''}$ are hydrogen;

a compound in which $G^{mh}$ is represented by the formula (MH-I), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, $R^{16h'}$ is hydrogen, $R^{17h'}$ is hydroxy, $R^{18h}$ is methyl, and all of $R^{20h}$, $R^{20h'}$, $R^{21h'}$ and $R^{21h''}$ are hydrogen;

a compound in which $G^{mh}$ is represented by the formula (MH-V), $R^{2h}$ is hydrogen, $R^{3h'}$ is hydroxy, $R^{6h}$ is methyl, $R^{6h'}$ is hydroxy, all of $R^{10h}$, $R^{12h}$ and $R^{16h}$ are methyl, all of $R^{16h'}$, $R^{17h'}R^{18h}$ and $R^{20h'}$ are hydrogen, $R^{20h}$ is methyl, $R^{21h'}$ is hydroxy, and $R^{21h''}$ is ethyl.

21. A compound represented by the formula (H-VI), a pharmacologically acceptable salt thereof or a hydrate of them

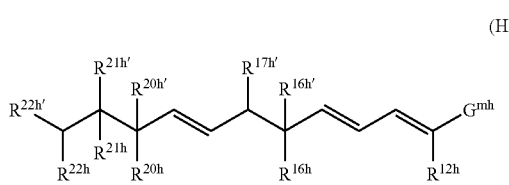

(H-VI)

In the formula, $R^{12h}$, $R^{16h}$, $R^{16h'}$, $R^{17h'}$, $R^{20h}$, $R^{20h'}$, $R^{21h}$, $R^{21h'}$, $R^{22h}$ and $R^{22h'}$ have the same meanings as the definitions in the formula (H-I) of claim 11; $G^{mh}$ has the same meaning as the definition in the formula (H-V) of claim 19.

22. A compound represented by the formula (H-VI) according to claim 21, a pharmacologically acceptable salt thereof or a hydrate of them, which is selected from the group consisting of a compound in which $G^{mh}$ is represented by the formula (MH-I), $R^{2h}$ is hydrogen, $R^{3h'}$ is hydroxy, both of $R^{5h}$ And $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, both of $R^{20h'}$ and $R^{21h}$ are hydrogen, both of $R^{21h'}$ and $R^{22h'}$ are hydroxy, and $R^{22h}$ is methyl; and a compound in which $G^{mh}$ is represented by the formula (MH-I), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, all of $R^{20h'}$, $R^{21h}$ and $R^{22h'}$ are hydrogen, $R^{21h'}$ is hydroxy, and $R^{22h}$ is methyl.

23. A compound represented by the formula (H-VII), a pharmacologically acceptable salt thereof or a hydrate of them

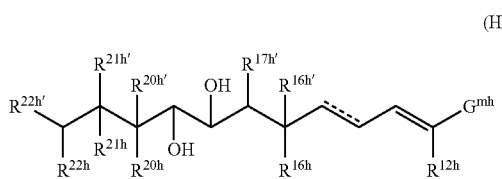

(H-VII)

In the formula, $G^{mh}$ has the same meaning as the definition in the formula (H-V) of claim 19; ===represents a single bond or a double bond; and $R^{12h}$, $R^{16h}$, $R^{16h'}$, $R^{17h'}$, $R^{20h}$, $R^{20h'}$, $R^{21h}$, $R^{21h'}$, $R^{22h}$ and $R^{22h'}$ have the same meanings as the definitions in the formula (H-I) of claim 11.

24. A compound represented by the formula (H-VII), a pharmacologically acceptable salt thereof or a hydrate of them, which is selected from the group consisting of a compound in which $G^{mh}$ is represented by the formula (MH-I), ===represents a double bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, all of $R^{20h'}$, $R^{21h}$ and $R^{22h'}$ are hydrogen, $R^{21h'}$ is hydroxy, and $R^{22h}$ is methyl;

a compound in which $G^{mh}$ is represented by the formula (MH-I), ===represents a single bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, all of $R^{20h'}$, $R^{21h}$ And $R^{22h'}$ are hydrogen, $R^{21h'}$ is hydroxy, and $R^{22h}$ is methyl; and a compound in which $G^{mh}$ is represented by the formula (MH-II), ===represents a double bond, $R^{2h}$ is hydrogen, $R^{3h'}$ is hydroxy, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{20h}$ is methyl, all of $R^{20h'}$, $R^{21h}$ and $R^{22h'}$ are hydrogen, $R^{21h'}$ hydroxy, and $R^{22h}$ is methyl.

25. A compound represented by the formula (H-VIII), a pharmacologically acceptable salt thereof or a hydrate of them

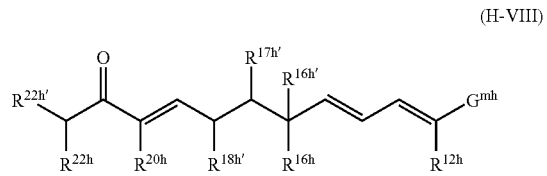

(H-VIII)

In the formula, $G^{mh}$, $R^{12h}$, $R^{16h}$, $R^{16h'}$, $R^{17h'}$, $R^{20h}$, $R^{22h}$ and $R^{22h'}$ have the same meanings as the formula (H-I) of claim 11; and $R^{18h'}$ represents hydrogen or hydroxy.

26. A compound, a pharmacologically acceptable salt thereof or a hydrate of them in the formula (H-VIII) according to claim 25, which is selected from the group consisting of a compound in which $G^{mh}$ is represented by the formula (MH-I), $R^{2h}$ is hydrogen, $R^{3h'}$ is hydroxy, both of $R^{5h}$ And $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{18h'}$ is hydroxy, $R^{20h}$ is methyl, $R^{22h'}$ is hydroxy, and $R^{22h}$ is methyl; and a compound in which $G^{mh}$ is represented by the formula (MH-I), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{16h'}$ and $R^{17h'}$ are hydrogen, $R^{18h'}$ is hydroxy, $R^{20h}$ is methyl, $R^{22h'}$ are hydrogen, and $R^{22h}$ is methyl.

27. A compound represented by the formula (H-IX), a pharmacologically acceptable salt thereof or a hydrate of them (H-IX)

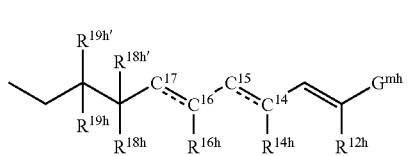

In the formula, $G^{mh}$ has the same meaning as the definition in the formula (H-V) of claim 19; $C^{14}$====$C^{15}$ and $C^{16}$====$C^{17}$ are the same as or different from each other and each represents a single bond or a double bond; $R^{12h}$, $R^{16h}$ and $R^{18h}$ have the same meanings as the definition in the formula (H-V) of claim 20; $R^{14h}$ represents hydrogen or methyl; $R^{18h'}$ represents hydrogen or hydroxy; $R^{19h}$ And $R^{19h'}$ are (1) the same as or different from each other and each represents hydrogen, methyl or hydroxy, or (2) $R^{19h}$ and $R^{19h'}$ are bound together to represent a ketone structure (==O).

28. A compound represented by the formula (H-IX) according to claim 27, a pharmacologically acceptable salt thereof or a hydrate of them, which is selected from the group consisting of a compound in which $G^{mh}$ is represented by the formula (MH-I), $C^{14}$====$C^{15}$ is a double bond, $C^{16}$====$C^{17}$ is a single bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, all of $R^{14h}$, $R^{18h}$ and $R^{19h}$ are hydrogen, and both of $R^{18h'}$ and $R^{19h'}$ are hydroxy;

a compound in which $G^{mh}$ is represented by the formula (MH-I), $C^{14}$====$C^{15}$ is a single bond, $C^{16}$====$C^{17}$ is a double bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, both of $R^{10h}$ and $R^{14h}$ are methyl, both of $R^{12h}$ and $R^{16h}$ are hydrogen, $R^{18h}$ is methyl, $R^{18h'}$ is hydroxy, and $R^{19h}$ and $R^{19h'}$ are bound together to form a ketone structure (==O); and a compound in which $G^{mh}$ is represented by the formula (MH-I), $C^{14}$====$C^{15}$ is a single bond, $C^{16}$====$C^{17}$ is a double bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, both of $R^{10h}$ and $R^{14h}$ are methyl, both of $R^{12h}$ and $R^{16h}$ are hydrogen, $R^{18h}$ is methyl, $R^{18h'}$ is hydroxy, $R^{19h}$ is hydrogen, and $R^{19h'}$ is hydroxy.

29. A compound represented by the formula (H-X), a pharmacologically acceptable salt thereof or a hydrate of them (H-X)

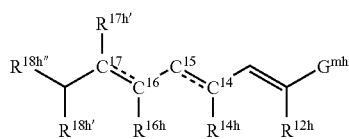

In the formula, $G^{mh}$, $R^{16h}$ and $R^{17h'}$ have the same meanings as the definitions in the formula (H-V) of claim 19; $R^{14h}$ represents hydrogen or methyl; $C^{14}$====$C^{15}$ and $C^{16}$====$C^{17}$ are the same as or different from each other and each represents a single bond or a double bond; $R^{18h'}$ is hydrogen or hydroxy; and $R^{18h''}$ represents (1) methyl or (2) the formula (R-F).

30. A compound, a pharmacologically acceptable salt thereof or a hydrate of them in the formula (H-X) according to claim 29, which is selected from the group consisting of a compound in which $G^{mh}$ is represented by the formula (MH-I), $R^{18h''}$ is represented by the formula (R-F), $C^{14}$====$C^{15}$ is a double bond, $C^{16}$====$C^{17}$ is a single bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{14h}$ and $R^{17h'}$ are hydrogen, $R^{18h'}$ is hydroxy, both of $R^{f3a}$ and $R^{f5}$ are methyl, both of $R^{f3b}$ and $R^{f4b}$ are hydrogen, and $R^{f4b}$ is hydroxy;

a compound in which $G^{mh}$ is represented by the formula (MH-I), $C^{14}$====$C^{15}$ is a single bond, $C^{16}$====$C^{17}$ is a double bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, both of $R^{10h}$ and $R^{14h}$ are methyl, all of $R^{12h}$, $R^{16h}$ and $R^{17h'}$ are hydrogen, $R^{18h'}$ is hydroxy, and $R^{18h''}$ is methyl; and a compound in which $G^{mh}$ is represented by the formula (MH-I), $C^{14}$====$C^{15}$ is a double bond, $C^{16}$====$C^{17}$ is a single bond, $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{14h}$ and $R^{18h'}$ are hydrogen, $R^{17h'}$ is hydroxy, and $R^{18h''}$ is methyl.

31. A compound represented by the formula (H-XI), a pharmacologically acceptable salt thereof or a hydrate of them (H-XI)

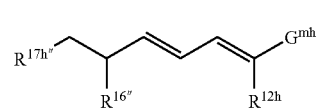

In the formula, $G^{mh}$ and $R^{12h}$ have the same meanings as the definitions in the formula (H-V) of claim 19; $R^{16h''}$ represents hydrogen, methyl or hydroxy; and $R^{17h''}$ represents (1) hydrogen or (2) the formula (R-F).

32. A compound represented by the formula (H-XI) according to claim 31, a pharmacologically acceptable salt thereof or a hydrate of them, which is selected from the group consisting of a compound in which $G^{mh}$ is represented by the formula (MH-I), $R^{7h''}$ is represented by the formula (R-F), $R^{2h}$ is hydrogen, $R^{3h'}$ is hydroxy, both of $R^{5h}$ and $R^{5h'}$ are hydrogen, $R^{6h}$ is methyl, $R^{6h'}$ is hydroxy, $R^{7h'}$ is acetoxy, all of $R^{10h}$, $R^{12h}$ and $R^{16h}$ are methyl, both of $R^{f3a}$ and $R^{f4a}$ are hydroxy, $R^{f3b}$ is hydrogen, $R^{f4b}$ is methyl, and $R^{f5}$ is ethyl; and a compound in which $G^{mh}$ is represented by the formula (MH-I), $R^{2h}$ is hydrogen, $R^{3h'}$ is hydroxy, all of $R^{5h}$, $R^{5h'}$ and $R^{6h'}$ are hydrogen, $R^{6h}$ is methyl, $R^{7h'}$ is acetoxy, both of $R^{10h}$ and $R^{12h}$ are methyl, $R^{16h''}$ is hydroxy, and $R^{7h''}$ is hydrogen.

33. A compound represented by the formula (15), a pharmacologically acceptable salt thereof or a hydrate of them (15)

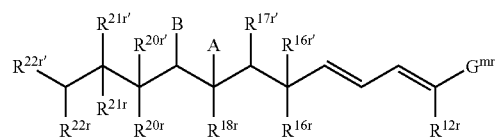

In the formula (15), $G^{mr}$ is represented by the formula (1):

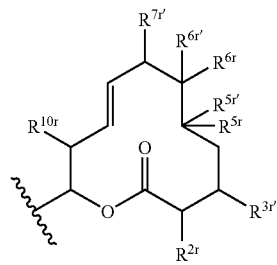
(MD-1)

(wherein $R^{2r}$, $R^{3r}$, $R^{5r}$, $R^{5r'}$, $R^{6r}$, $R^{6r'}$, $R^{7r'}$ and $R^{10r}$ are the same as or different from each other and each represents
1) hydrogen,
2) methyl which may have substituents,
3) —$OR^H$ (wherein $R^H$ is <1> hydrogen, <2> methyl or <3> acetyl),
4) —$OR^D$ (wherein $R^D$ represents
  <1> $C_{1-22}$ alkyl (provided that in case of methyl, it has always substituents),
  <2> —$CH_2Ar$,
  <3> $C_{3-22}$ acyl,
  <4> unsaturated $C_{3-22}$ acyl,
  <5> —$COR^{CO}$,
  <6> $C_{1-22}$ alkylsulfonyl,
  <7> benzenesulfonyl or
  <8> —$SiR^{s1}R^{s2}R^{s3}$, each of which may have substituents)
5) halogen or
6) —$R^M$—$NR^{N1}R^{N2}$ (Ar, $R^{CO}$, $R^{s1}$, $R^{s2}$, $R^{s3}$, $R^M$, $R^{N1}$ and $R^{N2}$ have the same meanings as the definitions of the formula 5 of claim 1), further, $R^{5r}$ and $R^{5r'}$ may be bound together to represent a ketone structure;
further, $R^{6r}$ or $R^{6r'}$ may be bound together to represent a spirooxyrane structure or an exo-methylene structure;
further, either of $R^{6r}$ or $R^{6r'}$, and $R^{7r'}$ may be bound together to represent a 1,3-dioxolane ring), the formula (2):

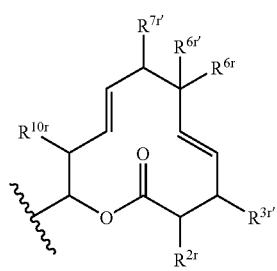
(MD-II)

(wherein $R^{2r}$, $R^{3r'}$, $R^{6r}$, $R^{6r'}$, $R^{7r'}$ and $R^{10r}$ have the same meanings as the above-mentioned definition), the formula (3):

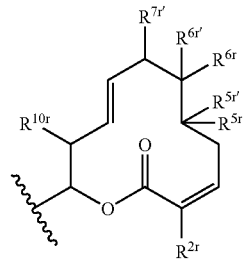
(MD-III)

(wherein $R^{2r}$, $R^{5r}$, $R^{5r'}$, $R^{6r}$, $R^{6r'}$, $R^{7r'}$ and $R^{10r}$ have the same meanings as the above-mentioned definition), the formula (4):

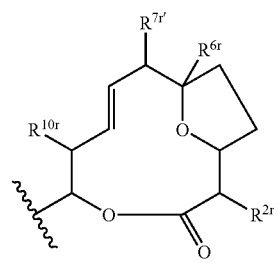
(MD-IV)

(wherein $R^{2r}$, $R^{6r}$, $R^{7r'}$ and $R^{10r}$ have the same meanings as the above-mentioned definition), or the formula (5):

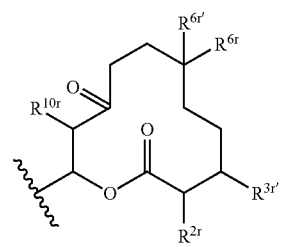
(MD-V)

(wherein $R^{2r}$, $R^{3r'}$, $R^{6r}$, $R^{6r'}$ and $R^{10r}$ have the same meanings as the above-mentioned definition);
$R^{12r}$, $R^{16r}$, $R^{16r'}$, $R^{17r'}$, $R^{18r}$, $R^{20r}$, $R^{20r'}$, $R^{21r}$, $R^{21r'}$, $R^{22r}$ and $R^{22r'}$ are the same as or different from each other and each represents
1) hydrogen,
2) methyl which may be optionally substituted,
3) —$OR^H$ (wherein $R^H$ represents <1> hydrogen, <2> methyl or <3> acetyl),
4) —$OR^D$ (wherein $R^D$ represents
  <1> $C_{1-22}$ alkyl (provided that in case of methyl, it has always substituents),
  <2> —$CH_2Ar$,
  <3> $C_{3-22}$ acyl,
  <4> unsaturated $C_{3-22}$ acyl,
  <5> —$COR^{CO}$,
  <6> $C_{1-22}$ alkylsulfonyl,
  <7> benzenesulfonyl, or <8> —SiR$^{s1}$R$^{s2}$R$^{s3}$, each of which may have substituents), 5) halogen or 6) —R$^M$—NR$^{N1}$R$^{N2}$ (Ar, R$^{CO}$, R$^{s1}$, R$^{s2}$, R$^{s3}$, R$^M$, R$^{N1}$ and R$^{N2}$ have the same meanings as the definitions in the formula 5 of claim 2);

further, R$^{21r}$ and R$^{21r'}$ may be bound together to represent <1> a ketone structure (=O) or an oxime structure (=NOR$^{OX}$: wherein R$^{OX}$ has the same meaning as the definition in the formula 5 of claim 2);

when either one of A and B is 1) halogen, or 2) <1> alkylsulfonyloxy, <2> benzenesulfonyloxy or <3> C$_{1-22}$ Alkoxy, each of which may have substituents, the other is 1) hydroxy, or 2) <1> C$_{1-22}$ Alkoxy or <2> C$_{2-22}$ acyloxy, each of which may have substituents.

34. A compound represented by the formula (16), a pharmacologically acceptable salt thereof or a hydrate of them

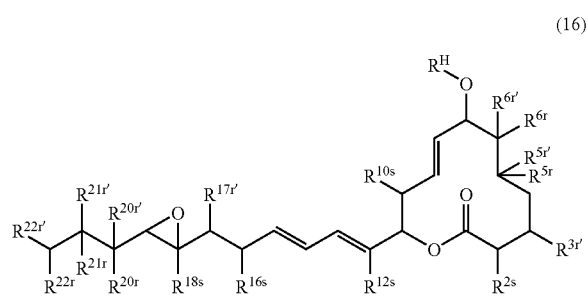

(16)

In the formula (16), R$^{3r'}$, R$^{5r}$, R$^{5r'}$, R$^{6r}$, R$^{6r'}$, R$^H$, R$^{17r'}$, R$^{20r}$, R$^{20r'}$, R$^{21r}$, R$^{21r'}$, R$^{22r}$ and R$^{22r'}$ have the same meanings as the definitions in the formula 15 of claim 33; and R$^{2s}$, R$^{10s}$, R$^{12s}$, R$^{16s}$ and R$^{18s}$ are the same as or different from each other and each represents hydrogen or methyl, provided that the restricted clause 3 according to claim 1 is included.

35. A compound represented by the formula (17), a pharmacologically acceptable salt thereof or a hydrate of them

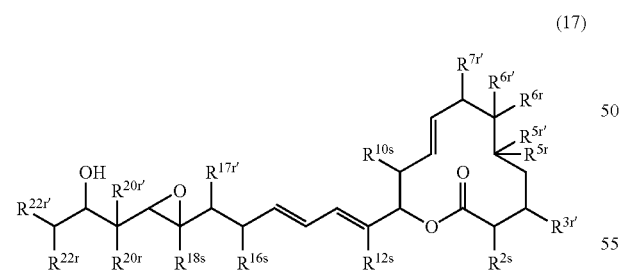

(17)

In the formula (17), R$^{3r'}$, R$^{5r}$, R$^{5r'}$, R$^{6r}$, R$^{6r'}$, R$^{7r'}$, R$^{17r'}$, R$^{20r}$, R$^{20r'}$, R$^{22r}$ and R$^{22r'}$ have the same meanings as the definitions in the formula 15 of claim 33; and R$^{2s}$, R$^{10s}$, R$^{12s}$, R$^{16s}$ and R$^{18s}$ have the same meanings as the definitions in the formula 16 of claim 34, provided that the restricted clauses 3 According to claim 1 is included.

36. A compound represented by the formula (18), a pharmacologically acceptable salt thereof or a hydrate of them

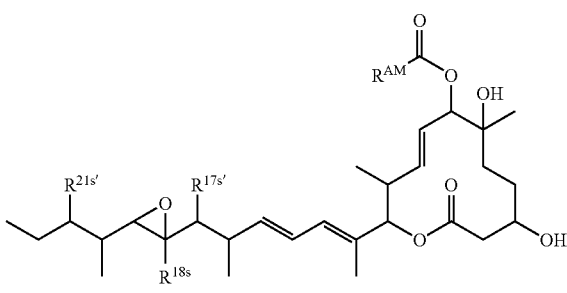

(18)

In the formula (18), R$^{17s'}$ represents hydrogen or hydroxy; R$^{18s}$ represents hydrogen or methyl; R$^{21s}$ represents hydroxy or methoxy; and R$^{AM}$ represents —NR$^{am1}$R$^{am2}$ (wherein R$^{am1}$ and R$^{am2}$ are (1) the same as or different from each other and each represents 1) hydrogen, or 2) <1> C$_{1-22}$ alkyl, <2> C$_{3-8}$ cycloalkyl, <3> unsaturated C$_{3-22}$ alkyl, <4> C$_{2-22}$ acyl, <5> unsaturated C$_{3-22}$ acyl, <6> C$_{6-14}$ aryl, <7> C$_{3-8}$ cycloalkenyl, <8> 5-membered to 14-membered heteroaryl, <9> aralkyl, <10> heteroaralkyl, <11> C$_{1-22}$ alkylsulfonyl, <12> benzenesulfonyl, <13> azetidin-2-yl, <14> pyrrolidin-3-yl, <15> piperazin-4-yl or <16> homopiperazin-4-yl, each of which may have substituents, or (2) —NR$^{am1}$R$^{am2}$ is bound together to represents an optionally substituted 3-membered to 14-membered nitrogen-containing non-aromatic heterocyclic ring).

37. A compound represented by the formula (18) of claim 36, a pharmacologically acceptable salt thereof or a hydrate of them, which is selected from the group of compounds consisting of, (1) a compound in which R$^{AM}$ is represented by

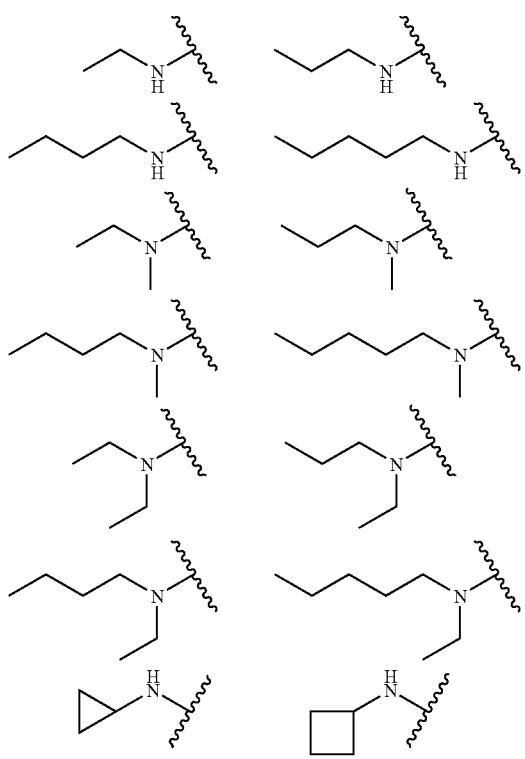

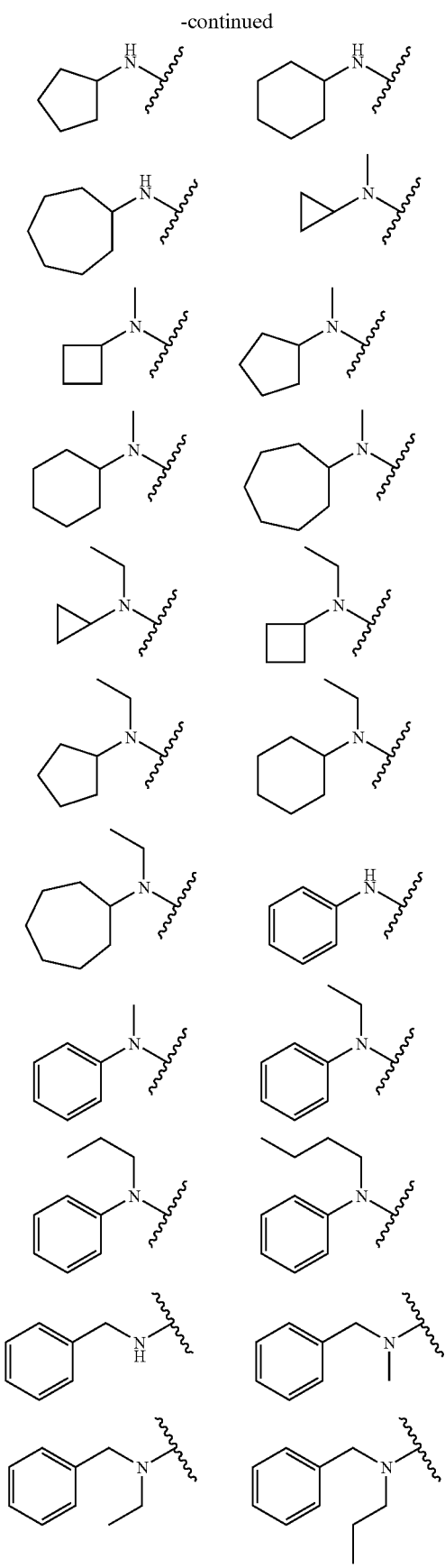

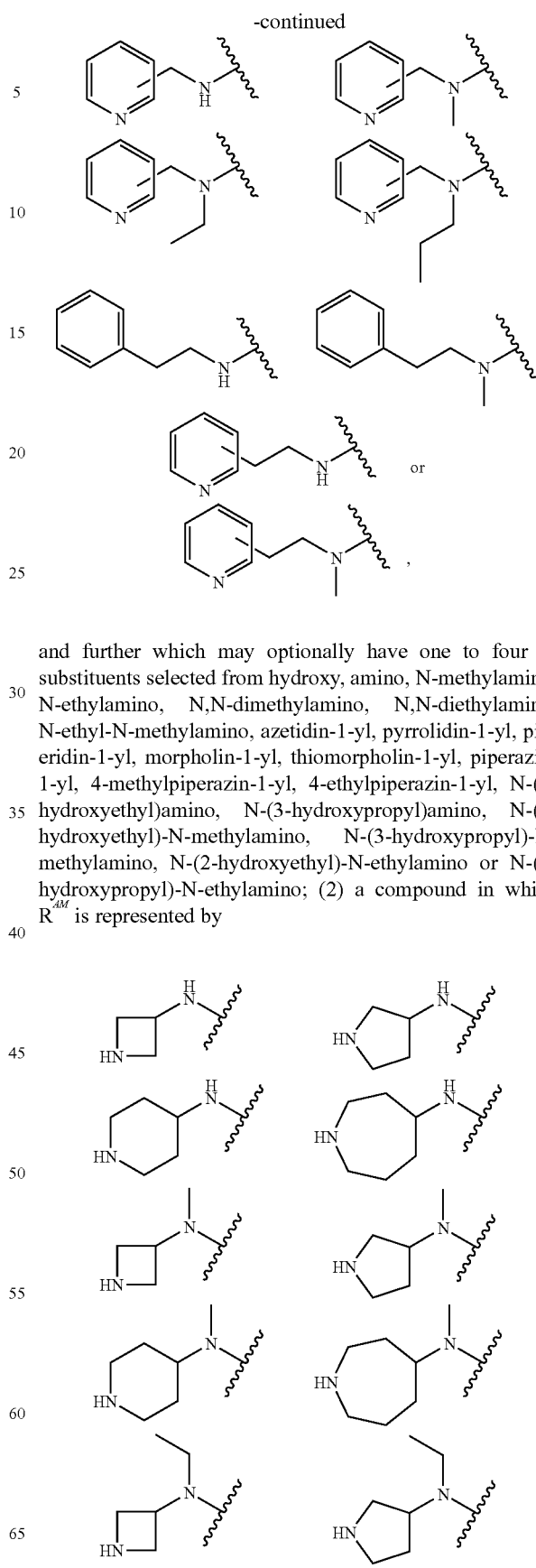

and further which may optionally have one to four of substituents selected from hydroxy, amino, N-methylamino, N-ethylamino, N,N-dimethylamino, N,N-diethylamino, N-ethyl-N-methylamino, azetidin-1-yl, pyrrolidin-1-yl, piperidin-1-yl, morpholin-1-yl, thiomorpholin-1-yl, piperazin-1-yl, 4-methylpiperazin-1-yl, 4-ethylpiperazin-1-yl, N-(2-hydroxyethyl)amino, N-(3-hydroxypropyl)amino, N-(2-hydroxyethyl)-N-methylamino, N-(3-hydroxypropyl)-N-methylamino, N-(2-hydroxyethyl)-N-ethylamino or N-(3-hydroxypropyl)-N-ethylamino; (2) a compound in which $R^{AM}$ is represented by -continued

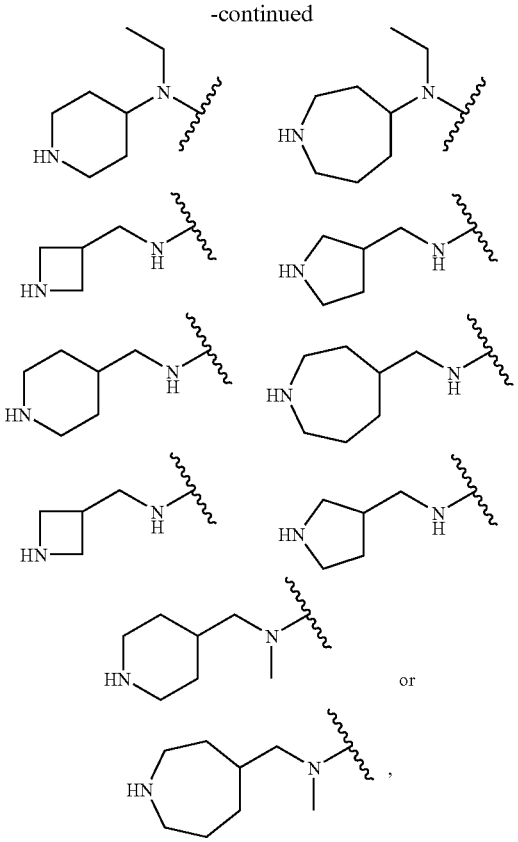

and further, which may optionally have one to four of substituents selected from methyl, ethyl, n-propyl, hydroxy, hydroxymethyl, 2-hydroxyethyl and 3-hydroxypropyl; and (3) a compound in which $R^{AM}$ is represented by

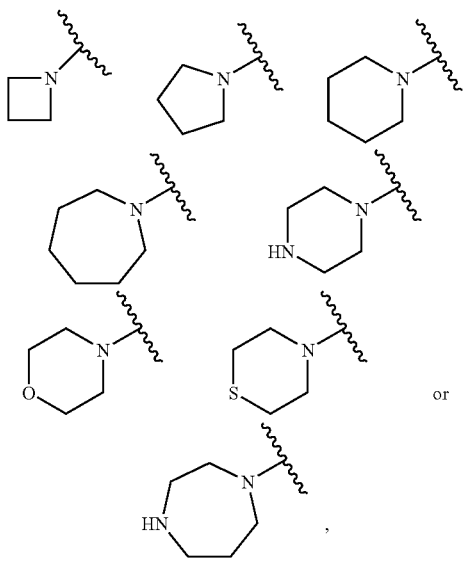

and further, which may optionally have one or two of substituents selected from methyl, ethyl, n-propyl, hydroxy, hydroxymethyl, 2-hydroxyethyl, 3-hydroxypropyl, amino, N-methylamino, N-ethylamino, N,N-dimethylamino, N,N-diethylamino, N-ethyl-N-methylamino, azetidin-1-yl, pyrrolidin-1-yl, piperidin-1-yl, morpholin-1-yl and thiomorpholin-1-yl.

38. A compound represented by the formula (19), a pharmacologically acceptable salt thereof or a hydrate of them

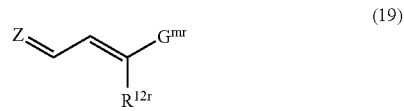

(19)

In the formula, $G^{mr}$ and $R^{12r}$ have the same meanings as the definitions in the formula (15) of claim 33; and Z represents oxygen or the formula:

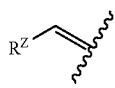

(wherein $R^Z$ represents (1) hydrogen or (2) a and $C_{1-8}$ alkyl, $C_{1-8}$ alkenyl or $C_{1-8}$ Alkynyl which may have substituents and an epoxy structure).

39. A compound represented by the formula (20), a pharmacologically acceptable salt thereof or a hydrate of them

(20)

In the formula, a' and B' are bound together with oxygen to represent an epoxy structure, or either one of them represents hydroxy and the other represents any one of chlorine, bromine, hydroxy and methoxy; $R^{21a'}$ and $R^{21b'}$ are bound together with oxygen to represent a ketone structure, or either one of them represents hydrogen and the other represents any one of hydroxy, methoxy and —$OR^M$; $R^{3''}$, $R^{6''}$ and $R^{7''}$ are the same as or different from each other and each represents hydrogen, acetyl or —$R^M$; $R^{16}$, $R^{17}$ and $R^{20}$ are the same as or different from each other and each represents hydrogen, hydroxy or —$OR^M$; $R^{12}$ represents methyl, —$CH_2OH$ or —$CH_2OR^M$ (wherein $R^M$ represents $C_1$–$C_8$ alkyl, $C_2$–$C_8$ acyl, $R^{bn}CH_2$, $R^{bn}CO$ or $R^{n1}R^{n2}NCO$; $R^{bn}$ represents $C_6$–$C_{10}$ aryl or $C_5$–$C_{14}$ heteroacyl which may optionally have one or more substituents described below, $R^{n1}$ and $R^{n2}$ are the same as or different from each other and each represents hydrogen, $C_1$–$C_8$ alkyl, $C_3$–$C_7$ cycloalkyl, benzyl which may optionally have one or more substituents described below, or $R^{n1}$ and $R^{n2}$ are bound together to represent pyrrolidine, piperidine, piperazine, N-substituted piperazine or morpholine;

The substituent described here indicates the following
a) $C_1$–$C_8$ alkyl, $C_1$–$C_8$ alkoxy, $C_2$–$C_8$ acyl,
b) fluoro, chloro, bromo, iodo, c) carboxylic acid, sulfonic acid, carboxylic acid ester, carboxamide which may optionally have substituents on nitrogen, d) nitro, amino, N-monosubstituted amino, N,N-disubstituted amino, e) a hydroxy group, mercaptane, $C_1$–$C_8$ alkylthio, $C_1$–$C_8$ alkylsulfoxide, $C_1$–$C_8$ alkylsulfone, provided that the restricted clauses 1, 2 and 3 According to claim 1 are included.

40. A compound represented by the formula (21), a pharmacologically acceptable salt thereof or a hydrate of them

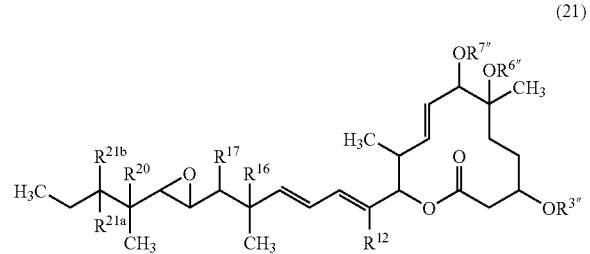

(21)

In the formula (21), $R^{3''}$ and $R^{6''}$ represent hydrogen; $R^{7''}$ represents hydrogen or acetyl; $R^{16}$, $R^{17}$ and $R^{20}$ are the same as or different from each other and each represents hydrogen or hydroxy; $R^{21a}$ And $R^{21b}$ are bound together with oxygen to represent a ketone structure, or either one of them represents hydroxy or methoxy and the other represents hydrogen; and $R^{12}$ represents methyl or —$CH_2OH$, provided that the restricted clauses 1, 2 and 3 According to claim 1 are included.

41. The compound according to claim 40, a pharmacologically acceptable salt thereof or a hydrate of them, wherein in the formula (21), $R^{3''}$, $R^{6''}$ and $R^{17}$ are hydrogen; $R^{7''}$ is hydrogen or acetyl; $R^{16}$ and $R^{20}$ are the same as or different from each other and each represents hydrogen or hydroxy; $R^{21a'}$ and $R^{21b'}$ are bound together with oxygen, or either one of them represents hydroxy and the other is hydrogen; and $R^{12'}$ is methyl.

42. The compound according to claim 40, a pharmacologically acceptable salt thereof or a hydrate of them, wherein in the formula (21), $R^{3''}$, $R^{6''}$ and $R^{17}$ are hydrogen; $R^{7''}$ is acetyl; $R^{16}$ and $R^{17}$ are the same as or different from each other and each represents hydrogen or hydroxy; $R^{21a}$ and $R^{21b}$ are bound together with oxygen, or either one of them represents hydroxy and the other is hydrogen; and $R^{12}$ represents methyl or —$CH_2OH$.

43. The compound according to claim 40, or a pharmacologically acceptable salt thereof or a hydrate of them, wherein in the formula (21), $R^{3''}$, $R^{6''}$, $R^{7''}$, $R^{17}$, $R^{20}$ and $R^{21a}$ are hydrogen; $R^{16}$ and $R^{21b}$ are hydroxy; and $R^{12}$ is methyl.

44. The compound according to claim 40, a pharmacologically acceptable salt thereof or a hydrate of them, wherein in the formula (21), $R^{3''}$, $R^{6''}$, $R^{7''}$, $R^{16}$, $R^{17}$, $R^{20}$ and $R^{21a}$ are hydrogen; $R^{20}$ and $R^{21b}$ are hydroxy; and $R^{12}$ is methyl.

45. The compound according to claim 40, a pharmacologically acceptable salt thereof or a hydrate of them, wherein in the formula (21), $R^{3''}$, $R^{6''}$, $R^{7''}$, $R^{16}$, $R^{17}$, $R^{20}$ and $R^{21a}$ are hydrogen; $R^{21b}$ is hydroxy; and $R^{12}$ is methyl.

46. The compound according to claim 40, a pharmacologically acceptable salt thereof or a hydrate of them, wherein in the formula (21), $R^{3''}$, $R^{6''}$, $R^{16}$, $R^{17}$ and $R^{21a}$ are hydrogen; $R^{20}$ and $R^{21b}$ are hydroxy; $R^{7''}$ is acetyl; and $R^{12}$ is methyl.

47. The compound according to claim 40, a pharmacologically acceptable salt thereof or a hydrate of them, wherein in the formula (21), $R^{3''}$, $R^{6''}$, $R^{17}$, $R^{20}$ and $R^{21a}$ are hydrogen; $R^{16}$ and $R^{21b}$ are hydroxy; $R^{7''}$ is acetyl; and $R^{12}$ is methyl.

48. The compound according to claim 40, a pharmacologically acceptable salt thereof or a hydrate of them, wherein in the formula (21), $R^{3''}$, $R^{6''}$, $R^{16}$, $R^{17}$ and $R^{20}$ are hydrogen; $R^{21a}$ and $R^{21b}$ are bound together with oxygen; $R^{7''}$ is acetyl; and $R^{12}$ is methyl.

49. The compound according to claim 40, a pharmacologically acceptable salt thereof or a hydrate of them, wherein in the formula (21), $R^{3''}$, $R^{6''}$, $R^{16}$, $R^{17}$, $R^{20}$ and $R^{21a}$ are hydrogen; $R^{21b}$ is hydroxy; $R^{7''}$ is acetyl; and $R^{12}$ is methyl.

50. A medicament comprising at least one selected from compounds according to claims 1 to 49, a pharmacologically acceptable salt thereof or a hydrate of them as an active ingredient, and a pharmaceutically acceptable carrier.

51. The medicament according to claim 50, as an agent for preventing or treating a disease against which gene expression control is efficacious.

52. The medicament according to claim 50, as an agent for preventing or treating a diseases against which VEGF production suppressing action is efficacious.

53. The medicament according to claim 50, as an agent for preventing or treating a disease against which an antiangiogenic effect is efficacious.

54. The medicament according to claim 50, as an antiangiogenic agent.

55. The medicament according to claim 50, as an antitumor agent.

56. The medicament according to claim 50, as an agent for treating hematoma.

57. The medicament according to claim 50, as an agent for supressing cancer metastasis.

58. The medicament according to claim 50, as an agent for treating retina angiogenic disease or an agent for treating diabetic retinopathy.

59. The medicament according to claim 50, as an agent for treating inflammatory disease.

60. The medicament according to claim 50, as an agent for treating inflammatory diseases consisting of osteoarthritis, rheumatoid arthritis, psoriasis or delayed hypersensitivity reaction.

61. The medicament according to claim 50, as an agent for treating atherosclerosis.

62. The medicament according to claim 50, as an agent for treating solid cancer.

63. The medicament according to claim 62, wherein the solid cancer is lung cancer, brain tumor, breast cancer, prostate cancer, ovarian cancer, colon cancer or melanoma.

64. The medicament according to claim 50, as an agent for treating leukemia.

65. The medicament according to claim 50, as an antitumor agent based on gene expression control.

66. The medicament according to claim 50, as an antitumor agent based on VEGF production suppressing action.

67. The medicament according to claim 50, as an antitumor agent based on an antiangiogenic effect.

68. A method for preventing or treating a disease against which gene expression control is efficacious, which comprises administering a pharmacologically effective dose of the medicament according to claim 50 to a patient.

69. A method for preventing or treating a disease against which the VEGF production suppressing action is efficacious, which comprises administering a pharmacologically effective dose of the medicament according to claim 50 to a patient.

70. A method for preventing or treating a disease against which an antiangiogenic effect is efficacious, which comprises administering a pharmacologically effective dose of the medicament according to claim 50 to a patient.

71. A method for preventing or treating a disease against which gene expression control is efficacious, a disease against which VEGF production suppressing action is efficacious, a disease against which antiangiogenic action is efficacious or solid cancers, which comprises administering to a patient in need thereof an effective dose of a compound according to any one of claims 1 to 49, a pharmacologically acceptable salt thereof, or a hydrate of said compound or said salt.

72. A production process of the compound according to any one of claims 1 to 49, a pharmacologically acceptable salt thereof or a hydrate of them, which comprises culturing *Streptomyces* sp. Mer. 11107, FERM P- 18144 or its variant in a nutrient culture medium, collecting the compound according to any one of claims 2 to 50 from the culture solution, and carrying out various modification synthesis by using the obtained compounds as a starting material to obtain derivatives thereof.

73. The compound according to claim 1, in which the compound is (8E,12E,14E)-7-acetoxy-3,6,21-trihydroxy-6,10,12,16,20-pentamethyl-18,19-epoxytricosa-8,12,14-trien-11-olide, (8E,12E,14E)-7-acetoxy-3,6,16,21-tetrahydroxy-6,10,12,16,20-pentamethyl-18,19-epoxytricosa-8,12,14-trien-11-olide, (8E,12E,14E)-7-acetoxy-3,5,6,21-tetrahydroxy-6,10,12,16,20-pentamethyl-18,19-epoxytricosa-8,12,14-trien-11-olide, (8E,12E,14E)-7-acetoxy-3,21-dihydroxy-10,12,16,20-tetramethyl-18,19-epoxy-6,6-epoxymethanotricosa-8,12,14-trien-11-olide, (8E,12E,14E)-7-acetoxy-3,6,21-trihydroxy-6,10,12,16,20-pentamethyl-5-oxo-18,19-epoxytricosa-8,12,14-trien-11-olide, (8E,12E,14E)-7-acetoxy-3,6-dihydroxy-6,10,12,16,20-pentamethyl-21-oxo-18,19-epoxytricosa-8,12,14-trien-11-olide, (4E,8E,12E,14E)-7-acetoxy-3,6,21-trihydroxy-6,10,12,16,20-pentamethyl-18,19-epoxytricosa-4,8,12,14-tetraen-11-olide, (8E,12E,14E)-7-acetoxy-3,6,21-trihydroxy-6,10,12,16,20-pentamethyl-18,19-epoxydocosa-8,12,14-trien-11-olide, (8E,12E,14E)-7-acetoxy-6-acetoxymethyl-3,6,21-trihydroxy-10,12,16,20-tetramethyl-18,19-epoxytricosa-8,12,14-trien-11-olide, (8E,12E,14E)-7-acetoxy-3,6,17,21-tetrahydroxy-6,10,12,16,20-pentamethyl-18,19-epoxytricosa-8,12,14-trien-11-olide, (8E,12E,14E)-6-acetoxymethyl-3,6,7,21-tetrahydroxy-10,12,16,20-tetramethyl-18,19-epoxytricosa-8,12,14-trien-11-olide, (8E,12E,14E)-7-acetoxy-3,5,21-trihydroxy-6,10,12,16,20-pentamethyl-18,19-epoxytricosa-8,12,14-trien-11-olide, (4E,8E,12E,14E)-7-acetoxy-3,21-dihydroxy-10,12,16,20-tetramethyl-18,19-epoxy-6,6-epoxymethanotricosa-4,8,12,14-tetraen-11-olide, (4E,8E,12E,14E)-6,7-diacetoxy-3,21-dihydroxy-6,10,12,16,20-pentamethyl-18,19-epoxytricosa-4,8,12,14-tetraen-11-olide, (8E,12E,14E)-7-acetoxy-3,6,16-trihydroxy-6,10,12,16,20-pentamethyl-21-oxo-18,19-epoxytricosa-8,12,14-trien-11-olide, (4E,8E,12E,14E)-7-acetoxy-3,6,17,21-tetrahydroxy-6,10,12,16,20-pentamethyl-18,19-epoxytricosa-4,8,12,14-tetraen-11-olide, or (8E,12E,14E)-7-acetoxy-3,6,17-trihydroxy-6,10,12,16,18-pentamethyl-18,19-epoxyhenicosa-8,12,14-trien-11-olide.

74. The compound according to claim 1, in which the compound is (8E,12E,14E)-7-acetoxy-3,6,21-trihydroxy-6,10,12,16,20-pentamethyl-18,19-epoxytricosa-8,12,14-trien-11-olide, (8E,12E,14E)-7-acetoxy-3,6,16,21-tetrahydroxy-6,10,12,16,20-pentamethyl-18,19-epoxytricosa-8,12,14-trien-11-olide, (8E,12E,14E)-7-acetoxy-3,5,6,21-tetrahydroxy-6,10,12,16,20-pentamethyl-18,19-epoxytricosa-8,12,14-trien-11-olide, (8E,12E,14E)-7-acetoxy-3,21-dihydroxy-10,12,16,20-tetramethyl-18,19-epoxy-6,6-epoxymethanotricosa-8,12,14-trien-11-olide, or (8E,12E,14E)-7-acetoxy-3,6,21-trihydroxy-6,10,12,16,20-pentamethyl-5-oxo-18,19-epoxytricosa-8,12,14-trien-11-olide.

75. The compound according to claim 1, in which the compound is (8E,12E,14E)-7-acetoxy-3,6-dihydroxy-6,10,12,16,20-pentamethyl-21-oxo-18,19-epoxytricosa-8,12,14-trien-11-olide, (4E,8E,12E,14E)-7-acetoxy-3,6,21-trihydroxy-6,10,12,16,20-pentamethyl-18,19-epoxytricosa-4,8,12,14-tetraen-11-olide, (8E,12E,14E)-7-acetoxy-3,6,21-trihydroxy-6,10,12,16,20-pentamethyl-18,19-epoxydocosa-8,12,14-trien-11-olide, (8E,12E,14E)-7-acetoxy-6-acetoxymethyl-3,6,21-trihydroxy-10,12,16,20-tetramethyl-18,19-epoxytricosa-8,12,14-trien-11-olide, (8E,12E,14E)-7-acetoxy-3,6,17,21-tetrahydroxy-6,10,12,16,20-pentamethyl-18,19-epoxytricosa-8,12,14-trien-11-olide, (8E,12E,14E)-6-acetoxymethyl-3,6,7,21-tetrahydroxy-10,12,16,20-tetramethyl-18,19-epoxytricosa-8,12,14-trien-11-olide, (8E,12E,14E)-7-acetoxy-3,5,21-trihydroxy-6,10,12,16,20-pentamethyl-18,19-epoxytricosa-8,12,14-trien-11-olide, (4E,8E,12E,14E)-7-acetoxy-3,21-dihydroxy-10,12,16,20-tetramethyl-18,19-epoxy-6,6-epoxymethanotricosa-4,8,12,14-tetraen-11-olide, (4E,8E,12E,14E)-6,7-diacetoxy-3,21-dihydroxy-6,10,12,16,20-pentamethyl-18,19-epoxytricosa-4,8,12,14-tetraen-11-olide, (8E,12E,14E)-7-acetoxy-3,6,16-trihydroxy-6,10,12,16,20-pentamethyl-21-oxo-18,19-epoxytricosa-8,12,14-trien-11-olide, (4E,8E,12E,14E)-7-acetoxy-3,6,17,21-tetrahydroxy-6,10,12,16,20-pentamethyl-18,19-epoxytricosa-4,8,12,14-tetraen-11-olide, or (8E,12E,14E)-7-acetoxy-3,6,17-trihydroxy-6,10,12,16,18-pentamethyl-18,19-epoxyhenicosa-8,12,14-trien-11-olide.

76. The compound according to claim 1, in which the compound is (8E,12E,14E)-7-acetoxy-3,6,21-trihydroxy-6,10,12,16, 20-pentamethyl-18,19-epoxytricosa-8,12,14-trien-11-olide.

77. The compound according to claim 1, in which the compound is (8E,12E,14E)-7-acetoxy-3,6,16,21-tetrahydroxy-6,10,12, 16,20-pentamethyl-18,19-epoxytricosa-8,12,14-trien-11-olide.

78. The compound according to claim 1, in which the compound is (8E,12E,14E)-7-acetoxy-3,5,6,21-tetrahydroxy-6,10,12, 16,20-pentamethyl-18,19-epoxytricosa-8,12,14-trien-11-olide.

79. The compound according to claim 1, in which the compound is (8E,12E,14E)-7-acetoxy-3,21-dihydroxy-10,12,16,20-tetramethyl-18,19-epoxy-6,6-epoxymethanotricosa-8,12, 14-trien-11-olide.

80. The compound according to claim 1, in which the compound is (8E,12E,14E)-7-acetoxy-3,6,21-trihydroxy-6,10,12,16, 20-pentamethyl-5-oxo-18,19-epoxytricosa-8,12,14-trien-11-olide.

81. The compound according to claim 1, in which the compound is (8E,12E,14E)-3,6,21-trihydroxy-6,10,12,16,20-pentamethyl-7-((4-methylpiperazin-1-yl)carbonyl)oxy-18,19-epoxytricosa-8,12,14-trien-11-olide, (8E,12E,14E)-7-(N-(2-N'N'-dimethylamino)ethyl)carbamoyloxy-3,6,21-trihydroxy-6,10,12,16,20-pentamethyl-18,19-epoxytricosa-8,12,14-trien-11-olide, (8E,12E,14E)-7-(N-(3-N'N'-dimethylamino)propyl)carbamoyloxy-3,6,21-trihydroxy-6,10,12,16,20-pentamethyl-18,19-epoxytricosa-8,12,14-trien-11-olide, (8E,12E,14E)-3,6,21-trihydroxy-6,10,12,16,20-pentamethyl-7-((piperazin-1-yl)carbonyl)oxy-18,19-epoxytricosa-8,12,14-trien-11-olide, (8E,12E,14E)-3,6,21-trihydroxy-6,10,12,16,20-pentamethyl-7-((4-methylhomopiperazin-1-yl)carbonyl)oxy-18,19-epoxytricosa-8,12,14-trien-11-olide, (8E,12E,14E)-3,6,21-trihydroxy-6,10,12,16,20-pentamethyl-7-((4-ethylpiperazin-1-yl)carbonyl)oxy-18,19-epoxytricosa-8,12,14-trien-11-olide, (8E,12E,14E)-3,6,21-trihydroxy-6,10,12,16,20-pentamethyl-7-((4-(2-hydroxyethyl)piperazin-1-yl)carbonyl)oxy-18,19-epoxytricosa-8,12,14-trien-11-olide, (8E,12E,14E)-3,6,21-trihydroxy-6,10,12,16,20-pentamethyl-((4-piperidin-1-yl)-piperidin-1-yl)carbonyl)oxy-18, 19-epoxytricosa-8,12,14-trien-11-olide, (8E,12E,14E)-7,21-diacetoxy-3,6-dihydroxy-6,10,12,16, 20-pentamethyl-18,19-epoxytricosa-8,12,14-trien-11-olide, (8E,12E,14E)-7-acetoxy-21-carbamoyloxy-3,6-dihydroxy-6,10,12,16,20-pentamethyl-18,19-epoxytricosa-8,12, 14-trien-11-olide, (8E,12E,14E)-3,6,21-trihydroxy-6,10,12,16,20-pentamethyl-7-((homopiperazin-1-yl)carbonyl)oxy-18,19-epoxytricosa-8,12,14-trien-11-olide, (8E,12E,14E)-3,6,21-trihydroxy-6,10,12,16,20-pentamethyl-7-N-(2-(piperidin-1-yl)ethyl)carbamoyloxy-18,19-epoxytricosa-8,12,14-trien-11-olide, (8E,12E,14E)-3,6,21-trihydroxy-6,10,12,16,20-pentamethyl-7-N-(2-(pyrrolidin-1-yl)ethyl)carbamoyloxy-18,19-epoxytricosa-8,12,14-trien-11-olide, (8E,12E,14E)-3,6,21-trihydroxy-6,10,12,16,20-pentamethyl-7-N-(1-methylpiperidin-4-yl)carbamoyloxy-18,19-epoxytricosa-8,12,14-trien-11-olide, (8E,12E,14E)-3,6,21-trihydroxy-6,10,12,16,20-pentamethyl-7-N-(3-(4-methylpiperazin-1-yl)propyl)carbamoyloxy-18,19-epoxytricosa-8,12,14-trien-11-olide, (8E,12E,14E)-3,6,21-trihydroxy-6,10,12,16,20-pentamethyl-7-((3,5-dimethylpiperazin-1-yl)carbonyl)oxy-18,19-epoxytricosa-8,12,14-trien-11-olide, (8E,12E,14E)-3,6,21-trihydroxy-6,10,12,16,20-pentamethyl-7-N-methyl-N-(1-methylpiperidin-4-yl)carbamoyloxy-18,19-epoxytricosa-8,12,14-trien-11-olide, (8E,12E,14E)-7-acetoxy-3,6-dihydroxy-21-methoxy-6, 10,12,16,20-pentamethyl-18,19-epoxytricosa-8,12,14-trien-11-olide, (8E,12E,14E)-7-acetoxy-3-hydroxy-6,21-dimethoxy-6, 10,12,16,20-pentamethyl-18,19-epoxytricosa-8,12,14-trien-11-olide, or (8E,12E,14E)-7-acetoxy-3,21-dihydroxy-6-methoxy-6, 10,12,16,20-pentamethyl-18,19-epoxytricosa-8,12,14-trien-11-olide.

82. The compound according to claim 1, in which the compound is (8E,12E,14E)-3,6,21-trihydroxy-6,10,12,16,20-pentamethyl-7-((4-methylpiperazin-1-yl)carbonyl)oxy-18,19-epoxytricosa-8,12,14-trien-11-olide, (8E,12E,14E)-7-(N-(2-N'N'-dimethylamino)ethyl)carbamoyloxy-3,6,21-trihydroxy-6,10,12,16,20-pentamethyl-18,19-epoxytricosa-8,12,14-trien-11-olide, (8E,12E,14E)-7-(N-(3-N'N'-dimethylamino)propyl)carbamoyloxy-3,6,21-trihydroxy-6,10,12,16,20-pentamethyl-18,19-epoxytricosa-8,12,14-trien-1-olide, (8E,12E,14E)-3,6,21-trihydroxy-6,10,12,16,20-pentamethyl-7-((piperazin-1-yl)carbonyl)oxy-18,19-epoxytricosa-8,12,14-trien-11-olide, (8E,12E,14E)-3,6,21-trihydroxy-6,10,12,16,20-pentamethyl-7-((4-methylhomopiperazin-1-yl)carbonyl)oxy-18,19-epoxytricosa-8,12,14-trien-11-olide, (8E,12E,14E)-3,6,21-trihydroxy-6,10,12,16,20-pentamethyl-7-((4-ethylpiperazin-1-yl)carbonyl)oxy-18,19-epoxytricosa-8,12, 14-trien-11-olide, (8E,12E,14E)-3,6,21-trihydroxy-6,10,12,16,20-pentamethyl-7-((4-(2-hydroxyethyl)piperazin-1-yl)carbonyl)oxy-18,19-epoxytricosa-8,12,14-trien-1-olide, or (8E,12E,14E)-3,6,21-trihydroxy-6,10,12,16,20-pentamethyl-7-((4-piperidin-1-yl)-piperidin-1-yl)carbonyl)oxy-18, 19-epoxytricosa-8,12,14-trien-11-olide.

83. The compound according to claim 1, in which the compound is (8E,12E,14E)-7,21-diacetoxy-3,6-dihydroxy-6,10,12,16, 20-pentamethyl-18,19-epoxytricosa-8,12,14-trien-11-olide, (8E,12E,14E)-7-acetoxy-21-carbamoyloxy-3,6-dihydroxy-6,10,12,16,20-pentamethyl-18,19-epoxytricosa-8,12, 14-trien-11-olide, (8E,12E,14E)-3,6,21-trihydroxy-6,10,12,16,20-pentamethyl-7-((homopiperazin-1-yl)carbonyl)oxy-18,19-epoxytricosa-8,12,14-trien-11-olide, (8E,12E,14E)-3,6,21-trihydroxy-6,10,12,16,20-pentamethyl-7-N-(2-(piperidin-1-yl)ethyl)carbamoyloxy-18,19-epoxytricosa-8,12,14-trien-11-olide, (8E,12E,14E)-3,6,21-trihydroxy-6,10,12,16,20-pentamethyl-7-N-(2-(pyrrolidin-1-yl)ethyl)carbamoyloxy-18,19-epoxytricosa-8,12,14-trien-11-olide, (8E,12E,14E)-3,6,21-trihydroxy-6,10,12,16,20-pentamethyl-7-N-(1-methylpiperidin-4-yl)carbamoyloxy-18,19-epoxytricosa-8,12,14-trien-11-olide, (8E,12E,14E)-3,6,21-trihydroxy-6,10,12,16,20-pentamethyl-7-N-(3-(4-methylpiperazin-1-yl)propyl)carbamoyloxy-18,19-epoxytricosa-8,12,14-trien-1-olide, (8E,12E,14E)-3,6,21-trihydroxy-6,10,12,16,20-pentamethyl-7-((3,5-dimethylpiperazin-1-yl)carbonyl)oxy-18,19-epoxytricosa-8,12,14-trien-11-olide, or (8E,12E,14E)-3,6,21-trihydroxy-6,10,12,16,20-pentamethyl-7-N-methyl-N-(1-methylpiperidin-4-yl)carbamoyloxy-18,19-epoxytricosa-8,12,14-trien-11-olide.

84. The compound according to claim 1, in which the compound is (8E,12E,14E)-7-acetoxy-3,6-dihydroxy-21-methoxy-6,10,12,16,20-pentamethyl-18,19-epoxytricosa-8,12,14-trien-11-olide, (8E,12E,14E)-7-acetoxy-3-hydroxy-6,21-dimethoxy-6,10,12,16,20-pentamethyl-18,19-epoxytricosa-8,12,14-trien-11-olide, or (8E,12E,14E)-7-acetoxy-3,21-dihydroxy-6-methoxy-6,10,12,16,20-pentamethyl-18,19-epoxytricosa-8,12,14-trien-11-olide.

85. The compound according to claim 1, in which the compound is (8E,12E,14E)-3,6,21-trihydroxy-6,10,12,16,20-pentamethyl-7-((4-methylpiperazin-1-yl)carbonyl)oxy-18,19-epoxytricosa-8,12,14-trien-11-olide.

86. The compound according to claim 1, in which the compound is (8E,12E,14E)-7-(N-(2-N'N'-dimethylamino)ethyl)carbamoyloxy-3,6,21-trihydroxy-6,10,12,16,20-pentamethyl-18,19-epoxytricosa-8,12,14-trien-11-olide.

87. The compound according to claim 1, in which the compound is (8E,12E,14E)-7-(N-(3-N'N'-dimethylamino)propyl)carbamoyloxy-3,6,21-trihydroxy-6,10,12,16,20-pentamethyl-18,19-epoxytricosa-8,12,14-trien-11-olide.

88. The compound according to claim 1, in which the compound is (8E,12E,14E)-3,6,21-trihydroxy-6,10,12,16,20-pentamethyl-7-((piperazin-1-yl)carbonyl)oxy-18,19-epoxytricosa-8,12,14-trien-11-olide.

89. The compound according to claim 1, in which the compound is (8E,12E,14E)-3,6,21-trihydroxy-6,10,12,16,20-pentamethyl-7-((4-methylhomopiperazin-1-yl)carbonyl)oxy-18,19-epoxytricosa-8,12,14-trien-11-olide.

90. The compound according to claim 1, in which the compound is (8E,12E,14E)-3,6,21-trihydroxy-6,10,12,16,20-pentamethyl-7-((4-ethylpiperazin-1-yl)carbonyl)oxy-18,19-epoxytricosa-8,12,14-trien-11-olide.

91. The compound according to claim 1, in which the compound is (8E,12E,14E)-3,6,21-trihydroxy-6,10,12,16,20-pentamethyl-7-((4-(2-hydroxyethyl)piperazin-1-yl)carbonyl)oxy-18,19-epoxytricosa-8,12,14-trien-11-olide.

92. The compound according to claim 1, in which the compound is (8E,12E,14E)-3,6,21-trihydroxy-6,10,12,16,20-pentamethyl-((4-piperidin-1-yl)-piperidin-1-yl)carbonyl)oxy-18,19-epoxytricosa-8,12,14-trien-11-olide.

* * * * *